(12) United States Patent
Bharathan et al.

(10) Patent No.: US 7,998,952 B2
(45) Date of Patent: Aug. 16, 2011

(54) THIOLACTAMS AND USES THEREOF

(75) Inventors: Indu T. Bharathan, Cambridge, MA (US); Matthew Duffey, Boston, MA (US); Amy Elder, Arlington, MA (US); Jianping Guo, Winchester, MA (US); Gang Li, Westborough, MA (US); Dominic Reynolds, Stoneham, MA (US); Francois Soucy, Stoneham, MA (US); Tricia J. Vos, Medford, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/631,144

(22) Filed: Dec. 4, 2009

(65) Prior Publication Data
US 2010/0179126 A1 Jul. 15, 2010

Related U.S. Application Data

(60) Provisional application No. 61/200,945, filed on Dec. 5, 2008.

(51) Int. Cl.
C07D 487/04 (2006.01)
A61K 31/55 (2006.01)
(52) U.S. Cl. .................. 514/212.06; 540/521
(58) Field of Classification Search .......... 540/521; 514/212.06
See application file for complete search history.

(56) References Cited

U.S. PATENT DOCUMENTS

| | | | |
|---|---|---|---|
| 5,827,849 A | 10/1998 | Himmelsbach et al. | |
| 5,854,236 A | 12/1998 | Albright et al. | |
| 6,686,352 B2 | 2/2004 | Masciadri et al. | |
| 2003/0083327 A1 | 5/2003 | Davies et al. | |
| 2003/0181439 A1 | 9/2003 | Meijer et al. | |
| 2003/0191143 A1 | 10/2003 | Pitts et al. | |
| 2005/0020830 A1 | 1/2005 | Allen et al. | |
| 2006/0100194 A1 | 5/2006 | Blackburn et al. | |
| 2009/0105213 A1 | 4/2009 | Blackburn et al. | |

FOREIGN PATENT DOCUMENTS

| JP | 06 172355 | 6/1994 |
|---|---|---|
| WO | WO 95/06640 A1 | 3/1995 |
| WO | WO 97/47601 A1 | 12/1997 |
| WO | WO 97/47624 A1 | 12/1997 |
| WO | WO 02/06288 A1 | 1/2002 |
| WO | WO 02/087513 A2 | 11/2002 |
| WO | WO 02/088079 A2 | 11/2002 |
| WO | WO 02/088080 A2 | 11/2002 |
| WO | WO 02/094834 A1 | 11/2002 |
| WO | WO 03/104230 A1 | 12/2003 |
| WO | WO 2004/076424 A1 | 9/2004 |
| WO | WO 2005/007655 A1 | 1/2005 |
| WO | WO 2005/037843 A1 | 4/2005 |
| WO | WO 2005/111039 A2 | 11/2005 |
| WO | WO 2006/041773 A2 | 4/2006 |
| WO | WO 2007/003536 A1 | 1/2007 |

OTHER PUBLICATIONS

U.S. Appl. No. 12/903,370, filed Oct. 13, 2010, Blackburn et al., Feb. 17, 2011.
International Search Report and Written Opinion dated Apr. 22, 2010 from International Application No. PCT/US2009/006391, which relates to U.S. Appl. No. 12/631,144, filed Dec. 4, 2009.
International Search Report and Written Opinion dated Jun. 3, 2006 from International Application No. PCT/US2005/035458, which relates to U.S. Appl. No. 11/242,413.
Chetoni, Fabio, et al., "Synthesis of Novel 1-Aryl[1]benzoxepino[5,4-c]pyrazole and [1]Benzoxepino[5,4-d]pyrimidine Derivatives," *Journal of Heterocyclic Chemistry*, vol. 30 (Dec. 1993), pp. 1653-1658.
Chen, Wen-Yean, et al., "Synthesis of 7-Phenylpyrimido[5,4-d][1]benzazepin-2-ones (1)," *Journal of Heterocyclic Chemistry*, vol. 20 (May-Jun. 1983), pp. 663-666.
Kunick, Conrad, et al., "Evaluation and Comparison of 3D-QSAR CoMSIA Models for CDK1, CDK5, and GSK-3 Inhibition by Paullones," *Journal of Medicinal Chemistry*, vol. 47, No. 1 (2004), pp. 22-36.
Link, Andreas, et al., "d-Fused [1]Benzazepines with Selective in Vitro Antitumor Activity: Synthesis and Structure-Activity Relationships," *Journal of Medicinal Chemistry*. vol. 41, No. 8 (1998), pp. 1299-1305.
Leost, Maryse, et al., "Paullones Are Potent Inhibitors of Glycogen Synthase Kinase-3β and Cyclin-Dependent Kinase 5/p25," *European Journal of Biochemistry*, vol. 267, No. 19 (2000), pp. 5983-5994.
Proctor, George R., et al., "Azabenzocycloheptenones. Part 19. Formation of Some Heterocyclic Annelated Compounds from 1,2,3,4-Tetrahydro-1-benzazepine Derivatives," *Journal of the Chemical Society. Perkin Transactions I* (1978), pp. 862-870.

*Primary Examiner* — Bruck Kifle
(74) *Attorney, Agent, or Firm* — Millennium Pharmaceuticals, Inc.

(57) ABSTRACT

This invention provides compounds of formula I:

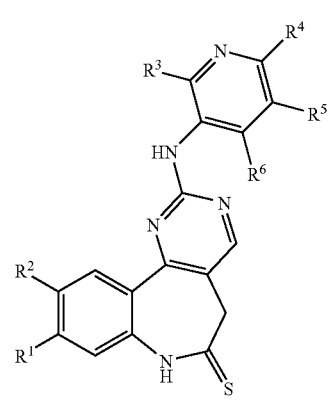

wherein $R^1$, $R^2$, $R^3$, $R^4$, $R^5$, and $R^6$ are as described in the specification. The compounds are inhibitors of PLK and are thus useful for treating proliferative, inflammatory, or cardiovascular disorders.

29 Claims, No Drawings

THIOLACTAMS AND USES THEREOF

The present application claims the benefit of U.S. Provisional Application Ser. No. 61/200,945, filed Dec. 5, 2008. The entire contents of U.S. Provisional Application Ser. No. 61/200,945 is incorporated herein by this reference.

BACKGROUND OF THE INVENTION

Protein kinases constitute a large family of structurally related enzymes that effect the transfer of a phosphate group from a nucleoside triphosphate to a protein acceptor. A vast array of cellular functions, including DNA replication, cell cycle progression, energy metabolism, and cell growth and differentiation, are regulated by reversible protein phosphorylation events mediated by protein kinases. Additionally, protein kinase activity has been implicated in a number of disease states. Accordingly, protein kinase targets have attracted substantial drug discovery efforts in recent years, with several protein kinase inhibitors achieving regulatory approval (reviewed in Fischer, *Curr. Med. Chem.*, 11:1563 (2004); Dancey and Sausville, *Nature Rev. Drug Disc.*, 2:296 (2003)).

PLK is a serine/threonine protein kinase that plays a key role in cell cycle control. PLK controls entry and progression through mitosis at multiple stages by regulating centrosome maturation, activation of initiating factors, degradation of inhibitory components, chromosome condensation, and exit from mitosis (reviewed in Barr et al., *Nature Reviews Mol Cell Biol.*, 5; 429 (2004); Petronczki et al., *Dev. Cell*, 5; 646 (2008)). PLK has been reported to be overexpressed in numerous cancers such as melanoma, prostate, ovarian, colorectal, pancreatic, non small cell lung, esophageal, endometrial, glioma, squamous cell carcinoma of the head and neck and non-Hodkins lymphoma (Kneisel et al., *J Cutan Pathol* 29: 354 (2002); Takai et al. *Cancer Lett* 169: 41 (2001); Takahashi et al *Cancer Sci.;* 94(2):148 (2003); Macmillan et al, *Ann. Surg. Oncol.* 8: 729 (2001); Gray et al. *Mol. Cancer. Ther.* 3: 641 (2004); Dietzmann et al. *J. Neurooncol.* 53:1 (2001); Ito et al. *Br. J. Cancer* 90:414 (2005); Weichert et al. *Pancreatology.* 5:259 (2005); Mito et al. *Leuk. Lymphoma* 46:225 (2005); Liu et al. *Oncology* 74:96 (2008); Yamamoto et al. *Oncology* 70(3):231 (2006); Weichert et al. *Cancer Sci.* 97(4):271 (2006)). Increased levels of expression are additionally correlated with poor prognosis and survival. (Takai et al. *Cancer Lett* 164: 41 (2001); Wolf et al. *Oncogene* 14: 543 (1997); Knecht et al. *Cancer Res,* 59 (1999); Strebhardt et al, *JAMA* 283:479 (2000); Weichert et al. *World J. Gastroenterol* 11:5644 (2005); Tokumitsu et al. *Int. J. Oncol.* 15: 687 (1999); Takai et al. *Cancer Lett.* 164:41 (2001); Weichert et al. *Prostate* 60:240 (2004); Kanaji et al. *Oncology* 70(2):126 (2006)). Overexpression of the kinase transforms cells, rendering them oncogenic such that they acquire the ability to form tumors in mice (Smith et al., *Biochem. Biophys. Res. Commun.* 234; 397 (1997)). PLK protein levels are also elevated in tumor relative to normal cell lines in culture. Downregulation of PLK protein expression by RNA interference in tumor cell lines results in a reduction of cell proliferation, mitotic arrest at prometaphase and the rapid progression into apoptosis (Spankuch-Schmitt et al. *J Natl. Cancer Inst.* 94(24):1863 (2002); Spankuch-Schmitt et al. *Oncogene* 21(20):3162 (2002)). This effect was not observed in normal cell lines. Moreover downregulation of PLK by short hairpin expression in mice with human xenografts reduced tumor growth to 18% (Spankuch et al. *J. Natl. Cancer Inst.* 96(11): 862 (2004); Kappel et al. *Nucleic Acids Res.* 34(16) 4527 (2006)). The key role of PLK in mitotic progression, its overexpression in a wide range of malignancies and the antiproliferative effect observed upon its inhibition demonstrate its feasibility as a therapeutic target.

Accordingly, inhibitors of PLK are useful for treating various diseases or conditions associated with PLK activity, and are especially needed in view of the inadequate treatments currently available for many of these disorders.

DETAILED DESCRIPTION OF THE INVENTION

1. General Description of Compounds of the Invention:

This invention provides compounds that are inhibitors of PLK, and accordingly are useful for the treatment of proliferative, inflammatory, or cardiovascular disorders. The compounds of this invention are represented by formula I:

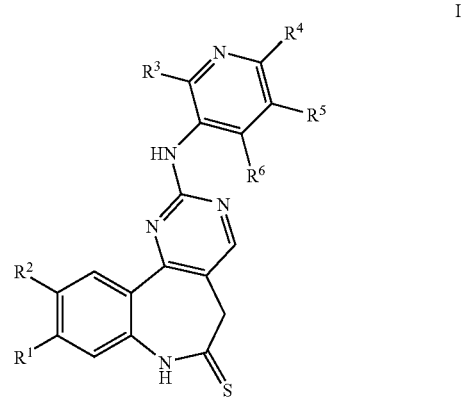

I or a pharmaceutically acceptable salt thereof, wherein:

$R^1$ is selected from hydrogen, —CN, halogen, optionally substituted $C_{1-6}$aliphatic, or —$YR^{1a}$, wherein Y is —O—, —S—, or —$NR^{1a}$, and each occurrence of $R^{1a}$ is independently hydrogen, or optionally substituted $C_{1-6}$aliphatic;

$R^2$ is selected from hydrogen, halogen, —$ZR^{2a}$, or —$OR^{2b}$, wherein Z is an optionally substituted $C_{1-6}$ alkylene chain, and $R^{2a}$ is —$OR^{2b}$, —$N(R^{2b})_2$, —$SR^{2b}$, —$C(O)N(R^{2b})_2$, —$N(R^{2b})C(O)R^{2b}$, —$SO_2N(R^{2b})_2$, —$NR^{2b}SO_2R^{2b}$, —$NR^{2b}C(O)N(R^{2b})_2$, or —$NR^{2b}SO_2N(R^{2b})_2$, wherein each occurrence of $R^{2b}$ is independently hydrogen or optionally substituted $C_{1-6}$alkyl, or two occurrences of $R^{2b}$, taken together with a nitrogen atom to which they are bound, form an optionally substituted 3-7-membered heterocyclyl ring;

$R^3$ is selected from hydrogen, halogen, optionally substituted $C_{1-4}$alkyl, or optionally substituted $C_{1-4}$alkoxy;

$R^4$ is selected from hydrogen, optionally substituted $C_{1-6}$aliphatic, an optionally substituted 3-7-membered heterocyclyl ring, —$(CH_2)_xNR^{4a}R^{4b}$, —$(CH_2)_xNR^{4a}C(O)R^{4b}$, —$(CH_2)_xNR^{4a}S(O)_2R^{4b}$, —$(CH_2)_xC(O)R^{4b}$, $(CH_2)_xC(O)NR^{4a}R^{4b}$, —$(CH2)_xS(O)_2NR^{4a}R^{4b}$, or —$(CH_2)_xOR^{4b}$, wherein each occurrence of x is independently 0-6;

wherein $R^{4a}$ is hydrogen or optionally substituted $C_{1-6}$aliphatic, and $R^{4b}$ is hydrogen, optionally substituted $C_{1-6}$aliphatic, optionally substituted $C_{3-7}$-heterocyclyl or $C_{3-7}$carbocyclyl ring, or is W—$R^{4c}$, wherein W is an optionally substituted $C_{2-6}$ alkylene chain, and $R^{4c}$ is an optionally substituted $C_{3-7}$-heterocyclyl ring, —$OR^{4d}$, —$N(R^{4d})_2$, —$SR^{4d}$, —C(O)N $(R^{4d})_2$, —N($R^{4d}$)C(O)$R^{4d}$, —SO$_2$N($R^{4d}$)$_2$, —N$R^{4d}$SO$_2$$R^{4d}$, —N$R^{4d}$C(O)N($R^{4d}$)$_2$, or —N$R^{4d}$SO$_2$N($R^{4d}$)$_2$, wherein each occurrence of $R^{4d}$ is independently hydrogen or optionally substituted $C_{1-6}$aliphatic, or two occurrences of $R^{4d}$, taken together with the nitrogen atom to which they are bound, form an optionally substituted 3-7-membered heterocyclyl ring;

or wherein $R^{4a}$ and $R^{4b}$, taken together with the nitrogen atom to which they are bound, form an optionally substituted 3-7-membered heterocyclyl ring;

$R^5$ is hydrogen, optionally substituted $C_{1-6}$aliphatic, an optionally substituted $C_{3-7}$-heterocyclyl ring, or is X—$R^{5a}$, wherein X is an optionally substituted $C_{2-6}$ alkylene chain or —N$R^{5c}$, wherein when X is an optionally substituted $C_{2-6}$ alkylene chain $R^{5a}$ is —O$R^{5b}$, —N($R^{5b}$)$_2$, —S$R^{5b}$, —C(O)N($R^{5b}$)$_2$, —N($R^{5b}$)C(O)$R^{5b}$, —SO$_2$N($R^{5b}$)$_2$, —N$R^{5b}$SO$_2$$R^{5b}$, —N$R^{5b}$C(O)N($R^{5b}$)$_2$, or —N$R^{5b}$SO$_2$N($R^{5b}$)$_2$; and when X is —N$R^{5c}$, $R^{5a}$ is hydrogen or optionally substituted $C_{1-6}$aliphatic, or $R^{5a}$ and $R^{5c}$, taken together with the nitrogen atom to which they are bound, form an optionally substituted 3-7-membered heterocyclyl ring;

wherein each occurrence of $R^{5b}$ and $R^{5c}$ is independently hydrogen or optionally substituted $C_{1-6}$aliphatic, or two occurrences of $R^{5b}$, or $R^{5a}$ and $R^5$c, taken together with the nitrogen atom to which they are bound, form an optionally substituted 3-7-membered heterocyclyl ring; or wherein $R^4$ and $R^5$, taken together, form an optionally substituted 5-7-membered cycloaliphatic or heterocyclyl ring; and $R^6$ is selected from hydrogen, halogen, optionally substituted $C_{1-4}$alkyl, or optionally substituted $C_{1-4}$alkoxy.

2. Compounds and Definitions:

Compounds of this invention include those described generally for formula I above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. Preferably, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $NR^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —OR$^+$, —SR$^\circ$, —S(O)R$^\circ$, —SO$_2$R$^\circ$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R$^\circ$, —NR$^+$CO$_2$R$^+$, —NR$^+$SO$_2$R$^\circ$, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R$^\circ$, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$, —C(R$^\circ$)=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl ring. Each R$^\circ$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R$^\circ$=N—NHSO$_2$R$^\circ$ or =N—R* where R$^\circ$ is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring, for example where a phenyl group is substituted with two occurrences of OR$^+$

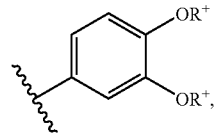

these two occurrences of R$^+$ are taken together with the oxygen atoms to which they are bound to form a fused 6-membered oxygen containing ring:

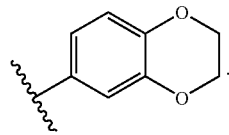

It will be appreciated that a variety of other rings (e.g., spiro and bridged rings) can be formed when two independent occurrences of R$^+$ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds:

In certain embodiments, for compounds of general formula I, $R^2$, $R^4$, and $R^6$ are each hydrogen.

In other embodiments, $R^2$, $R^5$, and $R^6$ are each hydrogen.

In still other embodiments, $R^1$ is optionally substituted $C_{1-4}$aliphatic, halogen, —CN, or —OMe. In yet other embodiments, $R^1$ is methyl, ethyl, —$CF_3$, Cl, —CN, —OMe, or cyclopropyl.

In still other embodiments, $R^2$ is hydrogen or —Z—$R^{2a}$, wherein Z is —$(CH_2)_{2-4}$ and $R^{2a}$ is $N(R^{2b})_2$, wherein each occurrence of $R^{2b}$ is selected from hydrogen or $C_{1-4}$alkyl, or two occurrences of $R^{2b}$, taken together with the nitrogen atom to which they are bound, form an optionally substituted $C_{3-7}$-heterocyclyl ring.

In yet other embodiments, $R^3$ is methyl or $CF_3$.

In still other embodiments, $R^4$ is methyl, or —$NR^{4a}R^{4b}$, wherein $R^{4a}$ and $R^{4b}$, taken together with the nitrogen atom to which they are bound, form an optionally substituted 3-7-membered heterocyclyl ring, or wherein $R^{4a}$ is hydrogen or $C_{1-4}$alkyl, and $R^{4b}$ is an optionally substituted $C_{3-7}$-heterocyclyl ring or is W—$R^{4c}$, wherein W is an optionally substituted $C_{2-6}$ alkylene chain, and $R^{4c}$ is an optionally substituted $C_{3-7}$-heterocyclyl ring.

In yet other embodiments, $R^5$ is an optionally substituted $C_{3-7}$-heterocyclyl ring or is X—$R^{5a}$, wherein X is an optionally substituted $C_{2-6}$ alkylene chain, and $R^{5a}$ is —$N(R^{5b})_2$, wherein each occurrence of $R^{5b}$ is independently hydrogen or $C_{1-6}$alkyl, or two occurrences of $R^{5b}$, taken together with the nitrogen atom to which they are bound, form an optionally substituted 3-7-membered heterocyclyl ring. In other embodiments, $R^4$ and $R^5$ are taken together to form a ring selected from:

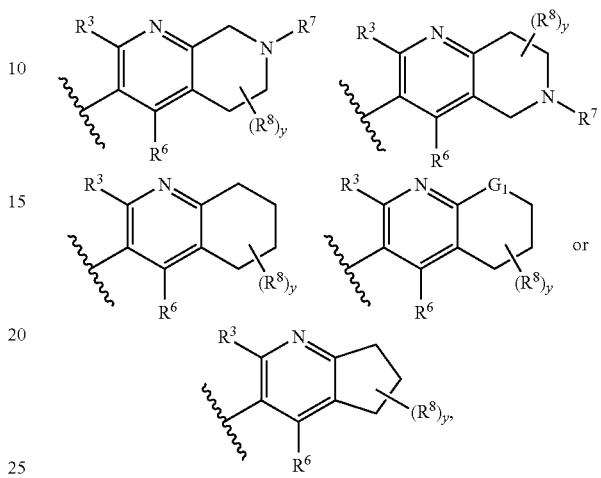

wherein
$G_1$ is —NH—, —O— or —N($CH_3$)—
$R^7$ is selected from hydrogen or optionally substituted $C_{1-6}$aliphatic,
$R^8$ is selected from fluoro, optionally substituted $C_{1-6}$aliphatic, or —$YR^{1a}$, wherein Y is —O—, —S—, or —$NR^{1a}$, and each occurrence of $R^{1a}$ is independently hydrogen, or optionally substituted $C_{1-6}$aliphatic; and
y is 0-4.

In yet other embodiments, compounds of the invention have the structure of formula I-A:

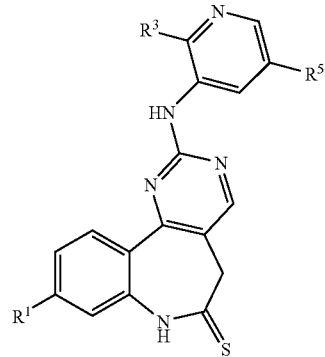

I-A

In some embodiments for compounds of formula I-A, $R^1$ is optionally substituted $C_{1-4}$aliphatic, halogen, —CN, or —OMe. In yet other embodiments, $R^1$ is methyl, ethyl, —$CF_3$, Cl, —CN, —OMe, or cyclopropyl.

In still other embodiments for compounds of formula I-A, $R^3$ is methyl or $CF_3$.

In yet other embodiments, $R^5$ is an optionally substituted $C_{3-7}$-heterocyclyl ring or is X—$R^{5a}$, wherein X is an optionally substituted $C_{2-6}$ alkylene chain, and $R^{5a}$ is —$N(R^{5b})_2$, wherein each occurrence of $R^{5b}$ is independently hydrogen or $C_{1-6}$alkyl, or two occurrences of $R^{5b}$, taken together with the nitrogen atom to which they are bound, form an optionally substituted 3-7-membered heterocyclyl ring.

In still other embodiments, $R^5$ is an optionally substituted pyrrolidinyl, morpholinyl, piperidinyl, or piperazinyl group, or is X—$R^{5a}$, wherein X is a $C_{2-4}$alkylene chain, and $R^{5a}$ is —N($R^{5b}$)$_2$, wherein each occurrence of $R^{5b}$ is independently hydrogen or $C_{1-6}$alkyl, or two occurrences of $R^{5b}$, taken together with the nitrogen atom to which they are bound, form an optionally substituted pyrrolidinyl, piperidinyl, piperazinyl, or morpholinyl group. In some embodiments, the pyrrolidinyl, morpholinyl, piperidinyl, or piperazinyl group is optionally substituted with 1-4 occurrences of $C_{1-4}$alkyl or $C_{1-4}$haloalkyl.

In still other embodiments for compounds of formula I-A:
a) $R^1$ is methyl, ethyl, propyl, —CF$_3$, Cl, —CN, —OMe, or cyclopropyl;
b) $R^3$ is methyl or CF$_3$; and
c) $R^5$ is an optionally substituted pyrrolidinyl, morpholinyl, piperidinyl, or piperazinyl group, or is X—$R^{5a}$, wherein X is a $C_{2-4}$alkylene chain, and $R^{5a}$ is —N($R^{5b}$)$_2$, wherein each occurrence of $R^{5b}$ is independently hydrogen or $C_{1-6}$alkyl, or two occurrences of $R^{5b}$, taken together with the nitrogen atom to which they are bound, form an optionally substituted pyrrolidinyl, piperidinyl, piperazinyl, or morpholinyl group.

In still other embodiments for compounds of formula I-A, $R^1$ is Cl or CF$_3$, and $R^3$ is methyl.

In yet other embodiments, compounds have the structure of formula I-B:

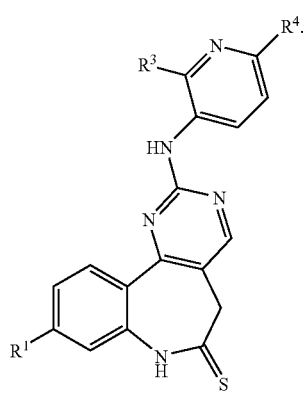

I-B

In still other embodiments, compounds have the structure of formula I-B, wherein $R^1$ is optionally substituted $C_{1-4}$aliphatic, halogen, —CN, or —OMe. In other embodiments, $R^1$ is methyl, ethyl, —CF$_3$, Cl, —CN, —OMe, or cyclopropyl.

In yet other embodiments for compounds of formula I-B, $R^3$ is methyl or CF$_3$.

In still other embodiments for compounds of formula I-B, $R^4$ is —NR$^{4a}$R$^{4b}$, wherein R$^{4a}$ and R$^{4b}$, taken together with the nitrogen atom to which they are bound, form an optionally substituted 3-7-membered heterocyclyl ring, or wherein R$^{4a}$ is hydrogen or C$_{1-4}$alkyl, and R$^{4b}$ is an optionally substituted C$_{3-7}$.heterocyclyl ring or is W—R$^{4c}$, wherein W is an optionally substituted C$_{2-4}$ alkylene chain, and R$^{4c}$ is an optionally substituted C$_{3-7}$-heterocyclyl ring, or —N(R$^{4d}$)$_2$, wherein each occurrence of R$^{4d}$ is independently hydrogen or C$_{1-6}$alkyl, or two occurrences of R$^{4d}$, taken together with the nitrogen atom to which they are bound, form an optionally substituted 3-7-membered heterocyclyl ring.

In other embodiments, R$^4$ is —NR$^{4a}$R$^{4b}$, wherein R$^{4a}$ and R$^{4b}$, taken together with the nitrogen atom to which they are bound, form an optionally substituted pyrrolidinyl, piperazinyl, piperidinyl, or morpholinyl ring, or wherein R$^{4a}$ is hydrogen or C$_{1-4}$alkyl, and R$^{4b}$ is an optionally substituted pyrrolidinyl, piperazinyl, piperidinyl, or morpholinyl ring, or is W—R$^{4c}$, wherein W is an optionally substituted C$_{2-4}$ alkylene chain, and R$^{4c}$ is an optionally substituted pyrrolidinyl, piperazinyl, piperidinyl, or morpholinyl ring, or —N(R$^{4d}$)$_2$, wherein each occurrence of R$^{4d}$ is independently hydrogen or C$_{1-6}$alkyl, or two occurrences of R$^{4d}$, taken together with the nitrogen atom to which they are bound, form an optionally substituted pyrrolidinyl, piperazinyl, piperidinyl, or morpholinyl ring.

In still other embodiments for compounds of formula I-B:
a) R$^1$ is methyl, ethyl, propyl, —CF$_3$, Cl, —CN, —OMe, or cyclopropyl;
b) R$^3$ is methyl or CF$_3$; and
c) R$^4$ is —NR$^{4a}$R$^{4b}$, wherein R$^{4a}$ and R$^{4b}$, taken together with the nitrogen atom to which they are bound, form an optionally substituted pyrrolidinyl, piperazinyl, piperidinyl, or morpholinyl ring, or wherein R$^{4a}$ is hydrogen or C$_{1-4}$alkyl, and R$^{4b}$ is an optionally substituted pyrrolidinyl, piperazinyl, piperidinyl, or morpholinyl ring, or is W—R$^{4c}$, wherein W is an optionally substituted C$_{2-4}$ alkylene chain, and R$^{4c}$ is an optionally substituted pyrrolidinyl, piperazinyl, piperidinyl, or morpholinyl ring, or —N(R$^{4d}$)$_2$, wherein each occurrence of R$^{4d}$ is independently hydrogen or C$_{1-6}$alkyl, or two occurrences of R$^{4d}$, taken together with the nitrogen atom to which they are bound, form an optionally substituted pyrrolidinyl, piperazinyl, piperidinyl, or morpholinyl ring.

In yet other embodiments for compounds of formula I-B, R$^1$ is Cl or CF$_3$, and R$^3$ is methyl.

Table 1 below depicts certain exemplary compounds of formula I:

TABLE 1

Exemplary Compounds of formula I:

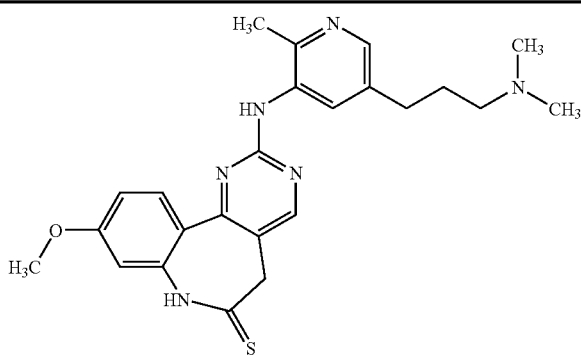

I-1

TABLE 1-continued
Exemplary Compounds of formula I:
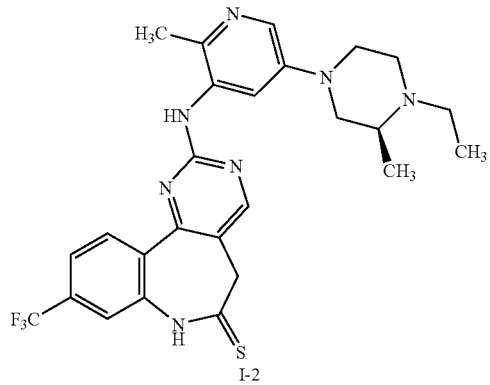
I-2
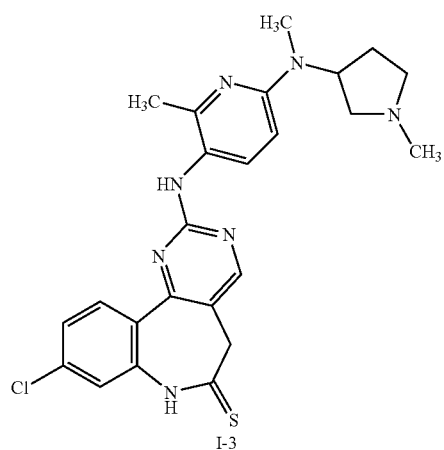
I-3
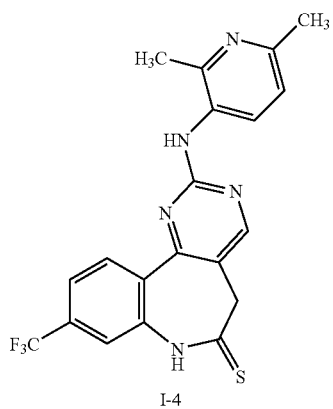
I-4
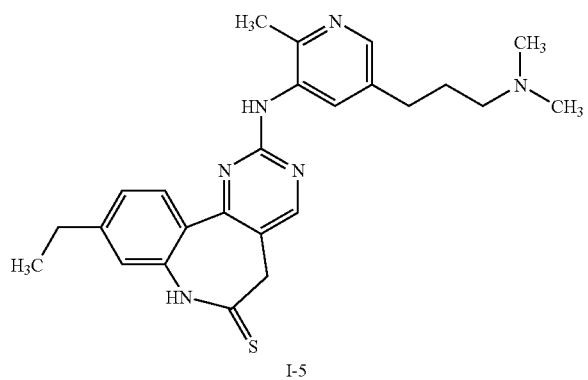
I-5

TABLE 1-continued
Exemplary Compounds of formula I:
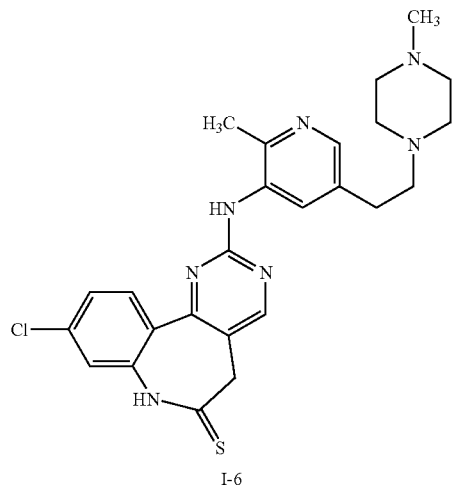
I-6
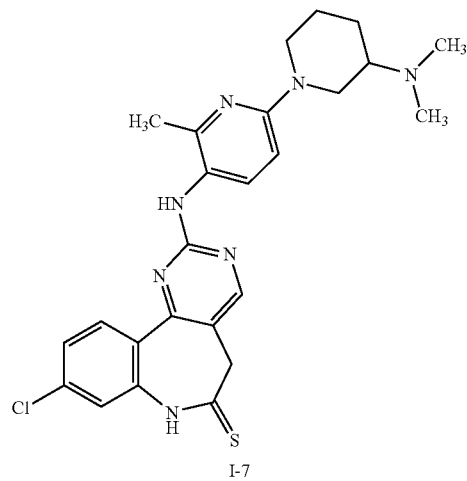
I-7
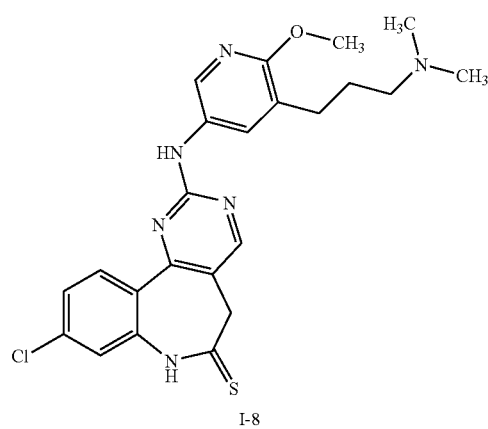
I-8

TABLE 1-continued
Exemplary Compounds of formula I:
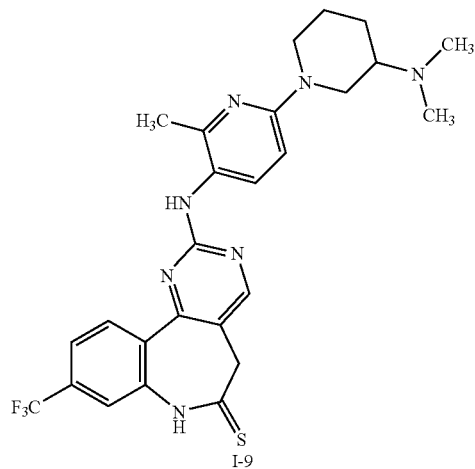
I-9
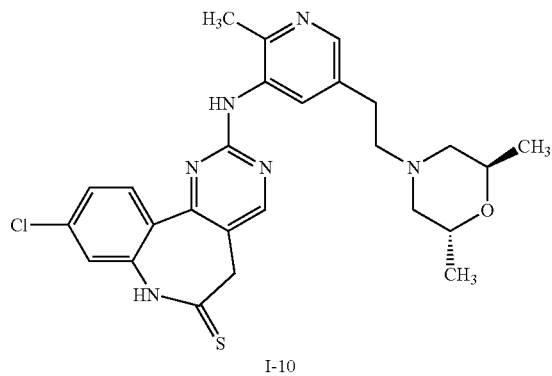
I-10
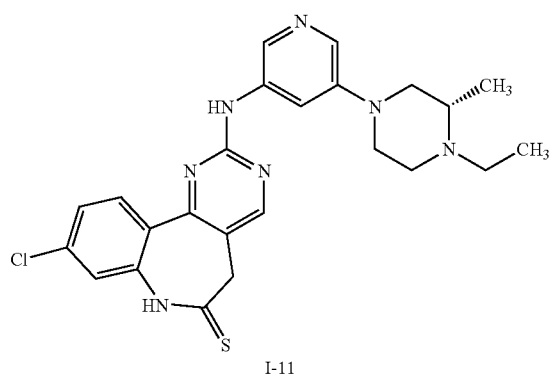
I-11
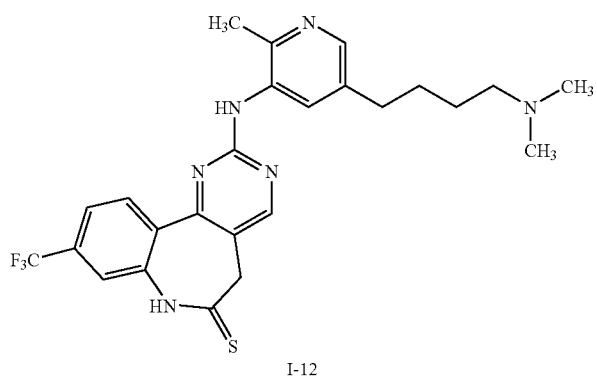
I-12

TABLE 1-continued
Exemplary Compounds of formula I:
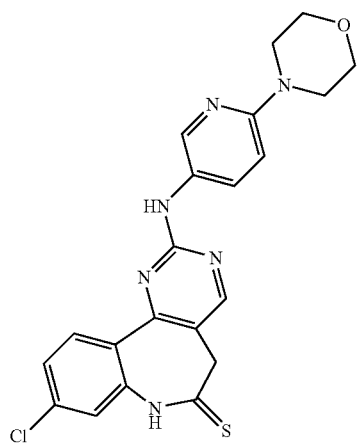
I-13
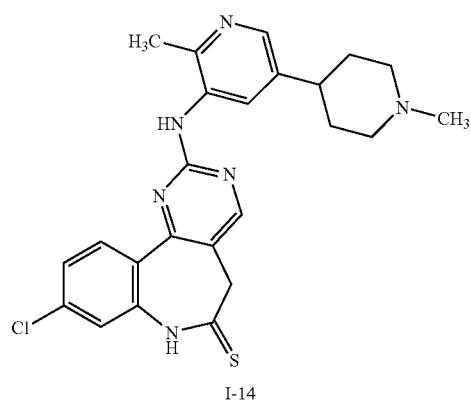
I-14
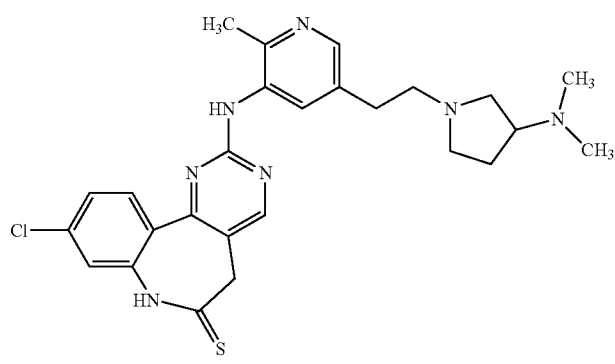
I-15

TABLE 1-continued
Exemplary Compounds of formula I:
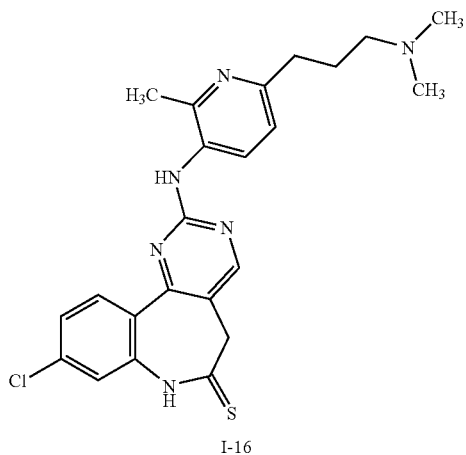
I-16
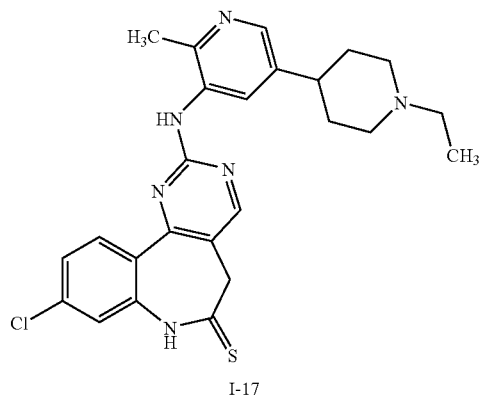
I-17
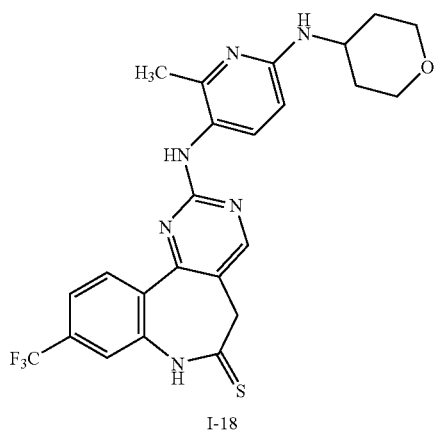
I-18

TABLE 1-continued
Exemplary Compounds of formula I:
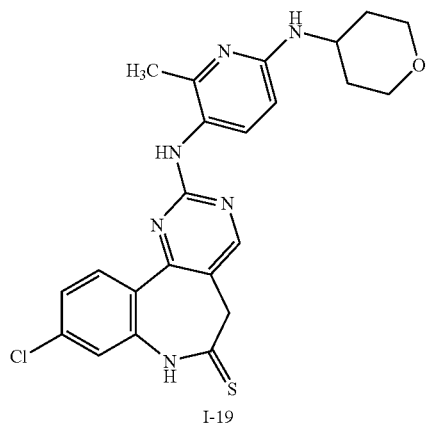
I-19
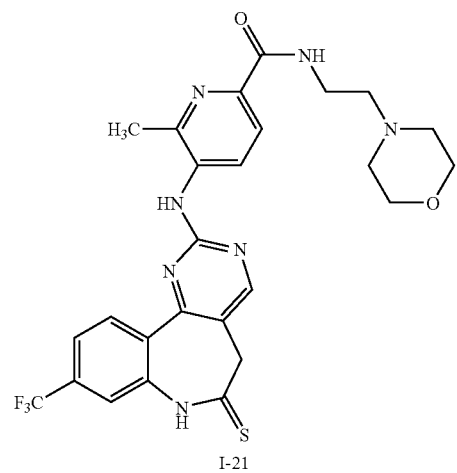
I-21
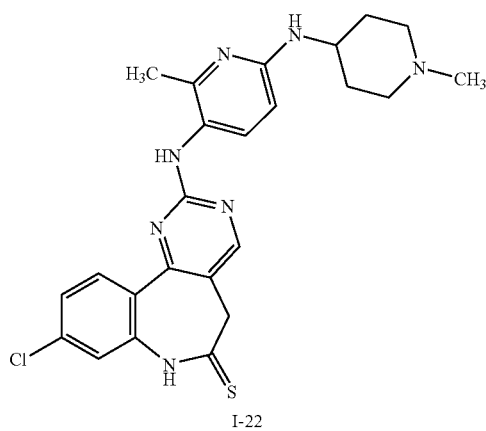
I-22

TABLE 1-continued
Exemplary Compounds of formula I:
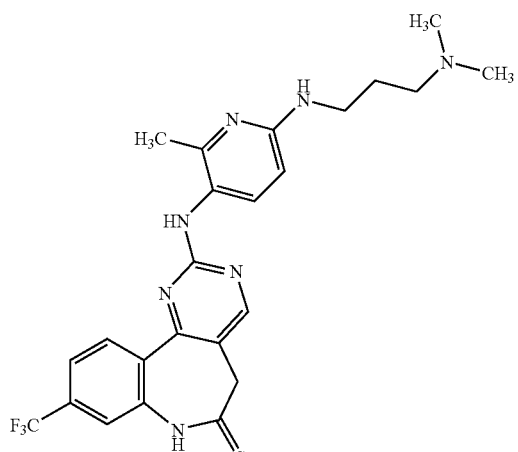
I-23
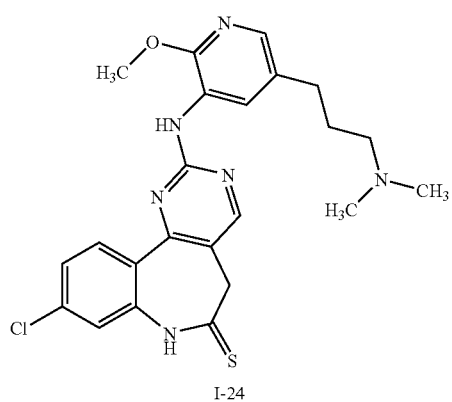
I-24
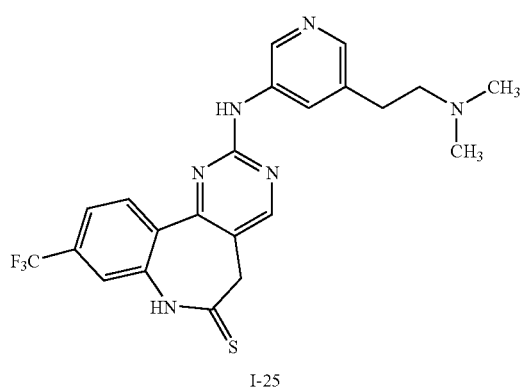
I-25

TABLE 1-continued
Exemplary Compounds of formula I:
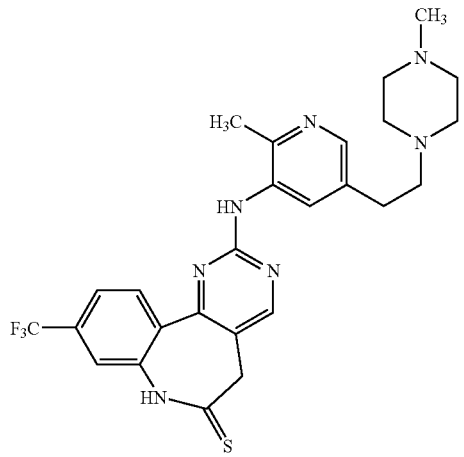
I-26
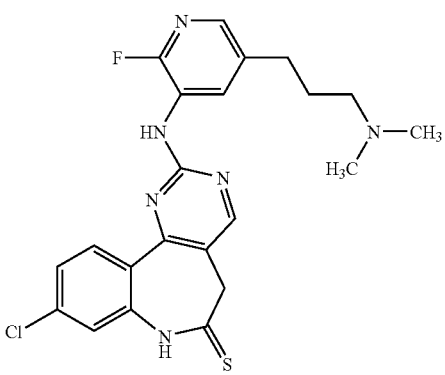
I-27
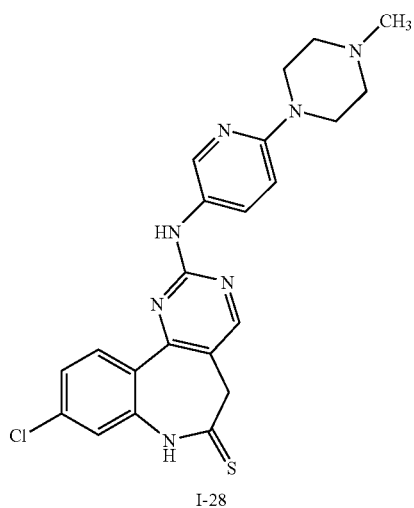
I-28

TABLE 1-continued
Exemplary Compounds of formula I:
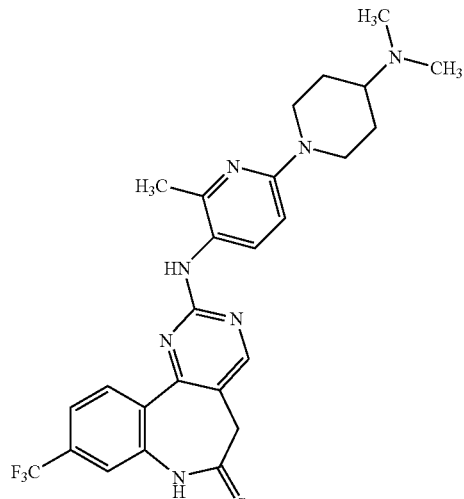
I-29
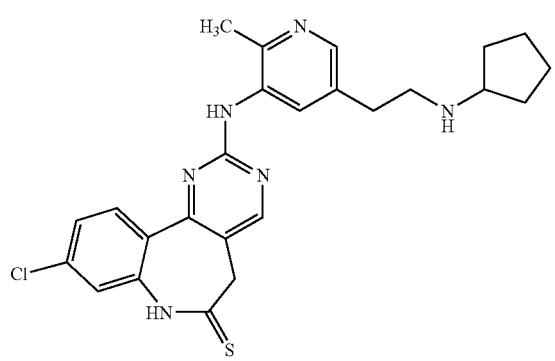
I-30
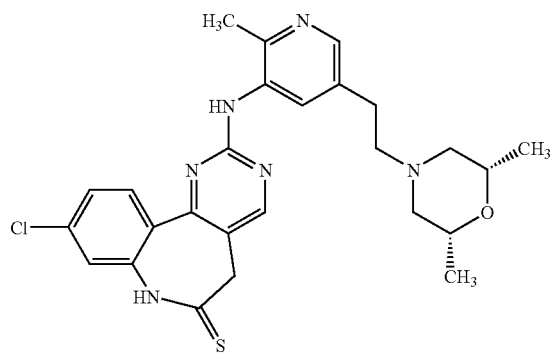
I-31

TABLE 1-continued
Exemplary Compounds of formula I:
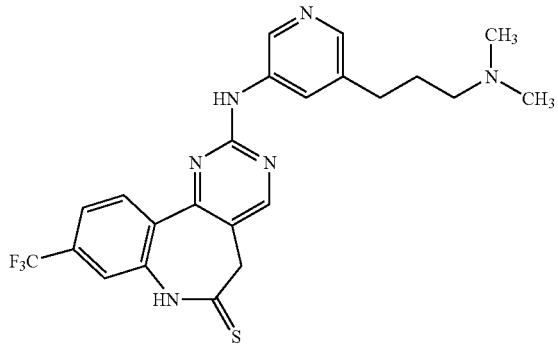
I-32
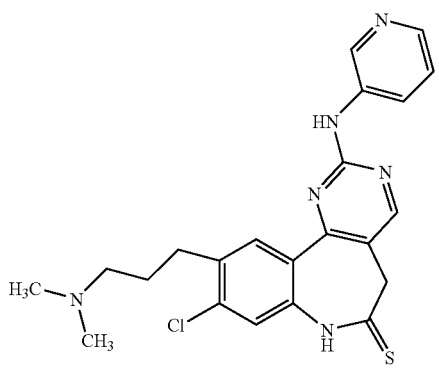
I-33
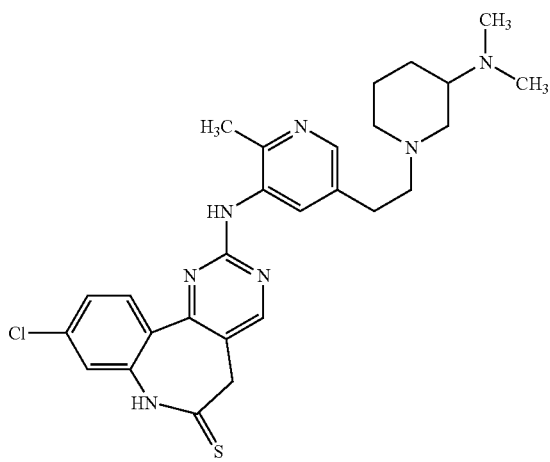
I-34

TABLE 1-continued
Exemplary Compounds of formula I:
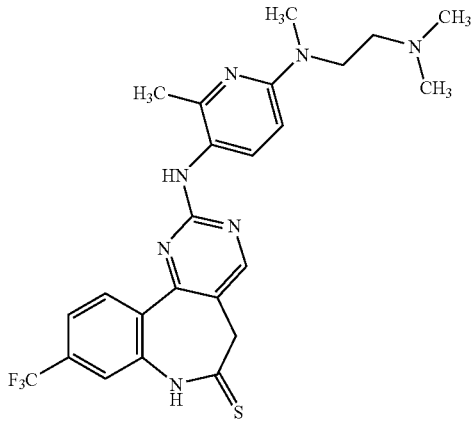
I-35
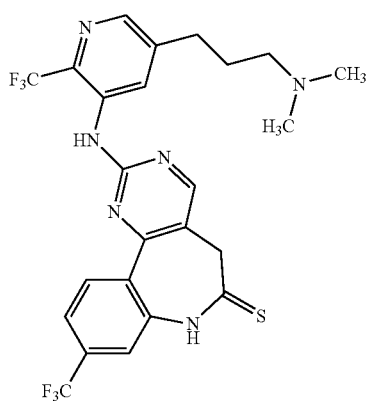
I-36
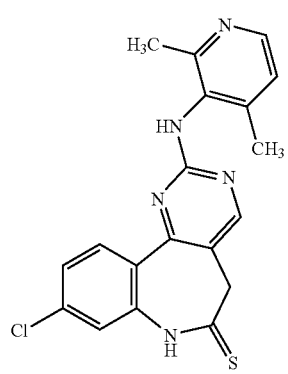
I-37

TABLE 1-continued
Exemplary Compounds of formula I:
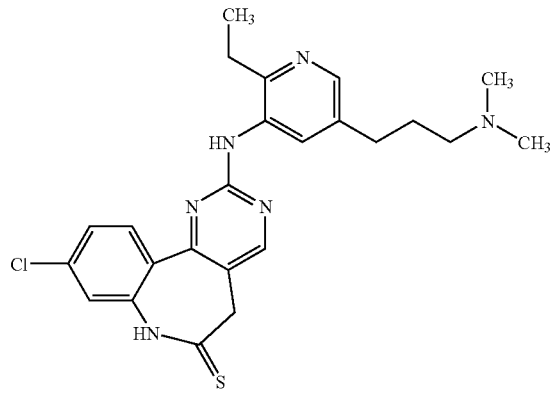
I-38
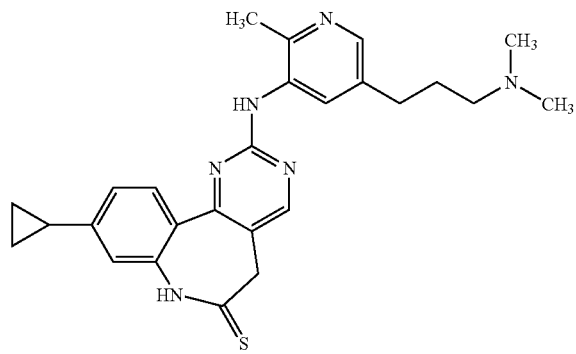
I-39
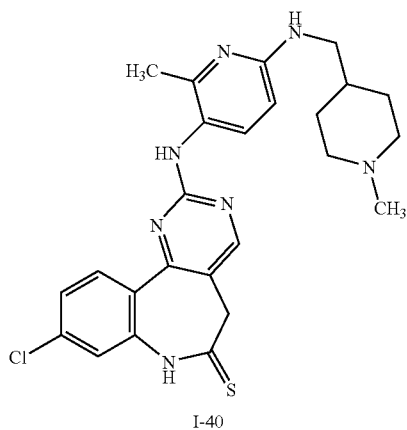
I-40

TABLE 1-continued
Exemplary Compounds of formula I:
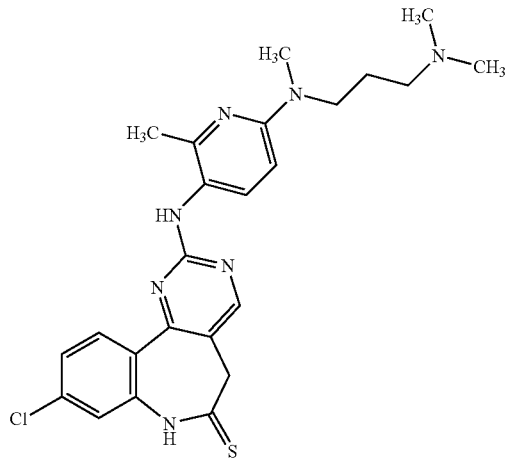
I-41
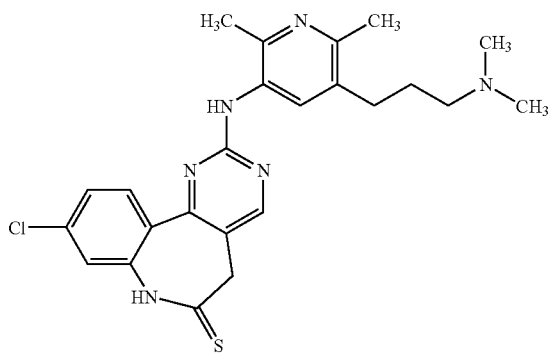
I-42
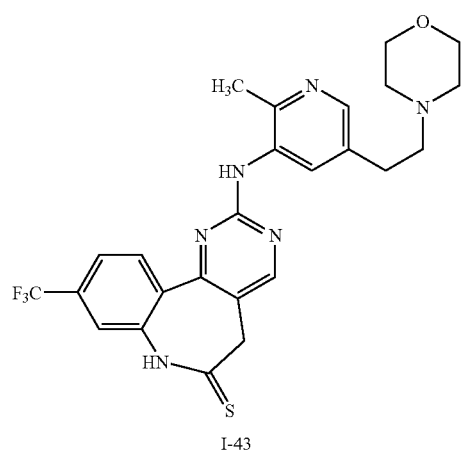
I-43

TABLE 1-continued
Exemplary Compounds of formula I:
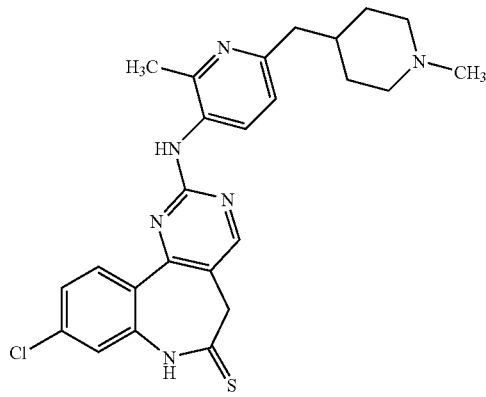
I-44
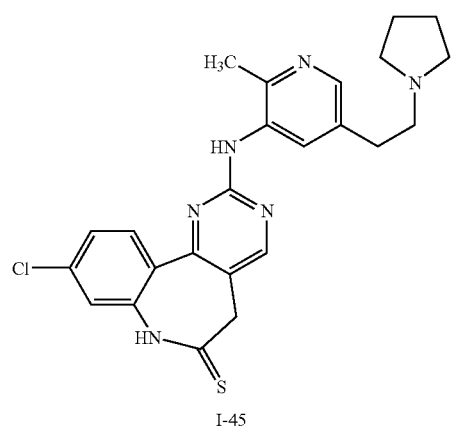
I-45
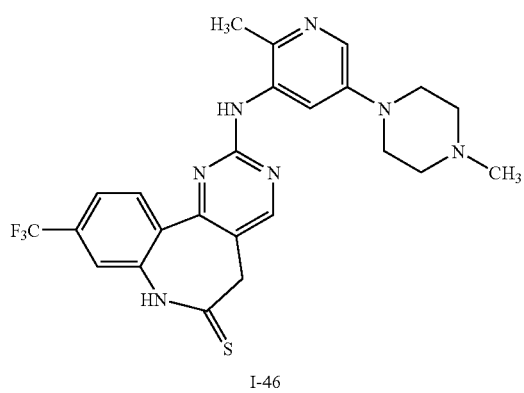
I-46

TABLE 1-continued
Exemplary Compounds of formula I:
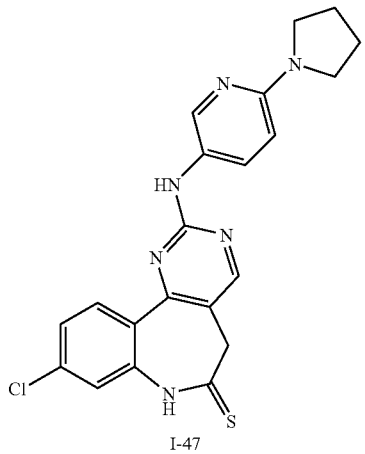
I-47
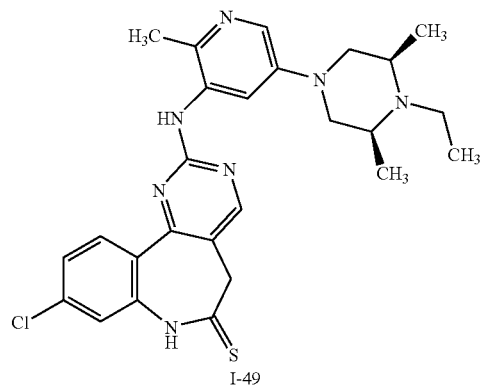
I-49
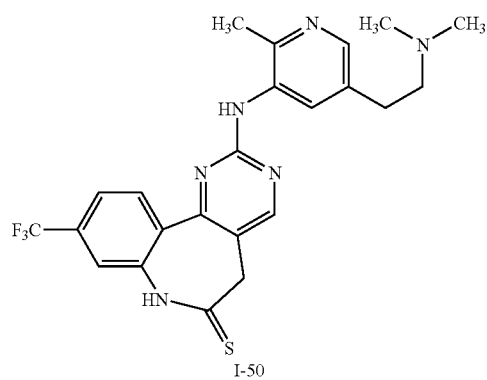
I-50
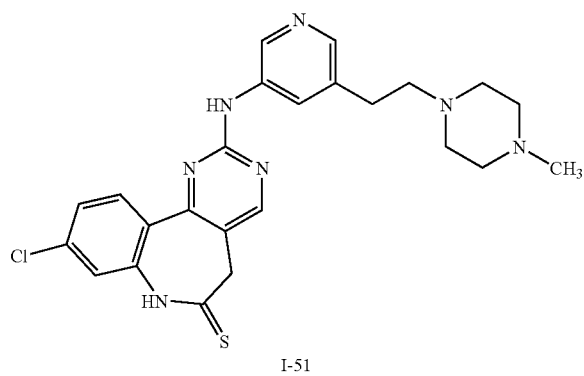
I-51

TABLE 1-continued
Exemplary Compounds of formula I:
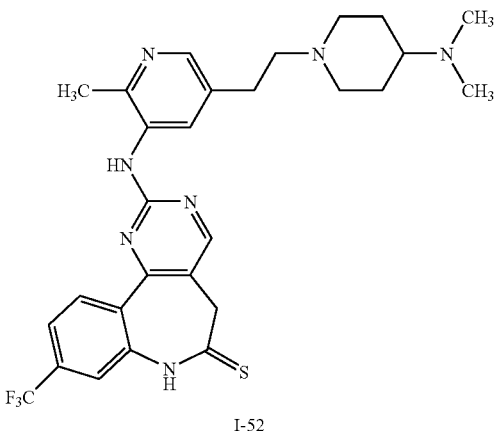
I-52
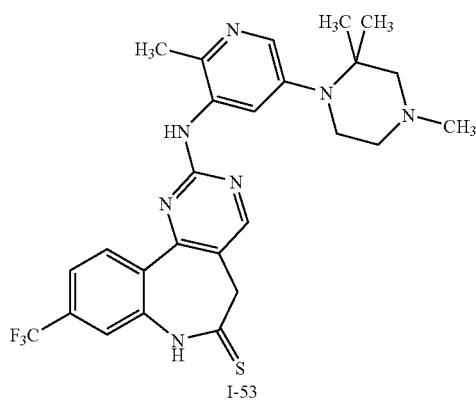
I-53
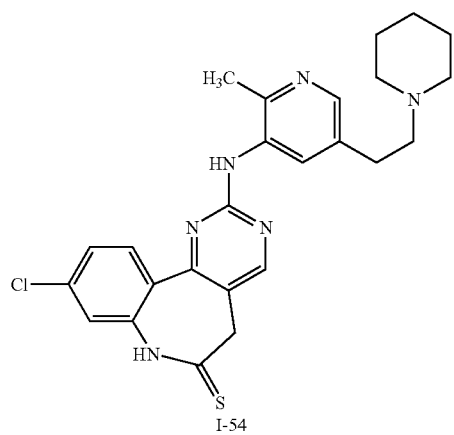
I-54
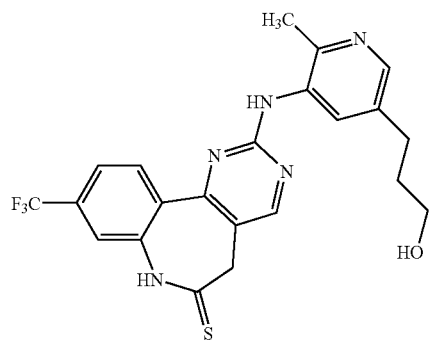

TABLE 1-continued
Exemplary Compounds of formula I:
I-55
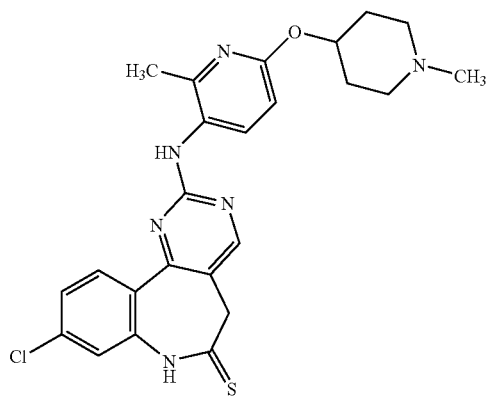
I-56
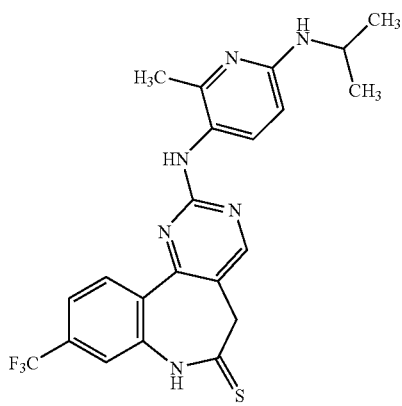
I-57
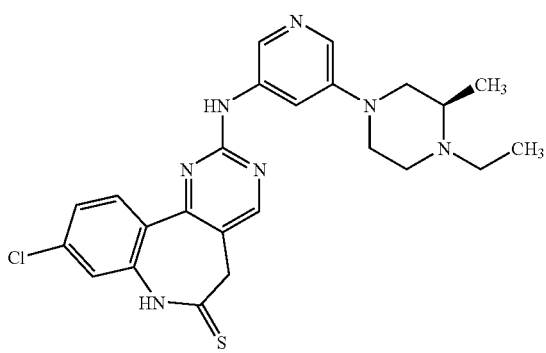
I-58

TABLE 1-continued
Exemplary Compounds of formula I:
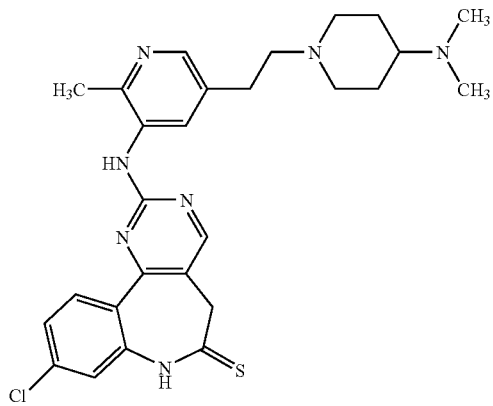
I-59
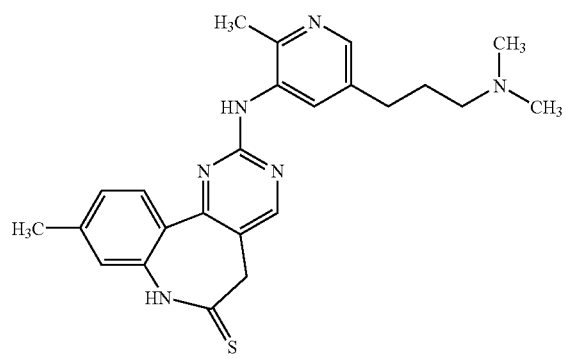
I-60
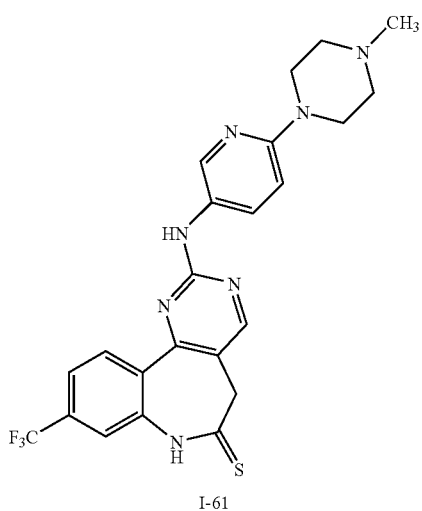
I-61

TABLE 1-continued
Exemplary Compounds of formula I:
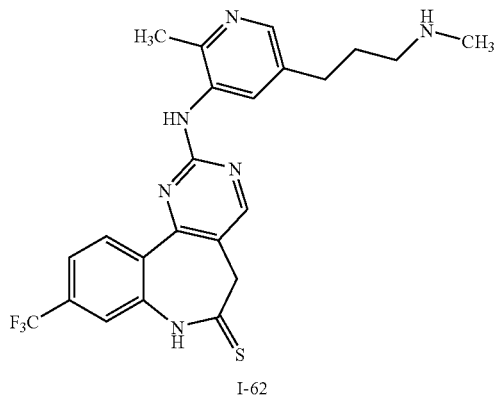
I-62
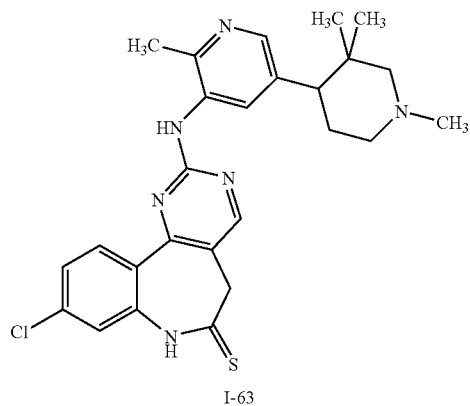
I-63
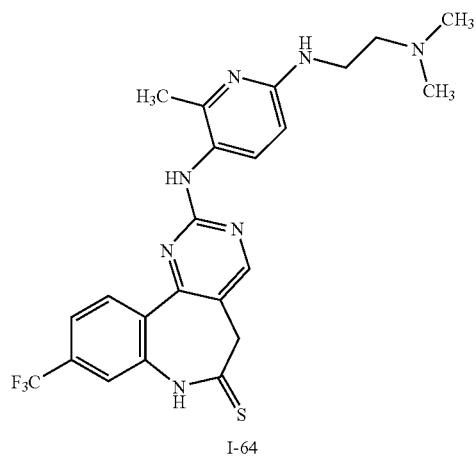
I-64

TABLE 1-continued
Exemplary Compounds of formula I:
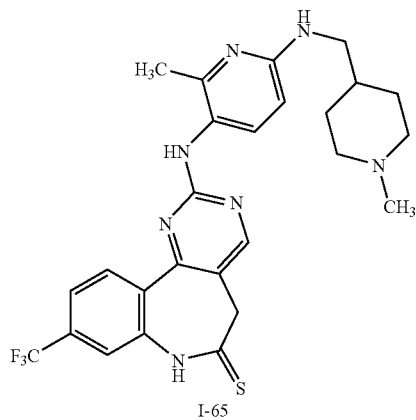
I-65
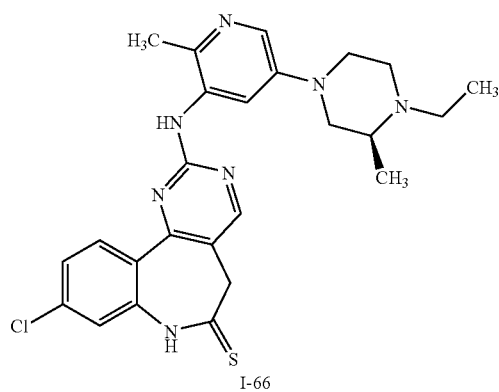
I-66
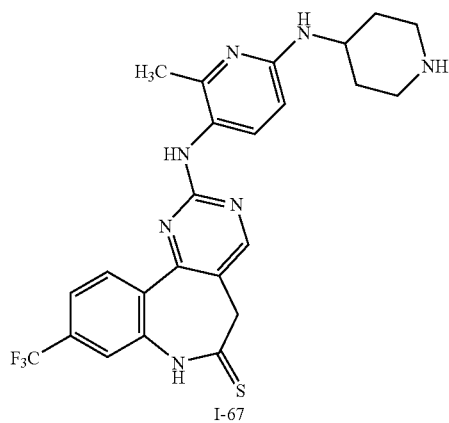
I-67
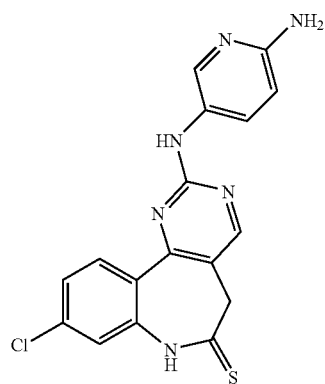

TABLE 1-continued
Exemplary Compounds of formula I:
I-68
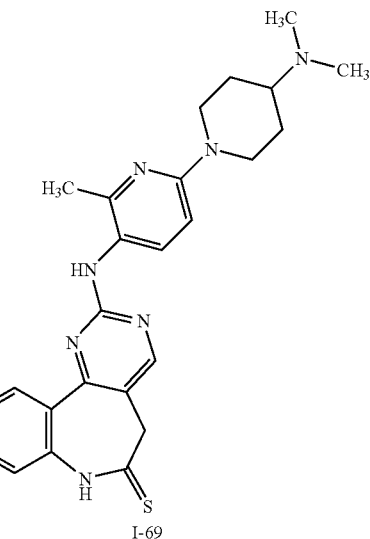
I-69
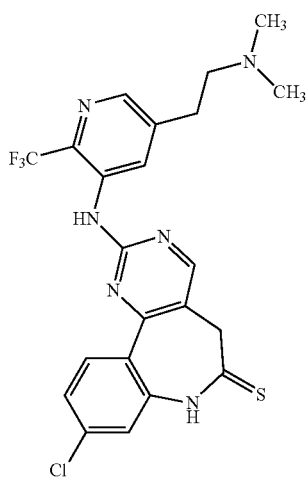
I-70
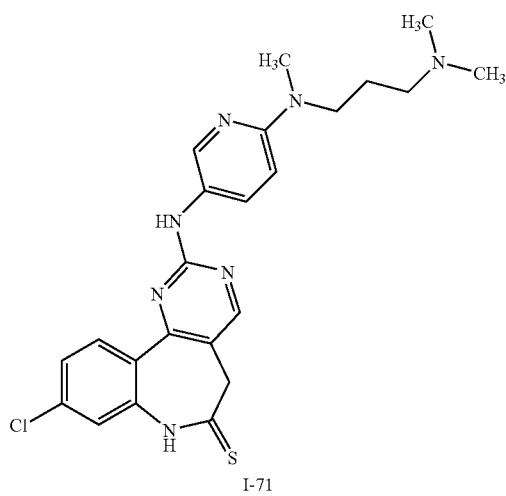
I-71

TABLE 1-continued
Exemplary Compounds of formula I:
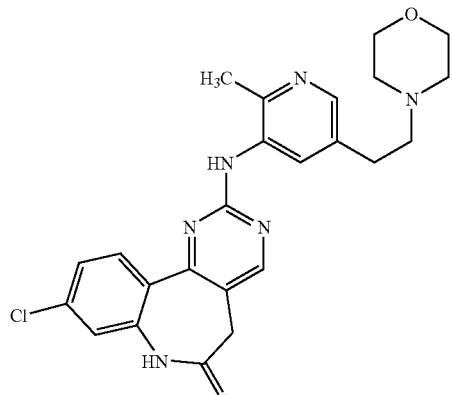
I-72
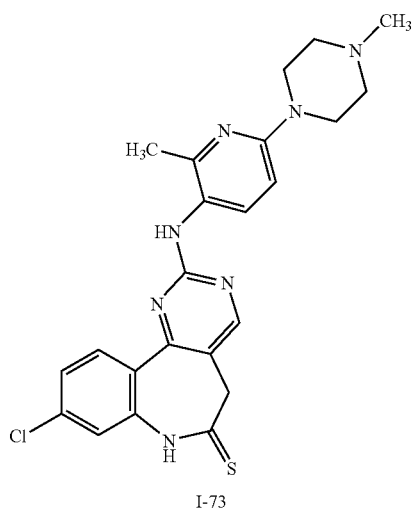
I-73
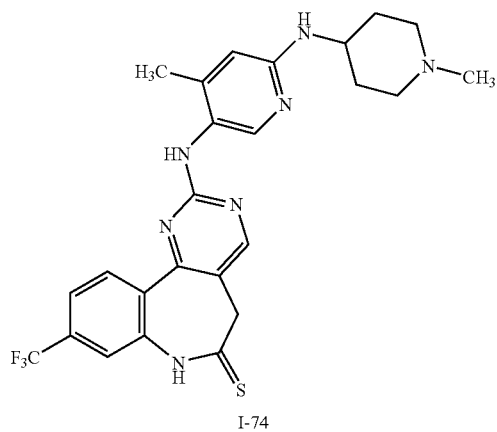
I-74

TABLE 1-continued
Exemplary Compounds of formula I:
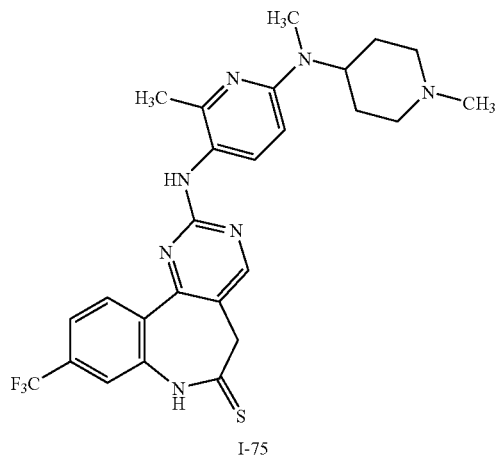
I-75
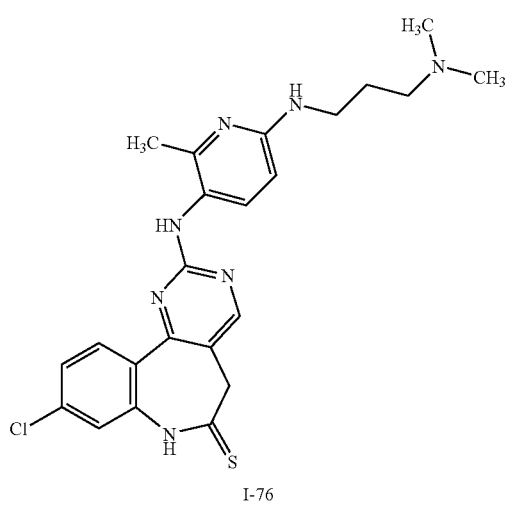
I-76
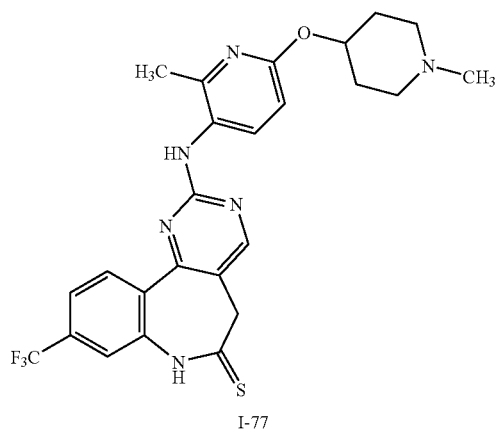
I-77

TABLE 1-continued
Exemplary Compounds of formula I:
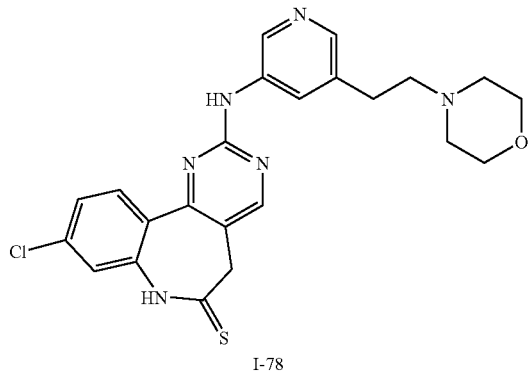
I-78
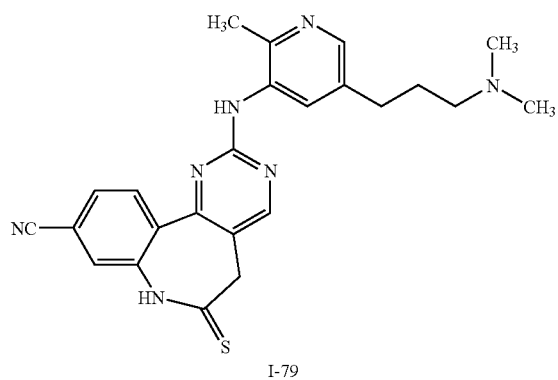
I-79
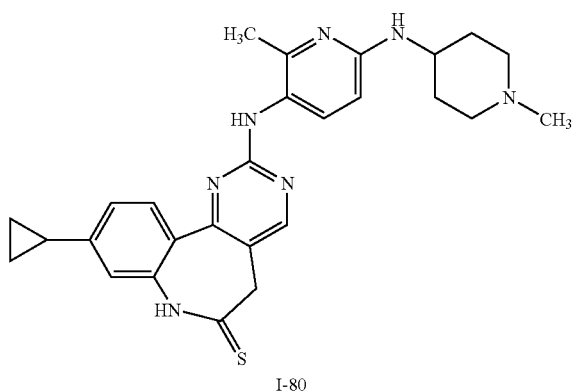
I-80
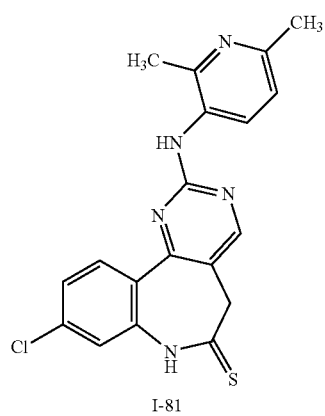
I-81

TABLE 1-continued
Exemplary Compounds of formula I:
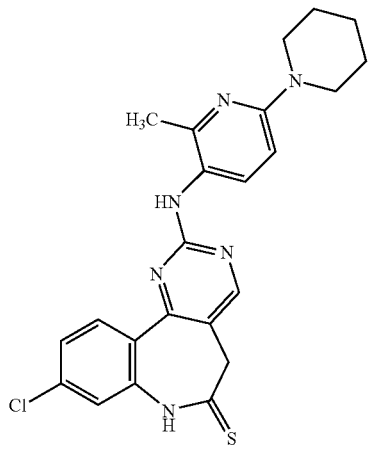
I-82
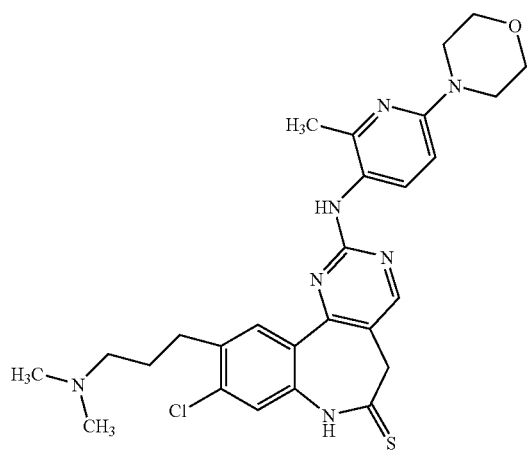
I-83
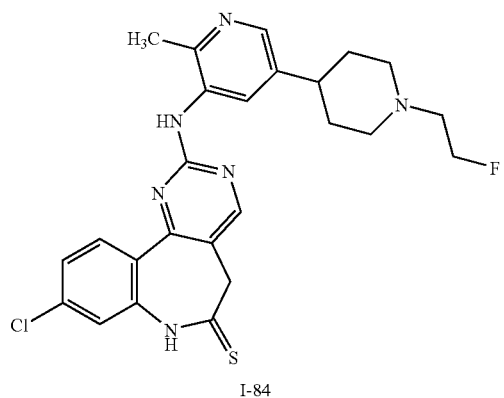
I-84

TABLE 1-continued
Exemplary Compounds of formula I:
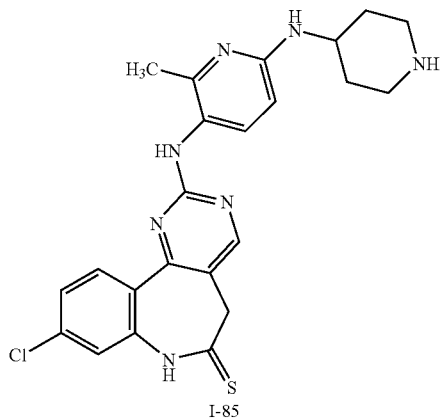
I-85
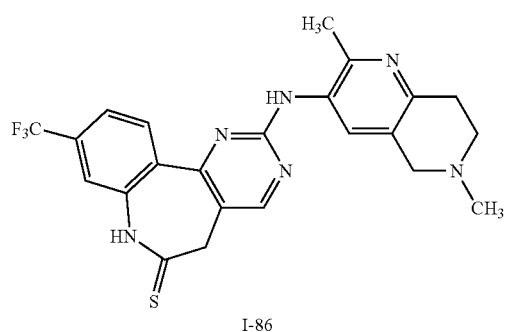
I-86
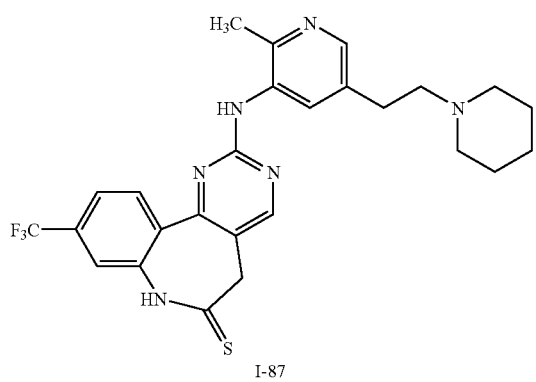
I-87
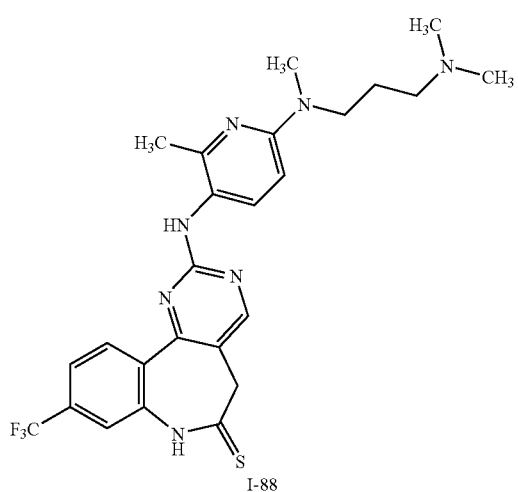
I-88

TABLE 1-continued
Exemplary Compounds of formula I:
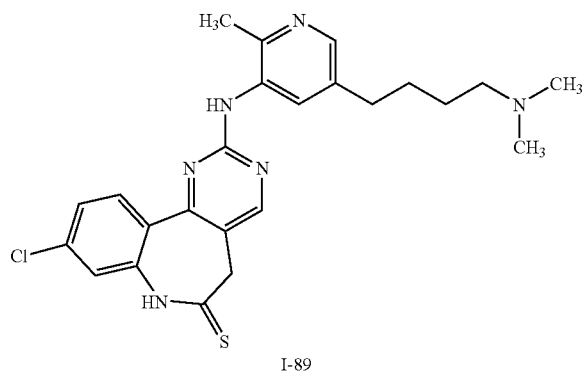
I-89
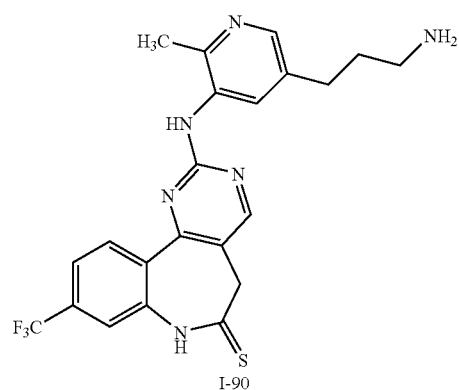
I-90
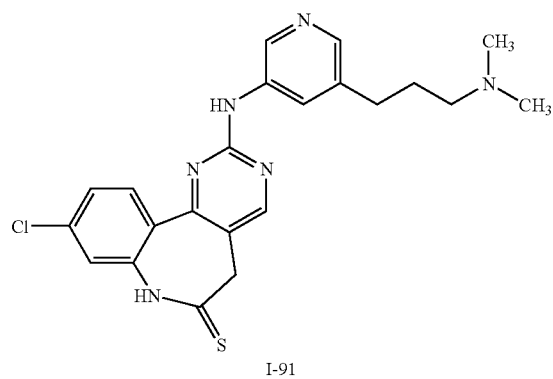
I-91
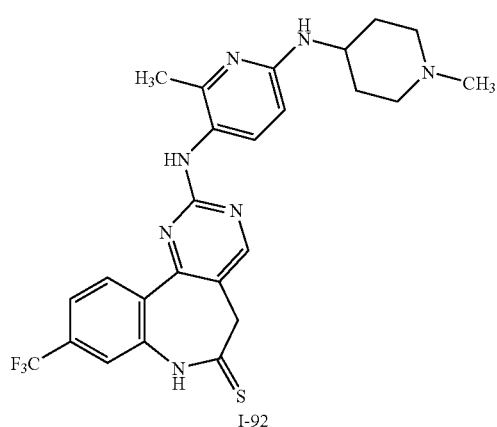
I-92

TABLE 1-continued
Exemplary Compounds of formula I:
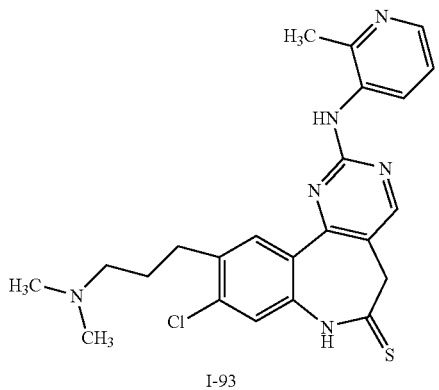
I-93
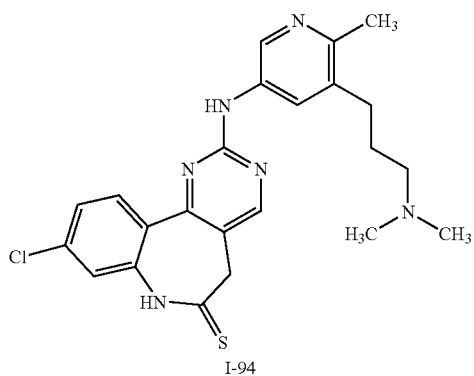
I-94
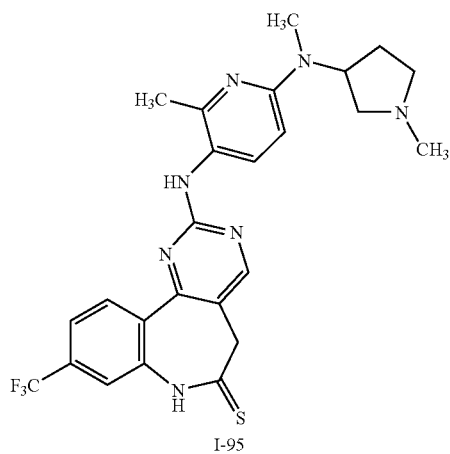
I-95
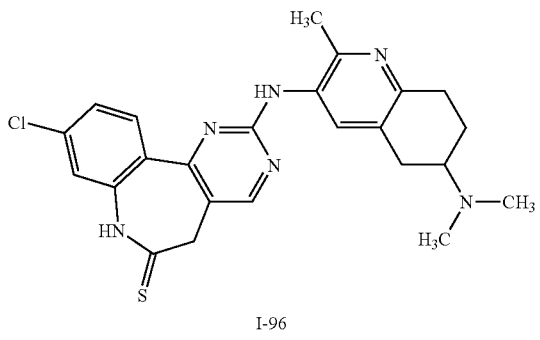
I-96

TABLE 1-continued
Exemplary Compounds of formula I:
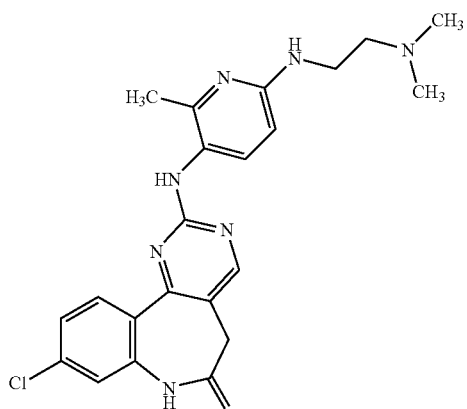
I-97
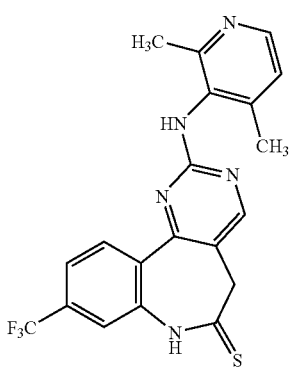
I-98
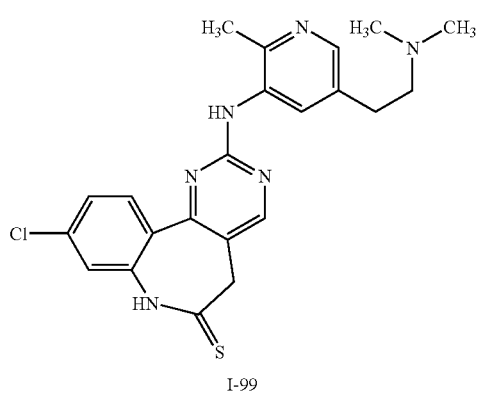
I-99

TABLE 1-continued
Exemplary Compounds of formula I:
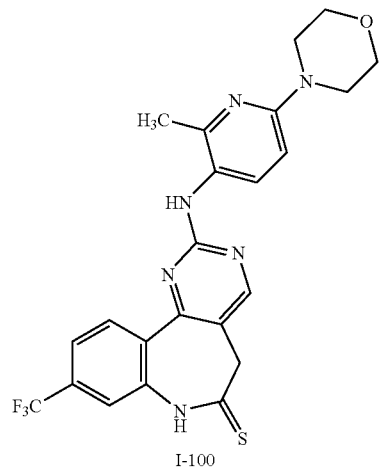
I-100
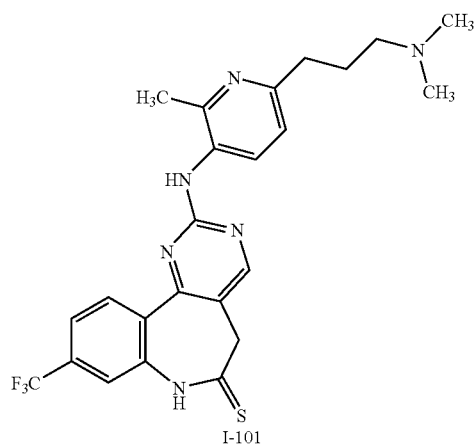
I-101
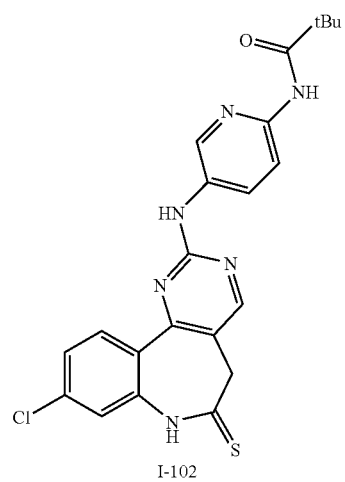
I-102

TABLE 1-continued
Exemplary Compounds of formula I:
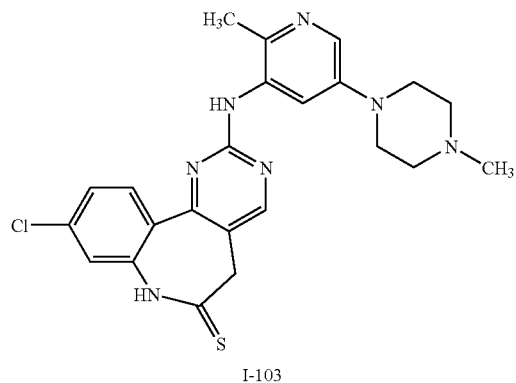
I-103
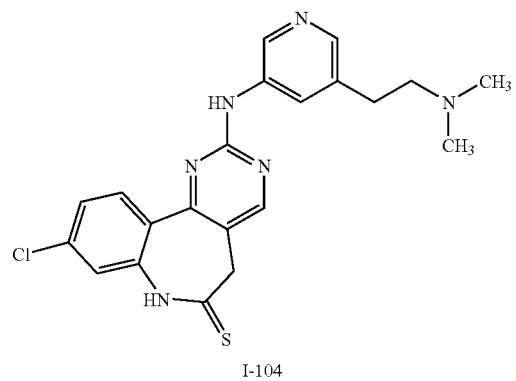
I-104
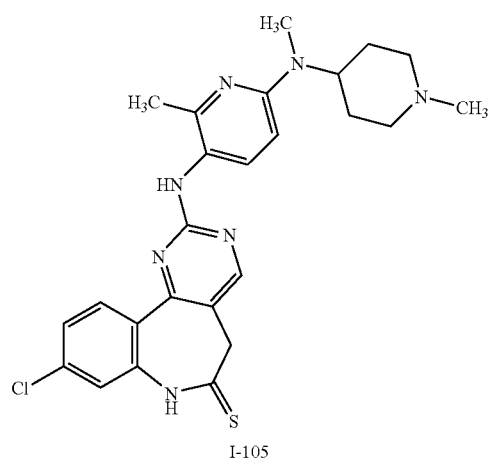
I-105

TABLE 1-continued
Exemplary Compounds of formula I:
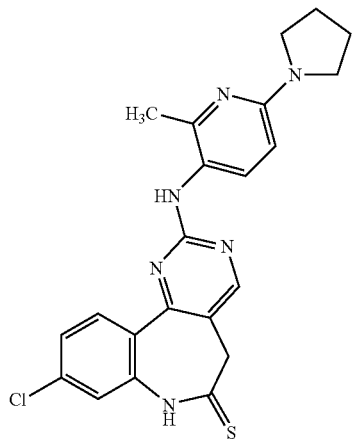
I-106
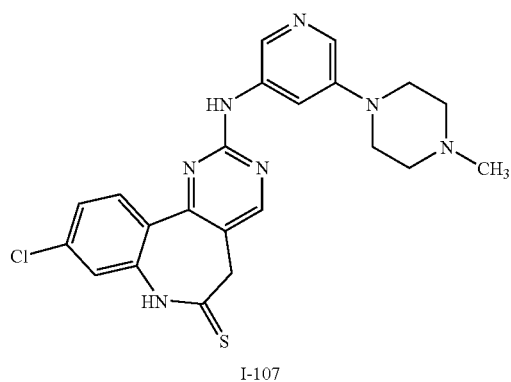
I-107
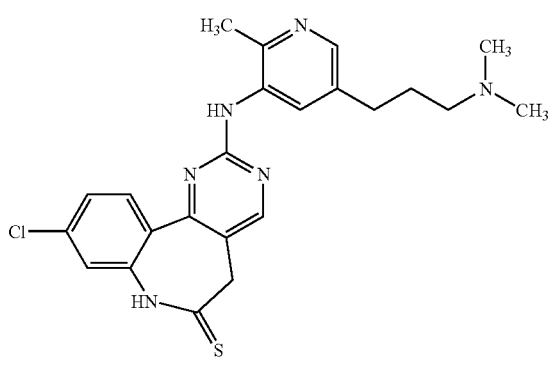
I-108

TABLE 1-continued
Exemplary Compounds of formula I:
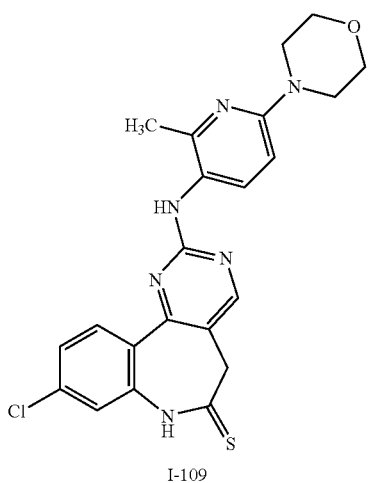
I-109
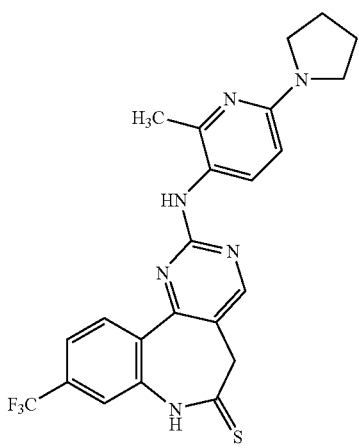
I-110
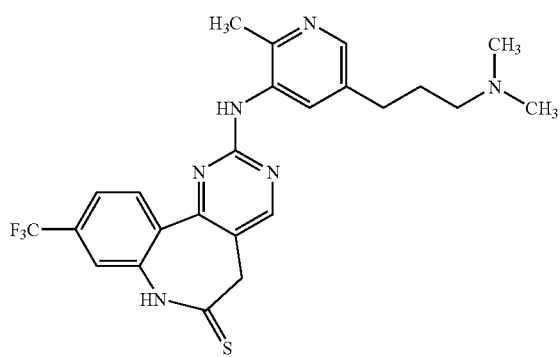
I-111

TABLE 1-continued
Exemplary Compounds of formula I:
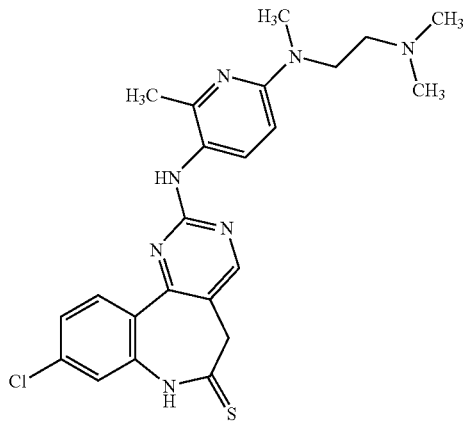
I-112
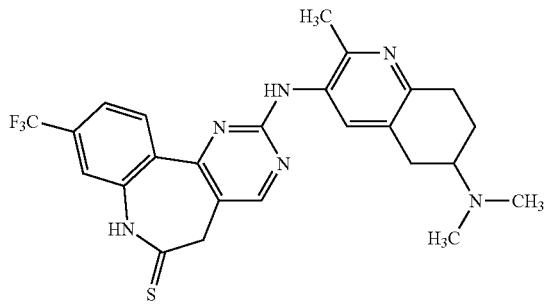
I-113
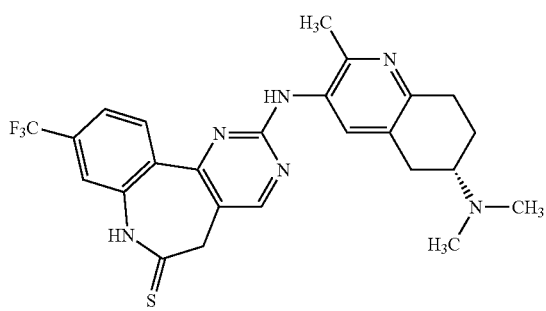
I-114
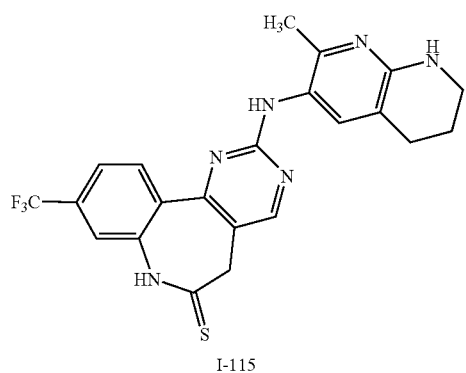
I-115

TABLE 1-continued
Exemplary Compounds of formula I:
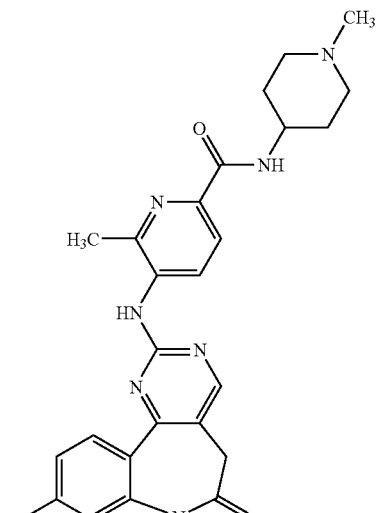
I-116
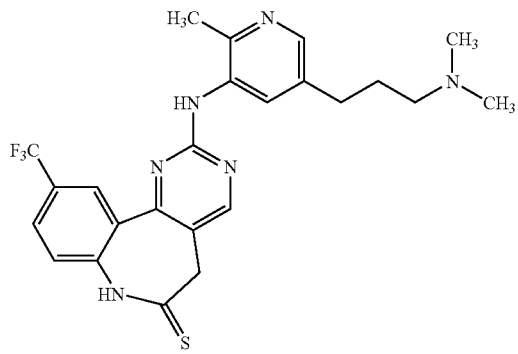
I-117
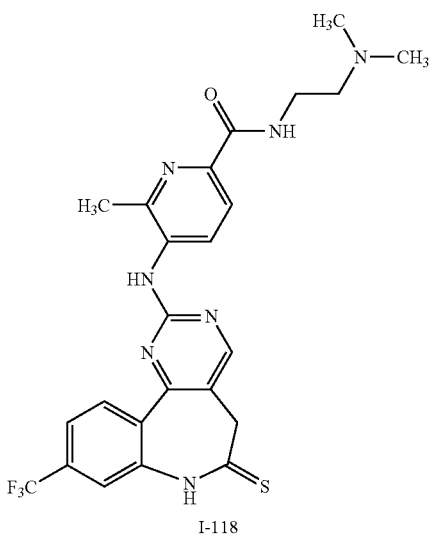
I-118

TABLE 1-continued
Exemplary Compounds of formula I:
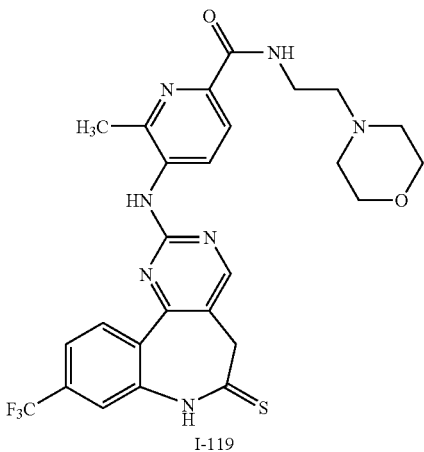
I-119
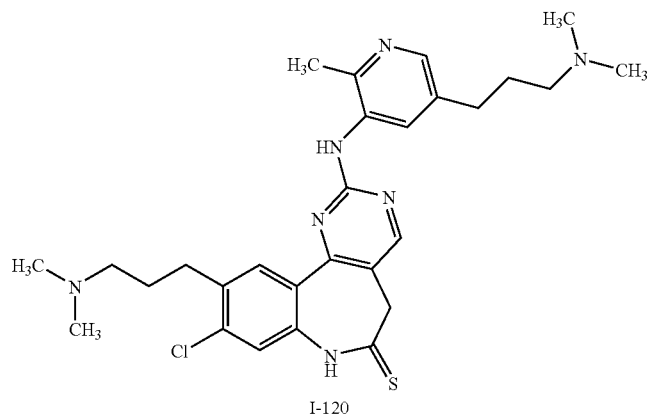
I-120
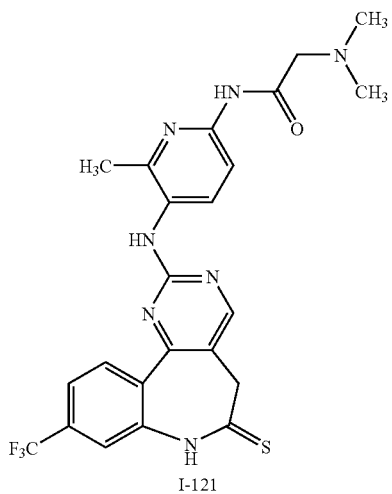
I-121

TABLE 1-continued

Exemplary Compounds of formula I:

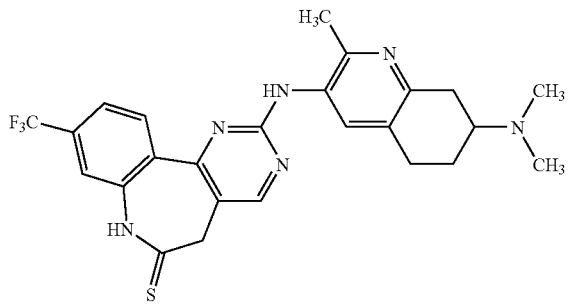

I-122

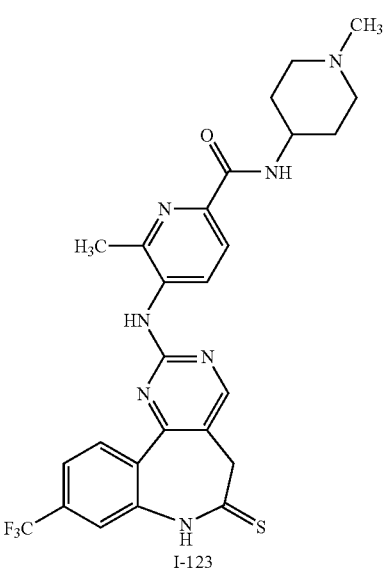

I-123

TABLE 2

Compound Names:

| | |
|---|---|
| I-1 | 2-({5-[3-(dimethylamino)propyl]-2-methylpyridin-3-yl}amino)-9-methoxy-5,7-dihydro-6H-pyrimido[5,4-d][1]benzazepine-6-thione |
| I-2 | 2-({5-[(3S)-4-ethyl-3-methylpiperazin-1-yl]-2-methylpyridin-3-yl}amino)-9-(trifluoromethyl)-5,7-dihydro-6H-pyrimido[5,4-d][1]benzazepine-6-thione |
| I-3 | 9-chloro-2-({2-methyl-6-[methyl(1-methylpyrrolidin-3-yl)amino]pyridin-3-yl}amino)-5,7-dihydro-6H-pyrimido[5,4-d][1]benzazepine-6-thione |
| I-4 | 2-[(2,6-dimethylpyridin-3-yl)amino]-9-(trifluoromethyl)-5,7-dihydro-6H-pyrimido[5,4-d][1]benzazepine-6-thione |
| I-5 | 2-({5-[3-(dimethylamino)propyl]-2-methylpyridin-3-yl}amino)-9-ethyl-5,7-dihydro-6H-pyrimido[5,4-d][1]benzazepine-6-thione |
| I-6 | 9-chloro-2-({2-methyl-5-[2-(4-methylpiperazin-1-yl)ethyl]pyridin-3-yl}amino)-5,7-dihydro-6H-pyrimido[5,4-d][1]benzazepine-6-thione |
| I-7 | 9-chloro-2-({6-[3-(dimethylamino)piperidin-1-yl]-2-methylpyridin-3-yl}amino)-5,7-dihydro-6H-pyrimido[5,4-d][1]benzazepine-6-thione |
| I-8 | 9-chloro-2-({5-[3-(dimethylamino)propyl]-6-methoxypyridin-3-yl}amino)-5,7-dihydro-6H-pyrimido[5,4-d][1]benzazapine-6-thione |
| I-9 | 2-({6-[3-(dimethylamino)piperidin-1-yl]-2-methylpyridin-3-yl}amino)-9-(trifluoromethyl)-5,7-dihydro-6H-pyrimido[5,4-d][1]benzazepine-6-thione |
| I-10 | 9-chloro-2-[5-{2-[(2R,6R)-2,6-dimethylmorpholin-4-yl]ethyl}-2-methylpyridin-3-yl)amino]-5,7-dihydro-6H-pyrimido[5,4-d][1]benzazepine-6-thione |
| I-11 | 9-chloro-2-({5-[(3S)-4-ethyl-3-methylpiperazin-1-yl]pyridin-3-yl}amino)-5,7-dihydro-6H-pyrimido[5,4-d][1]benzazepine-6-thione |
| I-12 | 2-({5-[4-(dimethylamino)butyl]-2-methylpyridin-3-yl}amino)-9-(trifluoromethyl)-5,7-dihydro-6H-pyrimido[5,4-d][1]benzazepine-6-thione |
| I-13 | 9-chloro-2-[(6-morpholin-4-ylpyridin-3-yl)amino]-5,7-dihydro-6H-pyrimido[5,4-d][1]benzazepine-6-thione |
| I-14 | 9-chloro-2-{[2-methyl-5-(1-methylpiperidin-4-yl)pyridin-3-yl]amino}-5,7-dihydro-6H-pyrimido[5,4-d][1]benzazepine-6-thione |

TABLE 2-continued

Compound Names:

| | |
|---|---|
| I-15 | 9-chloro-2-[(5-{2-[3-(dimethylamino)pyrrolindin-1-yl]ethyl}-2-methylpridin-3-yl)amino]-5,7-dihydro-6H-pyrimido[5,4-d][1]benzazepine-6-thione |
| I-16 | 9-chloro-2-({6-[3-(dimethylamino)propyl]-2-methylpyridin-3-yl}amino)-5,7-dihydro-6H-pyrimido[5,4-d][1]benzazepine-6-thione |
| I-17 | 9-chloro-2-{[5-(1-ethylpiperidin-4-yl)-2-methylpyridin-3-yl]amino}-5,7-dihydro-6H-pyrimido[5,4-d][1]benzazepine-6-thione |
| I-18 | 2-{[2-methyl-6-(tetrahydro-2H-pyran-4-ylamino)pyridin-3-yl]amino}-9-(trifluoromethyl)-5,7-dihydro-6H-pyrimido[5,4-d][1]benzazepine-6-thione |
| I-19 | 9-chloro-2-{[2-methyl-6-(tetrahydro-2H-pyran-4-ylamino)pyridin-3-yl]amino}-5,7-dihydro-6H-pyrimido[5,4-d][1]benzazepine-6-thione |
| I-21 | 6-methyl-N-(2-morpholin-4-ylethyl)-5-{[6-thioxo-9-(trifluoromethyl)-6,7-dihydro-5H-pyrimido[5,4-d][1]benzazepin-2-yl]amino}pyridine-2-carboxamide |
| I-22 | 9-chloro-2-({2-methyl-6-[(1-methylpiperidin-4-yl)amino]pyridin-3-yl}amino)-5,7-dihydro-6H-pyrimido[5,4-d][1]benzazepine-6-thione |
| I-23 | 2-[(6-{[3-(dimethylamino)propyl]amino}-2-methylpyridin-3-yl)amino]-9-(trifluoromethyl)-5,7-dihydro-6H-pyrimido[5,4-d][1]benzazepine-6-thione |
| I-24 | 9-chloro-2-({5-[3-(dimethylamino)propyl]-2-methoxypyridin-3-yl}amino)-5,7-dihydro-6H-pyrimido[5,4-d][1]benzazepine-6-thione |
| I-25 | 2-({5-[2-(dimethylamino)ethyl]pyridin-3-yl}amino)-9-(trifluoromethyl)-5,7-dihydro-6H-pyrimido[5,4-d][1]benzazepine-6-thione |
| I-26 | 2-({2-methyl-5-[2-(4-methylpiperazin-1-yl)ethyl]pyridin-3-yl}amino)-9-(trifluoromethyl)-5,7-dihydro-6H-pyrimido[5,4-d][1]benzazepine-6-thione |
| I-27 | 9-chloro-2-({5-[3-(dimethylamino)propyl]-2-fluoropyridin-3-yl}amino)-5,7-dihydro-6H-pyrimido[5,4-d][1]benzazepine-6-thione |
| I-28 | 9-chloro-2-{[6-(4-methylpiperazin-1-yl)pyridin-3-yl]amino}-5,7-dihydro-6H-pyrimido[5,4-d][1]benzazepine-6-thione |
| I-29 | 2-({6-[4-(dimethylamino)piperidin-1-yl]-2-methylpyridin-3-yl}amino)-9-(trifluoromethyl)-5,7-dihydro-6H-pyrimido[5,4-d][1]benzazepine-6-thione |
| I-30 | 9-chloro-2-({5-[2-(cyclopentylamino)ethyl]-2-methylpyridin-3-yl}amino)-5,7-dihydro-6H-pyrimido[5,4-d][1]benzazepine-6-thione |
| I-31 | 9-chloro-2-[(5-{2-[(2R,6S)-2,6-dimethylmorpholin-4-yl]ethyl}-2-methylpyridin-3-yl)amino]-5,7-dihydro-6H-pyrimido[5,4-d][1]benzazepine-6-thione |
| I-32 | 2-({5-[3-(dimethylamino)propyl]pyridin-3-yl}amino)-9-(trifluoromethyl)-5,7-dihydro-6H-pyrimido[5,4-d][1]benzazepine-6-thione |
| I-33 | 9-chloro-10-[3-(dimethylamino)propyl]-2-(pyridin-3-ylamino)-5,7-dihydro-6H-pyrimido[5,4-d][1]benzazepine-6-thione |
| I-34 | 9-chloro-2-[(5-{2-[3-(dimethylamino)piperidin-1-yl]ethyl}-2-methylpyridin-3-yl)amino]-5,7-dihydro-6H-pyrimido[5,4-d][1]benzazepine-6-thione |
| I-35 | 2-({6-[[2-(dimethylamino)ethyl](methyl)amino]-2-methylpyridin-3-yl}amino)-9-(trifluoromethyl)-5,7-dihydro-6H-pyrimido[5,4-d][1]benzazepine-6-thione |
| I-36 | 2-{[5-[3-(dimethylamino)propyl]-2-(trifluoromethyl)pyridin-3-yl]amino}-9-(trifluoromethyl)-5,7-dihydro-6H-pyrimido[5,4-d][1]benzazepine-6-thione |
| I-37 | 9-chloro-2-[(2,4-dimethylpyridin-3-yl)amino]-5,7-dihydro-6H-pyrimido[5,4-d][1]benzazepine-6-thione |
| I-38 | 9-chloro-2-({5-[3-(dimethylamino)propyl]-2-ethylpyridin-3-yl}amino)-5,7-dihydro-6H-pyrimido[5,4-d][1]benzazepine-6-thione |
| I-39 | 9-cyclopropyl-2-({5-[3-(dimethylamino)propyl]-2-methylpyridin-3-yl}amino)-5,7-dihydro-6H-pyrimido[5,4-d][1]benzazepine-6-thione |
| I-40 | 9-chloro-2-[(2-methyl-6-{[(1-methylpiperidin-4-yl)methyl]amino}pyridin-3-yl)amino]-5,7-dihydro-6H-pyrimido[5,4-d][1]benzazepine-6-thione |
| I-41 | 9-chloro-2-({6-[[3-(dimethylamino)propyl](methyl)amino]-2-methylpyridin-3-yl}amino)-5,7-dihydro-6H-pyrimido[5,4-d][1]benzazepine-6-thione |
| I-42 | 9-chloro-2-({5-[3-(dimethylamino)propyl]-2,6-dimethylpyridin-3-yl}amino)-5,7-dihydro-6H-pyrimido[5,4-d][1]benzazepine-6-thione |
| I-43 | 2-{[2-methyl-5-(2-morpholin-4-ylethyl)pyridin-3-yl]amino}-9-(trifluoromethyl)-5,7-dihydro-6H-pyrimido[5,4-d][1]benzazepine-6-thione |
| I-44 | 9-chloro-2-({2-methyl-6-[(1-methylpiperidin-4-yl)methyl]pyridin-3-yl}amino)-5,7-dihydro-6H-pyrimido[5,4-d][1]benzazepine-6-thione |
| I-45 | 9-chloro-2-{[2-methyl-5-(2-pyrrolidin-1-ylethyl)pyridin-3-yl]amino}-5,7-dihydro-6H-pyrimido[5,4-d][1]benzazepine-6-thione |
| I-46 | 2-{[2-methyl-5-(4-methylpiperazin-1-yl)pyridin-3-yl]amino}-9-(trifluoromethyl)-5,7-dihydro-6H-pyrimido[5,4-d][1]benzazepine-6-thione |
| I-47 | 9-chloro-2-[(6-pyrrolidin-1-ylpyridin-3-yl)amino]-5,7-dihydro-6H-pyrimido[5,4-d][1]benzazepine-6-thione |
| I-49 | 9-chloro-2-({5-[(3R,5S)-4-ethyl-3,5-dimethylpiperazin-1-yl]-2-methylpyridin-3-yl}amino)-5,7-dihydro-6H-pyrimido[5,4-d][1]benzazepine-6-thione |
| I-50 | 2-({5-[2-(dimethylamino)ethyl]-2-methylpyridin-3-yl}amino)-9-(trifluoromethyl)-5,7-dihydro-6H-pyrimido[5,4-d][1]benzazepine-6-thione |
| I-51 | 9-chloro-2-({5-[2-(4-methylpiperazin-1-yl)ethyl]pyridin-3-yl}amino)-5,7-dihydro-6H-pyrimido[5,4-d][1]benzazepine-6-thione |
| I-52 | 2-[(5-{2-[4-(dimethylamino)piperidin-1-yl]ethyl}-2-methylpyridin-3-yl)amino]-9-(trifluoromethyl)-5,7-dihydro-6H-pyrimido[5,4-d][1]benzazepine-6-thione |
| I-53 | 2-{[2-methyl-5-(1,3,3-trimethylpiperidin-4-yl)pyridin-3-yl]amino}-9-(trifluoromethyl)-5,7-dihydro-6H-pyrimido[5,4-d][1]benzazepine-6-thione |
| I-54 | 9-chloro-2-{[2-methyl-5-(2-piperidin-1-ylethyl)pyridin-3-yl]amino}-5,7-dihydro-6H-pyrimido[5,4-d][1]benzazepine-6-thione |
| I-55 | 2-{[5-(3-hydroxypropyl)-2-methylpyridin-3-yl]amino}-9-(trifluoromethyl)-5,7-dihydro-6H-pyrimido[5,4-d][1]benzazepine-6-thione |

TABLE 2-continued

Compound Names:

| | |
|---|---|
| I-56 | 9-chloro-2-({2-methyl-6-[(1-methylpiperidin-4-yl)oxy]pyridin-3-yl}amino)-5,7-dihydro-6H-pyrimido[5,4-d][1]benzazepine-6-thione |
| I-57 | 2-{[6-(isopropylamino)-2-methylpyridin-3-yl]amino}-9-(trifluoromethyl)-5,7-dihydro-6H-pyrimido[5,4-d][1]benzazepine-6-thione |
| I-58 | 9-chloro-2-({5-[(3R)-4-ethyl-3-methylpiperazin-1-yl]pyridin-3-yl}amino)-5,7-dihydro-6H-pyrimido[5,4-d][1]benzazepine-6-thione |
| I-59 | 9-chloro-2-[(5-{2-[4-(dimethylamino)piperidin-1-yl]ethyl}-2-methylpyridin-3-yl)amino]-5,7-dihydro-6H-pyrimido[5,4-d][1]benzazepine-6-thione |
| I-60 | 2-({5-[3-(dimethylamino)propyl]-2-methylpyridin-3-yl}amino)-9-methyl-5,7-dihydro-6H-pyrimido[5,4-d][1]benzazepine-6-thione |
| I-61 | 2-{[6-(4-methylpiperazin-1-yl)pyridin-3-yl]amino}-9-(trifluoromethyl)-5,7-dihydro-6H-pyrimido[5,4-d][1]benzazepine-6-thione |
| I-62 | 2-({2-methyl-5-[3-(methylamino)propyl]pyridin-3-yl}amino)-9-(trifluoromethyl)-5,7-dihydro-6H-pyrimido[5,4-d][1]benzazepine-6-thione |
| I-63 | 9-chloro-2-{[2-methyl-5-(1,3,3-trimethylpiperidin-4-yl)pyridin-3-yl]amino}-5,7-dihydro-6H-pyrimido[5,4-d][1]benzazepine-6-thione |
| I-64 | 2-[(6-{[2-(dimethylamino)ethyl]amino}-2-methylpyridin-3-yl)amino]-9-(trifluoromethyl)-5,7-dihydro-6H-pyrimido[5,4-d][1]benzazepine-6-thione |
| I-65 | 2-[(2-methyl-6-{[1-methylpiperidin-4-yl)methyl]amino}pyridin-3-yl)amino]-9-(trifluoromethyl)-5,7-dihydro-6H-pyrimido[5,4-d][1]benzazepine-6-thione |
| I-66 | 9-chloro-2-({5-[(3S)-4-ethyl-3-methylpiperazin-1-yl]-2-methylpyridin-3-yl}amino)-5,7-dihydro-6H-pyrimido[5,4-d][1]benzazepine-6-thione |
| I-67 | 2-{[2-methyl-6-(piperidin-4-ylamino)pyridin-3-yl]amino}-9-(trifluoromethyl)-5,7-dihydro-6H-pyrimido[5,4-d][1]benzazepine-6-thione |
| I-68 | 2-[(6-aminopyridin-3-yl)amino]-9-chloro-5,7-dihydro-6H-pyrimido[5,4-d][1]benzazepine-6-thione |
| I-69 | 9-chloro-2-({6-[4-(dimethylamino)piperidin-1-yl]-2-methylpyridin-3-yl}amino)-5,7-dihydro-6H-pyrimido[5,4-d][1]benzazepine-6-thione |
| I-70 | 9-chloro-2-{[5-[2-(dimethylamino)ethyl]-2-(trifluoromethyl)pyridin-3-yl]amino}-5,7-dihydro-6H-pyrimido[5,4-d][1]benzazepine-6-thione |
| I-71 | 9-chloro-2-({6-[[3-(dimethylamino)propyl](methyl)amino]pyridin-3-yl}amino)-5,7-dihydro-6H-pyrimido[5,4-d][1]benzazepine-6-thione |
| I-72 | 9-chloro-2-{[2-methyl-5-(2-morpholin-4-ylethyl)pyridin-3-yl]amino}-5,7-dihydro-6H-pyrimido[5,4-d][1]benzazepine-6-thione |
| I-73 | 9-chloro-2-{[2-methyl-6-(4-methylpiperazin-1-yl)pyridin-3-yl]amino}-5,7-dihydro-6H-pyrimido[5,4-d][1]benzazepine-6-thione |
| I-74 | 2-({4-methyl-6-[(1-methylpiperidin-4-yl)amino]pyridin-3-yl}amino)-9-(trifluoromethyl)-5,7-dihydro-6H-pyrimido[5,4-d][1]benzazepine-6-thione |
| I-75 | 2-({2-methyl-6-[methyl(1-methylpiperidin-4-yl)amino]pyridin-3-yl}amino)-9-(trifluoromethyl)-5,7-dihydro-6H-pyrimido[5,4-d][1]benzazepine-6-thione |
| I-76 | 9-chloro-2-[(6-{[3-(dimethylamino)propyl]amino}-2-methylpyridin-3-yl)amino]-5,7-dihydro-6H-pyrimido[5,4-d][1]benzazepine-6-thione |
| I-77 | 2-({2-methyl-6-[(1-methylpiperidin-4-yl)oxy]pyridin-3-yl}amino)-9-(trifluoromethyl)-5,7-dihydro-6H-pyrimido[5,4-d][1]benzazepine-6-thione |
| I-78 | 9-chloro-2-{[5-(2-morpholin-4-ylethyl)pyridin-3-yl]amino}-5,7-dihydro-6H-pyrimido[5,4-d][1]benzazepine-6-thione |
| I-79 | 2-({5-[3-(dimethylamino)propyl]-2-methylpyridin-3-yl}amino)-6-thioxo-6,7-dihydro-5H-pyrimido[5,4-d][1]benzazepine-9-carbonitrile |
| I-80 | 9-cyclopropyl-2-({2-methyl-6-[(1-methylpiperidin-4-yl)amino]pyridin-3-yl}amino)-5,7-dihydro-6H-pyrimido[5,4-d][1]benzazepine-6-thione |
| I-81 | 9-chloro-2-[(2,6-dimethylpyridin-3-yl)amino]-5,7-dihydro-6H-pyrimido[5,4-d][1]benzazepine-6-thione |
| I-82 | 9-chloro-2-[(2-methyl-6-piperidin-1-ylpyridin-3-yl)amino]-5,7-dihydro-6H-pyrimido[5,4-d][1]benzazepine-6-thione |
| I-83 | 9-chloro-10-[3-(dimethylamino)propyl]-2-[(2-methyl-6-morpholin-4-ylpyridin-3-yl)amino]-5,7-dihydro-6H-pyrimido[5,4-d][1]benzazepine-6-thione |
| I-84 | 9-chloro-2-({5-[1-(2-fluoroethyl)piperidin-4-yl]-2-methylpyridin-3-yl}amino)-5,7-dihydro-6H-pyrimido[5,4-d][1]benzazepine-6-thione |
| I-85 | 9-chloro-2-{[2-methyl-6-(piperidin-4-ylamino)pyridin-3-yl]amino}-5,7-dihydro-6H-pyrimido[5,4-d][1]benzazepine-6-thione |
| I-86 | 2-[(2,6-dimethyl-5,6,7,8-tetrahydro-1,6-naphthyridin-3-yl)amino]-9-(trifluoromethyl)-5,7-dihydro-6H-pyrimido[5,4-d][1]benzazepine-6-thione |
| I-87 | 2-{[2-methyl-5-(2-piperidin-1-ylethyl)pyridin-3-yl]amino}-9-(trifluoromethyl)-5,7-dihydro-6H-pyrimido[5,4-d][1]benzazepine-6-thione |
| I-88 | 2-({6-[[3-(dimethylamino)propyl](methyl)amino]-2-methylpyridin-3-yl}amino)-9-(trifluoromethyl)-5,7-dihydro-6H-pyrimido[5,4-d][1]benzazepine-6-thione |
| I-89 | 9-chloro-2-({5-[4-(dimethylamino)butyl]-2-methylpyridin-3-yl}amino)-5,7-dihydro-6H-pyrimido[5,4-d][1]benzazepine-6-thione |
| I-90 | 2-{[5-(3-aminopropyl)-2-methylpyridin-3-yl]amino}-9-(trifluoromethyl)-5,7-dihydro-6H-pyrimido[5,4-d][1]benzazepine-6-thione |
| I-91 | 9-chloro-2-({5-[3-(dimethylamino)propyl]pyridin-3-yl}amino)-5,7-dihydro-6H-pyrimido[5,4-d][1]benzazepine-6-thione |
| I-92 | 2-({2-methyl-6-[(1-methylpiperidin-4-yl)amino]pyridin-3-yl}amino)-9-(trifluoromethyl)-5,7-dihydro-6H-pyrimido[5,4-d][1]benzazepine-6-thione |
| I-93 | 9-chloro-10-[3-(dimethylamino)propyl]-2-[(2-methylpyridin-3-yl)amino]-5,7-dihydro-6H-pyrimido[5,4-d][1]benzazepine-6-thione |
| I-94 | 9-chloro-2-({5-[3-(dimethylamino)propyl]-6-methylpyridin-3-yl}amino)-5,7-dihydro-6H-pyrimido[5,4-d][1]benzazepine-6-thione |

TABLE 2-continued

Compound Names:

| | |
|---|---|
| I-95 | 2-({2-methyl-6-[methy(1-methylpyrrolidin-3-yl)amino]pyridin-3-yl}amino)-9-(trifluoromethyl)-5,7-dihydro-6H-pyrimido[5,4-d][1]benzazepine-6-thione |
| I-96 | 9-chloro-2-{[6-(dimethylamino)-2-methyl-5,6,7,8-tetrahydroquinolin-3-yl]amino}-5,7-dihydro-6H-pyrimido[5,4-d][1]benzazepine-6-thione |
| I-97 | 9-chloro-2-[(6-{[2-(dimethylamino)-ethyl]amino}2-methylpyridin-3-yl)amino]-5,7-dihydro-6H-pyrimido[5,4-d][1]benzazepine-6-thione |
| I-98 | 2-[(2,4-dimethylpyridin-3-yl)amino]-9-(trifluoromethyl)-5,7-dihydro-6H-pyrimido[5,4-d][1]benzazepine-6-thione |
| I-99 | 9-chloro-2-({5-[2-(dimethylamino)-ethyl]-2-methylpyridin-3-yl}amino)-5,7-dihydro-6H-pyrimido[5,4-d][1]benzazepine-6-thione |
| I-100 | 2-[(2-methyl-6-morpholin-4-ylpyridin-3-yl)amino]-9-(trifluoromethyl)-5,7-dihydro-6H-pyrimido[5,4-d][1]benzazepine-6-thione |
| I-101 | 2-({6-[3-(dimethylamino)propyl]-2-methylpyridin-3-yl}amino)-9-(trifluoromethyl)-5,7-dihydro-6H-pyrimido[5,4-d][1]benzazepine-6-thione |
| I-102 | N-{5-[(9-chloro-6-thioxo-6,7-dihydro-5H-pyrimido[5,4-d][1]benzazepin-2-yl)amino]pyridin-2-yl}-2,2-dimethylpropanamide |
| I-103 | 9-chloro-2-{[2-methyl-5-(4-methylpiperazin-1-yl)pyridin-3-yl]amino}-5,7-dihydro-6H-pyrimido[5,4-d][1]benzazepine-6-thione |
| I-104 | 9-chloro-2-({5-[2-(dimethylamino)ethyl]pyridin-3-yl}amino)-5,7-dihydro-6H-pyrimido[5,4-d][1]benzazepine-6-thione |
| I-105 | 9-chloro-2-({2-methyl-6-[methyl(1-methylpiperidin-4-yl)amino]pyridin-3-yl}amino)-5,7-dihydro-6H-pyrimido[5,4-d][1]benzazepine-6-thione |
| I-106 | 9-chloro-2-[(2-methyl-6-pyrrolidin-1-ylpyridin-3-yl)amino]-5,7-dihydro-6H-pyrimido[5,4-d][1]benzazepine-6-thione |
| I-107 | 9-chloro-2-{[5-(4-methylpiperazin-1-yl)pyridin-3-yl]amino}-5,7-dihydro-6H-pyrimido[5,4-d][1]benzazepine-6-thione |
| I-108 | 9-chloro-2-({5-[3-(dimethylamino)propyl]-2-methylpyridin-3-yl}amino)-5,7-dihydro-6H-pyrimido[5,4-d][1]benzazepine-6-thione |
| I-109 | 9-chloro-2-[(2-methyl-6-morpholin-4-ylpyridin-3-yl)amino]-5,7-dihydro-6H-pyrimido[5,4-d][1]benzazepine-6-thione |
| I-110 | 2-[(2-methyl-6-pyrrolidin-1-ylpyridin-3-yl)amino]-9-(trifluoromethyl)-5,7-dihydro-6H-pyrimido[5,4-d][1]benzazepine-6-thione |
| I-111 | 2-({5-[3-(dimethylamino)propyl]-2-methylpyridin-3-yl}amino)-9-(trifluoromethyl)-5,7-dihydro-6H-pyrimido[5,4-d][1]benzazepine-6-thione |
| I-112 | 9-chloro-2-({6-[[2-(dimethylamino)ethyl](methyl)amino]-2-methylpyridin-3-yl}amino)-5,7-dihydro-6H-pyrimido[5,4-d][1]benzazepine-6-thione |
| I-113 | 2-{[(6R)-6-(dimethylamino)-2-methyl-5,6,7,8-tetrahydroquinolin-3-yl]amino}-9-(trifluoromethyl)-5,7-dihydro-6H-pyrimido[5,4-d][1]benzazepine-6-thione |
| I-114 | 2-{[6S]-6-(dimethylamino)-2-methyl-5,6,7,8-tetrahydroquinolin-3-yl]amino}-9-(trifluoromethyl)-5,7-dihydro-6H-pyrimido[5,4-d][1]benzazepine-6-thione |
| I-115 | 2-[(2-methyl-5,6,7,8-tetrahydro-1,8-naphthyridin-3-yl)amino]-9-(trifluoromethyl)-5,7-dihydro-6H-pyrimido[5,4-d][1]benzazepine-6-thione |
| I-116 | 5-[(9-chloro-6-thioxo-6,7-dihydro-5H-pyrimido[5,4-d][1]benzazepin-2-yl)amino]-6-methyl-N-(1-methylpiperidin-4-yl)pyridine-2-carboxamide |
| I-117 | 2-({5-[3-(dimethylamino)propyl]-2-methylpyridin-3-yl}amino)-10-(trifluoromethyl)-5,7-dihydro-6H-pyrimido[5,4-d][1]benzazepine-6-thione |
| I-118 | N-[2-(dimethylamino)ethyl]-6-methyl-5-{[6-thioxo-9-(trifluoromethyl)-6,7-dihydro-5H-pyrimido[5,4-d][1]benzazepin-2-yl]amino}pyridine-2-carboxamide |
| I-119 | 6-methyl-N-(2-morpholin-4-ylethyl)-5-{[6-thioxo-9-(trifluoromethyl)-6,7-dihydro-5H-pyrimido[5,4-d][1]benzazepin-2-yl]amino}pyridine-2-carboxamide |
| I-120 | 9-chloro-10-[3-(dimethylamino)propyl]-2-({5-[3-(dimethylamino)propyl]-2-methylpyridin-3-yl}amino)-5,7-dihydro-6H-pyrimido[5,4-d][1]benzazepine-6-thione |
| I-121 | 2-(dimethylamino)-N-(6-methyl-5-{[6-thioxo-9-(trifluoromethyl)-6,7-dihydro-5H-pyrimido[5,4-d][1]benzazepin-2-yl]amino}pyridin-2-yl)acetamide |
| I-122 | 2-{[7-(dimethylamino)-2-methyl-5,6,7,8-tetrahydroquinolin-3-yl]amino}-9-(trifluoromethyl)-5,7-dihydro-6H-pyrimido[5,4-d][1]benzazepine-6-thione |
| I-123 | 6-methyl-N-(1-methylpiperidin-4-yl)-5-{[6-thioxo-9-(trifluoromethyl)-6,7-dihydro-5H-pyrimido[5,4-d][1]benzazepin-2-yl]amino}pyridine-2-carboxamide |

4. General Synthetic Methods and Intermediates:

The compounds of the present invention can be prepared by methods known to one of ordinary skill in the art and/or by reference to the schemes shown below and the synthetic examples that follow. Exemplary synthetic routes are set forth in Schemes 1 and 2 below, and in the Examples.

Scheme 1: General route for the synthesis of compounds of formula I

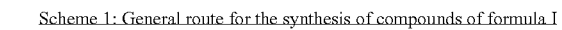

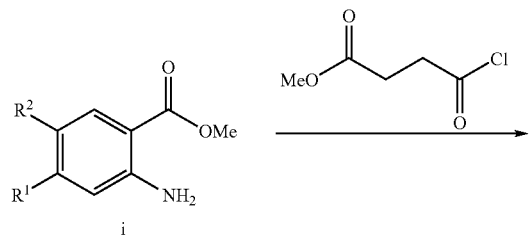

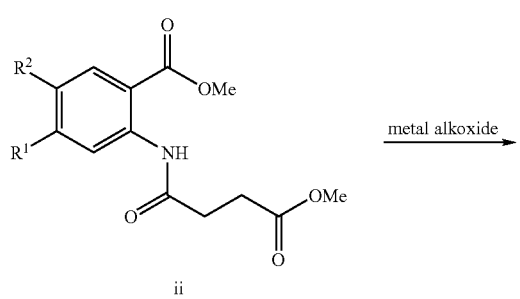

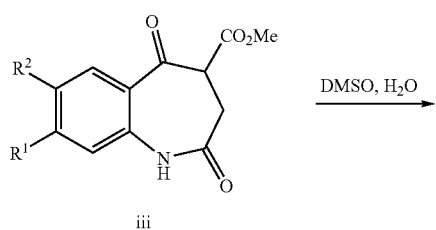

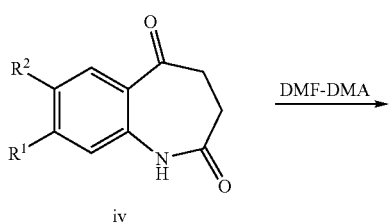

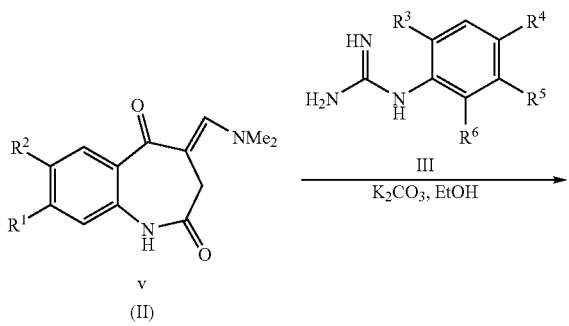

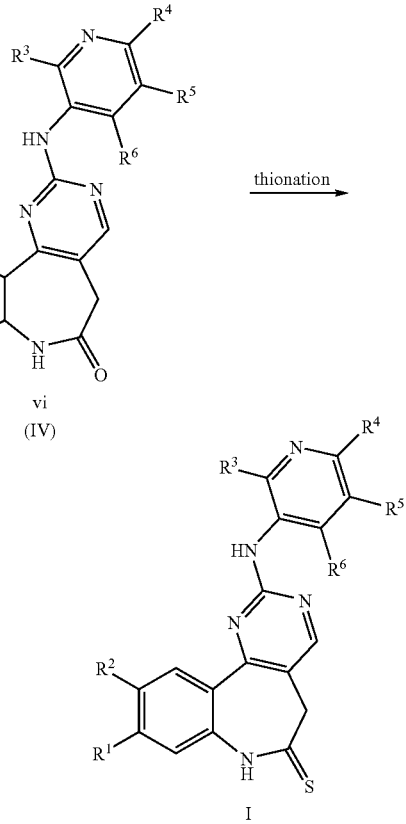

Scheme 1 above shows a general route for preparing compounds of formula I. Conversion of anilines i to acylated amino benzoic acid methyl esters of formula ii can be accomplished by coupling with appropriately substituted acyl chlorides with a suitable base, such as DIEA in the presence or absence of DMAP. Compounds iii can be prepared from ii by cyclization with a suitable base, such as a metal alkoxide (e.g., KOt-Bu or LiOt-Bu). Decarboxylation of iii to provide iv can be effected by heating in DMSO/$H_2O$ or NMP/$H_2O$. For compounds iv when $R^1$ is an iodo substituent, transformation of the iodide to a variety of functional groups can take place at this stage of the synthesis.

Treatment of compounds iv with DMF-DMA in refluxing THF is a method of preparing compounds v (formula II). Enamines v can be converted to the pyrimidines vi (formula IV) by treatment with appropriately substituted pyridyl guanidines of the formula III in the presence of a mild base in ethanol. Two methods for conversion of benzolactams vi to thiolactams I are treatment with $P_2S_5$ in pyridine or with Lawesson's reagent.

Scheme 2: Alternate route for the synthesis of compounds of formula I

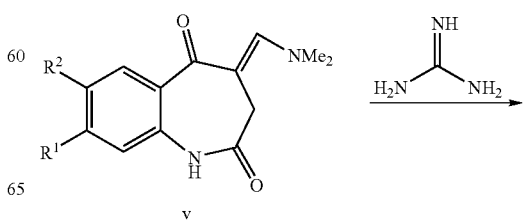

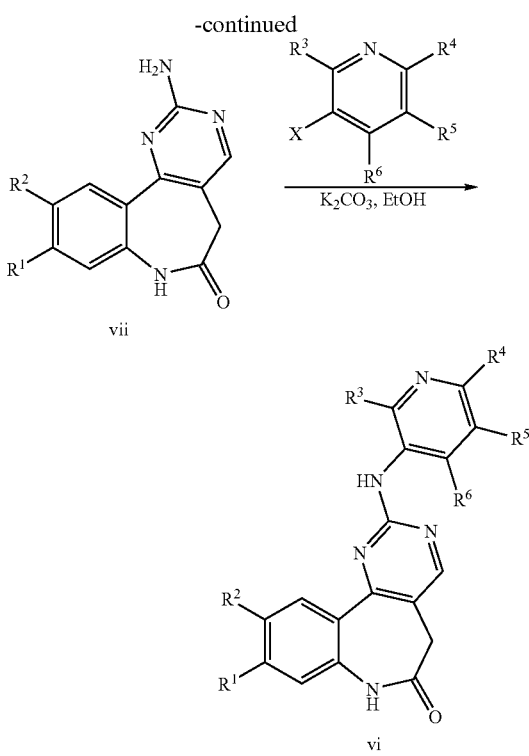

As an alternative procedure to using pyridyl guanidines to provide compounds of formula vi, guanidine itself can be reacted with enamines v to give compounds vii (Scheme 2). Treatment of amines vii with pyridyl halides under Buchwald conditions is a method of preparing compounds of formula I.

It will be appreciated that intermediates of formulas vi, vii, and v are also provided. In particular, intermediates of formula vi are provided, wherein variables $R^1$, $R^2$, $R^3$, $R^4$, $R^5$ and $R^6$ are as described generally and in subsets herein as for compounds of formula I.

In one aspect, the invention provides a process for preparing a compound of formula I:

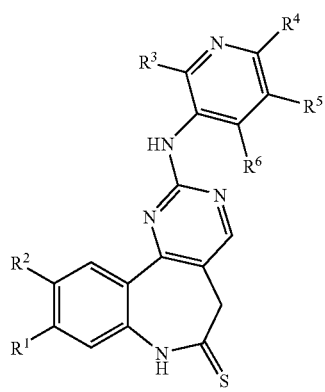

I or a salt thereof, wherein $R^1$ is selected from hydrogen, —CN, halogen, optionally substituted $C_{1-6}$aliphatic, or —$YR^{1a}$,
wherein Y is —O—, —S—, or —$NR^{1a}$, and each occurrence of $R^{1a}$ is independently hydrogen, or optionally substituted $C_{1-6}$aliphatic;

$R^2$ is selected from hydrogen, halogen, —$ZR^{2a}$, or —$OR^{2b}$,
wherein Z is an optionally substituted $C_{1-6}$ alkylene chain, and $R^{2a}$ is —$OR^{2b}$, —$N(R^{2b})_2$, —$SR^{2b}$, —C(O)N($R^{2b}$)$_2$, —N($R^{2b}$)C(O)$R^{2b}$, —SO$_2$N($R^{2b}$)$_2$, —$NR^{2b}SO_2R^{2b}$, —$NR^{2b}C(O)N(R^{2b})_2$, or —$NR^{2b}SO_2N(R^{2b})_2$, wherein each occurrence of $R^{2b}$ is independently hydrogen or optionally substituted $C_{1-6}$alkyl, or two occurrences of $R^{2b}$, taken together with a nitrogen atom to which they are bound, form an optionally substituted 3-7-membered heterocyclyl ring;

$R^3$ is selected from hydrogen, halogen, optionally substituted $C_{1-4}$alkyl, or optionally substituted $C_{1-4}$alkoxy;

$R^4$ is selected from hydrogen, optionally substituted $C_{1-6}$aliphatic, an optionally substituted 3-7-membered heterocyclyl ring, —(CH$_2$)$_x$NR$^{4a}$R$^{4b}$, —(CH$_2$)$_x$NR$^{4a}$C(O)R$^{4b}$, —(CH$_2$)$_x$NR$^{4a}$S(O)$_2$R$^{4b}$, —(CH$_2$)$_x$C(O)R$^{4b}$, —(CH$_2$)$_x$C(O)NR$^{4a}$R$^{4b}$, —(CH$_2$)$_x$S(O)$_2$NR$^{4a}$R$^{4b}$, or —(CH$_2$)$_x$OR$^{4b}$,
wherein
each occurrence of x is independently 0-6;
wherein $R^{4a}$ is hydrogen or optionally substituted $C_{1-6}$aliphatic, and
$R^{4b}$ is hydrogen, optionally substituted $C_{1-6}$aliphatic, optionally substituted $C_{3-7}$heterocyclyl or $C_{3-7}$carbocyclyl ring, or is W—$R^{4c}$, wherein W is an optionally substituted $C_{2-6}$ alkylene chain, and $R^{4c}$ is an optionally substituted $C_{3-7}$-heterocyclyl ring, —$OR^{4d}$, —$N(R^{4d})_2$, —C(O)N($R^{4d}$)$_2$, —N($R^{4d}$)C(O)$R^{4d}$, —SO$_2$N($R^{4d}$)$_2$, —$NR^{4d}SO_2R^{4d}$, —$NR^{4d}C(O)N(R^{4d})_2$, or —$NR^{4d}SO_2N(R^{4d})_2$, wherein each occurrence of $R^{4d}$ is independently hydrogen or optionally substituted $C_{1-6}$aliphatic, or two occurrences of $R^{4d}$, taken together with the nitrogen atom to which they are bound, form an optionally substituted 3-7-membered heterocyclyl ring;
or wherein $R^{4a}$ and $R^{4b}$, taken together with the nitrogen atom to which they are bound, form an optionally substituted 3-7-membered heterocyclyl ring;

$R^5$ is hydrogen, optionally substituted $C_{1-6}$aliphatic, an optionally substituted $C_{3-7}$heterocyclyl ring, or is X—$R^{5a}$,
wherein X is an optionally substituted $C_{2-6}$ alkylene chain or —$NR^{5c}$,
wherein when X is an optionally substituted $C_{2-6}$ alkylene chain $R^{5a}$ is —$OR^{5b}$, —$N(R^{5b})_2$, —$SR^{5b}$, —C(O)N($R^{5b}$)$_2$, —N($R^{5b}$)C(O)$R^{5b}$, —SO$_2$N($R^{5b}$)$_2$, —$NR^{5b}SO_2R^{5b}$, —$NR^{5b}C(O)N(R^{5b})_2$, or —$NR^{5b}SO_2N(R^{5b})_2$; and
when X is —$NR^{5c}$, $R^{5a}$ is hydrogen or optionally substituted $C_{1-6}$aliphatic, or $R^{5a}$ and $R^{5c}$, taken together with the nitrogen atom to which they are bound, form an optionally substituted 3-7-membered heterocyclyl ring;
wherein each occurrence of $R^{5b}$ and $R^{5c}$ is independently hydrogen or optionally substituted $C_{1-6}$aliphatic, or two occurrences of $R^{5b}$, or $R^{5a}$ and $R^{5c}$, taken together with the nitrogen atom to which they are bound, form an optionally substituted 3-7-membered heterocyclyl ring; or wherein $R^4$ and $R^5$, taken together, form an optionally substituted 5-7-membered cycloaliphatic or heterocyclyl ring; and $R^6$ is selected from hydrogen, halogen, optionally substituted $C_{1-4}$alkyl, or optionally substituted $C_{1-4}$alkoxy.

The process comprises the steps of:

(a-1) treating a compound of formula II:

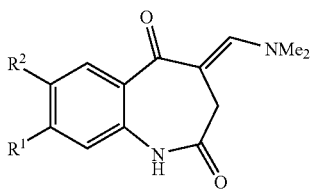

wherein variables $R^1$ and $R^2$ are as described generally and in subsets herein as for compounds of formula I; with a compound of formula III:

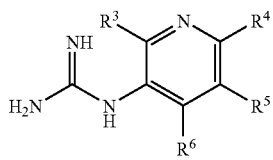

wherein variables $R^3$, $R^4$, $R^5$ and $R^6$ are as described generally and in subsets herein as for compounds of formula I; to form a compound of formula IV:

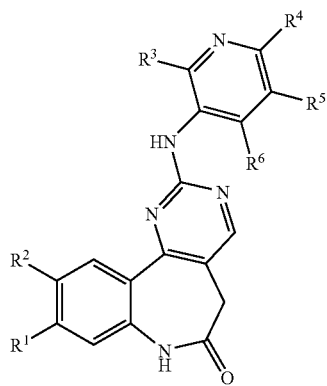

wherein variables $R^1$, $R^2$, $R^3$, $R^4$, $R^5$ and $R^6$ are as described generally and in subsets herein as for compounds of formula I; and (a-2) thionating the compound of formula IV to form the compound of formula I, In some embodiments, the thionation of a compound of formula IV is effected in the presence of $P_2S_5$ in pyridine or with Lawesson's reagent.

In another aspect, the invention provides a process for preparing a compound of formula IA:

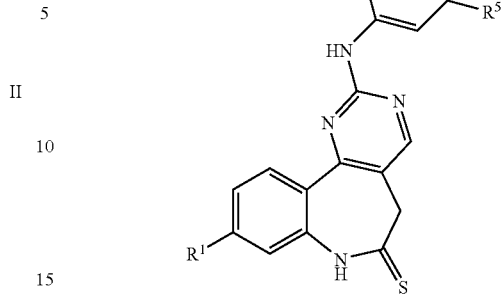

or a salt thereof, wherein $R^1$ is optionally substituted $C_{1-4}$aliphatic, halogen, —CN, or —OMe;

$R^3$ is methyl or $CF_3$; and $R^5$ is an optionally substituted $C_{3-7}$-heterocyclyl ring or is X—$R^{5a}$, wherein X is an optionally substituted $C_{2-6}$ alkylene chain, and $R^{5a}$ is —N($R^{5b}$)$_2$, wherein each occurrence of $R^{5b}$ is independently hydrogen or $C_{1-6}$alkyl, or two occurrences of $R^{5b}$, taken together with the nitrogen atom to which they are bound, form an optionally substituted 3-7-membered heterocyclyl ring.

The process comprises the steps of:

(b-1) treating a compound of formula II wherein $R^1$ is as described generally and in subsets herein as for compounds of formula I-A and $R^2$ is H; with an compound of formula III, wherein variables $R^3$ and $R^5$ are as described generally and in subsets herein as for compounds of formula I-A and $R^4$ and $R^6$ are each H; to form a compound of formula IV, wherein variables $R^1$, $R^3$, and $R^5$ are as described generally and in subsets herein as for compounds of formula I-A, and $R^2$, $R^4$ and $R^6$ are each H; and (b-2) thionating the compound of formula IV to form the compound of formula I-A.

In a further embodiment, the process for preparing a compound of formula I-A comprises the steps of:

(c-1) treating a compound of formula II, wherein $R^1$ is —$CF_3$ and $R^2$ is H; with a compound of formula III, wherein $R^4$ and $R^6$ are each H, $R^3$ is methyl, $R^5$ is X—$R^{5a}$, wherein X is an optionally substituted $C_3$ alkylene chain, and $R^{5a}$ is —N(Me)$_2$, in the presence of a mild base such as $K_2CO_3$ in a suitable solvent such as ethanol to form a compound of formula IV; and (c-2) thionating the compound of formula IV, in the presence of $P_2S_5$ in pyridine to form the compound of formula I-A.

In another embodiment, the process further comprises:

(c-3) treating the compound of formula I-A with HCl in a suitable solvent such as ethanol to form the HCl salt of formula I-A.

In another aspect, the invention provides a process for preparing a compound of formula I-B:

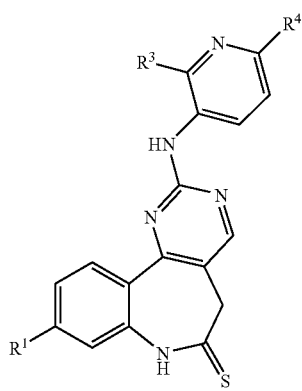

or a salt thereof, wherein $R^1$ is optionally substituted $C_{1-4}$aliphatic, halogen, —CN, or —OMe;

$R^3$ is methyl or $CF_3$; and $R^4$ is —$NR^{4a}R^{4b}$, wherein $R^{4a}$ and $R^{4b}$, taken together with the nitrogen atom to which they are bound, form an optionally substituted 3-7-membered heterocyclyl ring, or wherein $R^{4a}$ is hydrogen or $C_{1-4}$alkyl, and $R^{4b}$ is an optionally substituted $C_{3-7}$-heterocyclyl ring or is W—$R^{4c}$, wherein W is an optionally substituted $C_{2-4}$ alkylene chain, and $R^{4c}$ is an optionally substituted $C_{3-7}$-heterocyclyl ring, or —$N(R^{4d})_2$, wherein each occurrence of $R^{4d}$ is independently hydrogen or $C_{1-6}$alkyl, or two occurrences of $R^{4d}$, taken together with the nitrogen atom to which they are bound, form an optionally substituted 3-7-membered heterocyclyl ring.

The process comprises the steps of:

(d-1) treating a compound of formula II wherein $R^1$ is as described generally and in subsets herein as for compounds of formula I-B and $R^2$ is H; with an compound of formula III, wherein variables $R^3$ and $R^4$ are as described generally and in subsets herein as for compounds of formula I-B and $R^5$ and $R^6$ are each H; to form a compound of formula IV, wherein variables $R^1$, $R^3$, and $R^4$ are as described generally and in subsets herein as for compounds of formula I-B, and $R^2$, $R^5$ and $R^6$ are each H; and (d-2) thionating the compound of formula IV to form the compound of formula I-B.

In yet another aspect, the invention provides a process for preparing a compound of formula III:

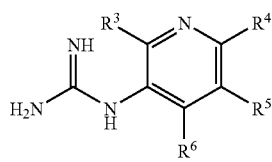

wherein $R^4$ and $R^6$ are each H, $R^3$ is methyl, $R^5$ is X—$R^{5a}$, wherein X is an optionally substituted $C_3$ alkylene chain, and $R^{5a}$ is —$N(Me)_2$, The process comprises the steps of:

(e-1) treating a compound of formula V:

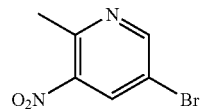

with a compound of formula VI:

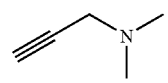

in the presence of $Pd(PPh_3)_2Cl_2$, CuI, and triethylamine to give a compound of formula VII:

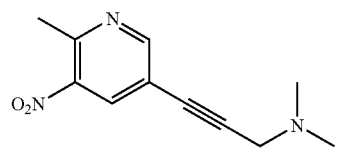

(e-2) hydrogenating the compound of formula VII with hydrogen and $Pd(OH)_2$ in the presence of a suitable solvent, such as isopropyl alcohol, followed by treatment with HCl to give a compound of formula VIII:

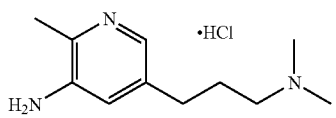

(e-3) treating the compound of formula VIII with a compound of formula IX:

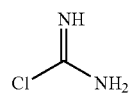

in the presence of acetic acid and acetonitrile to give the compound of formula III.

Another aspect of this invention relates to compounds of formula III:

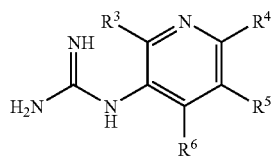

or a salt thereof, wherein variables $R^3$, $R^4$, $R^5$ and $R^6$ are as described generally and in subsets herein as for compounds of formula I, provided that:

i) at least one of $R^3$, $R^4$, $R^5$ and $R^6$ is other than H;

ii) when $R^3$, $R^5$ and $R^6$ are H, then $R^4$ is other than morpholinyl, —C(O)NH$_2$, —OMe, or —O-n-butyl;

iii) when $R^4$, $R^5$ and $R^6$ are H, then $R^3$ is other than chloro or —OMe; and iv) the compound of formula III is other than:

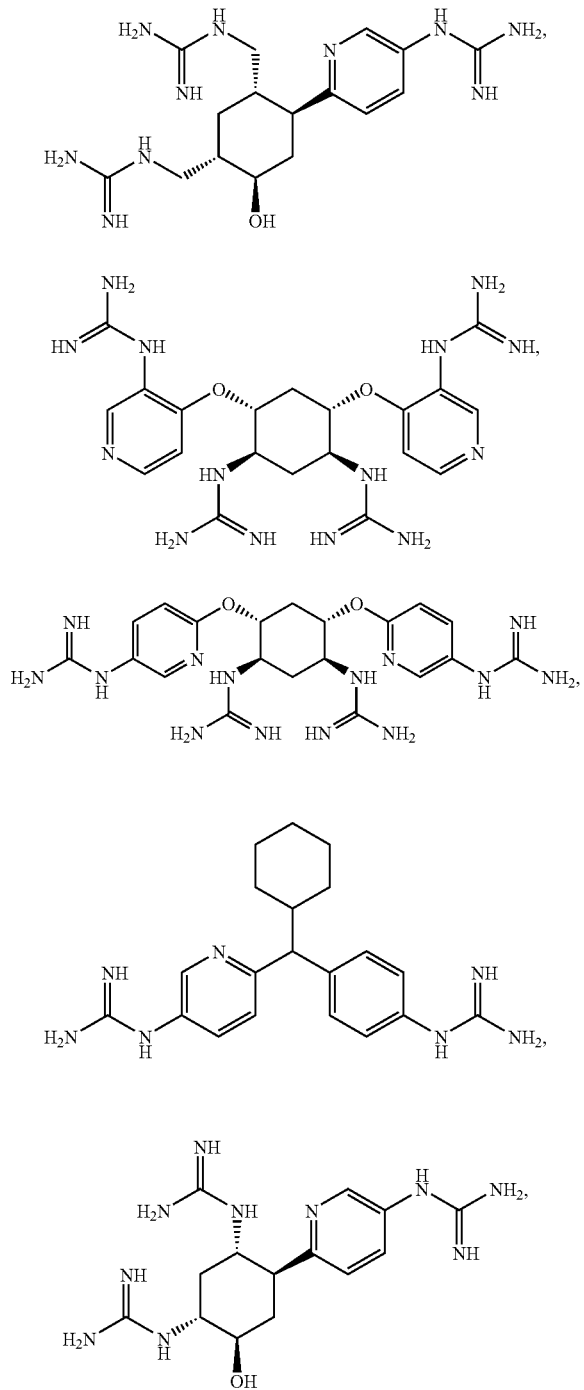

or a salt thereof.

Another aspect of this invention relates to compounds of formula IV:

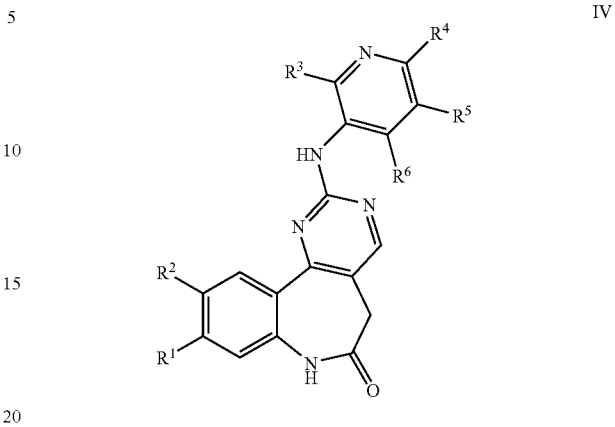

IV wherein variables $R^1$, $R^2$, $R^3$, $R^4$, $R^5$ and $R^6$ are as described generally and in subsets herein as for compounds of formula I.

5. Uses, Formulation and Administration

As discussed above, the present invention provides compounds that are useful as inhibitors of PLK enzymes, and thus the present compounds are useful for treating proliferative, inflammatory, or cardiovascular disorders such as tumor and/or cancerous cell growth mediated by PLK. In particular, the compounds are useful in the treatment of cancers in a subject, including, but not limited to, lung and bronchus, prostate, breast, pancreas, colon and rectum, thyroid, liver and intrahepatic bile duct, hepatocellular, gastric, glioma/glioblastoma, endometrial, melanoma, kidney, and renal pelvis, urinary bladder, utering corpus, uterine cervix, ovary, multiple myeloma, esophagus, acute myelogenous leukemia, chronic myelogenous leukemia, lymphocytic leukemia, myeloid leukemia, brain, oral cavity, and pharynx, small intestine, non-Hodgkin lymphoma, and villous colon adenoma.

In some embodiments, compounds of the invention are suitable for the treatment of breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of PLK.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylase, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, or cardiovascular disorder, or is that amount effective for treating cancer. In other embodiments, an "effective amount" of a compound is an amount which inhibits binding of PLK and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents, such as other inhibitors of PLK. In some embodiments, a compound of the invention is administered in conjunction with a therapeutic agent selected from the group consisting of cytotoxic agents, radiotherapy, and immunotherapy. It is understood that other combinations may be undertaken while remaining within the scope of the invention.

Another aspect of the invention relates to inhibiting PLK, activity in a biological sample or a patient, which method comprises administering to the patient, or contacting said biological sample with a compound of formula I or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where PLK kinase plays a role.

Experimental Procedures

Definitions
AcOH acetic acid
AHX aminohexanoic acid
ATP adenosine triphosphate
Bn benzyl
BOC tert-butoxycarbonyl
BSA bovine serum albumin
C Celsius
$CO_2$ Carbon Dioxide
DBU 1,8-diazabicyclo-undec-7-ene
DCM dichloromethane
DIEA diisopropylethylamine
DMAP 4-dimethylaminopyridine
DMF dimethylformamide
DMF-DMA dimethylformamide dimethylacetal
DMSO dimethylsulfoxide
DNA deoxyribonucleic acid
DTT dithiothreitol
EDC N-(3-dimethylaminopropyl)-N'-ethylcarbodiimide hydrochloride
EDTA ethylenediaminetetraacetic acid
EtOAc ethyl acetate
EtOH ethanol
FBS fetal bovine serum
h hours
$IC_{50}$ inhibitory concentration 50%
IgG immunoglobulin G
KCl Potassium Chloride
L length
Lawesson's Reagent 2,4-bis(4-methoxyphenyl)-2,4-dithioxo-1,3,2,4-dithiadiphosphetane
m/z mass to charge
MeOH methanol
min minutes
MS mass spectrum
NaCl Sodium Chloride
Ni Nickel
NMP N-methylpyrrolidinone
PBS phosphate-buffered saline
PBST phosphate-buffered saline Tween20
pHisH3 phosphorylated histone H3 on Serine 10
PLK1 polo-like kinase 1
rt room temperature
t-BuOK potassium tert-butoxide
STAB sodium triacetoxy borohydride
TBDPS tert-butyl diphenyl silyl
TBS tert-butyl dimethyl silyl
TEA triethylamine
THF tetrahydrofuran
TBTU O-(benzotriazol-1-yl)-N,N,N',N'-tetramethyluronium tetrafluoroborate
W width
Xphos 2-dicyclohexylphosphino-2',4',6'-tri-i-propyl-1,1'-biphenyl LCMS Conditions:

Method Formic Acid (FA): Spectra were run on a Phenominex Luna 5μ C18 50×4.6 mm column on a Hewlett-Packard HP1100 using acetonitrile containing zero to 100 percent 0.1% formic acid in water (2.5 mL/min for a 3 min run).

Method Formic Acid Long (FAL): Spectra were run on a Phenominex Luna 5μ C18 50×4.6 mm column on a Hewlett-Packard HP1100 using acetonitrile containing zero to 100 percent 0.1% formic acid in water (1.0 mL/min for a 16 min run).

Method Ammonium Acetate (AA): Spectra were run on a Phenominex Luna 5μ C18 50×4.6 mm column on a Hewlett-Packard HP1100 using acetonitrile containing zero to 100 percent 10 mM ammonium acetate in water (2.5 mL/min for a 3 min run).

Method Ammonium Acetate Long (AAL): Spectra were run on a Phenominex Luna 5μ C18 50×4.6 mm column on a Hewlett-Packard HP1100 using acetonitrile containing zero to 100 percent 10 mM ammonium acetate in water (1.0 mL/min for a 16 min run).

For the LCMS Methods FAP1, FAP2, and FAP3, Solvent A=99% Water+1% Acetonitrile+0.1% Formic Acid and Solvent B=95% Acetonitrile+5% Water +0.1% Formic Acid.

Method Formic Acid Purity 1 (FAP1): Spectra were obtained on an Agilent 1100 Series LC system connected to a Micromass mass spectrometer using Waters Symmetry C-18 4.6×100 mm column with a solvent gradient of 100% A to 100% B (1 mL/min for a 20 min run).

Method Formic Acid Purity 2 (FAP2): Spectra were obtained on an Agilent 1100 Series LC system connected to a Micromass mass spectrometer using Waters Symmetry C-18 4.6×100 mm column with a solvent gradient of 100% A to 100% B (1 mL/min for a 16.5 min run).

Method Formic Acid Purity 3 (FAP3): Spectra were obtained on Agilent 1100 Series LC system connected to a Micromass mass spectrometer using Waters Symmetry C-18 4.6×100 mm column with a solvent gradient of 95% A/5% B to 100% B (1 mL/min for a 10 min run).

Example 1

Synthesis of Compounds of Formula i

2-Amino-4-methoxy-benzoic acid methyl ester

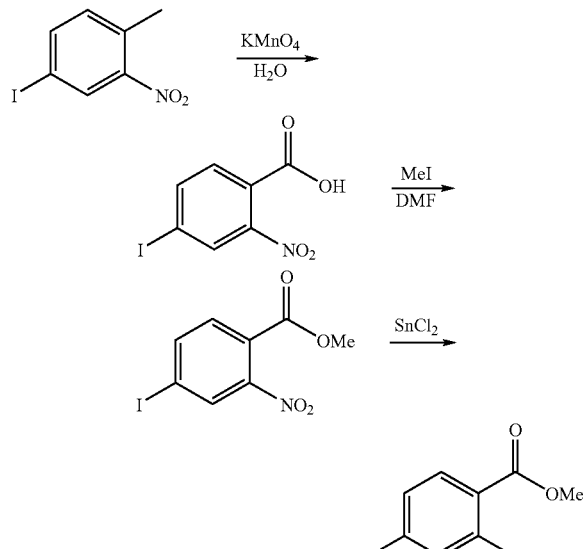

Step 1: 4-Iodo-2-nitrobenzoic acid

To a mixture of 4-iodo-2-nitrotoluene (9.0 g, 34 mmol) in $H_2O$ (340 mL) was added $KMnO_4$ (22.0 g, 139 mmol). The mixture was heated at reflux for 5 h and then cooled to rt and filtered through Celite®. The filtrate was acidified to pH=2 with conc. HCl. The precipitate that formed and was filtered and dried to give 4-iodo-2-nitrobenzoic acid (2.0 g, 20%). The filtrate was extracted with DCM (3×200 mL). The organic solutions were combined, dried over $Na_2SO_4$, filtered, and concentrated to provide a second lot of 4-iodo-2-nitrobenzoic acid (0.18 g, 2%).

Step 2: Methyl 4-iodo-2-nitrobenzoate

To a solution of 4-iodo-2-nitrobenzoic acid (2.3 g, 7.9 mmol) in DMF (30 mL) was added DBU (2.4 mL, 16 mmol) followed by iodomethane (1.5 mL, 24 mmol). The reaction mixture was allowed to stir at 0° C. for 15 min, then slowly allowed to warm to rt and to stir overnight. After 12 h, the reaction mixture was poured into 200 mL of $H_2O$ and extracted with EtOAc (2×100 mL). The organic solutions were combined, washed with $H_2O$ (2×100 mL), dried over $Na_2SO_4$, filtered and concentrated to give methyl 4-iodo-2-nitrobenzoate (2.3 g, 96%).

Step 3: Methyl 2-amino-4-iodobenzoate

To a solution of methyl 4-iodo-2-nitrobenzoate (2.3 g, 7.4 mmol) in DCM (5 mL) and EtOAc (5 mL) was added $SnCl_2 \cdot 2H_2O$ (10.8 g, 89.7 mmol). The mixture was allowed to stir for 12 h at rt. The solvents were evaporated, and the residue was partitioned between 200 mL of saturated aqueous $NaHCO_3$ and 200 mL of DCM. The organic solution was separated and the aqueous solution was extracted with DCM (2×100 mL). The organic solutions were combined, dried over $Na_2SO_4$, filtered and concentrated to give methyl 2-amino-4-iodobenzoate (1.85 g, 90%).

Methyl 2-amino-4-methoxybenzoate

Step 1: Methyl 4-methoxy-2-nitrobenzoate

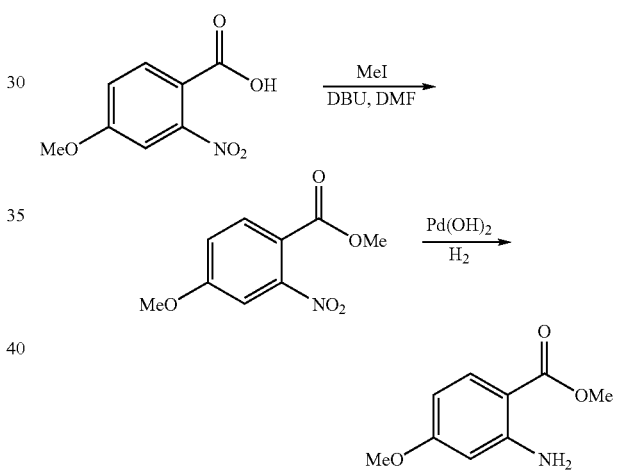

To a solution of 4-methoxy-2-nitrobenzoic acid (10.0 g, 50.7 mmol) in DMF (200 mL) at 0° C. was added DBU (15.2 mL, 101 mmol) followed by iodomethane (9.47 mL, 152 mmol). The reaction mixture was allowed to stir at 0° C. for 15 min then at rt overnight. The mixture was poured into water and extracted with EtOAc. The organic solutions were combined, washed with brine and dried over $MgSO_4$. The residue was purified by column chromatography to give methyl 4-methoxy-2-nitrobenzoate (50.7 mmol, 85%) as a yellow solid. LCMS (FA): m/z=212.1 (M+H).

Step 2: Methyl 2-amino-4-methoxybenzoate

A solution of methyl 4-methoxy-2-nitrobenzoate (9.0 g, 43 mmol) in MeOH (100 mL) was degassed and purged with nitrogen. To this solution was added 10% palladium hydroxide on carbon (1.2 g). The reaction mixture was degassed, purged with hydrogen and allowed to stir at rt overnight. The reaction mixture was filtered through Celite®, the Celite was washed with MeOH and the filtrate was concentrated to give methyl 2-amino-4-methoxybenzoate (7.80 g, 76%) as a brown solid. LCMS (FA): m/z=182.1 (M+H).

Methyl 2-amino-4-(trifluoromethyl)benzoate

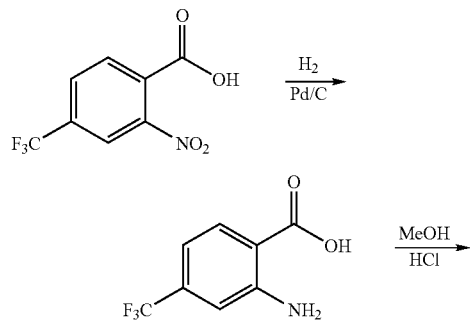

Step 1: 2-Amino-4-(trifluoromethyl)benzoic acid

A mixture of 2-nitro-4-(trifluoromethyl)benzoic acid (646 g, 2.75 mol) and 10% palladium on carbon (50% in water, 71 g) in MeOH (3.6 L) was allowed to stir at rt under an atmosphere of $H_2$ (15 psi). After 3 h, TLC (DCM:MeOH 10:1) showed no remaining starting material. The mixture was filtered and the filtrate was concentrated to give 2-amino-4-(trifluoromethyl)benzoic acid (520 g, 92%) as a white solid.

Step 2: Methyl 2-amino-4-(trifluoromethyl)benzoate

To a mixture of 2-amino-4-(trifluoromethyl)benzoic acid (150 g, 0.73 mol) in MeOH (2.5 L) was added conc. HCl (0.5 L, 16.5 mol). The reaction mixture was allowed to stir at reflux. After 3 h, an additional portion of HCl (0.5 L, 16.5 mol) was added and the reaction was allowed to continue to stir at 80° C. for 60 h. The reaction mixture was allowed to cool to rt and was concentrated. Water (0.5 L) was added to the residue, and the solution was basified with 10% aqueous NaOH solution. The resulting precipitate was filtered to give methyl 2-amino-4-(trifluoromethyl)benzoate (120 g, 75%) as a white solid.

Methyl 2-amino-4-chlorobenzoate

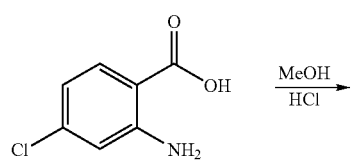

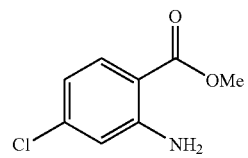

To a mixture of 2-amino-4-chlorobenzoic acid (150 g, 0.88 mol) in MeOH (2.6 L) was added conc. HCl (0.5 L, 16.5 mol) and the reaction mixture was allowed to stir at reflux. After 12 h, the reaction mixture was allowed to cool to rt and was concentrated. Water (0.5 L) was added to the residue and the solution basified with 10% aqueous NaOH. The resulting precipitate was filtered to give methyl 2-amino-4-chlorobenzoate (101 g, 62%).

Methyl 2-amino-4-chloro-5-iodobenzoate

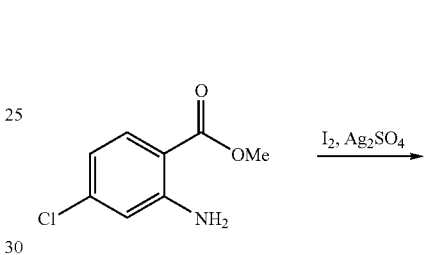

To a mixture of iodine (68 g, 0.27 mol) and silver sulfate (84 g, 0.27 mol) in absolute EtOH (2.5 L) was added methyl 2-amino-4-chlorobenzoate (50 g, 0.27 mol). The reaction mixture was allowed to stir at rt for 45 min. The reaction mixture was then filtered through a pad of Celite® and the filtrate was concentrated. The residue was dissolved in EtOAc (2 L) and washed with saturated aqueous $NaHCO_3$ (3×400 mL), water (3×400 mL), and brine. The organic solution was dried over $Na_2SO_4$, filtered, and concentrated to give methyl 2-amino-4-chloro-5-iodobenzoate (85 g, 99%).

Example 2

Synthesis of Compounds of Formula iv 8-iodo-3,4-dihydro-1H-1-benzazepine-2,5-dione

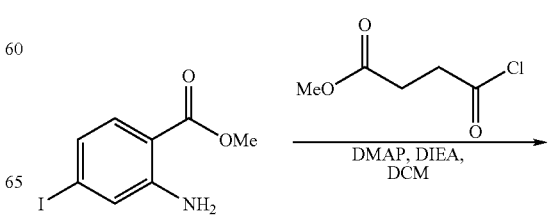

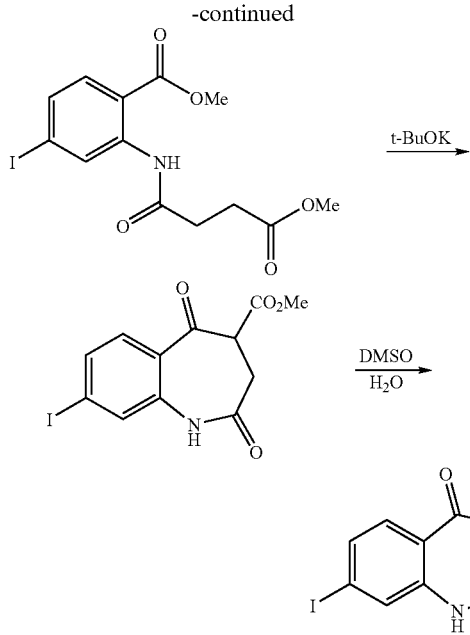

Step 1: Methyl 4-iodo-2-[(4-methoxy-4-oxobutanoyl)amino]benzoate

To a solution of methyl 2-amino-4-iodobenzoate (17 g, 61.3 mmol) in DCM (200 mL), was added DIEA (10.6 mL, 64.4 mmol) and DMAP (37.5 mg, 0.31 mmol). To this solution was added 3-(carbomethoxy)propionyl chloride (8.3 mL, 67.4 mmol) dropwise, and the reaction mixture was allowed to stir at rt for 2 h. To the reaction mixture was then added H$_2$O (80 mL) and the mixture was allowed to stir for 30 min. The organic solution was separated and the aqueous solution was extracted with DCM (2×100 mL). The organic solutions were combined, washed with H$_2$O (2×100 mL) and brine (1×100 mL), dried over Na$_2$SO$_4$, filtered and concentrated to give methyl 4-iodo-2-[(4-methoxy-4-oxobutanoyl)amino]benzoate (24,6 g, 99%).

Step 2: Methyl 8-iodo-2,5-dioxo-2,3,4,5-tetrahydro-1H-1-benzazepine-4-carboxylate To a solution of methyl 4-iodo-2-[(4-methoxy-4-oxobutanoyl)amino]benzoate (24.6 g, 63 mmol) in THF (240 mL) at 10° C. was added a 1 M solution of KOt-Bu in THF (185 mL, 185 mmol) dropwise over 30 min while maintaining the temperature at 10° C. After 2.5 h, 50 mL of H$_2$O followed by 190 mL of 1N HCl were added to bring the solution to pH=4. The resulting mixture was allowed to stir at rt for 40 min. The organic solution was separated and the aqueous solution was extracted with EtOAc (2×200 mL). The organic solutions were combined, dried over Na$_2$SO$_4$, filtered and concentrated to give methyl 8-iodo-2,5-dioxo-2,3,4,5-tetrahydro-1H-1-benzazepine-4-carboxylate (22 g, 97%).

Step 3: 8-Iodo-3,4-dihydro-1H-1-benzazepine-2,5-dione

A mixture of methyl 8-iodo-2,5-dioxo-2,3,4,5-tetrahydro-1H-1-benzazepine-4-carboxylate (74 g, 0.2 mol) in DMSO (560 mL) and H$_2$O (16 mL) was heated at 150° C. for 4 h. The reaction mixture was allowed to cool to rt, ice (1.0 L) was added, and the mixture was allowed to stir 12 h. To the flask was added 1N HCl (1.0 L) at 0° C. and the mixture allowed to stir for 3 h. The resulting precipitate was filtered and dried under reduced pressure to afford 8-iodo-3,4-dihydro-1H-1-benzazepine-2,5-dione (60 g, 97%).

8-(trifluoromethyl)-3,4-dihydro-1H-1-benzazepine-2,5-dione

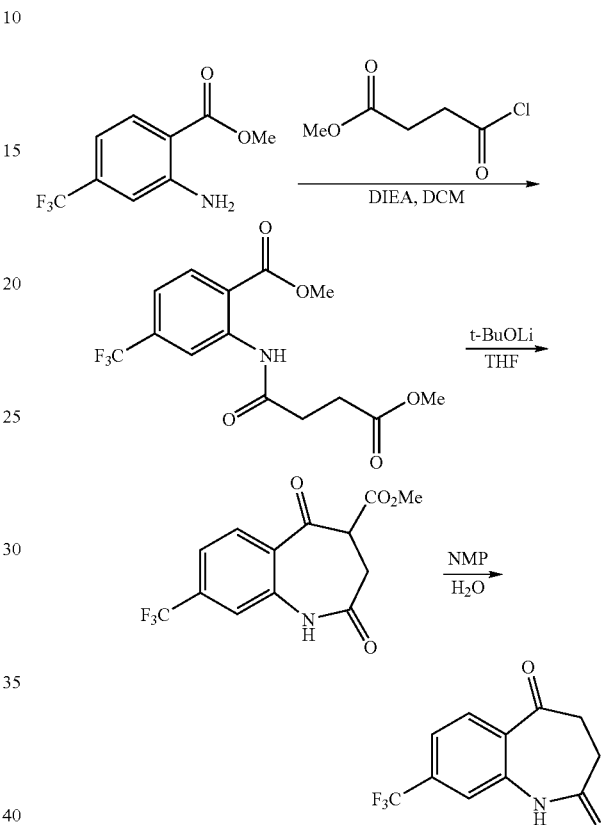

Step 1: Methyl 2-(4-methoxy-4-oxobutanamido)-4-(trifluoromethyl)benzoate

A 22 L reactor equipped with an overhead stirrer and a temperature probe was charged with methyl 2-amino-4-(trifluoromethyl)benzoate (680 g, 3.1 mol). DCM (5.4 L, 8 vol) was added to it and the resulting solution was cooled in an ice-water bath. DIEA (1.08 L, 6.2 mol, 2 equiv) was added to the solution. A solution of 4-chloro-4-oxo-butyrate (568 mL, 4.65 mol, 1.5 equiv) in DCM (1.4 L, 2 vol) was added dropwise maintaining the internal temperature below 15° C. (3 h). The ice-water bath was removed and the reaction was stirred for 3 h. The reaction was judged complete by HPLC analysis. Water (3.4 L, 5 vol) was added to the reaction and the biphasic mixture was stirred at ambient temperature overnight. The water layer was removed and saturated aqueous NaHCO$_3$ (3.4 L, 5 vol) was added to the DCM layer. The mixture was stirred for 30 min. The two layers were separated and another 3.4 L (5 vol) of saturated aqueous NaHCO$_3$ was added to the DCM layer. The mixture was stirred for 30 min. The two layers were separated and a 1:1 mixture of brine/water (3.4 L, 5 vol) was added to the DCM layer. The biphasic mixture was stirred for 30 min. The two layers were separated and the DCM layer was pumped down to a low volume (ca. 1.4 L, 2 vol). THF (6.8

L, 10 vol) was added to the solution and the solvent was evaporated under reduced pressure to a low volume (ca. 1.4 L) to obtain Methyl 2-(4-methoxy-4-oxobutanamido)-4-(trifluoromethyl)benzoate [1.032 kg, theoretical yield, 3.1 mol] as a solution in THF.

Step 2: Methyl 2,5-dioxo-8-(trifluoromethyl)-2,3,4,5-tetrahydro-1H-benzo[b]azepine-4-carboxylate A 22 L reactor equipped with an overhead stirrer and a temperature probe was charged with LiOBu$^t$ (1.24 kg, 15.5 mol, 5 equiv), and THF (5 L, 5 vol) was added slowly to obtain a solution (1 h). The internal temperature rose to 28° C. during this time. The solution was stirred until the temperature subsided to 22° C. The solution of Methyl 2-(4-methoxy-4-oxobutanamido)-4-(trifluoromethyl)benzoate [3.1 mol] in THF obtained above was further diluted with THF to make the total volume 5 L. This solution was added dropwise to the reactor maintaining the internal temperature below 35° C. (addition time 2 h). The reaction was stirred overnight at ambient temperature and was judged complete by HPLC analysis (Method 1, 15 min method). The reactor was cooled in an ice-water bath. The reaction was quenched by adding a mixture of AcOH (1.33 L, 23.25 mol, 7.5 equiv) and water (5 L, 5 vol) maintaining the internal temperature below 35° C. The pH of resulting biphasic mixture was 6-7. THF was removed resulting in a brown suspension. The solid was collected by filtration and the filter cake was washed with 5% THF in water (4 L, 4 vol). The solid was dried in a vacuum oven at 35° C. overnight to obtain Methyl 2,5-dioxo-8-(trifluoromethyl)-2,3,4,5-tetrahydro-1H-benzo[b]azepine-4-carboxylate [970 g, 103% recovery] as a brown solid. HPLC purity of this solid was 89.2% (AUC@226 nm).

Crude methyl 2,5-dioxo-8-(trifluoromethyl)-2,3,4,5-tetrahydro-1H-benzo[b]azepine-4-carboxylate obtained above was purified by recrystallization from IPA. Thus, a 12 L reactor equipped with a reflux condenser was charged with crude methyl 2,5-dioxo-8-(trifluoromethyl)-2,3,4,5-tetrahydro-1H-benzo[b]azepine-4-carboxylate (970 g) and IPA (6.8 L, 7 vol). The suspension was heated at 80° C. for 1.5 h resulting in a brown slurry. This was then cooled slowly to ambient temperature over a period of 3 h. The suspension that resulted was further cooled to −15° C. by using an ice-methanol bath. The suspension was stirred at this temperature for 2 h. The solid was filtered and the filter cake was washed with cold IPA (3.8 L, cooled in ice-methanol bath). The solid was dried in a vacuum oven at 35° C. to a constant weight to obtain methyl 2,5-dioxo-8-(trifluoromethyl)-2,3,4,5-tetrahydro-1H-benzo[b]azepine-4-carboxylate [671 g, 72% yield over two steps] as an off-white solid. $^1$H NMR (500 MHz, DMSO-d$_6$) δ ppm: 12.37 (s, 1H), 10.55 (s, 1H), 8.01 (d, 1H, J=10 Hz), 7.59 (d, 1H, J=10 Hz), 7.53 (s, 1H), 3.85 (s, 3H), 2.99 (s, 2H); ESI-MS m/z: 302 (M+H, 100%).

Step 3: 8-(trifluoromethyl)-3,4-dihydro-1H-1-benzazepine-2,5-dione

A 22 L reactor was charged with a solution of methyl 2,5-dioxo-8-(trifluoromethyl)-2,3,4,5-tetrahydro-1H-benzo[b]azepine-4-carboxylate [670 g, 2.22 mol] in NMP (4 L, 6 vol). Water (67 mL, 0.1 vol) was added and the resulting solution was slowly heated to 135° C. The reaction was continued for 15 h when HPLC analysis indicated >99% conversion. The reaction was cooled to ambient temperature. Water (8.7 L, 13 vol) was added slowly with vigorous stirring resulting in a suspension. The suspension was stirred at ambient temperature overnight. The solid was collected by filtration and the filter cake was washed with water (1.5 L). The solid was dried to a constant weight in a vacuum oven at 45° C. to obtain 8-(trifluoromethyl)-3,4-dihydro-1H-1-benzazepine-2,5-dione (522 g, 97% recovery) as an off-white solid.

$^1$H NMR (500 MHz, DMSO-d$_6$) δ ppm: 10.28 (s, 1H), 8.00 (d, 1H, J=8.0 Hz), 7.54 (s, 1H), 7.50 (d, 1H, J=8.0 Hz), 3.00-2.94 (m, 2H), 2.78-2.70 (m, 2H); ESI-MS m/z: 244 (M+H, 100%).

Compounds in the following table may be prepared from the appropriate starting materials using the procedures described above:

---

8-methoxy-3,4-dihydro-1H-1-benzazepine-2,5-dione
8-chloro-3,4-dihydro-1H-1-benzazepine-2,5-dione
8-chloro-7-iodo-3,4-dihydro-1H-1-benzazepine-2,5-dione

---

8-Methyl-3,4-dihydro-1H-1-benzazepine-2,5-dione

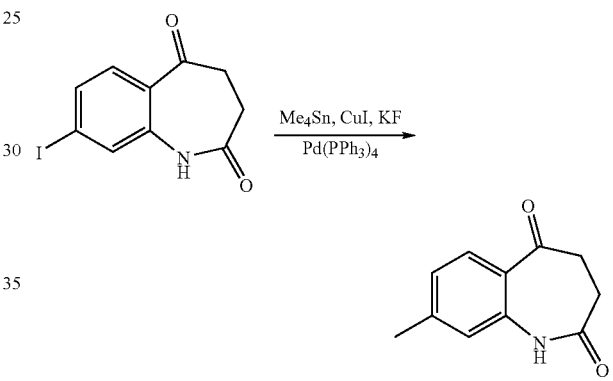

To a degassed solution of 8-iodo-3,4-dihydro-1H-1-benzazepine-2,5-dione (0.3 g, 1.0 mmol) in DMF (5 mL) was added CuI (19 mg, 0.1 mmol), KF (116 mg, 2.0 mmol), Me$_4$Sn (0.28 mL, 2.0 mmol), and Pd(PPh$_3$)$_4$ (116 mg, 0.1 mmol). The reaction mixture was allowed to stir at 120° C. for 4 h. After being allowed to cool to rt, EtOAc (50 mL) and a 1M aqueous KF solution (25 mL) were added and the solution was allowed to stir for an additional 40 min. The mixture was filtered over Celite®. The organic solution was separated, washed with brine, dried over Na$_2$SO$_4$, filtered and concentrated. The residue was purified by column chromatography to provide 8-methyl-3,4-dihydro-1H-1-benzazepine-2,5-dione (60 mg, 32%).

8-Ethyl-3,4-dihydro-1H-1-benzazepine-2,5-dione

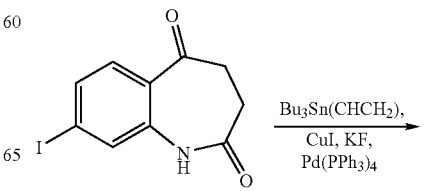

-continued

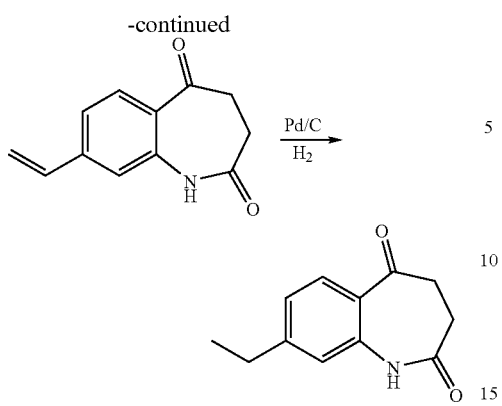

Step 1:
8-Vinyl-3,4-dihydro-1H-1-benzazepine-2,5-dione

To a degassed solution of 8-iodo-3,4-dihydro-1H-1-benzazepine-2,5-dione (0.3 g, 1.0 mmol) in DMF (5 mL) was added CuI (19 mg, 0.1 mmol), KF (116 mg, 2.0 mmol), tributylethenylstannane (0.58 mL, 2.0 mmol), and Pd(PPh$_3$)$_4$ (116 mg, 0.1 mmol). The reaction mixture was allowed to stir at 100° C. for 4 h. After being allowed to cool to rt, EtOAc (50 mL) and a 1M aqueous KF solution (25 mL) were added and the mixture was allowed to stir for an additional 40 min. The mixture was filtered over Celite® and the organic solution was separated, washed with brine, dried over Na$_2$SO$_4$, filtered and concentrated. The residue was treated with n-pentane and filtered. The resulting solid was purified by column chromatography to provide 8-vinyl-3,4-dihydro-1H-1-benzazepine-2,5-dione (80 mg, 40%).

Step 2:
8-Ethyl-3,4-dihydro-1H-1-benzazepine-2,5-dione

To a solution of 8-vinyl-3,4-dihydro-1H-1-benzazepine-2,5-dione (2.6 g, 13 mmol) in EtOH (160 mL) was added 10% (w/w) palladium on carbon (260 mg). The reaction mixture was allowed to stir under an atmosphere of H$_2$ (5 bar) at 70° C. until reaction was complete. The reaction mixture was filtered over Celite® and the filtrate was concentrated to give 8-ethyl-3,4-dihydro-1H-1-benzazepine-2,5-dione (2.4 g, 91%),

8-Cyclopropyl-3,4-dihydro-1H-1-benzazepine-2,5-dione

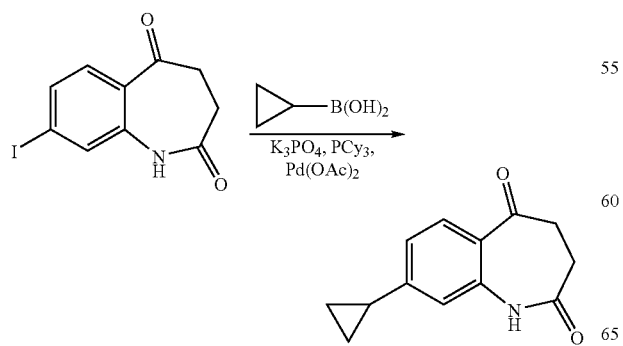

To a solution of 8-iodo-3,4-dihydro-1H-1-benzazepine-2,5-dione (0.6 g, 2.0 mmol) in toluene (9 mL) and H$_2$O (1 mL) under an atmosphere of N$_2$ was added cyclopropylboronic acid (0.34 g, 4.0 mmol), K$_3$PO$_4$ (1.27 g, 6.0 mmol), PCy$_3$ (1.2 mL, 0.8 mmol), and Pd(OAc)$_2$ (90 mg, 0.4 mmol). The reaction mixture was allowed to stir at 80° C. for 12 h and then allowed to cool to rt. To the mixture were added EtOAc (50 mL) and H$_2$O (50 mL), and the resulting solids were filtered over Celite®. The organic solution was separated and the aqueous solution was extracted with EtOAc (2×50 mL). The organic solutions were combined, dried over MgSO$_4$, filtered and concentrated. The residue was purified by column chromatography to provide 8-cyclopropyl-3,4-dihydro-1H-1-benzazepine-2,5-dione (100 mg, 23%).

8-Cyano-3,4-dihydro-1H-1-benzazepine-2,5-dione

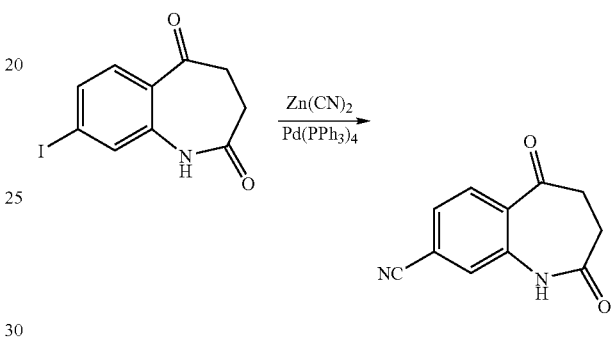

To a solution of 8-iodo-3,4-dihydro-1H-1-benzazepine-2,5-dione (0.3 g, 1.0 mmol) in DMF (5 mL) was added Zn(CN)$_2$ (0.12 g, 1.0 mmol) and Pd(PPh$_3$)$_4$ (116 mg, 0.1 mmol). The reaction mixture was allowed to stir at 80° C. for 3.5 h. After being allowed to cool to rt, EtOAc (20 mL) and H$_2$O (20 mL) were added, the organic solution was separated, and the aqueous solution was extracted with EtOAc (2×50 mL). The organic solutions were combined, washed with H$_2$O and brine, dried over MgSO$_4$, filtered and concentrated. The residue was purified by column chromatography to provide 8-cyano-3,4-dihydro-1H-1-benzazepine-2,5-dione (140 mg, 70%).

Example 3

Synthesis of Compounds of Formula v (Formula II)

(4Z)-8-chloro-4-[(dimethylamino)methylene]-7-iodo-3,4-dihydro-1H-1-benzazepine-2,5-dione

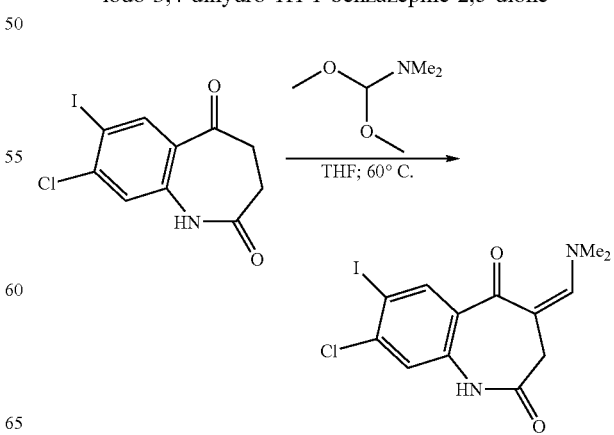

To a suspension of 8-chloro-7-iodo-3,4-dihydro-1H-1-benzazepine-2,5-dione (10.0 g, 29.8 mmol) in THF (44mL) was added DMF-DMA (21.1 mL, 149 mmol). The flask reaction mixture was allowed to stir 60° C. under an atmosphere of argon. A light orange solution containing a suspended solid resulted. After 17 h, the reaction mixture was allowed to cool to it. Ether (100 mL) was added and the solid was collected via suction filtration, washed with ether, and dried in a vacuum oven to yield (4Z)-8-chloro-4-[(dimethylamino)methylene]-7-iodo-3,4-dihydro-1H-1-benzazepine-2,5-dione (9.50g, 24.3 mmol, 82%) as a yellow solid. LCMS (FA): m/z=391 (M+H).

(4Z)-4-[(dimethylamino)methylene]-8-(trifluoromethyl)-3,4-dihydro-1H-1-benzazepine-2,5-dione

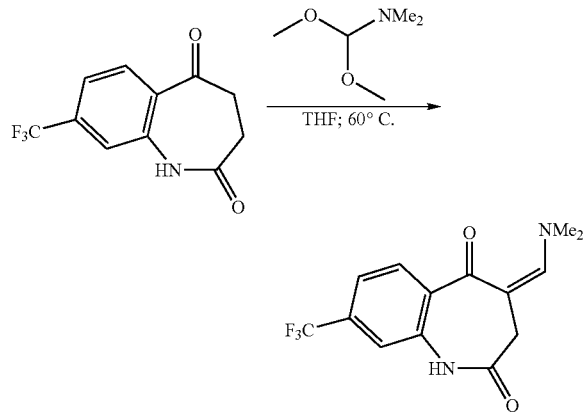

A 250 mL, round-bottom flask equipped with a magnetic stir bar and a reflux condenser was charged with 8-(trifluoromethyl)-3,4-dihydro-1H-1-benzazepine-2,5-dione [5 g, 0.02 mol] and THF (50 mL) was added to it. DMF-DMA (13.4 mL, 0.1 mol, 5 equiv) was added to the resulting suspension; the reaction was heated at 60° C. for 3 h and was judged complete by HPLC analysis. The reaction mixture was cooled to ambient temperature and the yellow solid that formed was collected by filtration. The filter cake was washed with 1:1 THF/MTBE (25 mL, 5 vol) followed by MTBE (10 mL). The solid was dried under high vacuum to obtain enamine (4Z)-4-[(dimethylamino)methylene]-8-(trifluoromethyl)-3,4-dihydro-1H-1-benzazepine-2,5-dione (5.28 g, 88% yield) as a yellow solid. $^1$H NMR (500 MHz, DMSO-$d_6$) δ ppm: 10.14 (s, 1H), 7.90 (d, 1H, J=8.0 Hz), 7.67 (s, 1H), 7.47 (d, 1H, J=8.0 Hz), 7.37 (s, 1H), 3.3 (s, 2H), 3.24 (s, 6H); ESI-MS m/z: 299 (M+H, 100%).

Compounds in the following table may be prepared from the appropriate starting materials using the procedures described above:

| |
|---|
| (4Z)-4-[(dimethylamino)methylene]-8-methoxy-3,4-dihydro-1H-1-benzazepine-2,5-dione |
| (4Z)-8-chloro-4-[(dimethylamino)methylene]-3,4-dihydro-1H-1-benzazepine-2,5-dione |
| (4Z)-4-[(dimethylamino)methylene]-2,5-dioxo-2,3,4,5-tetrahydro-1H-1-benzazepine-8-carbonitrile |
| (4Z)-4-[(dimethylamino)methylene]-8-ethyl-3,4-dihydro-1H-1-benzazepine-2,5-dione |
| (4Z)-8-cyclopropyl-4-[(dimethylamino)methylene]-3,4-dihydro-1H-1-benzazepine-2,5-dione |

Example 4

Synthesis of Compounds of Formula vi (Formula IV)

9-Chloro-2-({2-methyl-6-[(1-methylpiperidin-4-yl)amino]pyridin-3-yl}amino)-5,7-dihydro-6H-pyrimido[5,4-d][1]benzazepin-6-one

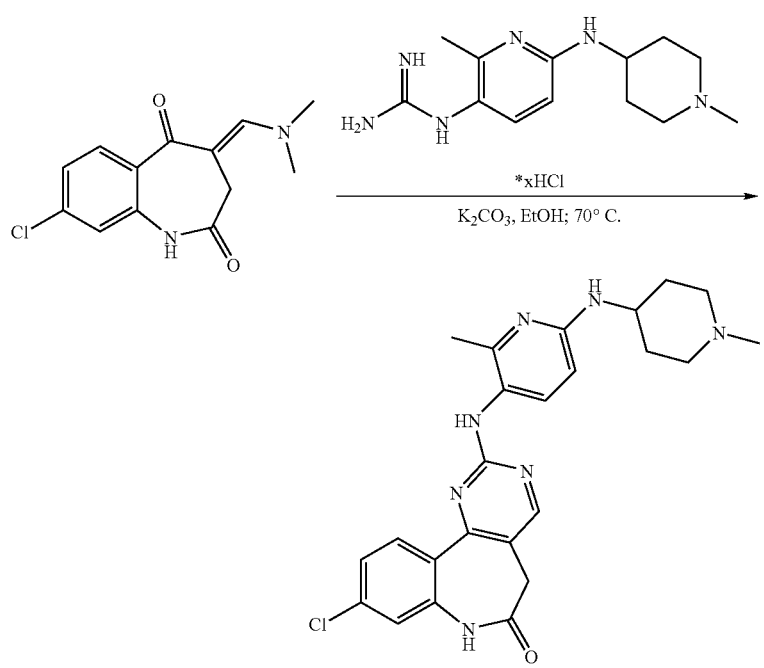

To (4E)-8-chloro-4-[(dimethylamino)methylene]-3,4-dihydro-1H-1-benzazepine-2,5-dione (3.25 g, 12.3 mmol) in EtOH (50 mL) were added N-{2-methyl-6-[(1-methylpiperidin-4-yl)amino]pyridin-3-yl}guanidine *xHCl (6.5 g, 14 mmol) and potassium carbonate (13.6 g, 98.3 mmol). The reaction mixture was allowed to stir for 2 days at 70° C. and then allowed to cool to room temperature. The solids were filtered and the filtrate was concentrated to give a thick red oil. Water was added to the residue and the aqueous solution was extracted with EtOAc. The organic solutions were combined, dried, filtered and concentrated to give 9-chloro-2-({2-methyl-6-[(1-methylpiperidin-4-yl)amino]pyridin-3-yl}amino)-5,7-dihydro-6H-pyrimido[5,4-d][1]benzazepin-6-one (5,3 g, 93%).

2-({5-[3-(dimethylamino)propyl]-2-methylpyridin-3-yl}amino)-9-(trifluoromethyl)-5,7-dihydro-6H-pyrimido[5,4-d][1]benzazepin-6-one

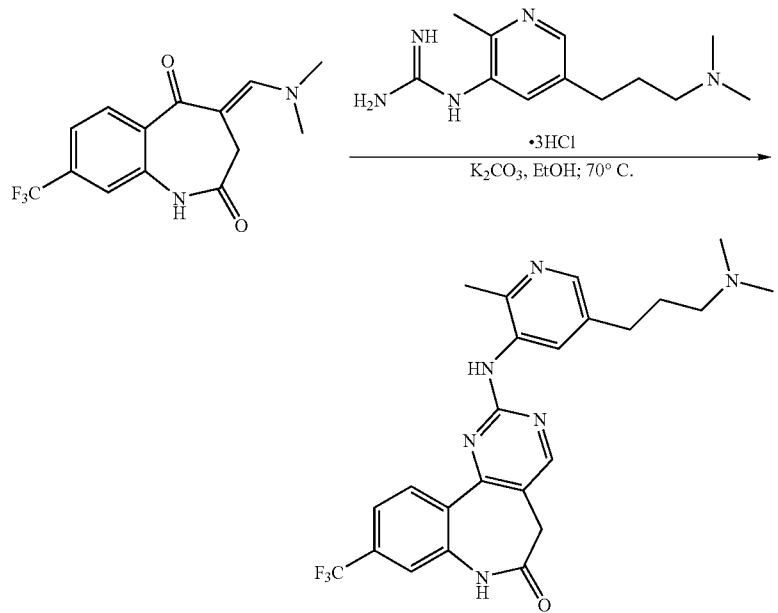

N-{5-[3-(dimethylamino)propyl]-2-methylpyridin-3-yl}guanidine.triHCl (233 g, 676 mol) was dissolved in ethanol (1.42 L) and to it was added powder potassium carbonate (359 g, 2.60 mol). The mixture was stirred at room temperature for 15 min. (4Z)-4-[(dimethylamino)methylene]-8-(trifluoromethyl)-3,4-dihydro-1H-1-benzazepine-2,5-dione (155 g, 520 mmol) was added to the reaction mixture. This mixture was slowly heated at 70° C. and held at 70° C. for 30 min. The reaction mixture was heated at 75° C. for 18 hours. HPLC indicated competition of the reaction. The reaction mixture was cooled to room temperature and filtered to remove potassium carbonate. The cake was washed with ethanol (200 mL) and the filtrate was concentrated to low volume (1.1 L). The mixture was heated at 70° C. while water (2.0 L) was slowly added. The suspension formed was stirred at 75° C. for 1 hour, then slowly cooled to room temperature. This solid was filtered and washed with 300 mL water/EtOH (2 vol/1 vol). Drying under vacuo at 40° C. overnight afforded 2-({5-[3-(dimethylamino)propyl]-2-methylpyridin-3-yl}amino)-9-(trifluoromethyl)-5,7-dihydro-6H-pyrimido[5,4-d][1]benzazepin-6-one as a light pink solid (175 g, >98% pure, 71.6% yield). LCMS (FA): $R_t$=5.72 min, m/z=469.2 (M−H).

Compounds in the following table may be prepared from the appropriate starting materials using the procedure described above:

2-{[2-methyl-5-(1,3,3-trimethylpiperidin-4-yl)pyridin-3-yl]amino}-9-(trifluoro-methyl)-5,7-dihydro-6H-pyrimido[5,4-d][1]benzazepin-6-one 2-({5-[3-(dimethylamino)propyl]-2-methylpyridin-3-yl}amino)-9-methoxy-5,7-dihydro-6H-pyrimido[5,4-d][1]benzazepin-6-one 9-chloro-2-{[2-methyl-5-(1,3,3-trimethylpiperidin-4-yl)pyridin-3-yl]amino}-5,7-dihydro-6H-pyrimido[5,4-d][1]benzazepin-6-one 9-chloro-2-({2-methyl-6-[(1-methylpiperidin-4-yl)methyl]pyridin-3-yl}amino)-5,7- dihydro-6H-pyrimido[5,4-d][1]benzazepin-6-one
9-chloro-2-({5-[3-(dimethylamino)propyl]-2-methoxypyridin-3-yl}amino)-5,7-dihydro-6H-pyrimido[5,4-d][1]benzazepin-6-one
9-chloro-2-({5-[3-(dimethylamino)propyl]-2-fluoropyridin-3-yl}amino)-5,7-dihydro-6H-pyrimido[5,4-d][1]benzazepin-6-one
9-chloro-10-[3-(dimethylamino)propyl]-2-[(2-methyl-6-morpholin-4-ylpyridin-3-yl)amino]-5,7-dihydro-6H-pyrimido[5,4-d][1]benzazepin-6-one
9-cyclopropyl-2-({2-methyl-6-[(1-methylpiperidin-4-yl)amino]pyridin-3-yl}amino)-5,7-dihydro-6H-pyrimido[5,4-d][1]benzazepin-6-one
2-({5-[3-(dimethylamino)propyl]-2-methylpyridin-3-yl}amino)-9-ethyl-5,7-dihydro-6H-pyrimido[5,4-d][1]benzazepin-6-one
2-({5-[3-(dimethylamino)propyl]-2-methylpyridin-3-yl}amino)-6-oxo-6,7-dihydro-5H-pyrimido[5,4-d][1]benzazepine-9-carbonitrile
2-({5-[3-(dimethylamino)propyl]-2-methylpyridin-3-yl}amino)-9-methyl-5,7-dihydro-6H-pyrimido[5,4-d][1]benzazepin-6-one
9-cyclopropyl-2-({5-[3-(dimethylamino)propyl]-2-methylpyridin-3-yl}amino)-5,7-dihydro-6H-pyrimido[5,4-d][1]benzazepin-6-one
2-({5-[3-(dimethylamino)propyl]pyridin-3-yl}amino)-9-(trifluoromethyl)-5,7-dihydro-6H-pyrimido[5,4-d][1]benzazepin-6-one
9-chloro-2-{[6-(dimethylamino)-2-methyl-5,6,7,8-tetrahydroquinolin-3-yl]amino}-5,7-dihydro-6H-pyrimido[5,4-d][1]benzazepin-6-one
2-({5-[2-(dimethylamino)ethyl]-2-methylpyridin-3-yl}amino)-9-(trifluoromethyl)-5,7-dihydro-6H-pyrimido[5,4-d][1]benzazepin-6-one
9-chloro-2-({5-[2-(dimethylamino)ethyl]-2-methylpyridin-3-yl}amino)-5,7-dihydro-6H-pyrimido[5,4-d][1]benzazepin-6-one
2-({2-methyl-5-[2-(4-methylpiperazin-1-yl)ethyl]pyridin-3-yl}amino)-9-(trifluoromethyl)-5,7-dihydro-6H-pyrimido[5,4-d][1]benzazepin-6-one
9-chloro-2-({2-methyl-5-[2-(4-methylpiperazin-1-yl)ethyl]pyridin-3-yl}amino)-5,7-dihydro-6H-pyrimido[5,4-d][1]benzazepin-6-one
9-chloro-2-({5-[3-(dimethylamino)propyl]-2-methylpyridin-3-yl}amino)-5,7-dihydro-6H-pyrimido[5,4-d][1]benzazepin-6-one
9-chloro-2-{[2-methyl-5-(2-piperidin-1-ylethyl)pyridin-3-yl]amino}-5,7-dihydro-6H-pyrimido[5,4-d][1]benzazepin-6-one
2-{[2-methyl-5-(2-piperidin-1-ylethyl)pyridin-3-yl]amino}-9-(trifluoromethyl)-5,7-dihydro-6H-pyrimido[5,4-d][1]benzazepin-6-one
9-chloro-2-{[2-methyl-5-(2-morpholin-4-ylethyl)pyridin-3-yl]amino}-5,7-dihydro-6H-pyrimido[5,4-d][1]benzazepin-6-one
2-{[2-methyl-5-(2-morpholin-4-ylethyl)pyridin-3-yl]amino}-9-(trifluoromethyl)-5,7-dihydro-6H-pyrimido[5,4-d][1]benzazepin-6-one
9-chloro-2-[(5-{2-[3-(dimethylamino)piperidin-1-yl]ethyl}-2-methylpyridin-3-yl)amino]-5,7-dihydro-6H-pyrimido[5,4-d][1]benzazepin-6-one
9-chloro-2-{[2-methyl-5-(2-pyrrolidin-1-ylethyl)pyridin-3-yl]amino}-5,7-dihydro-6H-pyrimido[5,4-d][1]benzazepin-6-one
9-chloro-2-({5-[4-(dimethylamino)butyl]-2-methylpyridin-3-yl}amino)-5,7-dihydro-6H-pyrimido[5,4-d][1]benzazepin-6-one
2-({5-[4-(dimethylamino)butyl]-2-methylpyridin-3-yl}amino)-9-(trifluoromethyl)-5,7-dihydro-6H-pyrimido[5,4-d][1]benzazepin-6-one
2-[(5-{2-[4-(dimethylamino)piperidin-1-yl]ethyl}-2-methylpyridin-3-yl)amino]-9-(trifluoromethyl)-5,7-dihydro-6H-pyrimido[5,4-d][1]benzazepin-6-one
9-chloro-2-[(5-{2-[4-(dimethylamino)piperidin-1-yl]ethyl}-2-methylpyridin-3-yl)amino]-5,7-dihydro-6H-pyrimido[5,4-d][1]benzazepin-6-one
9-chloro-2-[(5-{2-[(2R,6R)-2,6-dimethylmorpholin-4-yl]ethyl}-2-methylpyridin-3-yl)amino]-5,7-dihydro-6H-pyrimido[5,4-d][1]benzazepin-6-one
9-chloro-2-[(5-{2-[(2R,6S)-2,6-dimethylmorpholin-4-yl]ethyl}-2-methylpyridin-3-yl)amino]-5,7-dihydro-6H-pyrimido[5,4-d][1]benzazepin-6-one
9-chloro-2-[(5-{2-[3-(dimethylamino)pyrrolidin-1-yl]ethyl}-2-methylpyridin-3-yl)amino]-5,7-dihydro-6H-pyrimido[5,4-d][1]benzazepin-6-one
2-({6-[4-(dimethylamino)piperidin-1-yl]-2-methylpyridin-3-yl}amino)-9-(trifluoromethyl)-5,7-dihydro-6H-pyrimido[5,4-d][1]benzazepin-6-one
9-chloro-2-({5-[3-(dimethylamino)propyl]-6-methylpyridin-3-yl}amino)-5,7-dihydro-6H-pyrimido[5,4-d][1]benzazepin-6-one
9-chloro-2-[(6-{[3-(dimethylamino)propyl]amino}-2-methylpyridin-3-yl)amino]-5,7-dihydro-6H-pyrimido[5,4-d][1]benzazepin-6-one
2-{[6-(isopropylamino)-2-methylpyridin-3-yl]amino}-9-(trifluoromethyl)-5,7-dihydro-6H-pyrimido[5,4-d][1]benzazepin-6-one
2-{[2-methyl-6-(tetrahydro-2H-pyran-4-ylamino)pyridin-3-yl]amino}-9-(trifluoromethyl)-5,7-dihydro-6H-pyrimido[5,4-d][1]benzazepin-6-one
9-chloro-2-({2-methyl-6-[methyl(1-methylpiperidin-4-yl)amino]pyridin-3-yl}amino)-5,7-dihydro-6H-pyrimido[5,4-d][1]benzazepin-6-one
9-chloro-2-[(6-{[2-(dimethylamino)ethyl]amino}-2-methylpyridin-3-yl)amino]-5,7-dihydro-6H-pyrimido[5,4-d][1]benzazepin-6-one
2-[(6-{[2-(dimethylamino)ethyl]amino}-2-methylpyridin-3-yl)amino]-9-(trifluoromethyl)-5,7-dihydro-6H-pyrimido[5,4-d][1]benzazepin-6-one
2-({6-[[2-(dimethylamino)ethyl](methyl)amino]-2-methylpyridin-3-yl}amino)-9-(trifluoromethyl)-5,7-dihydro-6H-pyrimido[5,4-d][1]benzazepin-6-one
9-chloro-2-({6-[[2-(dimethylamino)ethyl](methyl)amino]-2-methylpyridin-3-yl}amino)-5,7-dihydro-6H-pyrimido[5,4-d][1]benzazepin-6-one
9-chloro-2-({6-[[3-(dimethylamino)propyl](methyl)amino]-2-methylpyridin-3-yl}amino)-5,7-dihydro-6H-pyrimido[5,4-d][1]benzazepin-6-one
2-({6-[[3-(dimethylamino)propyl](methyl)amino]-2-methylpyridin-3-yl}amino)-9-

-continued (trifluoromethyl)-5,7-dihydro-6H-pyrimido[5,4-d][1]benzazepin-6-one
2-({2-methyl-6-[methyl(1-methylpiperidin-4-yl)amino]pyridin-3-yl}amino)-9-(trifluoromethyl)-5,7-dihydro-6H-pyrimido[5,4-d][1]benzazepin-6-one
2-({2-methyl-6-[(1-methylpiperidin-4-yl)amino]pyridin-3-yl}amino)-9-(trifluoromethyl)-5,7-dihydro-6H-pyrimido[5,4-d][1]benzazepin-6-one
9-chloro-2-{[2-methyl-6-(tetrahydro-2H-pyran-4-ylamino)pyridin-3-yl]amino}-5,7-dihydro-6H-pyrimido[5,4-d][1]benzazepin-6-one
9-chloro-2-({6-[3-(dimethylamino)piperidin-1-yl]-2-methylpyridin-3-yl}amino)-5,7-dihydro-6H-pyrimido[5,4-d][1]benzazepin-6-one
2-({6-[3-(dimethylamino)piperidin-1-yl]-2-methylpyridin-3-yl}amino)-9-(trifluoromethyl)-5,7-dihydro-6H-pyrimido[5,4-d][1]benzazepin-6-one
2-({6-[3-(dimethylamino)propyl]-2-methylpyridin-3-yl}amino)-9-(trifluoromethyl)-5,7-dihydro-6H-pyrimido[5,4-d][1]benzazepin-6-one
9-chloro-2-({6-[3-(dimethylamino)propyl]-2-methylpyridin-3-yl}amino)-5,7-dihydro-6H-pyrimido[5,4-d][1]benzazepin-6-one
2-({2-methyl-6-[(1-methylpiperidin-4-yl)oxy]pyridin-3-yl}amino)-9-(trifluoromethyl)-5,7-dihydro-6H-pyrimido[5,4-d][1]benzazepin-6-one
2-[(2,4-dimethylpyridin-3-yl)amino]-9-(trifluoromethyl)-5,7-dihydro-6H-pyrimido[5,4-d][1]benzazepin-6-one
9-chloro-2-[(2,4-dimethylpyridin-3-yl)amino]-5,7-dihydro-6H-pyrimido[5,4-d][1]benzazepin-6-one
9-chloro-2-[(2,6-dimethylpyridin-3-yl)amino]-5,7-dihydro-6H-pyrimido[5,4-d][1]benzazepin-6-one
2-[(2,6-dimethylpyridin-3-yl)amino]-9-(trifluoromethyl)-5,7-dihydro-6H-pyrimido[5,4-d][1]benzazepin-6-one
2-[(2-methyl-6-morpholin-4-ylpyridin-3-yl)amino]-9-(trifluoromethyl)-5,7-dihydro-6H-pyrimido[5,4-d][1]benzazepin-6-one
9-chloro-2-[(2-methyl-6-morpholin-4-ylpyridin-3-yl)amino]-5,7-dihydro-6H-pyrimido[5,4-d][1]benzazepin-6-one
9-chloro-2-[(2-methyl-6-piperidin-1-ylpyridin-3-yl)amino]-5,7-dihydro-6H-pyrimido[5,4-d][1]benzazepin-6-one
9-chloro-2-[(2-methyl-6-piperidin-1-ylpyridin-3-yl)amino]-5,7-dihydro-6H-pyrimido[5,4-d][1]benzazepin-6-one
2-[(2-methyl-6-pyrrolidin-1-ylpyridin-3-yl)amino]-9-(trifluoromethyl)-5,7-dihydro-6H-pyrimido[5,4-d][1]benzazepin-6-one
9-chloro-2-{[2-methyl-6-(4-methylpiperazin-1-yl)pyridin-3-yl]amino}-5,7-dihydro-6H-pyrimido[5,4-d][1]benzazepin-6-one
9-chloro-2-({2-methyl-6-[(1-methylpiperidin-4-yl)oxy]pyridin-3-yl}amino)-5,7-dihydro-6H-pyrimido[5,4-d][1]benzazepin-6-one
2-[(6-{[3-(dimethylamino)propyl]amino}-2-methylpyridin-3-yl)amino]-9-(trifluoromethyl)-5,7-dihydro-6H-pyrimido[5,4-d][1]benzazepin-6-one
9-chloro-2-{[2-methyl-6-(piperidin-4-ylamino)pyridin-3-yl]amino}-5,7-dihydro-6H-pyrimido[5,4-d][1]benzazepin-6-one
9-chloro-2-({6-[4-(dimethylamino)piperidin-1-yl]-2-methylpyridin-3-yl}amino)-5,7-dihydro-6H-pyrimido[5,4-d][1]benzazepin-6-one
2-({2-methyl-6-[methyl(1-methylpyrrolidin-3-yl)amino]pyridin-3-yl}amino)-9-(trifluoromethyl)-5,7-dihydro-6H-pyrimido[5,4-d][1]benzazepin-6-one
9-chloro-2-({2-methyl-6-[methyl(1-methylpyrrolidin-3-yl)amino]pyridin-3-yl}amino)-5,7-dihydro-6H-pyrimido[5,4-d][1]benzazepin-6-one
9-chloro-2-{[2-methyl-5-(1-methylpiperidin-4-yl)pyridin-3-yl]amino}-5,7-dihydro-6H-pyrimido[5,4-d][1]benzazepin-6-one
9-chloro-2-{[5-(1-ethylpiperidin-4-yl)-2-methylpyridin-3-yl]amino}-5,7-dihydro-6H-pyrimido[5,4-d][1]benzazepin-6-one
9-chloro-2-({5-[1-(2-fluoroethyl)piperidin-4-yl]-2-methylpyridin-3-yl}amino)-5,7-dihydro-6H-pyrimido[5,4-d][1]benzazepin-6-one
9-chloro-2-({5-[3-(dimethylamino)propyl]-2-ethylpyridin-3-yl}amino)-5,7-dihydro-6H-pyrimido[5,4-d][1]benzazepin-6-one
2-({2-methyl-5-[3-(methylamino)propyl]pyridin-3-yl}amino)-9-(trifluoromethyl)-5,7-dihydro-6H-pyrimido[5,4-d][1]benzazepin-6-one
2-{[2-methyl-6-(piperidin-4-ylamino)pyridin-3-yl]amino}-9-(trifluoromethyl)-5,7-dihydro-6H-pyrimido[5,4-d][1]benzazepin-6-one
6-methyl-N-(2-morpholin-4-ylethyl)-5-{[6-oxo-9-(trifluoromethyl)-6,7-dihydro-5H-pyrimido[5,4-d][1]benzazepin-2-yl]amino}pyridine-2-carboxamide
9-chloro-2-[(2-methyl-6-{[(1-methylpiperidin-4-yl)methyl]amino}pyridin-3-yl)amino]-5,7-dihydro-6H-pyrimido[5,4-d][1]benzazepin-6-one
2-[(2-methyl-6-{[(1-methylpiperidin-4-yl)methyl]amino}pyridin-3-yl)amino]-9-(trifluoromethyl)-5,7-dihydro-6H-pyrimido[5,4-d][1]benzazepin-6-one
2-({4-methyl-6-[(1-methylpiperidin-4-yl)amino]pyridin-3-yl}amino)-9-(trifluoromethyl)-5,7-dihydro-6H-pyrimido[5,4-d][1]benzazepin-6-one
2-[(2,6-dimethyl-5,6,7,8-tetrahydro-1,6-naphthyridin-3-yl)amino]-9-(trifluoromethyl)-5,7-dihydro-6H-pyrimido[5,4-d][1]benzazepin-6-one
2-{[5-(3-hydroxypropyl)-2-methylpyridin-3-yl]amino}-9-(trifluoromethyl)-5,7-dihydro-6H-pyrimido[5,4-d][1]benzazepin-6-one
2-{[2-methyl-5-(4-methylpiperazin-1-yl)pyridin-3-yl]amino}-9-(trifluoromethyl)-5,7-dihydro-6H-pyrimido[5,4-d][1]benzazepin-6-one
9-chloro-2-{[2-methyl-5-(4-methylpiperazin-1-yl)pyridin-3-yl]amino}-5,7-dihydro-6H-pyrimido[5,4-d][1]benzazepin-6-one
9-chloro-2-({5-[(3S)-4-ethyl-3-methylpiperazin-1-yl]-2-methylpyridin-3-yl}amino)-5,7-dihydro-6H-pyrimido[5,4-d][1]benzazepin-6-one
9-chloro-2-({5-[(3R,5S)-4-ethyl-3,5-dimethylpiperazin-1-yl]-2-methylpyridin-3- yl}amino)-5,7-dihydro-6H-pyrimido[5,4-d][1]benzazepin-6-one
2-({5-[(3S)-4-ethyl-3-methylpiperazin-1-yl]-2-methylpyridin-3-yl}amino)-9-(trifluoromethyl)-5,7-dihydro-6H-pyrimido[5,4-d][1]benzazepin-6-one
9-chloro-2-({5-[3-(dimethylamino)propyl]pyridin-3-yl}amino)-5,7-dihydro-6H-pyrimido[5,4-d][1]benzazepin-6-one 9-Chloro-2-({5-[3-(dimethylamino)propyl]-6-methoxypyridin-3-yl}amino)-5,7-dihydro-6H-pyrimido[5,4-d][1]benzazepin-6-one

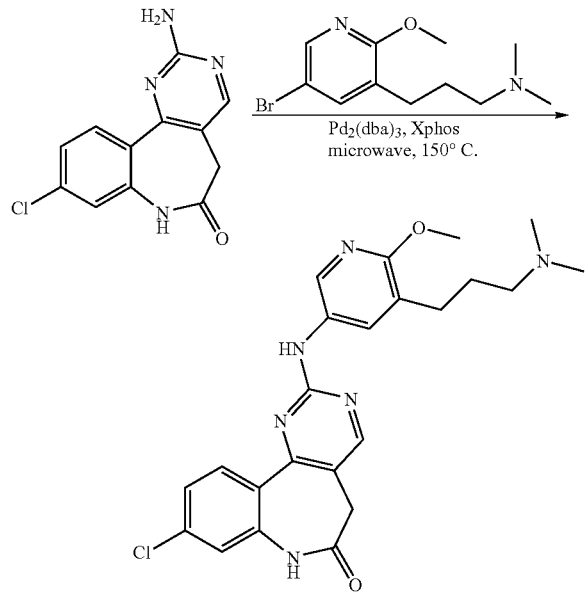

A mixture of 2-amino-9-chloro-5,7-dihydro-6H-pyrimido[5,4-d][1]benzazepin-6-one (0.36 g, 1.38 mmol), 3-(5-bromo-2-methoxypyridin-3-yl)-N,N-dimethylpropan-1-amine (0.38 g, 1.38 mmol), xphos (0.047 g, 0.099 mmol), and tris(dibenzyllideneacetone)dipalladium(0) (0.023 g, 0.026 mmol) in a sealed microwave tube was evacuated and purged with nitrogen three times. To the solids were added tert-butyl alcohol (3.6 mL) and t-BuOK (1M in t-BuOH, 2.63 mL) via syringe. The mixture was stirred well and then subjected to microwave irradiation (150 watts) while heating at 150° C. for 45 min. The reaction mixture was then poured into water (25 mL) with vigorous stirring. The precipitate that formed was filtered, washed with water, and air dried. The residue was purified by column chromatography to give 9-chloro-2-({5-[3-(dimethylamino)propyl]-6-methoxypyridin-3-yl}amino)-5,7-dihydro-6H-pyrimido[5,4-d][1]benzazepin-6-one (0.125 g, 18%).

Compounds in the following table were prepared from the appropriate starting materials using the procedures described above:

2-{[6-(4-methylpiperazin-1-yl)pyridin-3-yl]amino}-9-(trifluoromethyl)-5,7-dihydro-6H-pyrimido[5,4-d][1]benzazepin-6-one
9-chloro-2-[(6-morpholin-4-ylpyridin-3-yl)amino]-5,7-dihydro-6H-pyrimido[5,4-d][1]benzazepin-6-one
9-chloro-2-{[6-(4-methylpiperazin-1-yl)pyridin-3-yl]amino}-5,7-dihydro-6H-pyrimido[5,4-d][1]benzazepin-6-one
9-chloro-2-({6-[[3-(dimethylamino)propyl](methyl)amino]pyridin-3-yl}amino)-5,7-dihydro-6H-pyrimido[5,4-d][1]benzazepin-6-one
N-{5-[(9-chloro-6-oxo-6,7-dihydro-5H-pyrimido[5,4-d][1]benzazepin-2-yl)amino]pyridin-2-yl}-2,2-dimethylpropanamide
9-chloro-2-[(6-pyrrolidin-1-ylpyridin-3-yl)amino]-5,7-dihydro-6H-pyrimido[5,4-d][1]benzazepin-6-one
9-chloro-2-{[5-[2-(dimethylamino)ethyl]-2-(trifluoromethyl)pyridin-3-yl]amino}-5,7-dihydro-6H-pyrimido[5,4-d][1]benzazepin-6-one
9-chloro-2-({5-[2-(cyclopentylamino)ethyl]-2-methylpyridin-3-yl}amino)-5,7-dihydro-6H-pyrimido[5,4-d][1]benzazepin-6-one
2-({5-[2-(dimethylamino)ethyl]pyridin-3-yl}amino)-9-(trifluoromethyl)-5,7-dihydro-6H-pyrimido[5,4-d][1]benzazepin-6-one
9-chloro-2-({5-[2-(dimethylamino)ethyl]pyridin-3-yl}amino)-5,7-dihydro-6H-pyrimido[5,4-d][1]benzazepin-6-one
9-chloro-2-{[5-(2-morpholin-4-ylethyl)pyridin-3-yl]amino}-5,7-dihydro-6H-pyrimido[5,4-d][1]benzazepin-6-one
9-chloro-2-({5-[2-(4-methylpiperazin-1-yl)ethyl]pyridin-3-yl}amino)-5,7-dihydro-6H-pyrimido[5,4-d][1]benzazepin-6-one
9-chloro-2-{[5-(4-methylpiperazin-1-yl)pyridin-3-yl]amino}-5,7-dihydro-6H-pyrimido[5,4-d][1]benzazepin-6-one
9-chloro-2-({5-[(3R)-4-ethyl-3-methylpiperazin-1-yl]pyridin-3-yl}amino)-5,7-dihydro-6H-pyrimido[5,4-d][1]benzazepin-6-one
9-chloro-2-({5-[(3S)-4-ethyl-3-methylpiperazin-1-yl]pyridin-3-yl}amino)-5,7-dihydro-6H-pyrimido[5,4-d][1]benzazepin-6-one

9-Chloro-10-[3-(dimethylamino)propyl]-2-[(2-methylpyridin-3-yl)amino]-5,7-dihydro-6H-pyrimido[5,4-d][1]benzazepin-6-one

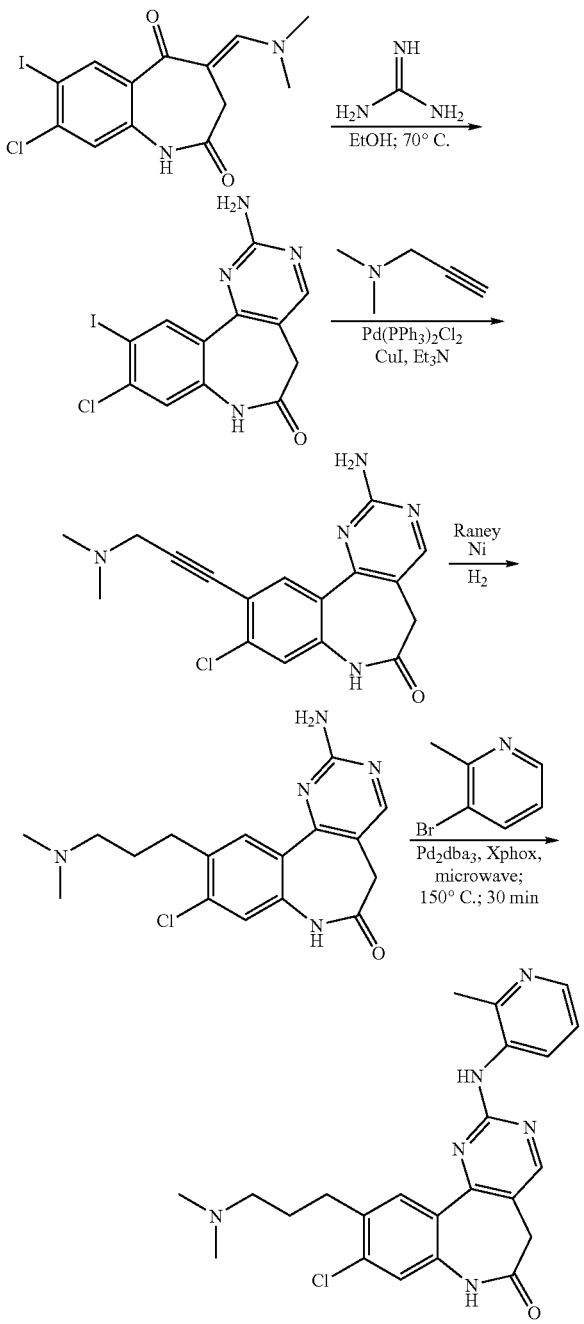

Step 1: 2-Amino-9-chloro-10-iodo-5,7-dihydro-6H-pyrimido[5,4-d][1]benzazepin-6-one A suspension of (4Z)-8-chloro-4-[(dimethylamino)methylene]-7-iodo-3,4-dihydro-1H-1-benzazepine-2,5-dione (9.50 g, 24.3 mmol), guanidine hydrochloride (2.56 g, 26.8 mmol), and potassium carbonate (11.1 g, 80.3 mmol) in EtOH (143) was allowed to stir while heating at 70° C. in a sealed reaction vessel. After 19 h, the reaction mixture was allowed to cool to room temperature then added to water (200 mL) and allowed to stir for 1 h. The resulting tan solid was collected via suction filtration, washed with water, and dried in a vacuum oven to give 2-amino-9-chloro-10-iodo-5,7-dihydro-6H-pyrimido[5,4-d][1]benzazepin-6-one (7.69 g, 82%). LCMS (FA): m/z=387 (M+H).

Step 2: 2-Amino-9-chloro-10-[3-(dimethylamino)prop-1-yn-1-yl]-5,7-dihydro-6H-pyrimido[5,4-d][1]benzazepin-6-one A solution of 2-amino-9-chloro-10-iodo-5,7-dihydro-6H-pyrimido[5,4-d][1]benzazepin-6-one (1.66 g, 4.29 mmol) and propargyl(dimethylamine) (0.74 mL, 6.89 mmol) in triethylamine (7 mL) and DMF (7 mL) was degassed with argon. To this solution was added bis(triphenylphosphine)palladium(II)chloride (0.30 g, 0.43 mmol) and copper iodide (0.163 g, 0.86 mmol). The reaction mixture was allowed to stir at 75° C. overnight. After the reaction mixture was allowed to cool to rt, water was added. The precipitate that formed was filtered and dried to give 2-amino-9-chloro-10-[3-(dimethylamino)prop-1-yn-1-yl]-5,7-dihydro-6H-pyrimido[5,4-d][1]benzazepin-6-one (1.61 g, 98%) as a brown solid. LCMS (FA): m/z=342 (M+H).

Step 3: 2-Amino-9-chloro-10-[3-(dimethylamino)propyl]-5,7-dihydro-6H-pyrimido[5,4-d][1]benzazepin-6-one A slurry of Raney Ni (3.0 mL) in water was added to 2-amino-9-chloro-10-[3-(dimethylamino)prop-1-yn-1-yl]-5,7-dihydro-6H-pyrimido[5,4-d][1]benzazepin-6-one (0.30 g, 0.88 mmol) in THF (6 mL). The reaction mixture was allowed to stir under an atmosphere of H$_2$ at rt overnight. The reaction mixture was filtered over Celite and the filter cake was washed with THF. The filtrate was concentrated and the resulting solid was triturated with MeOH, diethyl ether, and hexanes. The solid was collected via suction filtration to give 2-amino-9-chloro-10-[3-(dimethylamino)propyl]-5,7-dihydro-6H-pyrimido[5,4-d][1]benzazepin-6-one (0.158 g, 52%) as a light yellow solid. LCMS (FA): m/z=346 (M+H).

Step 4: 9-Chloro-10-[3-(dimethylamino)propyl]-2-[(2-methylpyridin-3-yl)amino]-5,7-dihydro-6H-pyrimido[5,4-d][1]benzazepin-6-one To a mixture of 2-amino-9-chloro-10-[3-(dimethylamino)propyl]-5,7-dihydro-6H-pyrimido[5,4-d][1]benzazepin-6-one (0.10 g, 0.29 mmol), Xphos (8.6 mg, 0.018 mmol), tris(dibenzylideneacetone)dipalladium (4.7 mg, 0.0052 mmol) and 3-bromo-2-methylpyridine (50 mg, 0.29 mmol) in a dry, sealed microwave tube under an atmosphere of argon was added tert-butyl alcohol (1.0 mL) followed by a 1.0 M solution of potassium tert-butoxide in tert-butyl alcohol (0.58 mL, 0.58 mmol). The mixture was heated under microwave irradiation at 150° C. for 30 min. The reaction mixture was allowed to cool to rt and then added to water (50 mL). The precipitated solid was collected via suction filtration, washed with water, and dried to produce 9-chloro-10-[3-(dimethylamino)propyl]-2-[(2-methylpyridin-3-ylamino]-5,7-dihydro-6H-pyrimido[5,4-d][1]benzazepin-6-one (95 mg, 0.21 mmol, 75%) as a brown solid. LCMS (FA): m/z=453.5 (M+H).

Compounds in the following table were prepared from the appropriate starting materials using the procedures described above:

9-chloro-10-[3-(dimethylamino)propyl]-2-(pyridin-3-ylamino)-5,7-dihydro-6H-pyrimido[5,4-d][1]benzazepin-6-one
9-chloro-2-({5-[3-(dimethylamino)propyl]-2,6-dimethylpyridin-3-yl}amino)-5,7-dihydro-6H-pyrimido[5,4-d][1]benzazepin-6-one 2-{[5-(3-Aminopropyl)-2-methylpyridin-3-yl]amino}-9-(trifluoromethyl)-5,7-dihydro-6H-pyrimido[5,4-d][1]benzazepin-6-one

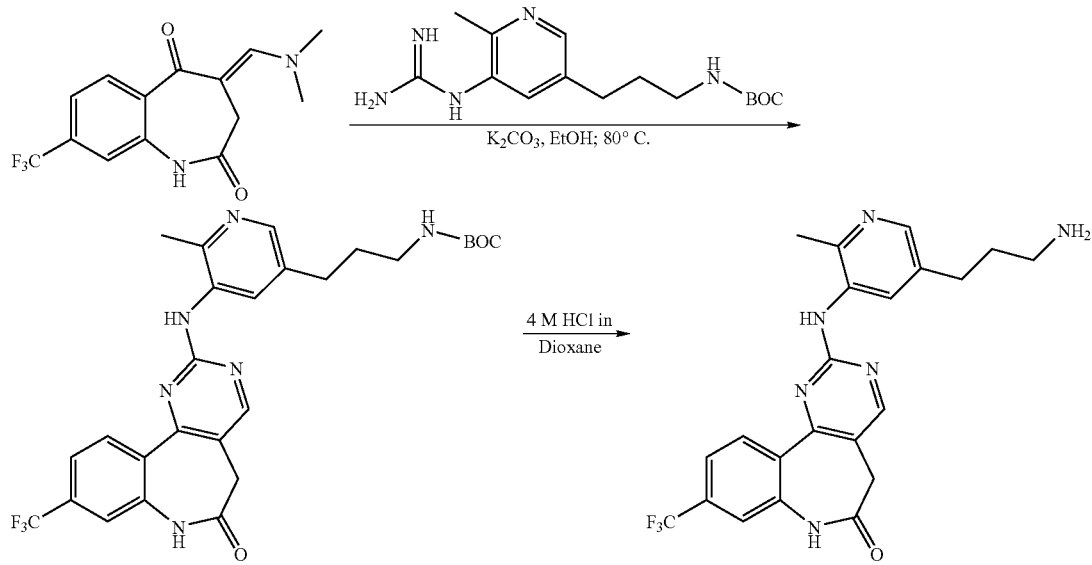

Step 1: tert-Butyl[3-(6-methyl-5-{[6-oxo-9-(trifluoromethyl)-6,7-dihydro-5H-pyrimido[5,4-d][1]benzazepin-2-yl]amino}pyridin-3-yl)propyl]carbamate To a solution of (4Z)-4-[(dimethylamino)methylene]-8-(trifluoromethyl)-3,4-dihydro-1H-1-benzazepine-2,5-dione (1.05 g, 3.51 mmol) and tert-butyl[3-(5-{[amino(imino)methyl]amino}-6-methylpyridin-3-yl)propyl]carbamate (1.62 g, 5.27 mmol) in EtOH (50 mL) was added potassium carbonate (2.91 g, 21.1 mmol). The reaction mixture was allowed to stir at 80° C. overnight. The reaction mixture was diluted with water (100 mL) and EtOAc (50 mL). The organic solution was separated and the aqueous solution was extracted with EtOAc (2×50 mL). The organic solutions were combined, washed with brine (100 mL), dried over MgSO$_4$, filtered and concentrated to give tert-butyl[3-(6-methyl-5-{[6-oxo-9-(trifluoromethyl)-6,7-dihydro-5H-pyrimido[5,4-d][1]benzazepin-2-yl]amino}pyridin-3-yl)propyl]carbamate (2.13 g, >99%) as a dark brown solid. LCMS (FA): R$_t$=1.79 min, m/z=543.0 (M+H).

Step 2: 2-{[5-(3-Aminopropyl)-2-methylpyridin-3-yl]amino}-9-(trifluoromethyl)-5,7-dihydro-6H-pyrimido[5,4-d][1]benzazepin-6-one To a 4M solution of HCl in dioxane (20 mL) was added tert-butyl[3-(6-methyl-5-{[6-oxo-9-(trifluoromethyl)-6,7-dihydro-5H-pyrimido[5,4-d][1]benzazepin-2-yl]amino}pyridin-3-yl)propyl]carbamate (1.10 g, 2.04 mmol). The reaction mixture was allowed to stir at rt overnight and then concentrated to give 2-{[5-(3-aminopropyl)-2-methylpyridin-3-yl]amino}-9-(trifluoromethyl)-5,7-dihydro-6H-pyrimido[5,4-d][1]benzazepin-6-one (1.35 g, 2.30 mmol, >99%) as a brown solid. LCMS (FA): R$_t$=0.55 min, m/z=443.0 (M+H).

2-[(6-Aminopyridin-3-yl)amino]-9-chloro-5,7-dihydro-6H-pyrimido[5,4-d][1]benzazepin-6-one

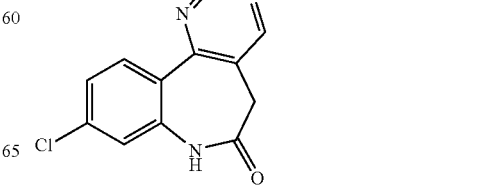

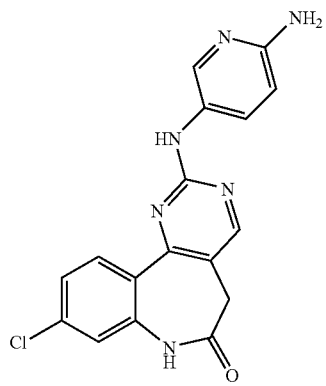

To a solution of N-{5-[(9-chloro-6-oxo-6,7-dihydro-5H-pyrimido[5,4-d][1]benzazepin-2-yl)amino]pyridin-2-yl}-2,2-dimethylpropanamide (0.220 g, 0.38 mmol) in THF (3 mL) and MeOH (4 mL) at rt was added 6M HCl in water (5 mL). The solution was allowed to stir at 100° C. for 22 h. The organic solvents were allowed to boil off and the aqueous mixture was allowed to cool to rt. Solid K₂CO₃ was added and the mixture was filtered. The resulting solid was collected and purified by column chromatography to give 2-[(6-aminopyridin-3-yl)amino]-9-chloro-5,7-dihydro-6H-pyrimido[5,4-d][1]benzazepin-6-one (0.095 g, 71%).

2-{[5-[3-(Dimethylamino)propyl]-2-(trifluoromethyl)pyridin-3-yl]amino}-9-(trifluoromethyl)-5,7-dihydro-6H-pyrimido[5,4-d][1]benzazepin-6-one

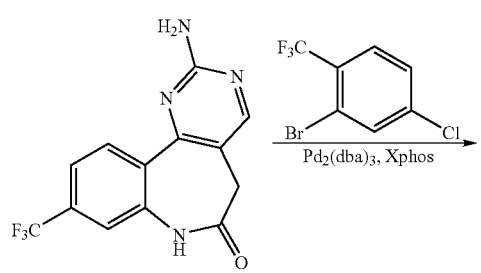

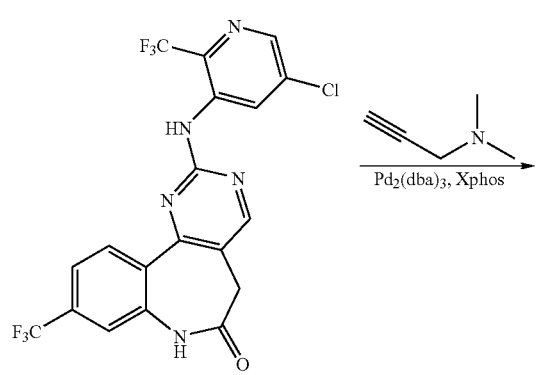

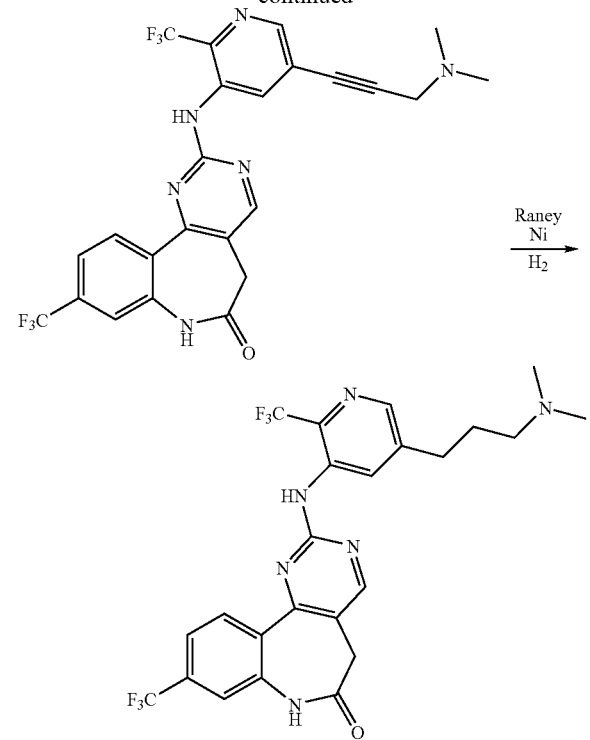

Step 1: 2-{[5-Chloro-2-(trifluoromethyl)pyridin-3-yl]amino)-9-(trifluoromethyl)-5,7-dihydro-6H-pyrimido[5,4-d][1]benzazepin-6-one A mixture of 2-amino-9-(trifluoromethyl)-5,7-dihydro-6H-pyrimido[5,4-d][1]benzazepin-6-one (0.42 g, 1.44 mmol), 3-bromo-5-chloro-2-(trifluoromethyl)pyridine (0.37 g, 1.44 mmol), Xphos (0.054 g, 0.115 mmol), and tris(dibenzylideneacetone)dipalladium(0) (0.052 g, 0.057 mmol) in a sealed microwave tube was evacuated and purged with argon 3 times. To the vial were added tert-butyl alcohol (5.3 mL) and 1.00 M of t-BuOK in tert-butyl alcohol (2.0 mL, 2.0 mol) via syringe. The mixture was allowed to stir to mix well, then was subjected to microwave irradiation at 150° C. for 1200 sec. The mixture was allowed to cool to rt and THF (6 mL) was added. The mixture was filtered and the solid was washed with THF. The organic solutions were combined and concentrated. The residue was purified by column chromatography to give 2-{[5-chloro-2-(trifluoromethyl)pyridin-3-yl]amino}-9-(trifluoromethyl)-5,7-dihydro-6H-pyrimido[5,4-d][1]benzazepin-6-one (0.081g, 12%) as a solid.

Step 2: 2-{[5-[3-(Dimethylamino)prop-1-yn-1-yl]-2-(trifluoromethyl)pyridin-3-yl]amino}-9-(trifluoromethyl)-5,7-dihydro-6H-pyrimido[5,4-d][1]benzazepin-6-one A mixture of 2-{[5-chloro-2-(trifluoromethyl)pyridin-3-yl]amino}-9-(trifluoromethyl)-5,7-dihydro-6H-pyrimido[5,4-d][1]benzazepin-6-one (0.058 g, 0.12 mmol), propargyl (dimethylamine) (0.016 mL, 0.15 mmol) and cesium carbonate (0.080 g, 0.25 mmol) in DMF (0.60 ml) was degassed for 15 min with argon. To the suspension were added bis(acetonitrile)palladium(II)chloride (0,0020 g, 0.0061 mmol) and Xphos (0.0076 g, 0.016 mmol). The suspension was purged three times with nitrogen and was then allowed to stir at 150° C. for 48 h. The mixture was filtered through celite and the filtrate was concentrated. The residue was purified by column chromatography to give 2-{[5-[3-(dimethylamino)prop-1-yn-1-yl]-2-(trifluoromethyl)pyridin-3-yl]amino}-9-(trifluoromethyl)-5,7-dihydro-6H-pyrimido[5,4-d][1]benzazepin-6-one (0.042g, 66%) as a solid.

Step 3: 2-{[5-[3-(Dimethylamino)propyl]-2-(trifluoromethyl)pyridin-3-yl]amino}-9-(trifluoromethyl)-5,7-dihydro-6H-pyrimido[5,4-d][1]benzazepin-6-one To a round bottom flask were added 2-{[5-[3-(dimethylamino)prop-1-yn-1-yl]-2-(trifluoromethyl)pyridin-3-yl]amino}-9-(trifluoromethyl)-5,7-dihydro-6H-pyrimido[5,4-d][1]benzazepin-6-one (0.042 g, 0.081 mmol), EtOH (5 mL), THF (1 mL), and Raney nickel (20 mg). The resulting mixture was allowed to stir under a hydrogen balloon overnight. The mixture was filtered through celite and the filtrate was concentrated. The residue was purified by column chromatography to give 2-{[5-[3-(dimethylamino)propyl]-2-(trifluoromethyl)pyridin-3-yl]amino}-9-(trifluoromethyl)-5,7-dihydro-6H-pyrimido[5,4-d][1]benzazepin-6-one (0.033g, 78%) as a solid.

Example 5

Separation of enantiomers of 10-{[6-(dimethylamino)-2-methyl-5,6,7,8-tetrahydroquinolin-3-yl]amino}-3-(trifluoromethyl)-5,7-dihydro-6H-dibenzo[b,d]azepin-6-one

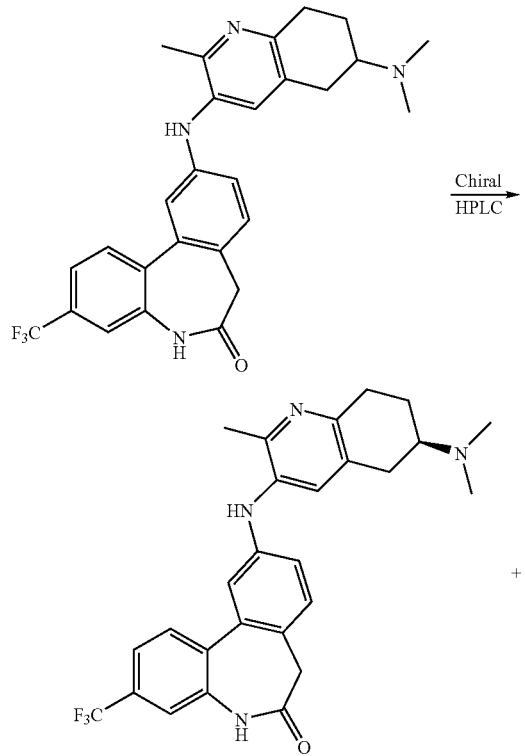

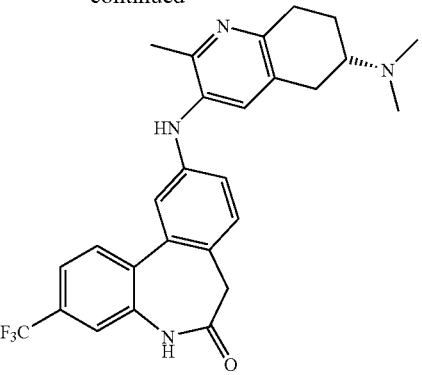

The enantiomers of 10-{[6-(dimethylamino)-2-methyl-5,6,7,8-tetrahydroquinolin-3-yl]amino}-3-(trifluoromethyl)-5,7-dihydro-6H-dibenzo[b,d]azepin-6-one were separated on a Vision HPLC fitted with a Chiralpak IC (20×250 mm) column using a isocratic solvent system of 80% hexane:10% iso-propyl alcohol:10% ethanol:0.1% diethylamine at a flow rate of 20 mL/min.

Example 6

Synthesis of Compounds of Formula I 2-({5-[3-(Dimethylamino)propyl]-2-methylpyridin-3-yl}amino)-9-(trifluoromethyl)-5,7-dihydro-6H-pyrimido[5,4-d][1]benzazepine-6-thione (I-111)

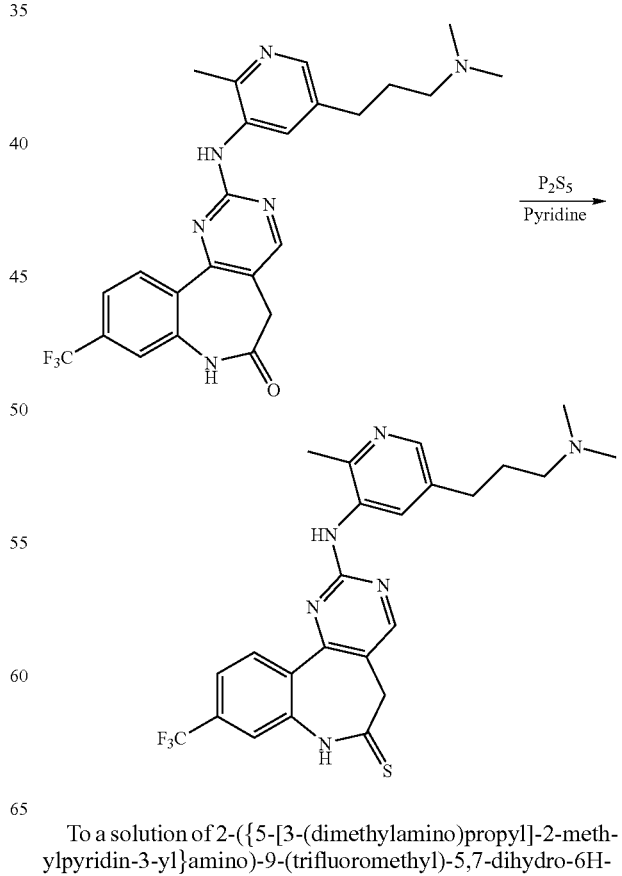

To a solution of 2-({5-[3-(dimethylamino)propyl]-2-methylpyridin-3-yl}amino)-9-(trifluoromethyl)-5,7-dihydro-6H- pyrimido[5,4-d][1]benzazepin-6-one (545 mg, 1.16 mmol) in pyridine (10 mL) was added phosphorus pentasulfide (810 mg, 3.6 mmol). The resulting suspension was allowed to stir at 60-65° C. for 18 h. The suspension was cooled to 10-15° C. and 2 mL of water were added. The mixture was then allowed to stir at rt for 5-10 min, during which time the solids dissolved. The solution was added slowly to 1M aq. NaHCO$_3$ (80 ml) with stirring, The resulting mixture was allowed to stir for 2 h and was then extracted with EtOAc (3×60 mL). The organic solutions were combined, washed with brine (50mL), dried over Na$_2$SO$_4$, filtered and concentrated. The residue was purified by HPLC to give 2-({5-[3-(dimethylamino)propyl]-2-methylpyridin-3-yl}amino)-9-(trifluoromethyl)-5,7-dihydro-6H-pyrimido[5,4-d][1]benzazepine-6-thione as the formate salt (378 mg, 61%) LCMS (FAP1): R$_t$=8.3 min., m/z=487.3 (M+H).

The formate salt of 2-({5-[3-(dimethylamino)propyl]-2-methylpyridin-3-yl}amino)-9-(trifluoromethyl)-5,7-dihydro-6H-pyrimido[5,4-d][1]benzazepine-6-thione (1.63g, 3.06 mmol) was dissolved in water (50 ml) and the resulting solution was added to a mixture of sat. NaHCO$_3$ (30 ml), 1M Na$_2$CO$_3$ (30 ml) and EtOAc with vigorous stirring. Brine (30 ml) was added and the mixture was allowed to stir for 15 min. The aqueous solution was separated and extracted with EtOAc (2×30 ml). The organic solutions were combined, washed with brine (2×40 ml), dried over Na$_2$SO$_4$, filtered and concentrated to give 2-({5-[3-(dimethylamino)propyl]-2-methylpyridin-3-yl}amino)-9-(trifluoromethyl)-5,7-dihydro-6H-pyrimido[5,4-d][1]benzazepine-6-thione (1.41g, 95%).

A solution of 2-({5-[3-(dimethylamino)propyl]-2-methylpyridin-3-yl}amino)-9-(trifluoromethyl)-5,7-dihydro-6H-pyrimido[5,4-d][1]benzazepine-6-thione in a mixture of MeOH (1.6 ml) and MeCN (10 ml) was allowed to stir under gentle reflux. To this solution was added 12 M HCl (15 ul, 0.19 mmol). The solution was seeded and allowed to cool slowly to rt. The resulting slurry was left at rt for 18 hrs. The solid was collected by filtration and dried under high vacuum to give the monohydrochloride salt of 2-({5-[3-(dimethylamino)propyl]-2-methylpyridin-3-yl}amino)-9-(trifluoromethyl)-5,7-dihydro-6H-pyrimido[5,4-d][1]benzazepine-6-thione (69 mg, 71%).

2-({5-[3-(Dimethylamino)propyl]-2-methylpyridin-3-yl}amino)-9-(trifluoromethyl)-5,7-dihydro-6H-pyrimido[5,4-d][1]benzazepine-6-thione (I-111)

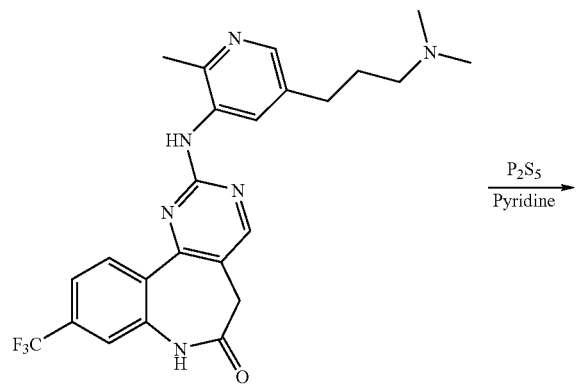

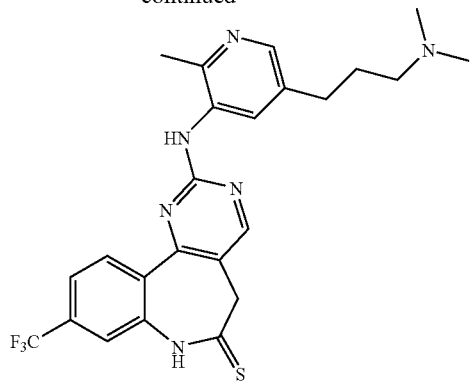

A mixture of 2-({5-[3-(dimethylamino)propyl]-2-methylpyridin-3-yl}amino)-9-(trifluoromethyl)-5,7-dihydro-6H-pyrimido[5,4-d][1]benzazepin-6-one (175 g, 372 mmol), phosphorus pentasulfide (82.7 g, 372 mmol) and pyridine (1.35 L) was heated at 50° C. for 18 hours. HPLC analysis showed completion of the reaction. After the reaction mixture was cooled below room temperature, a solution of sodium carbonate (525 g, 4.95 mol) in 5.1 L of water was slowly added while the temperature was kept at below room temperature. The resulting biphasic solution was separated and the organic layer was washed with the same amount of sodium carbonate solution two times. The organic phase was then reduced to ca. 1.1 L in volume. The solution was diluted with water (1.0 L) and stirred at room temperature overnight resulting in a yellow suspension. The solid was filtered and washed with 200 mL EtOH/water (1 vol/2 vol), and water 200 mL. After drying overnight under vacuo at 40° C., the crude product was dissolved in 1.2 L of EtOH at reflux. Water (2.0 L) was slowly added at 75° C. to induce crystallization. The suspension was then slowly cooled to room temperature and stirred overnight. The solid 2-({5-[3-(Dimethylamino)propyl]-2-methylpyridin-3-yl}amino)-9-(trifluoromethyl)-5,7-dihydro-6H-pyrimido[5,4-d][1]benzazepine-6-thione was filtered and dried under vac at 40° C. to a constant weight (140.0 g, HPLC purity>98%, 77% yield). LCMS (FA): R$_t$=6.26 min, m/z=485.2 (M–H).

Compounds in the following table may be prepared from the appropriate starting materials as either the formate or hydrochloride salt using the procedures described above:

| I-53  | LCMS (FAL): R$_t$ = 4.60 min, m/z = 493.6 (M + H). |
|-------|----------------------------------------------------|
| I-63  | LCMS (FAL): R$_t$ = 5.07 min, m/z = 527.7 (M + H). |
| I-44  | LCMS (FAP1): R$_t$ = 7.56 min, m/z = 479.6 (M + H). |
| I-24  | LCMS (FAP1): R$_t$ = 7.66 min, m/z = 469.5 (M + H). |
| I-27  | LCMS (FAP1): R$_t$ = 7.23 min, m/z = 457.5 (M + H). |
| I-8   | LCMS (FAP1): R$_t$ = 7.43 min, m/z = 469.4 (M + H). |
| I-93  | LCMS (FA): R$_t$ = 6.60 min, m/z = 453.5 (M + H).  |
| I-33  | LCMS (FA): R$_t$ = 4.95 min, m/z = 439.4 (M + H).  |
| I-61  | LCMS (FA): R$_t$ = 4.95 min, m/z = 486.2 (M + H).  |
| I-13  | LCMS (FA): R$_t$ = 5.59 min, m/z = 439.2 (M + H).  |
| I-28  | LCMS (FA): R$_t$ = 4.55 min, m/z = 452.2 (M + H).  |
| I-71  | LCMS (FA): R$_t$ = 8.10 min, m/z = 468.6 (M + H).  |
| I-102 | LCMS (FA): R$_t$ = 12.04 min, m/z = 453.4 (M + H). |
| I-47  | LCMS (FA): R$_t$ = 7.30 min, m/z = 423.4 (M + H).  |
| I-83  | LCMS (FA): R$_t$ = 4.05 min, m/z = 538.7 (M + H).  |
| I-80  | LCMS (FAP1): R$_t$ = 8.0 min, m/z = 486 (M + H).   |
| I-5   | LCMS (AAL): R$_t$ = 7.5 min, m/z = 447 (M + H).    |
| I-79  | LCMS (FAP1): R$_t$ = 4.5 min, m/z = 444 (M + H).   |
| I-60  | LCMS (FAP1): R$_t$ = 3.6 min, m/z = 432 (M + H).   |
| I-39  | LCMS (FAP1): R$_t$ = 4.0 min, m/z = 459 (M + H).   |
| I-32  | LCMS (FA): R$_t$ = 6.02 min, m/z = 473.4 (M + H).  |

-continued

| | |
|---|---|
| I-90 | LCMS (FAL): $R_t$ = 4.02 min, m/z = 459.1 (M + H). |
| I-22 | LCMS (FA): $R_t$ = 3.54 min, m/z = 480.4 (M + H). |
| I-1 | LCMS (FAP1): $R_t$ = 3.7 min, m/z = 449 (M + H). |
| I-91 | LCMS (FAL): $R_t$ = 3.91 min, m/z = 439.2 (M + H). |
| I-108 | LCMS (FAL): $R_t$ = 3.38 min, m/z = 453.2 (M + H). |
| I-50 | LCMS (FAL): $R_t$ = 4.01 min, m/z = 473 (M + H). |
| I-99 | LCMS (FAP1): $R_t$ = 7.46 min, m/z = 437.5 (M − H). |
| I-26 | LCMS (FAL): $R_t$ = 5.28 min, m/z = 528.7 (M + H). |
| I-6 | LCMS (FAL): $R_t$ = 5.28 min, m/z = 528.7 (M + H). |
| I-87 | LCMS (FAP1): $R_t$ = 8.91 min, m/z = 513.7 (M + H). |
| I-54 | LCMS (FAP1): $R_t$ = 7.99 min, m/z = 479 (M + H). |
| I-72 | LCMS (FAP1): $R_t$ = 7.61 min, m/z = 482 (M + H). |
| I-43 | LCMS (FAP1): $R_t$ = 8.53 min, m/z = 516 (M + H). |
| I-30 | LCMS (FAL): $R_t$ = 5.97 min, m/z = 479.5 (M + H). |
| I-34 | LCMS (FAL): $R_t$ = 3.48 min, m/z = 522.1 (M + H). |
| I-25 | LCMS (FAP1): $R_t$ = 5.96 min, m/z = 460 (M + H). |
| I-104 | LCMS (FAP1): $R_t$ = 5.49 min, m/z = 425 (M + H). |
| I-78 | LCMS (AAL): $R_t$ = 6.83 min, m/z = 467.3 (M + H). |
| I-51 | LCMS (AAL): $R_t$ = 5.99 min, m/z = 480.4 (M + H). |
| I-45 | LCMS (FAP1): $R_t$ = 7.66 min, m/z = 465 (M + H). |
| I-89 | LCMS (FAL): $R_t$ = 3.62 min, m/z = 467 (M + H). |
| I-12 | LCMS (FAL): $R_t$ = 3.84 min, m/z = 501 (M + H). |
| I-52 | LCMS (FAL): $R_t$ = 3.60 min, m/z = 556.3 (M + H). |
| I-59 | LCMS (FAP1): $R_t$ = 5.56 min, m/z = 522.5 (M + H). |
| I-15 | LCMS (FAP1): $R_t$ = 5.92 min, m/z = 508.5 (M + H). |
| I-29 | LCMS (FAP1): $R_t$ = 8.90 min, m/z = 528.6 (M + H). |
| I-94 | LCMS (FAP1): $R_t$ = 5.15 min, m/z = 453 (M + H). |
| I-95 | LCMS (FAP1): $R_t$ = 10.84 min, m/z = 514.6 (M + H). |
| I-3 | LCMS (FAP1): $R_t$ = 9.70 min, m/z = 480.5 (M + H). |
| I-69 | LCMS (FAP1): $R_t$ = 7.88 min, m/z = 494.5 (M + H). |
| I-85 | LCMS (FAP1): $R_t$ = 6.95 min, m/z = 466.5 (M + H). |
| I-23 | LCMS (FAP1): $R_t$ = 5.47 min, m/z = 502 (M + H). |
| I-56 | LCMS (FAP1): $R_t$ = 7.23 min, m/z = 481.3 (M + H). |
| I-76 | LCMS (FAP1): $R_t$ = 3.84 min, m/z = 469 (M + H). |
| I-88 | LCMS (FAP1): $R_t$ = 8.60 min, m/z = 516.6 (M + H). |
| I-41 | LCMS (FAP1): $R_t$ = 7.83 min, m/z = 482.5 (M + H). |
| I-92 | LCMS (FA): $R_t$ = 3.88 min, m/z = 515 (M + H). |
| I-7 | LCMS (FAP1): $R_t$ = 9.72 min, m/z = 494.5 (M + H). |
| I-19 | LCMS (FAP2): $R_t$ = 6.94 min, m/z = 467.6 (M + H). |
| I-9 | LCMS (FAP1): $R_t$ = 8.90 min, m/z = 528.5 (M + H). |
| I-75 | LCMS (FAP1): $R_t$ = 3.93 min, m/z = 528 (M + H). |
| I-57 | LCMS (FAP1): $R_t$ = 7.77 min, m/z = 459.6 (M + H). |
| I-18 | LCMS (FAP1): $R_t$ = 7.44 min, m/z = 501.6 (M + H). |
| I-105 | LCMS (FAP1): $R_t$ = 7.66 min, m/z = 494.6 (M + H). |
| I-64 | LCMS (FAP1): $R_t$ = 8.51 min, m/z = 488.6 (M + H). |
| I-97 | LCMS (FAP2): $R_t$ = 5.21 min, m/z = 454.6 (M + H). |
| I-112 | LCMS (FA): $R_t$ = 4.62 min, m/z = 468 (M + H). |
| I-35 | LCMS (FAP1): $R_t$ = 7.25 min, m/z = 502.6 (M + H). |
| I-81 | LCMS (FAP1): $R_t$ = 10.26 min, m/z = 382.5 (M + H). |
| I-4 | LCMS (FAP1): $R_t$ = 7.27 min, m/z = 416.4 (M + H). |
| I-100 | LCMS (FAP1): $R_t$ = 8.95 min, m/z = 487.4 (M + H). |
| I-77 | LCMS (FAP1): $R_t$ = 7.74 min, m/z = 515.6 (M + H). |
| I-101 | LCMS (FAP1): $R_t$ = 8.53 min, m/z = 487.5 (M + H). |
| I-98 | LCMS (FAP1): $R_t$ = 7.14 min, m/z = 416.4 (M + H). |
| I-16 | LCMS (FAP1): $R_t$ = 7.62 min, m/z = 453.4 (M + H). |
| I-37 | LCMS (FAP3): $R_t$ = 4.38 min, m/z = 382.2 (M + H). |
| I-82 | LCMS (FAP1): $R_t$ = 8.10 min, m/z = 451.5 (M + H). |
| I-110 | LCMS (FAP1): $R_t$ = 7.69 min, m/z = 471.4 (M + H). |
| I-106 | LCMS (FAP1): $R_t$ = 11.24 min, m/z = 437.6 (M + H). |
| I-73 | LCMS (FAP1): $R_t$ = 9.91 min, m/z = 466.5 (M + H). |
| I-109 | LCMS (FAP1): $R_t$ = 8.09 min, m/z = 453.5 (M + H). |
| I-14 | LCMS (FAP1): $R_t$ = 7.08 min, m/z = 465.6 (M + H). |
| I-84 | LCMS (FAP1): $R_t$ = 7.42 min, m/z = 497.2 (M + H). |
| I-17 | LCMS (FAP1): $R_t$ = 3.62 min, m/z = 479.1 (M + H). |
| I-38 | LCMS (FAP1): $R_t$ = 5.47 min, m/z = 467.4 (M + H). |
| I-42 | LCMS (FAP1): $R_t$ = 6.89 min, m/z = 467.5 (M + H). |
| I-62 | LCMS (FAL): $R_t$ = 4.06 min, m/z = 473.0 (M + H). |
| I-67 | LCMS (FAL): $R_t$ = 4.09 min, m/z = 500.4 (M + H). |
| I-40 | LCMS (FAL): $R_t$ = 3.57 min, m/z = 494 (M + H). |
| I-65 | LCMS (FAL): $R_t$ = 3.90 min, m/z = 528.4 (M + H). |
| I-74 | LCMS (FAL): $R_t$ = 3.96 min, m/z = 512.4 (M + H). |
| I-46 | LCMS (FA): $R_t$ = 1.38 min, m/z = 500.2 (M + H). |
| I-103 | LCMS (FAP1): $R_t$ = 3.64 min, m/z = 466.1 (M + H). |
| I-66 | LCMS (FAP1): $R_t$ = 3.77 min, m/z = 494.0 (M + H). |
| I-49 | LCMS (FAP1): $R_t$ = 3.82 min, m/z = 508.0 (M + H). |
| I-2 | LCMS (FAP1): $R_t$ = 3.91 min, m/z = 528.0 (M + H). |
| I-58 | LCMS (FAP1): $R_t$ = 7.22 min, m/z = 480.5 (M + H). |
| I-107 | LCMS (FAP1): $R_t$ = 7.56 min, m/z = 452.0 (M + H). |
| I-11 | LCMS (FAP1): $R_t$ = 8.06 min, m/z = 480.4 (M + H). |

9-Chloro-2-{[5-[2-(dimethylamino)ethyl]-2-(trifluoromethyl)pyridin-3-yl]amino}-5,7-dihydro-6H-pyrimido[5,4-d][1]benzazepine-6-thione (I-70)

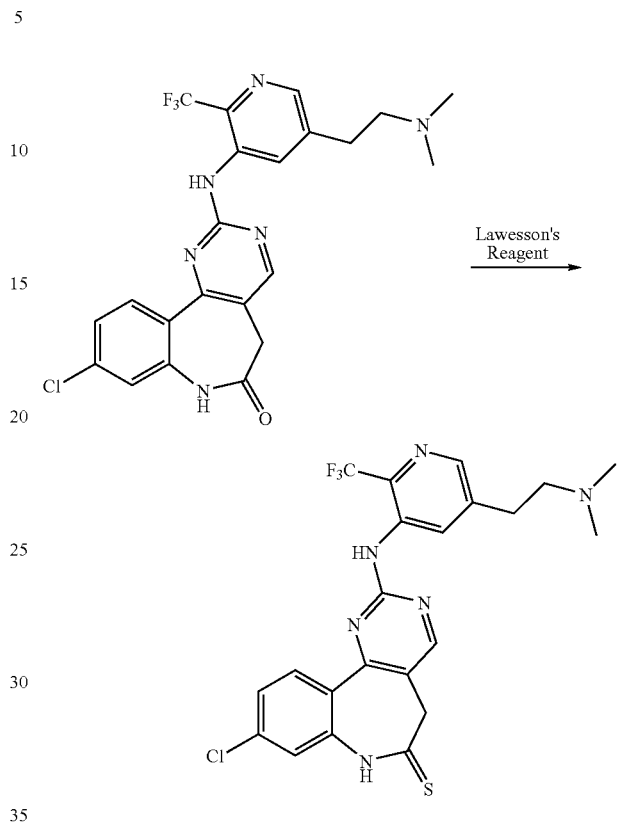

To a solution of 9-chloro-2-{[5-[2-(dimethylamino)ethyl]-2-(trifluoromethyl)pyridin-3-yl]amino}-5,7-dihydro-6H-pyrimido[5,4-d][1]benzazepin-6-one (0.011 g, 0.023 mmol) in THF (1.5 ml) was added Lawesson's reagent (0.028 g, 0.069 mmol). The resulting mixture was allowed to stir for 3 h at 65° C. and then allowed to cool to rt. HCl (6 mL, 1M in ether) was added. The mixture was filtered and the solid was washed with THF and saturated NaHCO₃. The residue was purified by column chromatography to give 9-chloro-2-{[5-[2-(dimethylamino)ethyl]-2-(trifluoromethyl)pyridin-3-yl]amino}-5,7-dihydro-6H-pyrimido[5,4-d][1]benzazepine-6-thione (I-70) as the formate salt (7.0 mg, 56%). LCMS (FA): $R_t$=7.10 min, m/z=493.1 (M+H).

Compounds in the following table were prepared from the appropriate starting materials as either the formate or hydrochloride salt using the procedures described above:

| | |
|---|---|
| I-68 | LCMS (FA): $R_t$ = 4.40 min, m/z = 369.2 (M + H). |
| I-96 | LCMS (FA): $R_t$ = 6.92 min, m/z = 465.6 (M + H). |
| I-36 | LCMS (FA): $R_t$ = 5.74 min, m/z = 541.6 (M + H). |
| I-10 | LCMS (FAP1): $R_t$ = 8.19 min, m/z = 509.5 (M + H). |
| I-31 | LCMS (FAL): $R_t$ = 4.22 min, m/z = 509.2 (M + H). |
| I-86 | LCMS (FA): $R_t$ = 1.23 min, m/z = 471.3 (M + H). |
| I-114 | LCMS (FAL): $R_t$ = 7.79 min, m/z = 499.5 (M + H). |
| I-113 | LCMS (FAL): $R_t$ = 7.79 min, m/z = 499.1 (M + H). |
| I-21 | LCMS (FAP1): $R_t$ = 7.56 min, m/z = 558.6 (M + H). |

Example 6

Synthesis of 2-{[5-(3-Hydroxypropyl)-2-methylpyridin-3-yl]amino}-9-(trifluoromethyl)-5,7-dihydro-6H-pyrimido[5,4-d][1]benzazepine-6-thione (I-55)

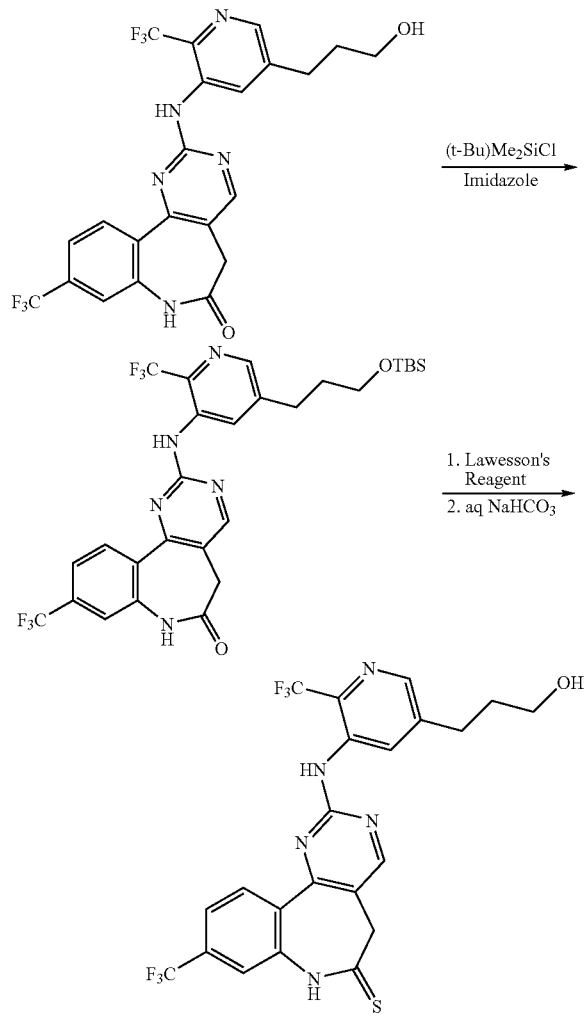

Step 1: 2-{[5-(3-{[tert-Butyl(dimethyl)silyl]oxy}propyl)-2-methylpyridin-3-yl]amino}-9-(trifluoromethyl)-5,7-dihydro-6H-pyrimido[5,4-d][1]benzazepin-6-one To a solution of 2-{[5-(3-hydroxypropyl)-2-methylpyridin-3-yl]amino}-9-(trifluoromethyl)-5,7-dihydro-6H-pyrimido[5,4-d][1]benzazepin-6-one (0.25 g, 0.564 mmol) in THF (10 ml) were added imidazole (0.077 g, 1.13 mmol) and tert-butyldimethylsilyl chloride (0.10 g, 0.676 mmol). The reaction mixture was allowed to stir overnight at rt and was then concentrated. Water (10 ml) and saturated NaHCO₃ (10 ml) were added. The resulting mixture was allowed to stir for 1 h at rt. The mixture was extracted with EtOAc (2×30 mL). The organic solutions were combined, dried over Na₂SO₄, filtered and concentrated. The residue was purified by column chromatography to give 2-{[5-(3-{[tert-butyl(dimethyl)silyl]oxy}propyl)-2-methylpyridin-3-yl]amino}-9-(trifluoromethyl)-5,7-dihydro-6H-pyrimido[5,4-d][1]benzazepin-6-one (0.16g, 0.29 mmol, 51%).

Step 2: 2-{[5-(3-Hydroxypropyl)-2-methylpyridin-3-yl]amino}-9-(trifluoromethyl)-5,7-dihydro-6H-pyrimido[5,4-d][1]benzazepine-6-thione (I-55)

To a solution of 2-{[5-(3-{[tert-butyl(dimethyl)silyl]oxy}propyl)-2-methylpyridin-3-yl]amino}-9-(trifluoromethyl)-5,7-dihydro-6H-pyrimido[5,4-d][1]benzazepin-6-one (0.16 g, 0.29 mmol) in THF (7 mL) was added 2,4-bis(4-methoxyphenyl)-2,4-dithioxo-1,3,2,4-dithiadiphosphetane (0.23 g, 0.574 mmol). The resulting mixture was allowed to stir for 6 h at rt. The mixture was concentrated. Water (20 mL) and saturated NaHCO₃ (20 mL) were added. The mixture was extracted with DCM (2×30 mL). The organic solutions were combined, dried over Na₂SO₄, filtered and concentrated. The residue was purified by column chromatography to give 2-{[5-(3-hydroxypropyl)-2-methylpyridin-3-yl]amino}-9-(trifluoromethyl)-5,7-dihydro-6H-pyrimido[5,4-d][1]benzazepine-6-thione as the formate salt (0.055g, 0.11 mmol, 38%) as a solid. LCMS (FA): $R_t$=5.10 min, m/z=460.3 (M+H).

Example 7

Synthesis of 2-{[5-(3-aminopropyl)-2-methylpyridin-3-yl]amino}-9-(trifluoromethyl)-5,7-dihydro-6H-pyrimido[5,4-d][1]benzazepin-6-one

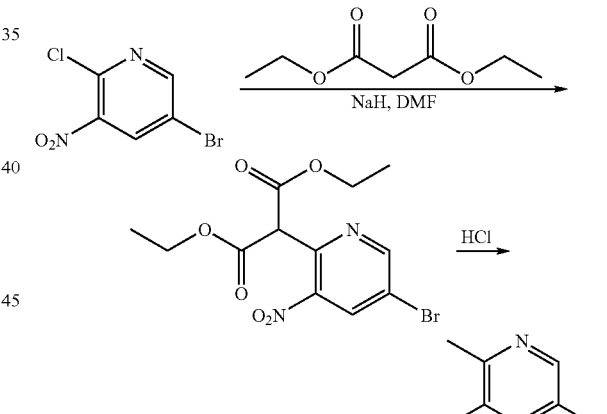

Step 1: Diethyl(5-bromo-3-nitropyridin-2-yl)malonate

To a suspension of NaH (60% in mineral oil, 27.9 g, 0.69 mol) in DMF (300 mL) at 5-10° C. was slowly added ethyl malonate (125 mL, 0.69 mol) over 30 min. The mixture was allowed to stir for 20 min at rt, during which time the suspension became a solution. A solution of 5-bromo-2-chloro-3-nitropyridine (75 g, 0.32 mol) in DMF (75 mL) was added slowly at 5-10° C. The resulting dark red mixture was allowed to stir at 40° C. for 2 h. The reaction mixture was then poured into 1M AcOH (0.75 L) and extracted with DCM (3×250 mL). The organic solutions were combined, washed with water and brine, dried over MgSO₄, filtered and concentrated.

The residue was purified by column chromatography to give diethyl(5-bromo-3-nitropyridin-2-yl)malonate (260 g, 99%) as a yellow oil.

Step 2: 5-Bromo-2-methyl-3-nitropyridine

To diethyl(5-bromo-3-nitropyridin-2-yl)malonate (66 g, 0.18 mol) was added water (250 mL) and 12 M HCl (360 mL, 4.32 mol). The mixture was heated at 105° C. until TLC showed starting material was consumed. The reaction mixture was then allowed to cool to rt and brine (0.67 L) was added. The organic solution was separated and the aqueous solution was extracted with DCM (3×0.67 L). The organic solutions were combined, washed with brine, sat, aq. NaHCO$_3$, and brine again, dried over Na$_2$SO$_4$, filtered and concentrated to give 5-bromo-2-methyl-3-nitropyridine (34.7 g, 75%) as a yellow solid.

Compounds in the following table were prepared from the appropriate starting materials using the procedures described above:

| |
|---|
| 5-bromo-2-ethyl-3-nitropyridine |

Example 8

Synthesis of Guanidines of Formula III Used for the Preparation of Compounds of Formula vi (Formula IV)

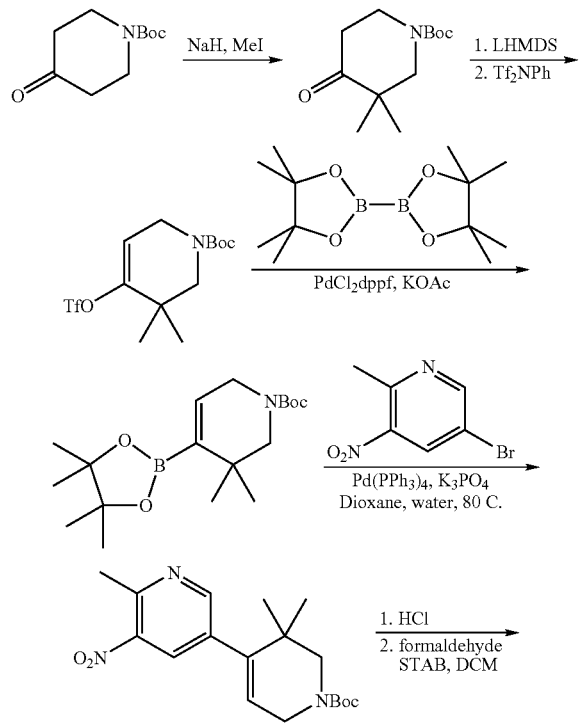

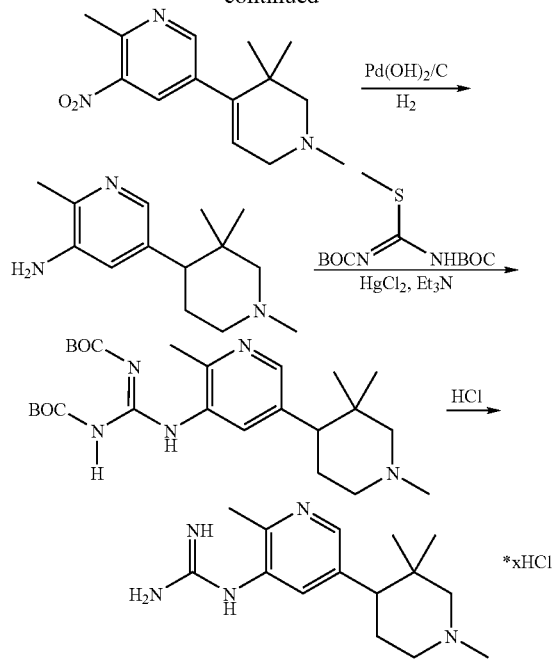

N-[2-methyl-5-(1,3,3-trimethylpiperidin-4-yl)pyridine-3-yl]guanidine

Step 1: tert-Butyl-3,3-dimethyl-4-oxopiperidine-1-carboxylate

To a solution of tert-butyl 4-oxopiperidine-1-carboxylate (15,0 g, 75.3 mmol) in THF (400 mL) at 0° C. was added sodium hydride (3.63 g, 151 mmol) slowly. The reaction mixture was allowed to stir for 5 min and then methyl iodide (11.7 mL, 188 mmol) was added dropwise. The reaction mixture was allowed to stir for 30 min at 0° C. and at rt overnight. The reaction mixture was diluted with water (200 mL). The aqueous solution was extracted with DCM. The organic solutions were combined, washed with brine, dried over Na$_2$SO$_4$, filtered and concentrated. The residue was purified by column chromatography to give tert-butyl-3,3-dimethyl-4-oxopiperidine-1-carboxylate (7.0 g, 40%) as a white solid. LCMS (FA): R$_f$=1.77 min, m/z=228,3 (M+H).

Step 2: tert-Butyl-3,3-dimethyl-4-{[(trifluoromethyl)sulfonyl]oxy}-3,6-dihydropyridine-1(2H)-carboxylate To a solution of tert-butyl 3,3-dimethyl-4-oxopiperidine-1-carboxylate (2.18 g, 9.59 mmol) in THF (20 mL) was added lithium bis(trimethylsilyl)amide (1.0M in THF, 10.5 mL) dropwise at −78° C. The reaction mixture was allowed to stir for 30 min and then N-phenylbis(trifluoromethanesulphonimide (3.70 g, 10.4 mmol) in THF (10 mL) was added dropwise. The reaction mixture was allowed to warm to 0° C. then rt, and allowed to stir overnight. The mixture was quenched by the addition of sat. aq. NH$_4$Cl (40 mL) and brine (80 mL). After stirring for 30 min, the aqueous solution was extracted with DCM. The organic solutions were combined, dried over Na$_2$SO$_4$, filtered and concentrated. The residue was purified by column chromatography to give tert-butyl-3,3-dimethyl- 4-{[(trifluoromethyl)sulfonyl]oxy}-3,6-dihydropyridine-1(2H)-carboxylate (2.3 g, 67%). LCMS (FA): $R_t$=2.34 min, m/z=360.1 (M+H).

Step 3:tert-Butyl-3,3-dimethyl-4-(4,4,5,5-tetramethyl-1,3,2-dioxaborolan-2-yl)-3,6-dihydropyridine-1(2H)-carboxylate To a solution of tert-butyl 3,3-dimethyl-4-{[(trifluoromethyl)sulfonyl]-oxy}-3,6-dihydropyridine-1(2H)-carboxylate (1.55 g, 4.31 mmol) in 1,4-dioxane (30 mL) were added bis(pinacolato)diboron (1.20 g, 4.74 mmol), 1,1'-bis(diphenylphosphino)ferrocenepalladium(II)dichloride, dichloromethane (106 mg, 0.129 mmol), 1,1'-bis(diphenylphosphino)ferrocene (71.7 mg, 0.129 mmol) and potassium acetate (1.27 g, 12.9 mmol). The reaction mixture was flushed with nitrogen gas and allowed to stir for 5 h at 80° C. The reaction mixture was filtered through Celite® and the filter cake was washed with EtOAc. The filtrate was washed with brine, dried over $Na_2SO_4$, filtered and concentrated. The residue was purified by column chromatography to give tert-butyl-3,3-dimethyl-4-(4,4,5,5-tetramethyl-1,3,2-dioxaborolan-2-yl)-3,6-dihydropyridine-1(2H)-carboxylate (0.55 g, 38%) as a white solid. LCMS (FA): $R_t$=2.51 min, m/z=338.3 (M+H).

Step 4:tert-Butyl-3',3',6-trimethyl-5-nitro-3',6'-dihydro-3,4'-bipyridine-1'(2'H)-carboxylate To a solution of tert-butyl-3,3-dimethyl-4-(4,4,5,5-tetramethyl-1,3,2-dioxaborolan-2-yl)-3,6-dihydropyridine-1(2H)-carboxylate (2.12 g, 6.28 mmol) in 1,4-dioxane (90 mL) were added 5-bromo-2-methyl-3-nitropyridine (1.64 g, 7.54 mmol), tetrakis(triphenylphosphine)palladium (642 mg, 0.556 mmol), potassium phosphate (4.96 g, 23.4 mmol) and water (22 mL). The reaction mixture was flushed with nitrogen gas and allowed to stir for 24 h at 80° C. The reaction mixture was filtered through a Celite® pad and washed with DCM. The filtrate was washed with brine, dried over $Na_2SO_4$, filtered and concentrated. The residue was purified by column chromatography to give tert-butyl-3',3',6-trimethyl-5-nitro-3',6'-dihydro-3,4'-bipyridine-1'(2'H)-carboxylate (1.3 g, 60%) as a white solid. LCMS (FA): $R_t$=2.16 min, m/z=348.3 (M+H).

Step 5: 3',3',6-Trimethyl-5-nitro-1',2',3',6'-tetrahydro-3,4'-bipyridine[HCl]

To a solution of tert-butyl-3',3',6-trimethyl-5-nitro-3',6'-dihydro-3,4'-bipyridine-1'(2'H)-carboxylate (1.30 g, 3.70 mmol) in MeOH (30 mL) was added hydrochloric acid (4.0 M in 1,4-dioxane, 40 mL). The reaction mixture was allowed to stir for 2 h at rt. The reaction mixture was concentrated to give 3',3',6-trimethyl-5-nitro-1',2',3',6'-tetrahydro-3,4'-bipyridine as the hydrochloride salt (1.12 g, 100%) as a white solid. LCMS (FA): $R_t$=0.89 min, m/z=248.3 (M+H).

Step 6: 1',3',3',6-Tetramethyl-5-nitro-1',2',3',6'-tetrahydro-3,4'-bipyridine

To a solution of 3',3',6-trimethyl-5-nitro-1',2',3',6'-tetrahydro-3,4'-bipyridine[HCl] (1.12 g, 3.50 mmol) in DCM (55 mL) were added formaldehyde (37% in water, 4.0 mL) and sodium triacetoxyborohydride (4.45 g, 21.0 mmol). The reaction mixture was allowed to stir for 2 h at rt. The mixture was quenched by the addition of sat. aq. sodium bicarbonate (40 mL). After stirring for 10 min, the aqueous solution was extracted with DCM. The organic solutions were combined, dried over $Na_2SO_4$, filtered and concentrated. The residue was purified by column chromatography to give 1',3',3',6-tetramethyl-5-nitro-1',2',3',6'-tetrahydro-3,4'-bipyridine (0.914 g, 100%). LCMS (FA): $R_t$=0.85 min, m/z=262.4 (M+H).

Step 7: 2-Methyl-5-(1,3,3-trimethylpiperidin-4-yl)pyridine-3-amine

To a solution of 1',3',3',6-tetramethyl-5-nitro-1',2',3',6'-tetrahydro-3,4'-bipyridine (0.912 g, 3.49 mmol) in MeOH (70 mL) was added palladium hydroxide (20 wt. % Pd (dry basis) on carbon, 808 mg). The reaction mixture was flushed with hydrogen gas and allowed to stir at rt overnight under an atmosphere of hydrogen. The reaction mixture was filtered through a Celite® pad and washed with MeOH. The filtrate was concentrated to give 2-methyl-5-(1,3,3-trimethylpiperidin-4-yl)pyridine-3-amine (0.814 g, 100%). LCMS (FA): $R_t$=0.24 min, m/z=234.4 (M+H).

Step 8:Di-tert-butyl((Z)-{[2-methyl-5-(1,3,3-trimethylpiperidin-4-yl)pyridine-3-yl]amino}methylylidene)biscarbamate To a solution of 2-methyl-5-(1,3,3-trimethylpiperidin-4-yl)pyridine-3-amine (0.814 g, 3.49 mmol) in DCM (50 mL) were added 1,3-bis(tert-butoxycarbonyl)-2-methyl-2-thiopsendourea (1.52 g, 5.23 mmol), mercury(II)chloride (1.42 g, 5.23 mmol) and TEA (2.92 mL, 20.9 mmol). The reaction mixture was allowed to stir overnight at rt then filtered through a Celite® pad and washed with DCM. The filtrate was washed with brine, dried over $Na_2SO_4$, filtered and concentrated. The residue was purified by column chromatography to give di-tert-butyl((Z)-{[2-methyl-5-(1,3,3-trimethylpiperidin-4-yl)pyridine-3-yl]amino}methylylidene)biscarbamate (0.79 g, 48%) as a white solid. LCMS (FAL): $R_t$=5.08 min, m/z=476.6 (M+H).

Step 9:N-[2-Methyl-5-(1,3,3-trimethylpiperidin-4-yl)pyridine-3-yl]guanidine

To a solution of di-tert-butyl((Z)-{[2-methyl-5-(1,3,3-trimethylpiperidin-4-yl)pyridine-3-yl]amino}methylylidene)biscarbamate (0.78 g, 1.60 mmol) in DCM (10 mL) was added hydrochloric acid (4.0 M in 1,4-dioxane, 20 mL). The reaction mixture was allowed to stir at rt overnight. The reaction mixture was concentrated to give the hydrochloride salt of N-[2-methyl-5-(1,3,3-trimethylpiperidin-4-yl)pyridine-3-yl]guanidine (750 mg, 110%) as a white solid.

Steps 7-9 in the synthesis of N-[2-methyl-5-(1,3,3-trimethylpiperidin-4-yl)pyridine-3-yl]guanidine represent General Method 1.

Compounds in the following table were prepared as the hydrochloride salts from the appropriate starting materials using the procedures described above:

N-[2-methyl-5-(1-methylpiperidin-4-yl)pyridin-3-yl]guanidine
N-[5-(1-ethylpiperidin-4-yl)-2-methylpyridin-3-yl]guanidine
N-{5-[1-(2-fluoroethyl)piperidin-4-yl]-2-methylpyridin-3-yl}guanidine

N-{2-methyl-6-[(1-methylpiperidin-4-yl)methyl]pyridine-3-yl}guanidine

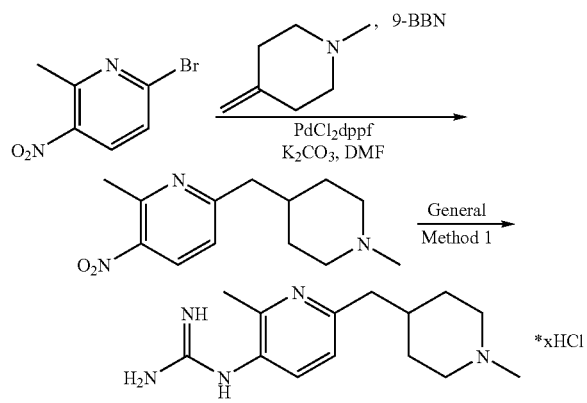

Step 1: 2-Methyl-6-[(1-methylpiperidin-4-yl)-methyl]-3-nitropyridine

To a solution of 9-BBN in THF (0.5 M, 4.93 mL, 2.46 mmol) was added 1-methyl-4-methylenepiperidine (274 mg, 2.46 mmol). The reaction mixture was allowed to stir at 75° C. for 1 h and was then allowed to cool to rt. The resulting solution was transferred into a solution of 2-methyl-5-nitro-6-methylpyridine (486 mg, 2.24 mmol) in DMF (11 mL). To the mixture were added [1,1'-bis(diphenylphosphino)ferrocene]-dichloropalladium(II) (1:1 complex with DCM, 54.9 mg, 0.0672 mmol) and potassium carbonate (402 mg, 2.91 mmol). The reaction mixture was allowed to stir for 3 h at rt. The mixture was quenched by the addition of water (10 mL). The aqueous solution was extracted with DCM. The organic solutions were combined, washed with brine, dried over $Na_2SO_4$, filtered and concentrated. The residue was purified by column chromatography to give 2-methyl-6-[(1-methylpiperidin-4-yl)-methyl]-3-nitropyridine (64 mg, 10%) as a white solid. LCMS (FAL): $R_f$=3.38 min, m/z=250.2 (M+H).

Step 2: N-{2-methyl-6[(1-methylpiperidin-4-yl)methyl]pyridine-3-yl}guanidine The hydrochloride salt of N-{2-methyl-6[(1-methylpiperidin-4-yl)methyl]pyridine-3-yl}guanidine was prepared as a white solid from 2-methyl-6-[(1-methylpiperidin-4-yl)-methyl]-3-nitropyridine following the procedures of General Method 1.

N-{5-[3-(Dimethylamino)propyl]-2-methoxypyridin-3-yl}guanidine

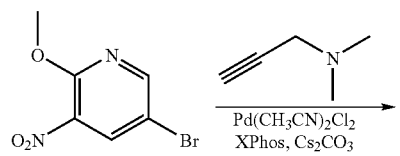

Step 1: 3-(6-Methoxy-5-nitropyridin-3-yl)-N,N-dimethylprop-2-yn-1-amine

To a solution of 5-bromo-2-methoxy-3-nitropyridine (1.50 g, 6.44 mmol) in DMF (30 mL) were added bis(acetonitrile)palladium(II)chloride (83.5 mg, 0.322 mmol), 2-dicyclohexylphosphino-2',4',6'-tri-i-propyl-1-1'-biphenyl (399 mg, 0.837 mmol), cesium carbonate (4.19 g, 12.9 mmol) and propargyl(dimethylamine) (0.832 mL, 7.72 mmol). The reaction mixture was flushed with nitrogen gas and allowed to stir for 4 h at 50° C. The reaction mixture was diluted with EtOAc and washed with brine, dried over $Na_2SO_4$, filtered and concentrated. The residue was purified by column chromatography to give 3-(6-methoxy-5-nitropyridin-3-yl)-N,N-dimethylprop-2-yn-1-amine (0.41 g, 27%) as a white solid. LCMS (FA): $R_f$=0.85 min, m/z=236.2 (M+H).

Step 2: N-{2-Methyl-6[(1-methylpiperidin-4-yl)methyl]pyridine-3-yl}guanidine N-{2-Methyl-6[(1-methylpiperidin-4-yl)methyl]pyridine-3-yl}guanidine was prepared as the hydrochloride salt as a white solid from 3-(6-methoxy-5-nitropyridin-3-yl)-N,N-dimethylprop-2-yn-1-amine following the procedures of General Method 1.

N-{5-[3-(Dimethylamino)propyl]-2-methylpyridin-3-yl}guanidine

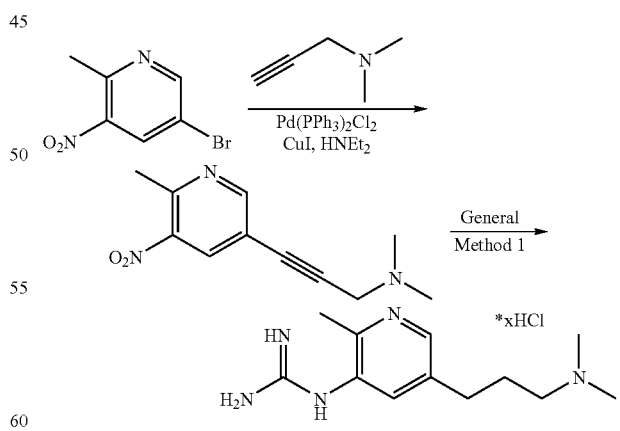

Step 1: N,N-Dimethyl-3-(6-methyl-5-nitropyridin-3-yl)prop-2-yn-1-amine

To a mixture of 5-bromo-2-methyl-3-nitropyridine (6.50 g, 30.0 mmol), copper iodide (280 mg, 1.5 mmol) and bis(triphenylphosphine)palladium(II)chloride (520 mg, 0.75 mmol) in diethylamine (17 mL) was added propargyl(dimethylamine) (4.04 mL, 37.5 mmol). The reaction mixture was allowed to stir for 15 h at rt. The resulting mixture was diluted with EtOAc (200 mL) and 1M aqueous $Na_2CO_3$ (150 mL). After stirring for 30 min, the organic solution was separated and the aqueous solution was extracted with EtOAc (2×100 mL). The organic solutions were combined, washed with water and brine, dried over $Na_2SO_4$, filtered and concentrated. The residue was purified by column chromatography to give N,N-dimethyl-3-(6-methyl-5-nitropyridin-3-yl)prop-2-yn-1-amine (5.98 g, 91%) as a dark oil. LCMS (FA): $R_f$=0.77 min, m/z=220.1 (M+H).

Step 2: 5-[3-(Dimethylamino)propyl]-2-methylpyridin-3-amine

To a solution of N,N-dimethyl-3-(6-methyl-5-nitropyridin-3-yl)prop-2-yn-1-amine (3.18 g, 13.8 mmol) in EtOH (50 mL) under an atmosphere of $N_2$ was added Raney 2800 nickel (50% water slurry; 760 mg, 4 mmol) using 5 mL of ethanol to transfer. The mixture was purged with $H_2$ (1 atm) and allowed to stir at rt under an atmosphere of $N_2$ for 20 h. More Raney nickel (620 mg, 3.6 mmol) was added using 5 mL of ethanol to transfer. The mixture was purged with $H_2$ (1 atm) and allowed to stir at rt under an atmosphere of $H_2$ for 20 h. The mixture was filtered through Celite® and the filtrate was concentrated to give 5-[3-(dimethylamino)propyl]-2-methylpyridin-3-amine (2.45 g, 93%) as a brown solid. LCMS (AAL): $R_f$=0.98 min, m/z=194.4 (M+H).

Step 3: N-{5-[3-(Dimethylamino)propyl]-2-methylpyridin-3-yl}guanidine

The hydrochloride salt of N-{5-[3-(dimethylamino)propyl]-2-methylpyridin-3-yl}guanidine was prepared from 5-[3-(dimethylamino)propyl]-2-methylpyridin-3-amine following General Method 1, with the exception that the hydrogenation step was performed using Raney Ni as described in Step 2. LCMS (AAL): $R_f$=0.82 min, m/z=236.6 (M+H).

N-{5-[3-(Dimethylamino)propyl]-2-methylpyridin-3-yl}guanidine trihydrochloride

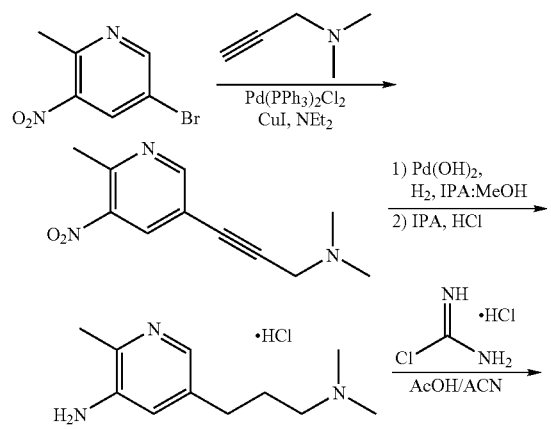

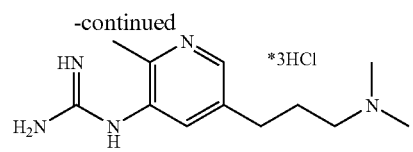

Step 1: N,N-dimethyl-3-(6-methyl-5-nitropyridin-3-yl)prop-2-yn-1-amine

A 12 L reactor equipped with an overhead stirrer and $N_2$ bubbler was charged with a solution of 5-bromo-2-methyl-3-nitropyridine (945 g, 4.35 mol) in EtOAc (5.7 L, 6 vol). To the reaction mixture, Pd(PPh$_3$)$_2$Cl$_2$ (15.4 g, 0.022 mol, 0.005 equiv), CuI (8.28 g, 0.0435 mol, 0.01 equiv) and Et$_3$N (3 L, 21.75 mol, 5 equiv) were added. Nitrogen was bubbled through the solution for 15 min and 3-dimethylamino-1-propyne (556 mL, 5.22 mol, 1.2 equiv) was added. The reaction-temperature setting was increased to 60° C. stepwise. The maximum temperature attained was 66° C. The reaction was continued for 3 h at this temperature (60° C.) and was judged complete by HPLC analysis. The reaction was cooled to ambient temperature and the inorganic salts were filtered off by passing the reaction mixture through a pad of celite. The filter cake was washed with EtOAc (2 L, 2 vol). The filtrate was transferred into a 20 L separatory funnel. The EtOAc layer was washed with 5% aqueous $Na_2CO_3$ solution (2×5 L, 5 vol). The layers were separated. The EtOAc layer was then washed with 10% brine in water (5 L, 5 vol). The layers were separated and the EtOAc layer was pumped down to a low volume (ca. 2 L, 2 vol) under reduced pressure. IPA (5 L, 5 vol) was added to the solution and the solvent was again evaporated to a low volume (ca. 2 L, 2 vol). The solution of N,N-dimethyl-3-(6-methyl-5-nitropyridin-3-yl-1-amine was subjected to hydrogenation in two batches using the procedure described in step 2, below,

Step 2: 5-(3-(dimethylamino)propyl)-2-methylpyridin-3-amine hydrochloride

The solution of N,N-dimethyl-3-(6-methyl-5-nitropyridin-3-yl)prop-2-yn-1-amine (2.17 mol) in IPA (ca. 1 L) obtained in the previous step was diluted with IPA to make the total volume 2.3 L, and MeOH (2.3 L, 5 vol) was added to the solution. This was then transferred into an 8 L Parr reactor. The reactor was purged with $N_2$. The catalyst [Pd(OH)$_2$, 20 wt % on carbon wet with 50% water, 15 wt %, 72 g] was charged into the reactor as a slurry in IPA (500 mL). The chiller temperature was set at 20° C. The reactor was purged with $N_2$ (twice) and then with $H_2$ (twice). The pressure was set at 30 psi. The internal temperature increased up to 62° C. even with the chiller temperature set at 20° C. After the exotherm subsided and the temperature cooled down to 35° C. (2 h), the chiller temperature was increased to 30° C. The reaction was continued at this temperature for 1 h. No additional exotherm was observed. The chiller temperature was increased to 40° C. and the reaction was continued for 1 h. No exotherm was observed. Finally, the chiller temperature was set at 55° C. (internal temperature was 48° C.). Next, the pressure was ramped up to 100 psi in increments of 10 psi over a period of 2 h. The reaction was continued for 20 h when $^1$H NMR analysis indicated complete conversion. The reaction was cooled to ambient temperature and the catalyst was filtered off. The filtrate was used for the HCl salt formation.

The filtrates from Batch 1 and Batch 2 were combined. The combined filtrates were pumped down to a low volume (ca. 2

L). IPA (10 L, 10 vol) was added and the solvent was evaporated to a low volume (ca. 2 L). IPAc (2 L) was added and the resulting solution was cooled in an ice-water bath. A solution of 5.95 N HCl in IPA (585 mL, 3.48 mol, 0.8 equiv) was added dropwise maintaining the internal temperature below 15° C. The suspension that resulted was stirred at ice-water bath temperature for 3 h. The solid was collected by filtration and the filter cake was washed with 1:1 IPA/IPAc (2 L). The solid was dried to a constant weight in a vacuum oven at 35° C. to obtain 5-(3-(dimethylamino)propyl)-2-methylpyridin-3-amine hydrochloride [620 g, 62% yield over two steps] as an off-white solid. Solid separated out from the filtrate after letting it stand overnight at ambient temperature. The solid was collected by filtration to obtain a second crop of 5-(3-(dimethylamino)propyl)-2-methylpyridin-3-amine hydrochloride [40 g, 4% recovery] as an off-white solid. The combined yield was 660 g (66% yield over two steps), $^1$H NMR (500 MHz, CD$_3$OD) δ ppm: 7.63 (s, 1H), 7.05 (s, 1H), 3.12-3.09 (m, 2H), 2.85 (s, 6H), 2.63 (t, 2H, J=7.5 Hz), 2.34 (s, 3H), 2.05-1.98 (m, 2H); ESI-MS m/z: 194 (M+H, 100%), Step 3: N-{5-[3-(Dimethylamino)propyl]-2-methylpyridin-3-yl}guanidine trihydrochloride A 1 L, three-neck, round-bottom flask equipped with an overhead stirrer, a reflux condenser, an N$_2$ inlet tube, and a temperature probe was charged with 5-(3-(dimethylamino)propyl)-2-methylpyridin-3-amine hydrochloride (25 g, 0.109 mol). Acetonitrile (275 mL, 11 vol) was added to it followed by acetic acid (25 mL, 1 vol). The initial suspension turned into a clear solution after the addition of acetic acid. Chloroformamidine hydrochloride (15.6 g, 0.136 mol, 1.25 equiv) was added to the solution resulting in a suspension. The reaction was heated at 40° C. for 30 min and at 50° C. for another 30 min. Then the temperature was raised to 60° C. and the reaction was continued at this temperature. After 1-2 h at 60° C., the reaction mixture became turbid and after 3-4 h, solid started separating out. The reaction was continued at 60° C. for 20 h and was judged complete by LC-MS analysis. The reaction was cooled to ambient temperature and the solid was collected by filtration (N$_2$ flow was used during the filtration). The filter cake was washed with acetonitrile (50 mL, 2 vol). The solid was dried under high vacuum overnight to obtain N-{5-[3-(Dimethylamino)propyl]-2-methylpyridin-3-yl}guanidine trihydrochloride (32.1 g, 85% recovery) as a light brown solid. Elemental analysis Calcd: C, 41.81; H, 7.02; Cl, 30.85; N, 20.32. Found: C, 41.09; H, 6.72; Cl, 31.51; N, 20.47; $^1$H NMR (500 MHz, D$_2$O) δ ppm: 8.57 (s, 1H), 8.45 (s, 1H), 3.22-3.19 (m, 2H), 2.90 (t, 2H, J=10 Hz), 2.86 (s, 6H), 2.69 (s, 3H), 2.15-2.07 (m, 2H); ESI-MS m/z 236 (M+H, 100%).

Compounds in the following table may be prepared as the hydrochloride salts from the appropriate starting materials using the procedures described above:

N-{6-[3-(dimethylamino)propyl]-2-methylpyridin-3-yl}guanidine
N-{5-[3-(dimethylamino)propyl]-6-methylpyridin-3-yl}guanidine
N-{5-[3-(dimethylamino)propyl]-2-ethylpyridin-3-yl}guanidine
N-{2-methyl-5-[3-(methylamino)propyl]pyridin-3-yl}guanidine
N-[5-(3-hydroxypropyl)-2-methylpyridin-3-yl]guanidine
N-{5-[3-(dimethylamino)propyl]pyridin-3-yl}guanidine N-(2-Methyl-6-morpholin-4-ylpyridin-3-yl)guanidine

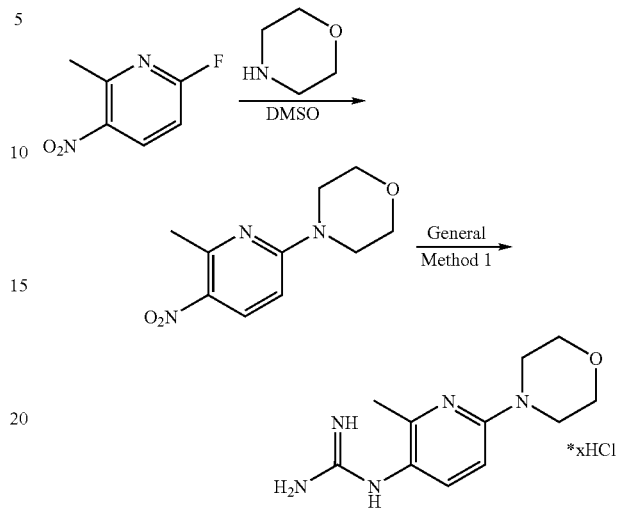

Step 1: 4-(6-Methyl-5-nitropyridin-2-yl)morpholine

To a solution of 2-fluoro-5-nitro-6-picoline (3.0 g, 19.2 mmol) in DMSO (26 mL) were added morpholine (3.35 mL, 38.4 mmol) and potassium carbonate (6.64 g, 48.0 mmol). The reaction mixture was allowed to stir overnight, at 70° C. The reaction mixture was then partitioned between EtOAc (40 mL) and water (40 mL). The organic solution was separated and the aqueous solution was extracted with EtOAc (2×40 mL). The organic solutions were combined, washed with brine, dried over MgSO$_4$, filtered and concentrated to give 4-(6-methyl-5-nitropyridin-2-yl)morpholine (4.0 g, 99%), as a muddy green solid. LCMS (FA): R$_t$=1.59 min, m/z=224.0 (M+H).

Step 2: N-(2-Methyl-6-morpholin-4-ylpyridin-3-yl)guanidine

The hydrochloride salt of N-(2-methyl-6-morpholin-4-ylpyridin-3-yl)guanidine was prepared from 4-(6-methyl-5-nitropyridin-2-yl)morpholine following the procedures of General Method 1.

Compounds in the following table were prepared as the hydrochloride salts from the appropriate starting materials using the procedures described above:

N-{6-[4-(dimethylamino)piperidin-1-yl]-2-methylpyridin-3-yl}guanidine
N-{2-methyl-6-[methyl(1-methylpyrrolidin-3-yl)amino]pyridin-3-yl}guanidine
N-{2-methyl-6-[(1-methylpiperidin-4-yl)amino]pyridin-3-yl}guanidine
N-(6-{[3-(dimethylamino)propyl]amino}-2-methylpyridin-3-yl)guanidine
N-{2-methyl-6-[(1-methylpiperidin-4-yl)oxy]pyridin-3-yl}guanidine
N-(2-methyl-6-piperidin-1-ylpyridin-3-yl)guanidine
N-(2-methyl-6-pyrrolidin-1-ylpyridin-3-yl)guanidine
N-[2-methyl-6-(4-methylpiperazin-1-yl)pyridin-3-yl]guanidine
N-[2-methyl-6-(piperidin-4-ylamino)pyridin-3-yl]guanidine
N-[6-(isopropylamino)-2-methylpyridin-3-yl]guanidine
N-[2-methyl-6-(tetrahydro-2H-pyran-4-ylamino)pyridin-3-yl]guanidine
N-{2-methyl-6-[methyl(1-methylpiperidin-4-yl)amino]pyridin-3-yl}guanidine
N-(6-{[2-(dimethylamino)ethyl]amino}-2-methylpyridin-3-yl)guanidine -continued N-{6-[[2-(dimethylamino)ethyl](methyl)amino]-2-methylpyridin-3-yl}guanidine
N-{6-[[3-(dimethylamino)propyl](methyl)amino]-2-methylpyridin-3-yl}guanidine
N-(6-{[3-(dimethylamino)propyl]amino}-2-methylpyridin-3-yl)guanidine
N-{6-[3-(dimethylamino)piperidin-1-yl]-2-methylpyridin-3-yl}guanidine
N-[2-methyl-6-(piperidin-4-ylamino)pyridin-3-yl]guanidine
N-(2-methyl-6-{[(1-methylpiperidin-4-yl)methyl]amino}pyridin-3-yl)guanidine
N-{4-methyl-6-[(1-methylpiperidin-4-yl)amino]pyridin-3-yl}guanidine

N-[6-(Dimethylamino)-2-methyl-5,6,7,8-tetrahydroquinolin-3-yl]guanidine

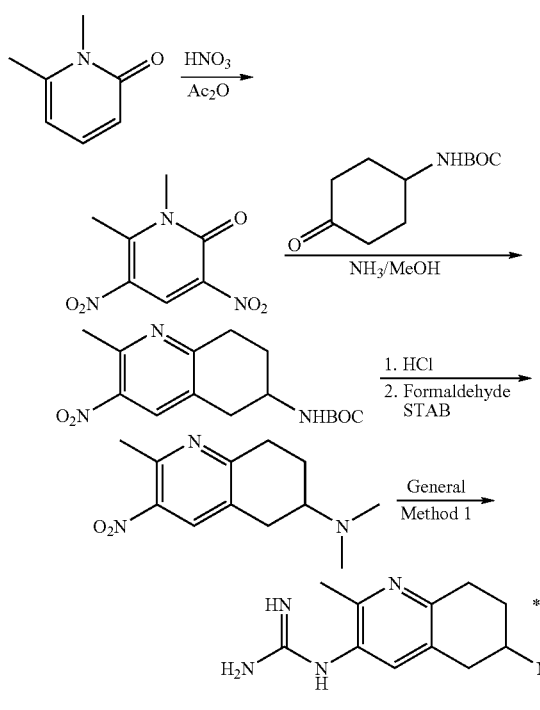

Step 1: 1,6-Dimethyl-3,5-dinitropyridin-2(1H)-one

To a solution of 1,6-dimethylpyridin-2(1H)-one (3.40 g, 27.60 mmol) in acetic anhydride (35 mL) was added fuming nitric acid (15 mL) dropwise over 3 h. The reaction mixture was allowed to stir for an additional 3 h, then the reaction mixture was cooled to 0° C. and water (30 mL) was added. The mixture was filtered and the solid was purified by column chromatography to give 1,6-dimethyl-3,5-dinitropyridin-2(1H)-one (1.82 g, 30%).

Step 2: 1,6-tert-Butyl (2-methyl-3-nitro-5,6,7,8-tetrahydroquinolin-6-yl)carbamate To a sealed tube was added 1,6-dimethyl-3,5-dinitropyridin-2(1H)-one (0.16 g, 0.76 mmol), tert-butyl(4-oxocyclohexyl)carbamate (0.19 g, 0.91 mmol), and ammonia (1M in methanol, 9 mL). The resulting mixture was allowed to stir for 5 h at 60° C. and then allowed to cool to rt and concentrated. The residue was purified by column chromatography to give tert-butyl(2-methyl-3-nitro-5,6,7,8-tetrahydroquinolin-6-yl)carbamate (0.066 g, 28%) as a solid.

Step 3: N,N-2-Trimethyl-3-nitro-5,6,7,8-tetrahydroquinolin-6-amine

To a round bottom flask was added tert-butyl(2-methyl-3-nitro-5,6,7,8-tetrahydroquinolin-6-yl)carbamate (0.14 g, 0.46 mmol) and HCl (4M in dioxane, 8 mL). The resulting mixture was allowed to stir for 5 h. The mixture was concentrated, and then water (10 mL), sodium triacetoxyborohydride (0.29 g, 1.38 mmol), and formaldehyde (37% in water, 6 mL) were added. The resulting mixture was allowed to stir for 80 min. Solid NaOH was added until the solution was basic. The mixture was extracted with EtOAc (2×30 mL). The organic solutions were combined, dried over $Na_2SO_4$, filtered and concentrated to give N,N-2-trimethyl-3-nitro-5,6,7,8-tetrahydroquinolin-6-amine (0.11 g, 97%) as a solid.

Step 4: N-[6-(Dimethylamino)-2-methyl-5,6,7,8-tetrahydroquinolin-3-yl]guanidine The hydrochloride salt of N-[6-(dimethylamino)-2-methyl-5,6,7,8-tetrahydroquinolin-3-yl]guanidine was prepared from N,N-2-trimethyl-3-nitro-5,6,7,8-tetrahydroquinolin-6-amine following the procedures of General Method 1. LCMS (FA): $R_t$=0.24 min, m/z=248.2 (M+H).

Compounds in the following table were prepared as the hydrochloride salts from the appropriate starting materials using the procedures described above:

| |
|---|
| N-(2,6-dimethyl-5,6,7,8-tetrahydro-1,6-naphthyridin-3-yl)guanidine |

N-{5-[2-(Dimethylamino)ethyl]-2-methylpyridin-3-yl}guanidine

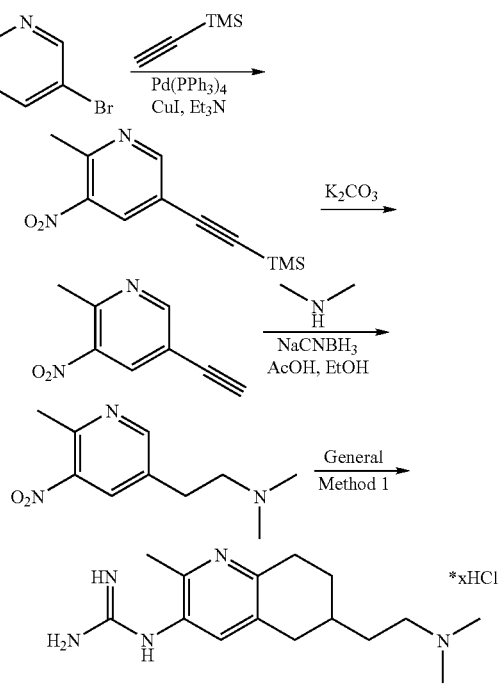

155
Step 1: 2-Methyl-3-nitro-5-[(trimethylsilyl)ethynyl]pyridine

To a solution of 5-bromo-2-methyl-3-nitropyridine (9.38 g, 43.2 mmol) and (trimethylsilyl)acetylene (9.16 mL, 64.8 mmol) in triethylamine (300 mL) were added bis(triphenylphosphine)palladium(II)chloride (3.34 g, 4.75 mmol) and copper(I) iodide (1.64 g, 8.64 mmol). The reaction mixture was allowed to stir for 4 h at 80° C. and then cooled to rt and filtered through Celite®. The filter pad was washed with EtOAc and the filtrate was washed with saturated aqueous NaHCO$_3$ (500 mL) then brine (500 mL). The organic solution was dried over Mg$_2$SO$_4$, filtered and concentrated. The residue was purified by column chromatography to give 2-methyl-3-nitro-5-[(trimethylsilyl)ethynyl]pyridine (9.22 g, 91%). LCMS (FAL): R$_t$=11.04 min, m/z=235.1 (M+H).

Step 2: 5-Ethynyl-2-methyl-3-nitropyridine

A solution of 2-methyl-3-nitro-5-[(trimethylsilyl)ethynyl]pyridine (2.32 g, 9.90 mmol) in methanol (22 mL) was cooled to 0° C. and potassium carbonate (137 mg, 0.99 mmol) was added. The reaction mixture was allowed to warm and stir at rt for 10 min, during which time a yellow precipitate formed. The reaction mixture was then concentrated and diluted with ether (200 mL). The organic solution was washed with water (200 mL) and brine (200 mL), dried over MgSO$_4$, filtered and concentrated to give 5-ethynyl-2-methyl-3-nitropyridine (1.48 g, 92%) as a solid. LCMS (FA): R$_t$=1.64 min, m/z=163.0 (M+H).

Step 3: N,N-Dimethyl-2-(6-methyl-5-nitropyridin-3-yl)ethanamine

To a solution of 5-ethynyl-2-methyl-3-nitropyridine (930 mg, 5.74 mmol) in EtOH (7 mL) were added dimethylamine hydrochloride (2.34 g, 28.7 mmol) and sodium cyanoborohydride (0.721 g, 11.5 mmol). The reaction mixture was allowed to stir at reflux for 24 h, concentrated, and treated with 4N NaOH (10 mL). The solution was extracted with DCM (2×200 mL). The organic solutions were combined, washed with brine (200 mL), dried over MgSO$_4$, filtered and concentrated. The residue was purified by column chromatography to give N,N-dimethyl-2-(6-methyl-5-nitropyridin-3-yl)ethanamine (489 mg, 41%). LCMS (AA): R$_t$=1.35 min, m/z 210 (M+H).

Step 4: N-{5-[2-(dimethylamino)ethyl]-2-methylpyridin-3-yl}guanidine

The hydrochloride salt of N-{5-[2-(dimethylamino)ethyl]-2-methylpyridin-3-yl}guanidine was prepared from N,N-dimethyl-2-(6-methyl-5-nitropyridin-3-yl)ethanamine following the procedures of General Method 1.

Compounds in the following table were prepared as the hydrochloride salt from the appropriate starting materials using the procedures described above:

---

N-[2-methyl-5-(2-piperidin-1-ylethyl)pyridin-3-yl]guanidine
N-[2-methyl-5-(2-morpholin-4-ylethyl)pyridin-3-yl]guanidine
N-(5-{2-[3-(dimethylamino)piperidin-1-yl]ethyl}-2-methylpyridin-3-yl)guanidine
N-[2-methyl-5-(2-pyrrolidin-1-ylethyl)pyridin-3-yl]guanidine
N-(5-{2-[4-(dimethylamino)piperidin-1-yl]ethyl}-2-methylpyridin-3-yl)guanidine

156
N-{2-Methyl-5-[2-(4-methylpiperazin-1-yl)ethyl]pyridin-3-yl}guanidine

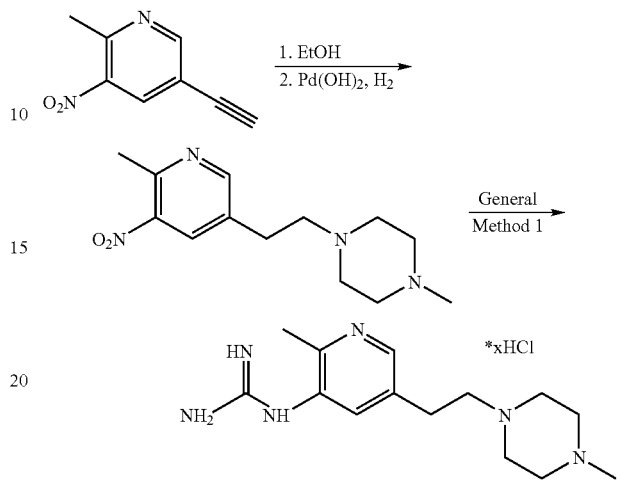

Step 1: 2-Methyl-5-[2-(4-methylpiperazin-1-yl)ethyl]pyridin-3-amine

To a solution of 5-ethynyl-2-methyl-3-nitropyridine (600 mg, 3.70 mmol) in EtOH (10 mL) was added 1-methylpiperazine (1.64 mL, 14.8 mmol). The reaction mixture was allowed to stir at reflux overnight. The reaction mixture was allowed to cool to rt and palladium hydroxide on carbon (0.060 g) was added to the solution. The reaction mixture was purged with hydrogen and then allowed to stir under an atmosphere of H$_2$ at rt overnight. The reaction mixture was filtered through celite and the filatrate was concentrated. The residue was purified by column chromatography to give 2-methyl-5-[2-(4-methylpiperazin-1-yl)ethyl]pyridin-3-amine (0.664 g, 77%).

Step 2: N-{2-Methyl-5-[2-(4-methylpiperazin-1-yl)ethyl]pyridin-3-yl}guanidine The hydrochloride salt of N-{2-methyl-5-[2-(4-methylpiperazin-1-yl)ethyl]pyridin-3-yl}guanidine was prepared from 2-methyl-5-[2-(4-methylpiperazin-1-yl)ethyl]pyridin-3-amine following the procedures of General Method 1.

Compounds in the following table were prepared as the hydrochloride salts from the appropriate starting materials using the procedures described above:

---

N-{5-[2-(cyclopentylamino)ethyl]-2-methylpyridin-3-yl}guanidine
N-{5-[2-(2,6-dimethylmorpholin-4-yl)ethyl]-2-methylpyridin-3-yl}guanidine
N-(5-{2-[3-(dimethylamino)pyrrolidin-1-yl]ethyl}-2-methylpyridin-3-yl)guanidine

157 tert-Butyl[3-(5-{[amino(imino)methyl]amino}-6-methylpyridin-3-yl)propyl]carbamate

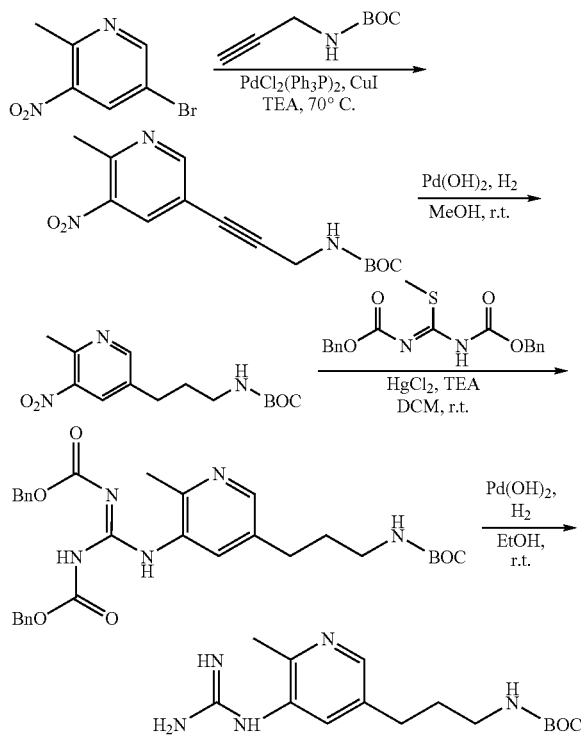

Step 1: tert-Butyl[3-(6-methyl-5-nitropyridin-3-yl)prop-2-yn-1-yl]carbamate To a solution of 5-bromo-2-methyl-3-nitropyridine (2.81 g, 12.9 mmol) in TEA (25 mL) was added tert-butyl prop-2-yn-1-ylcarbamate (2.58 g, 16.6 mmol). The solution was degassed with argon. To the reaction mixture were added bis(triphenylphosphine)palladium(II)chloride (0.18 g, 0.26 mmol) and copper(I)iodide (0.098 g, 0.52 mmol). The reaction mixture was allowed to stir at 70° C. for 2.5 h and was then concentrated and diluted with EtOAc (100 mL). The mixture was filtered over a pad of Celite® and the resulting filtrate was washed with sat. aq. NaHCO₃ (100 mL). The organic solution was dried over MgSO₄, filtered and concentrated. The residue was purified by column chromatography to give tert-butyl[3-(6-methyl-5-nitropyridin-3-yl)prop-2-yn-1-yl]carbamate (2.98 g, 79%) as a yellow solid. LCMS (FA): $R_t$=1.81 min, m/z=292.0 (M+H).

Step 2: tert-Butyl[3-(5-amino-6-methylpyridin-3-yl)propyl]carbamate

To a solution of tert-butyl[3-(6-methyl-5-nitropyridin-3-yl)prop-2-yn-1-yl]carbamate (2.98 g, 10.2 mmol) in MeOH (100 mL) was added palladium hydroxide on carbon (0.72 g). The reaction vessel was flushed with H₂ and then the reaction mixture was allowed to stir at rt under an atmosphere of hydrogen overnight. The reaction mixture was filtered over a pad of Celite® and the filtrate was concentrated to give tert-butyl[3-(5-amino-6-methylpyridin-3-yl)propyl]carbamate (2.97 g, >99%) as a yellow oil. LCMS (FA): $R_t$=0.85 min, m/z=266.0 (M+H).

158

Step 3: Dibenzyl{(Z)-[(5-{3-[(tert-butoxycarbonyl)amino]propyl}-2-methylpyridin-3-yl)amino]methylylidene}biscarbamate To a solution of tert-butyl[3-(5-amino-6-methylpyridin-3-yl)propyl]carbamate (2.99 g, 11.3 mmol), 1,3,-bis(benzyloxycarbonyl)-2-methyl-2-thiopseudourea (3.41 g, 9.51 mmol), and mercury(II)chloride (3.37 g, 12.4 mmol) in DCM (100 mL) was added TEA (5.19 mL, 37.3 mmol) dropwise via syringe. The reaction mixture was allowed to stir at rt overnight. The reaction mixture was filtered over a pad of Celite® and the resulting filtrate was concentrated. The residue was purified by column chromatography to give dibenzyl{(Z)-[(5-{3-[(tert-butoxycarbonyl)amino]propyl}-2-methylpyridin-3-yl)amino]methylylidene}biscarbamate (3.34 g, 61%) as a white solid. LCMS (FA): $R_t$=1.90 min, m/z=576.0 (M+H).

Step 4: tert-butyl[3-(5-{[amino(imino)methyl]amino}-6-methylpyridin-3-yl)propyl]carbamate To a solution of dibenzyl{(Z)[(5-{3-[(tert-butoxycarbonyl)amino]propyl}-2-methylpyridin-3-yl)amino]methylylidene}biscarbamate (3.34 g, 5.80 mmol) in MeOH (100 mL) was added palladium hydroxide on carbon (0.41 g). The reaction vessel was flushed with hydrogen gas and then allowed to stir at rt under an atmosphere of hydrogen gas overnight. The reaction mixture was filtered over a pad of Celite® and the filtrate was concentrated to give tert-butyl[3-(5-{[amino(imino)methyl]amino}-6-methylpyridin-3-yl)propyl]carbamate (1.77 g, 5.76 mmol, 99%) as a white solid. LCMS (FA): $R_t$=0.76 min, m/z=308.0 (M+H).

N-{5-[3-(Dimethylamino)propyl]-2-fluoropyridin-3-yl}guanidine

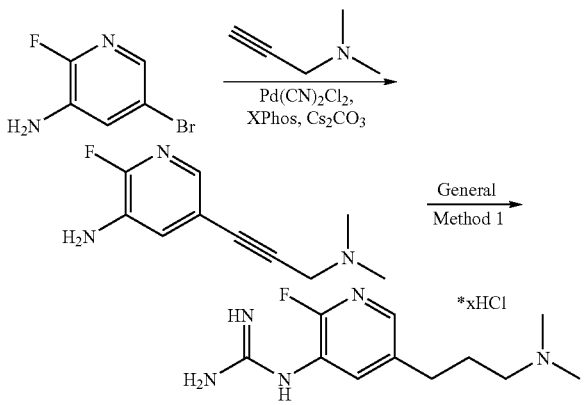

Step 1: 5-[3-(Dimethylamino)prop-1-yn-1-yl]-2-fluoropyridin-3-amine

A mixture of 5-bromo-2-fluoropyridin-3-amine (1.00 g, 5.24 mmol), N,N-dimethylprop-2-yn-1-amine (0.68 mL, 6.28 mmol), and cesium carbonate (3.41 g, 10.5 mmol) in DMF (25 mL) was degassed with argon for 15 min. To this slurry were added bis(acetonitrile)palladium(II)chloride (0.068 g, 0.26 mmol) and Xphos (0.324 g, 0.68 mmol). The suspension was allowed to stir at 50° C. for 4 h under an atmosphere of nitrogen and was then concentrated. The residue was purified by column chromatography to give 5-[3-(dimethylamino)prop-1-yn-1-yl]-2-fluoropyridin-3-amine (0.46 g, 45%).

Step 2: N-{5-[3-(Dimethylamino)propyl]-2-fluoropyridin-3-yl}guanidine

The hydrochloride salt of N-{5-[3-(dimethylamino)propyl]-2-fluoropyridin-3-yl}guanidine was prepared from 5-[3-(dimethylamino)prop-1-yn-1-yl]-2-fluoropyridin-3-amine following the procedures of General Method 1.

N-{5-[3-(Dimethylamino)propyl]pyridin-3-yl}guanidine

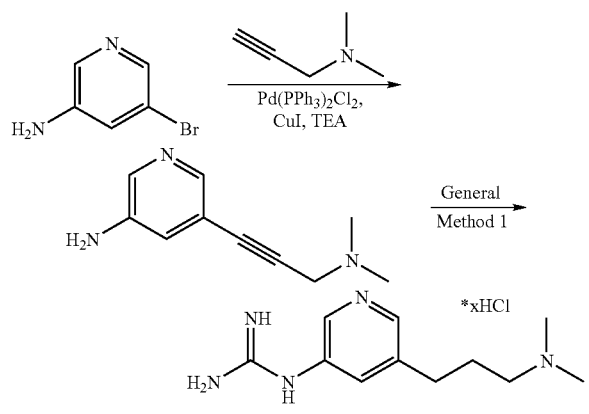

Step 1:
5-[3-(Dimethylamino)prop-1-yn-1-yl]pyridin-3-amine

To a degassed solution of 5-bromopyridin-3-amine (1.00 g, 5.78 mmol) and N,N-dimethylprop-2-yn-1-amine (1.57 mL, 14.6 mmol) in TEA (26 mL) were added bis(triphenylphosphine)palladium(II)chloride (0.203 g, 0.29 mmol) and copper iodide (0.110 g, 0.58 mmol). The reaction mixture was allowed to stir under an atmosphere of argon at 80° C. for 14 h. The reaction mixture was allowed to cool to rt and then filtered through Celite. The filter pad was washed with EtOAc and the filtrate was concentrated. The residue was purified by column chromatography to give 5-[3-(dimethylamino)prop-1-yn-1-yl]pyridin-3-amine (0.55 g, 54%).

Step 2: N-{5-[3-(Dimethylamino)propyl]pyridin-3-yl}guanidine

The hydrochloride salt of N-{5-[3-(dimethylamino)propyl]pyridin-3-yl}guanidine was prepared from 5-[3-(dimethylamino)prop-1-yn-1-yl]pyridin-3-amine following the procedures of General Method 1.

Compounds in the following table were prepared as the hydrochloride salts from the appropriate starting materials using the procedures described above:

| N-{5-[4-(dimethylamino)butyl]-2-methylpyridin-3-yl}guanidine |
| --- |

N-(2,4-Dimethylpyridin-3-yl)guanidine

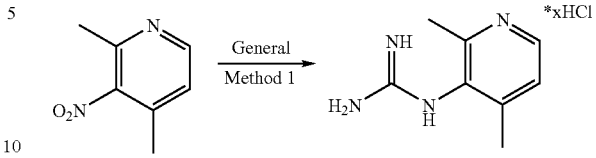

The hydrochloride salt of N-(2,4-dimethylpyridin-3-yl)guanidine was prepared from 2,4-dimethyl-3-nitropyridine following the procedures of General Method 1.

Compounds in the following table were prepared as the hydrochloride salts from the appropriate starting materials using the procedures described above:

| N-(2,6-dimethylpyridin-3-yl)guanidine |
| --- |

5-{[Amino(imino)methyl]amino}-6-methyl-N-(2-morpholin-4-ylethyl)pyridine-2-carboxamide

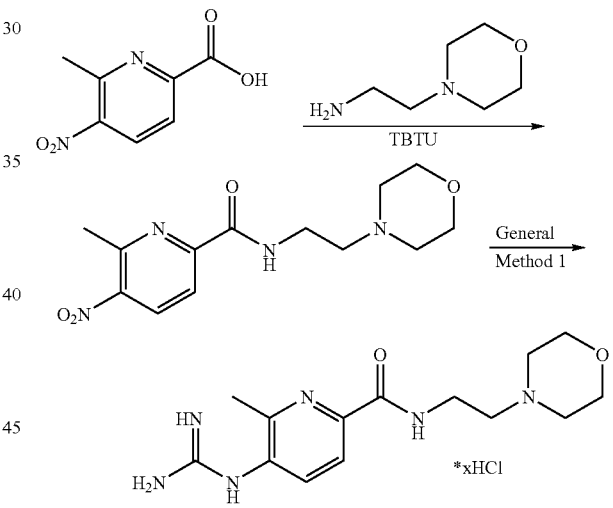

Step 1: 6-Methyl-N-(2-morpholin-4-ylethyl)-5-nitropyridine-2-carboxamide

To a solution of 6-methyl-5-nitropyridine-2-carboxylic acid (0.500 g, 3.0 mmol) in DCM (7 mL) were added 2-morpholin-4-ylethanamine (1.0 mL, 7.7 mmol), TBTU (0.992 g, 3.1 mmol), and DIEA (1.34 mL, 7.7 mmol). The reaction mixture was allowed to stir at rt overnight and then quenched with water. The organic solution was separated and the aqueous solution was extracted with DCM. The organic solutions were combined and concentrated. The residue was purified by column chromatography to give 6-methyl-N-(2-morpholin-4-ylethyl)-5-nitropyridine-2-carboxamide (0.27 g, 30%).

Step 2: 5-{[Amino(imino)methyl]amino}-6-methyl-N-(2-morpholin-4-ylethyl)pyridine-2-carboxamide The hydrochloride salt of 5-{[amino(imino)methyl]amino}-6-methyl-N-(2-morpholin-4-ylethyl)pyridine-2-car-

161 boxamide was prepared from 6-methyl-N-(2-morpholin-4-ylethyl)-5-nitropyridine-2-carboxamide from the appropriate starting materials following the procedures of General Method 1.

N-[2-Methyl-5-(4-methylpiperazin-1-yl)pyridin-3-yl]guanidine

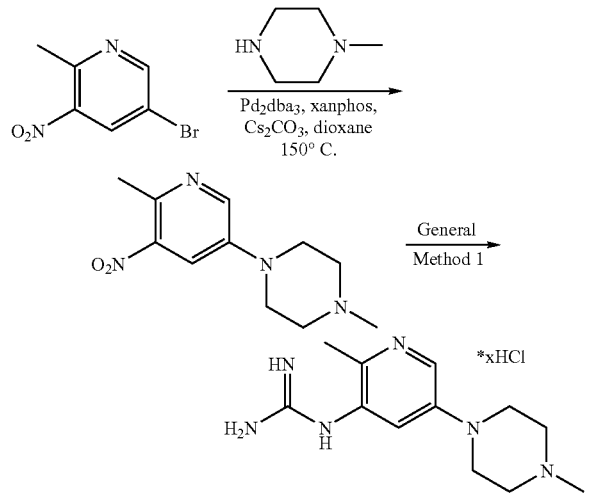

Step 1: 1-Methyl-4-(6-methyl-5-nitropyridin-3-yl)piperazine

1-Methylpiperazine (1.79 mL, 16.1 mmol) was added to a suspension of 5-bromo-2-methyl-3-nitropyridine (1.00 g, 4.61 mmol), 4,5-bis(diphenylphosphino)-9,9-dimethylxanthene (267 mg, 0.461 mmol), tris(dibenzylideneacetone)dipalladium(0) (170 mg, 0.180 mmol) and cesium carbonate (3.00 g, 9.22 mmol) in 1,4-dioxane (20.0 mL) under argon in a sealed reaction vessel. The reaction mixture was allowed to stir for 22 h, at 150° C. The reaction mixture was next partitioned between EtOAc (50 mL) and water (50 mL). The organic solution was separated and the aqueous solution was extracted with EtOAc (3×50 mL). The organic solutions were combined, washed with brine (twice), dried over $MgSO_4$, filtered and concentrated. The residue was purified by column chromatography to give 1-methyl-4-(6-methyl-5-nitropyridin-3-yl)piperazine (0.77 g, 71%) as a brown solid, LCMS (FA): $R_t$=1.07 min, m/z=237.3 (M+H).

Step 2: N-[2-Methyl-5-(4-methylpiperazin-1-yl)pyridin-3-yl]guanidine

The hydrochloride salt of N-[2-methyl-5-(4-methylpiperazin-1-yl)pyridin-3-yl]guanidine was prepared from 1-methyl-4-(6-methyl-5-nitropyridin-3-yl)piperazine following the procedures of General Method 1.

Compounds in the following table were prepared as the hydrochloride salts from the appropriate starting materials using the procedures described above:

---

N-{5-[(3S)-4-ethyl-3-methylpiperazin-1-yl]-2-methylpyridin-3-yl}guanidine
N-{5-[(3R,5S)-4-ethyl-3,5-dimethylpiperazin-1-yl]-2-methylpyridin-3-yl}guanidine
N-{5-[(3S)-4-ethyl-3-methylpiperazin-1-yl]-2-methylpyridin-3-yl}guanidine

---

162

Example 9

Synthesis of Pyridyl Halides Used for the Preparation of Compounds of Formula vi

3-(5-Bromo-2-methoxypyridin-3-yl)-N,N-dimethylpropan-1-amine

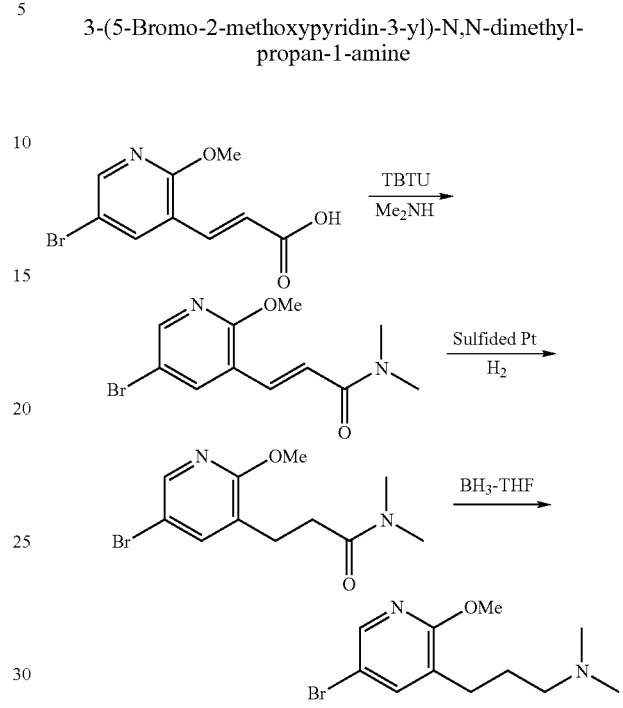

Step 1: (2E)-3-(5-Bromo-2-methoxypyridin-3-yl)-N,N-dimethylacrylamide

To a solution of (2E)-3-(5-bromo-2-methoxypyridin-3-yl) acrylic acid (1.00 g, 3.87 mmol) in DCM (10 mL) were added dimethylamine (2.0 M in THF, 5.80 mmol), DIEA (2.02 mL, 11.6 mmol) and TBTU (1.49 g, 4.65 mmol). The reaction mixture was allowed to stir at rt overnight. The reaction was quenched with water and then the aqueous solution was extracted with DCM. The organic solutions were combined, washed with brine, dried over $Na_2SO_4$, filtered and concentrated. The residue was purified by column chromatography to give (2E)-3-(5-bromo-2-methoxypyridin-3-yl)-N,N-dimethylacrylamide (1.05 g, 95%) as a white solid. LCMS (FA): $R_t$=1.68 min, m/z=285.1 (M+H).

Step 2: 3-(5-Bromo-2-methoxypyridin-3-yl)-N,N-dimethylpropanamide

To a solution of (2E)-3-(5-bromo-2-methoxypyridin-3-yl)-N,N-dimethylacryamide (1.05 g, 3.68 mmol) in EtOH (50 mL) was added platinum on sulfided carbon (5% Pt, 600 mg). The reaction mixture was flushed with hydrogen gas and allowed to stir at rt for 1 h under an atmosphere of hydrogen. The reaction mixture was filtered through a Celite® pad and washed with MeOH. The filtrate was concentrated to give 3-(5-bromo-2-methoxypyridin-3-yl)-N,N-dimethylpropanamide (1.0 g, 94%) as an oil. LCMS (FA): $R_t$=1.64 min, m/z=287.2 (M+H).

Step 3: 3-(5-Bromo-2-methoxypyridin-3-yl)-N,N-dimethylpropan-1-amine

To a solution of 3-(5-bromo-2-methoxypyridin-3-yl)-N,N-dimethylpropanamide (1.0 g, 3.0 mmol) in THF (40 mL) was added borane-tetrahydrofuran (1.0 M in THF, 8.71 mL) slowly. The reaction mixture was allowed to stir for 3 h at 50° C. The mixture was allowed to cool to rt and then concentrated to dryness. To the residue, a solution of HCl (3.0 M in water, 40 mL) was added. The resulting mixture was allowed to stir for 2 h at 80° C. The mixture was allowed to cool to rt and then was basified to pH>10 with a potassium hydroxide solution. The aqueous solution was extracted with DCM. The organic solutions were combined, washed with brine, dried over $Na_2SO_4$, filtered and concentrated. The residue was purified by column chromatography to give 3-(5-bromo-2-methoxypyridin-3-yl)-N,N-dimethylpropan-1-amine (0.377 g, 40%) as an oil. LCMS (FA): $R_t$=1.03 min, m/z=273.1 (M+H).

3-(5-Bromo-2-methoxypyridin-3-yl)-N,N-dimethylpropan-1-amine

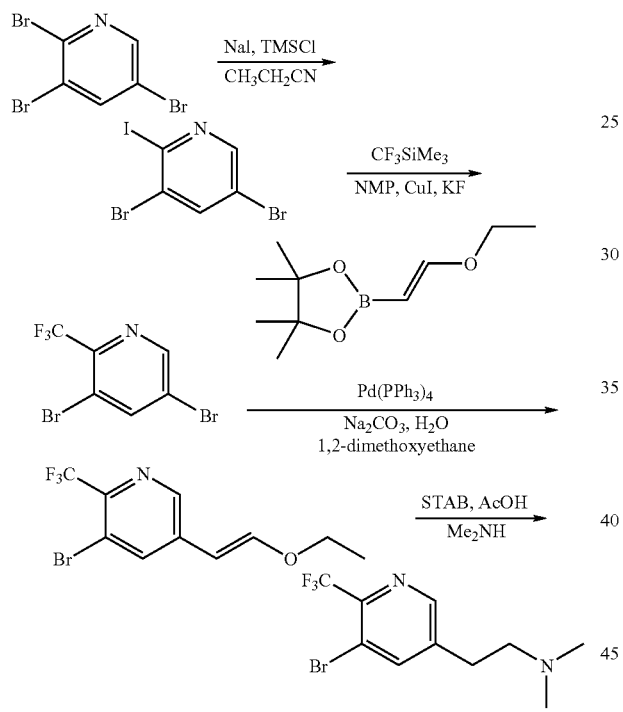

Step 1: 2-Iodo-3,5-dibromopyridine

To a sealed tube was added 2,3,5-tribromopyridine (5.63 g, 17.83 mol), sodium iodide (8.02 g, 53.50 mol), propanenitrile (45 mL), and chlorotrimethylsilane (2.26 mL, 17.83 mol). The resulting mixture was allowed to stir for 50 min at 105° C. The mixture was allowed to cool to rt and 2M NaOH (50 mL) was added. The mixture was extracted with EtOAc (2×80 mL). The organic solutions were combined, dried over $Na_2SO_4$, filtered and concentrated. The residue was purified by column chromatography to give 2-iodo-3,5-dibromopyridine (5.4 g, 83%) as a solid.

Step 2: 3,5-Dibromo-2-(trifluoromethyl)pyridine

To a solution of 2-iodo-3,5-dibromopyridine (4.21 g, 11.60 mmol) in NMP (25 mL) were added copper(I)iodide (4.42 g, 23.21 mmol), potassium fluoride (1.35 g, 23.21 mmol), and (trifluoromethyl)trimethylsilane (5.61 mL, 35.90 mmol). The resulting mixture was allowed to stir overnight at 50° C. The mixture was poured into 12% aqueous ammonia, and then extracted with $Et_2O$ (2×120 mL). The organic solutions were combined, dried over $Na_2SO_4$, filtered and concentrated. The residue was purified by column chromatography to give 3,5-dibromo-2-(trifluoromethyl)pyridine (1.63 g, 46%) as a liquid.

Step 3: 3-Bromo-5-[(E)-2-ethoxyvinyl]-2-(trifluoromethyl)pyridine

To a solution of 3,5-dibromo-2-(trifluoromethyl)pyridine (1.11 g, 3.65 mmol) in water (9 mL) were added 2-[(E)-2-ethoxyvinyl]-4,4,5,5-tetramethyl-1,3,2-dioxaborolane (0.72 g, 3.65 mmol), tetrakis(triphenylphosphine)-palladium(0) (0.42 g, 0.36 mmol), 1,2-dimethoxyethane (16.7 mL), and sodium carbonate (1.16 g, 11.0 mmol). The resulting mixture was allowed to stir overnight at 60° C. After the reaction was allowed to cool to rt, EtOAc (50 mL) was added. The organic solution was separated, dried over $Na_2SO_4$, filtered and concentrated. The residue was purified by column chromatography to give 3-bromo-5-[(E)-2-ethoxyvinyl]-2-(trifluoromethyl)pyridine (0.41 g, 38%), Step 4: 2-[5-Bromo-6-(trifluoromethyl)pyridin-3-yl]-N,N-dimethylethanamine To a solution of 3-bromo-5-[(E)-2-ethoxyvinyl]-2-(trifluoromethyl)-pyridine (0.35 g, 1.18 mmol) in AcOH (9 mL) was added water (3 mL). The resulting mixture was allowed to stir overnight at 105° C. The mixture was allowed to cool to rt. Dimethylamine hydrochloride (0.96 g, 11.8 mmol) and DCM (40 mL) were added. The resulting mixture was allowed to stir for 2 h. Sodium triacetoxyborohydride (0.50 g, 2.36 mmol) was added in portions over 50 min. The resulting mixture was allowed to stir for 3 h and was then concentrated. To the residue was added saturated $NaHCO_3$ (40 mL), and the mixture was extracted with EtOAc (2×30 mL). The organic solutions were combined, dried over $Na_2SO_4$, filtered and concentrated. The residue was purified by column chromatography to give 2-[5-bromo-6-(trifluoromethyl)pyridin-3-yl]-N,N-dimethylethanamine (0.052 g, 15%) as a solid. LCMS (AA): $R_t$=1.24 min, m/z=297.0 (M+H).

4-[2-(5-Bromopyridin-3-yl)ethyl]morpholine

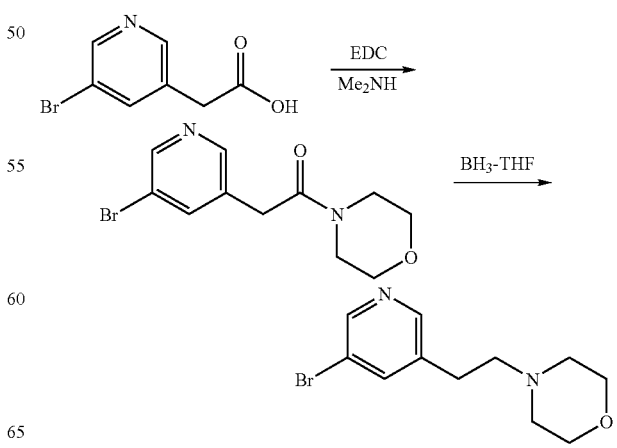

Step 1: 4-[(5-Bromopyridin-3-yl)acetyl]morpholine

To a solution of (5-bromopyridin-3-yl)acetic acid (1.00 g, 4.63 mmol) and morpholine (0.50 mL, 5.73 mmol) in DCM (50 mL) was added EDC (1.78 g, 9.30 mmol) and 1-hydroxybenzotriazole (1.25 g, 9.26 mmol). The reaction mixture was allowed to stir at rt for 50 min and then diluted with DCM (50 mL) and 1N HCl (100 mL). The organic solution was separated and discarded. The aqueous solution was neutralized with sat. aq. NaHCO$_3$ (100 mL) and was extracted with DCM (3×50 mL). The organic solutions were combined, dried over MgSO$_4$, filtered and concentrated to give 4-[(5-bromopyridin-3-yl)acetyl]morpholine (1.26 g, 4.40 mmol, 95%) as a light brown solid. LCMS (FA): R$_t$=1.11 min, m/z=287.0 (M+H).

Step 2: 4-[2-(5-Bromopyridin-3-yl)ethyl]morpholine

To a solution of 4-[(5-bromopyridin-3-yl)acetyl]morpholine (1.26 g, 4.40 mmol) in THF (15 mL) was added a 1M solution of borane in THF (23.2 mL, 23.2 mmol). The reaction mixture was allowed to stir at 55° C. overnight and then was allowed to cool to rt and then diluted with water (100 mL) and EtOAc (100 mL). The organic solution was separated and the aqueous solution was extracted with EtOAc (2×50 mL). The organic solutions were combined, dried over MgSO$_4$, filtered and concentrated to give a yellow oil, which was dissolved in 1N HCl (100 mL). This solution was allowed to stir at 80° C. overnight. The reaction mixture was neutralized with sat. aq. NaHCO$_3$ (100 mL) and then extracted with EtOAc (3×50 mL). The combined organic solutions were washed with brine, dried over MgSO$_4$, filtered and concentrated to give 4-[2-(5-bromopyridin-3-yl)ethyl]morpholine (0.631 g, 2.33 mmol, 53%) as a light yellow oil. LCMS (FA): R$_t$=0.50 min, m/z=273.0 (M+H).

Compounds in the following table were prepared from the appropriate starting materials using the procedures described above:

---
2-(5-bromopyridin-3-yl)-N,N-dimethylethanamine
1-[2-(5-bromopyridin-3-yl)ethyl]-4-methylpiperazine
---

5-Bromo-2-(pyrrolidin-1-yl)pyridine

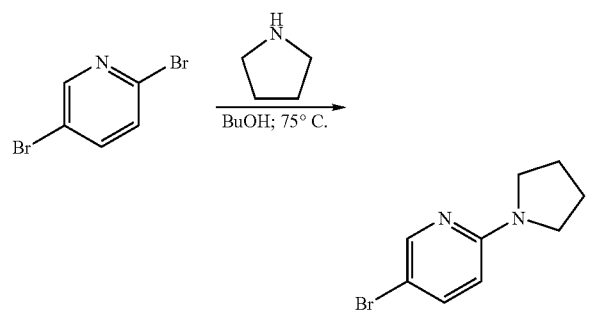

A solution of 2,5-dibromopyridine (1.60 g, 6.76 mmol) and pyrrolidine (5.64 mL, 67.6 mol) in 1-butanol (10.0 mL) was allowed to stir in a sealed reaction vessel while heating at 75° C. for 16 h. The reaction solvent was evaporated to produce an oily solid which was purified by column chromatography to give 5-bromo-2-(pyrrolidin-1-yl)pyridine (1.50 g, 6.60 mmol, 98%) as a white solid. LCMS (FA): m/z=229.1 (M+H).

Compounds in the following table were prepared from the appropriate starting materials using the procedure described above:

---
1-(5-bromopyridin-2-yl)-4-methylpiperazine
4-(5-bromopyridin-2-yl)morpholine
N-(5-bromopyridin-2-yl)-N,N',N'-trimethylpropane-1,3-diamine
---

N-(5-Chloropyridin-2-yl)-2,2-dimethylpropanamide

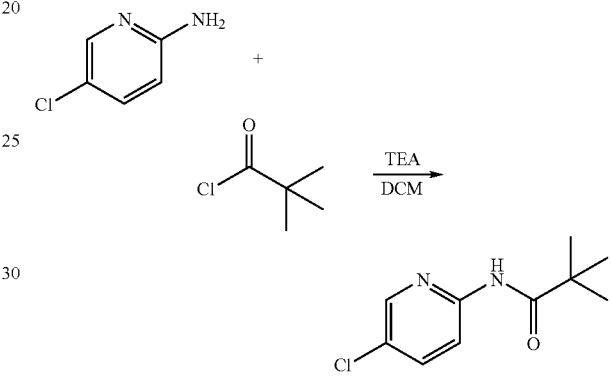

TEA (6.78 mL, 48.6 mmol) was added to a suspension of 2-amino-5-chloropyridine (5.00 g, 38.9 mmol) in DCM (75 mL). The resulting solution was cooled to 0° C. and a solution of 2,2-dimethylpropanoyl chloride (5.74 mL, 46.7 mmol) in DCM (10.0 mL) was added dropwise over a 5 min period. The resulting mixture was allowed to stir at rt for 1 h. The reaction mixture was then transferred to a separatory funnel and washed with a saturated aqueous solution of NaHCO$_3$. The organic solution was dried over MgSO$_4$, filtered and concentrated. The residue was purified by column chromatography to give N-(5-chloropyridin-2-yl)-2,2-dimethylpropanamide (8.0 g, 40 mmol, 99%). LCMS (FA): m/z=215.1 (M+H).

3-(5-Bromo-2,6-dimethylpyridin-3-yl)-N,N-dimethylprop-2-yn-1-amine

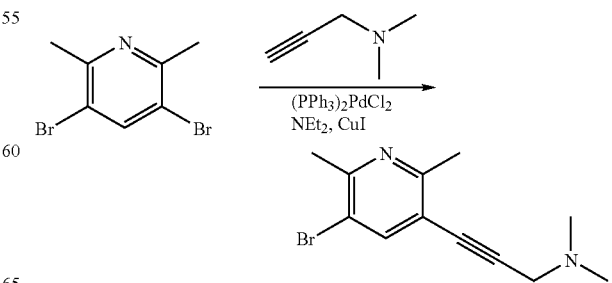

To a mixture of 3,5-dibromo-2,6-dimethylpyridine (605 mg, 2.54 mmol), copper iodide (22 mg, 0.11 mmol) and bis(triphenylphosphine)palladium(II)chloride (41 mg, 0.058 mmol) in diethylamine (3.0 mL) was added propargyl(dimethylamine) (0.27 mL, 2.50 mmol). The reaction mixture was allowed to stir for 15 h at 50° C. and was then allowed to cool to rt. The resulting mixture was diluted with EtOAc (30 mL) and 1M aqueous $Na_2CO_3$ (20 mL). After stirring for 30 min, the organic solution was separated and the aqueous solution was extracted with EtOAc (2×15 mL). The organic solutions were combined, washed with water and brine, dried over $Na_2SO_4$, filtered and concentrated. The residue was purified by column chromatography to give 3-(5-bromo-2,6-dimethylpyridin-3-yl)-N,N-dimethylprop-2-yn-1-amine (313 mg, 51%) as a dark oil. LCMS (AA): $R_t$=1.47 min, m/z=267.1 (M−H), 269.1 (M+H).

1-(5-Bromopyridin-3-yl)-4-methylpiperazine

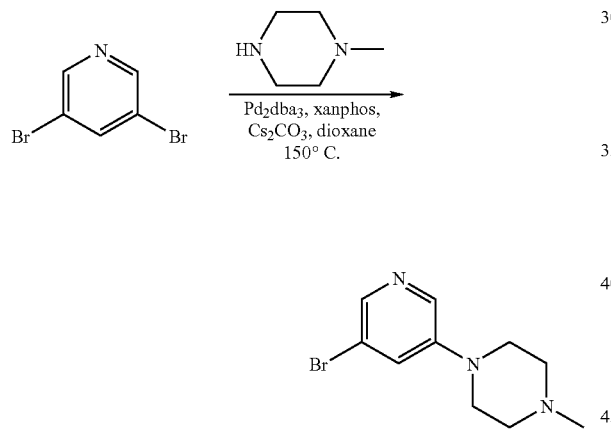

To a suspension of 3,5-dibromopyridine (0.30 g, 4.6 mmol), 4,5-bis(diphenylphosphino)-9,9-dimethylxanthene (57 mg, 0.098 mmol), tris(dibenzylideneacetone)dipalladium(0) (32 mg, 0.035 mmol) and cesium carbonate (830 mg, 2.5 mmol) in 1,4-dioxane (4.0 mL) in a sealed rxn vessel was added 1-methylpiperazine (0.170 mL, 1.5 mmol) under argon. The reaction mixture was heated for 30 min in a microwave reactor, at 150° C. The reaction mixture was diluted with EtOAc (50 mL), washed with brine and water, dried over $Na_2SO_4$, then filtered and concentrated. The crude reaction product was purified by column chromatography to give 1-(5-bromopyridin-3-yl)-4-methylpiperazine (0.13 g, 39%) as a brown oil. LCMS (FA): $R_t$=1.03 min, m/z=258.0 (M+H).

Compounds in the following table were prepared from the appropriate starting materials using the procedure described above:

| |
|---|
| (2R)-4-(5-bromopyridin-3-yl)-1-ethyl-2-methylpiperazine |
| (2S)-4-(5-bromopyridin-3-yl)-1-ethyl-2-methylpiperazine |

Example 10

Synthesis of 2-({5-[3-(Dimethylamino)propyl]-2-methylpyridin-3-yl}amino)-9-(trifluoromethyl)-5,7-dihydro-6H-pyrimido[5,4-d][1]benzazepine-6-thione Monohydrochloride Salt

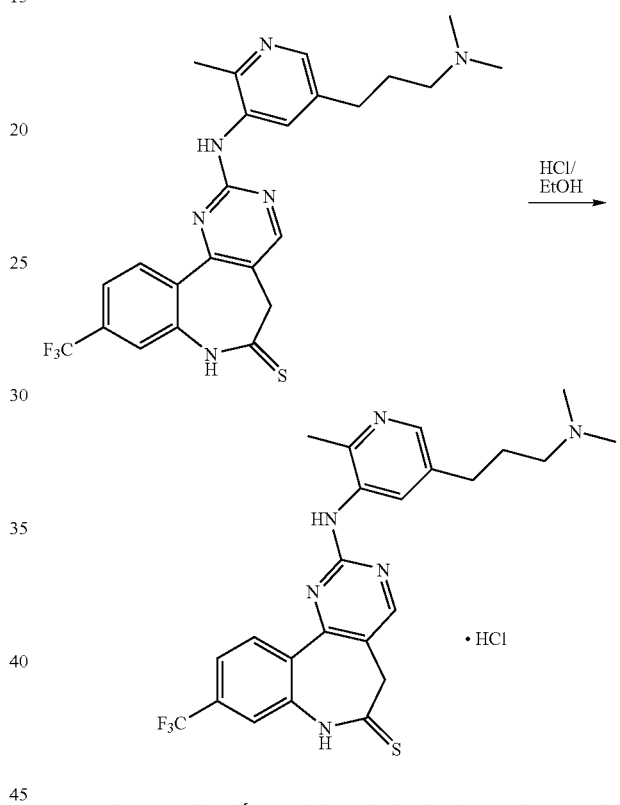

A mixture of 2-({5-[3-(Dimethylamino)propyl]-2-methylpyridin-3-yl}amino)-9-(trifluoromethyl)-5,7-dihydro-6H-pyrimido[5,4-d][1]benzazepine-6-thione (131.0 g, 269 mmol) in 200 P ethanol (1.05 L) was heated to reflux. A solution formed. Hydrochloric acid (1.25 M in ethanol, 43 mL, 53.8 mmol) was added slowly. Seeds were added. More hydrochloric acid (1.25 M in ethanol, 172 mL, 215 mmol) was added dropwise over 4 hours. The suspension formed was kept at reflux for 1 hour, then allowed to cool down to room temperature in 5 hours. The product was collected by filtration then washed with EtOH (20 mL). Drying under vacuo at 35° C. overnight afforded 2-({5-[3-(Dimethylamino)propyl]-2-methylpyridin-3-yl}amino)-9-(trifluoromethyl)-5,7-dihydro-6H-pyrimido[5,4-d][1]benzazepine-6-thione Monohydrochloride Salt as a light yellow solid (128 g, HPLC purity>99%, 90.9% yield). LCMS (FA): $R_t$=6.08 min, m/z 485.2 (M−H). FTIR: 1575, 1434, 1408, 1334, 1315, 1173, 1136, 1116, 1087, 787 $cm^{-1}$.

Example 11

Synthesis of 2-({5-[3-(Dimethylamino)propyl]-2-methylpyridin-3-yl}amino)-9-(trifluoromethyl)-5,7-dihydro-6H-pyrimido[5,4-d][1]benzazepine-6-thione Dihydrochloride Salt

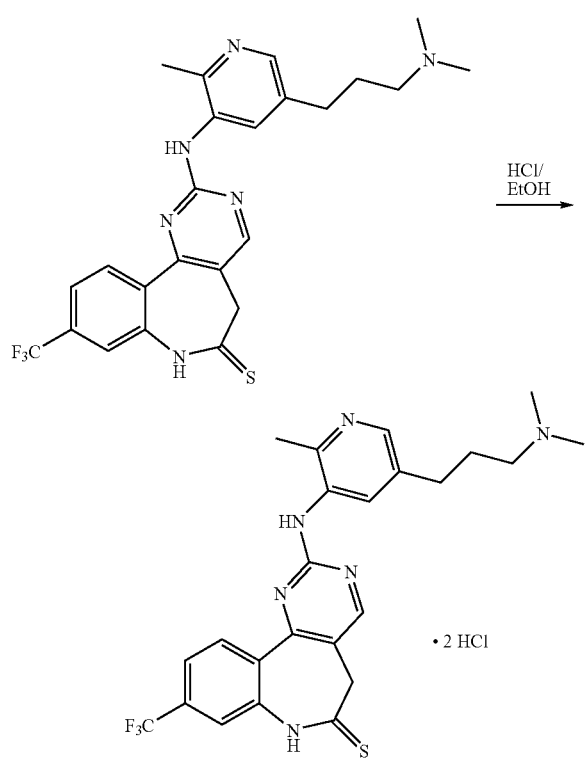

To a solution of 2-({5-[3-(Dimethylamino)propyl]-2-methylpyridin-3-yl}amino)-9-(trifluoromethyl)-5,7-dihydro-6H-pyrimido[5,4-d][1]benzazepine-6-thione (153 mg, 0.314 mmol) in Ethanol (5.1 mL, 87 mmol) under gentle reflux (oil bath at 85° C.) was added 0.89 M of Hydrochloric acid in Ethanol (7.0E2 µL, 0.63 mmol)(850 µl of conc. HCl in 10 ml of ethanol tritrated). The resulting solution was seeded and shortly thereafter solid formed. The mixture was allowed to cool at room temperature in the oil bath and was left overnight at room temperature. The solid was filtered off and dried under high vacuum to afford 2-({5-[3-(Dimethylamino)propyl]-2-methylpyridin-3-yl}amino)-9-(trifluoromethyl)-5,7-dihydro-6H-pyrimido[5,4-d][1]benzazepine-6-thione Dihydrochloride Salt as a yellow solid (163 mg, 92.6% yield).

Expression and Purification of Protein Kinase Enzymes

Example 12

PLK1 Enzyme Expression and Purification

Recombinant human PLK1 was expressed in *E. coli* as an N-terminal Smt fusion protein using a proprietary vector (pSGX4) by Structural Genomics (SGX). The fusion partner was removed through cleavage with Ulp1 after an initial purification using a Ni2+ affinity column.

Example 13

Protein Kinase Enzyme Assays

PLK1 DELFIA® Kinase Assay

The human PLK1 enzymatic reaction totaled 30 µL contained 50 mM Tris-HCl (pH 8.0), 10 mM $MgCl_2$, 0.02% BSA, 10% glycerol, 1 mM DTT, 100 mM NaCl, 3.3% DMSO, 50 µM ATP, 2 µM peptide substrate (Biotin-AHX-LDET-GHLDSSGLQEVHLA-$CONH_2$) and 0.3 nM recombinant human PLK1[2-369]T210D. The enzymatic reaction mixture, with or without PLK inhibitors, was incubated 90 minutes at room temperature before termination with 50 µL of STOP buffer containing 1% BSA, 0.05% Tween20, 100 mM EDTA. 50 µL of the stopped enzyme reaction mixture was transferred to a Neutravidin-coated 384-well plate (Pierce) and incubated at room temperature for 60 minutes. The wells were washed with wash buffer (25 mM Tris, 3 mM KCl, 14 mM NaCl and 0.1% Tween-20) and incubated for 1 hour with 50 µL of antibody reaction mixture containing 1% BSA, 0.05% Tween-20, anti-phospho-cdc25c rabbit monoclonal antibody (325 pM, Millennium Pharmaceuticals), europium labeled anti-rabbit IgG (2 nM, Perkin Elmer) in DELPHIA assay buffer (Perkin Elmer). The wells were washed and then the bound europium was liberated using 50 µL of Enhancement Solution (Perkin Elmer). Quantification of europium was done using a Pherastar (BMG Labtech)

The following compounds have PLK1 Delfia $IC_{50}$<5 nM: I-1, I-2, I-4, I-5, I-6, I-7, I-8, I-9, I-10, I-11, I-12, I-13, I-14, I-15, I-17, I-18, I-19, I-21, I-22, I-23, I-24, I-25, I-26, I-27, I-28, I-29, I-31, I-32, I-34, I-38, I-39, I-40, I-42, I-43, I-45, I-46, I-47, I-49, I-50, I-51, I-52, I-53, I-54, I-55, I-57, I-58, I-59, I-60, I-61, I-62, I-63, I-64, I-65, I-66, I-67, I-68, I-69, I-72, I-73, I-74, I-75, I-76, I-77, I-78, I-80, I-81, I-84, I-85, I-86, I-87, I-88, I-89, I-90, I-91, I-92, I-94, I-95, I-96, I-99, I-100, I-103, I-104, I-105, I-106, I-107, I-108, I-109, I-111, I-113, I-114, I-115, I-119

The following compounds have PLK1 Delfia $IC_{50}$ 5-25 nM:
I-3, I-16, I-33, I-35, I-36, I-41, I-44, I-56, I-70, I-71, I-79, I-82, I-83, I-93, I-97, I-101, I-102, I-110, I-112, I-116, I-117, I-118, I-121, I-122, I-123

The following compounds have PLK1 Delfia $IC_{50}$>25 nM: I-30, I-37, I-98, I-120

Example 14

Cellular Assays

PLK1 Phosphorylation Assay

Inhibition of PLK1 activity in whole cell systems can be assessed by determination of decreased phosphorylation of PLK1 substrates. For example, determining decreased phosphorylation of cdc25c on Threonine 96, a PLK1 substrate can be used to measure inhibition of PLK1 activity in a whole cell system. Alternatively, any known PLK1 substrate can be used in similar assay methods to assess inhibition of PLK1 activity.

In a specific example, HeLa cells were seeded in a 96-well cell culture plate ($4.5 \times 10^3$ cells/well) in Minimum Essential Medium supplemented with 10% FBS and incubated overnight at 37° C., 5% $CO_2$. pSGcdc25C (0.05 ug) and pCDNA3.1 PLK T210D (0.02 ug) DNA were transfected using 0.15 µl Fugene 6 (Roche) transfection reagent in each well. Cells were incubated with PLK1 inhibitors for 2 hours at 37° C., fixed with 4% paraformaldehyde for 15 minutes and then permeabilized for 15 minutes with 0.5% TritonX-100 in PBS. 100 µl of Roche blocking buffer was added to the wells prior to incubation with rabbit anti-pcdc25c T96 (1:2500, Millennium Pharmaceuticals) and mouse anti-myc (clone 9E10) (1:250, Millennium Pharmaceuticals Inc.) antibodies overnight at 4° C. After washing with PBS the cells were stained with anti-rabbit IgG Alexa 488 (1:500, Molecular Probes) and anti-mouse IgG Alexa 660 (1:500) for 45 minutes at room temperature. DNA was then stained with Hoechst solution (2 μg/ml). The percentage of pcdc25c and anti-myc positive cells were quantified using the Opera instrument and Acapella Image Analysis (Perkin Elmer.)

Mitotic Index Assay

HT29 cells (2.5×10$^3$ cells/well) in 75 μl of McCoy's 5A media (Invitrogen) supplemented with 10% FBS (Invitrogen) were seeded in wells of a 96-well Optilux plate (BD bioscience) and incubated for 24 hours at 37° C., 5% $CO_2$. 25 μl of serially diluted test compounds in McCoy's 5A media supplemented with 10% FCS (Gibco) were added to the wells. Cells were incubated for 24 hrs at 37° C. and then fixed with the addition of 50 μl of 4% paraformaldehyde for 10 minutes and permeabilizd for 10 minutes with the addition of 50 μl 0.5% TritonX-100 in PBS. After washing with PBST, 50 μl of 0.5% Roche blocking buffer was added to the wells and incubated for 1 hour at room temperature. Cells were then incubated with mouse anti-pHisH3 (1:500, Millennium Pharmaceuticals) for 1 hour at room temperature. After washing with PBST the cells were stained with anti-mouse IgG Alexa 594 (1:200) for 1 hour at room temperature. DNA was then stained with Hoechst solution (2 μg/ml). The percentage of pHisH3 cells were quantified using Discovery-1 and Meta-Morph (Molecular Devices.)

Anti-Proliferation Assays

8 μl of serially diluted test compounds were added to 75 μl of HT29 (2.66×10$^4$ cells/ml) cells in McCoy's 5A media supplemented with 10% FBS (Invitrogen) in Biocoat Poly-D lysine 384 well Black/Clear plates (BD Biosciences). Cells were incubated for 72 hrs at 37° C., 5% $CO_2$. Supernatant was aspirated from the wells, leaving 25 μl in each well. ATP-lite 1 step reagent (25 μl, Perkin Elmer) was added to each well and luminescence for each plate was read on the LeadSeeker (Amersham Biosciences). Percent inhibition was calculated using the values from a DMSO control set to 100%.

Example 15

In Vivo Assays

In Vivo Tumor Efficacy

HT29 human colon cancer cells with p53 deficiency are cultured in McCoy's 3A medium containing 10% FCS and incubated at 37° C., 5% $CO_2$. The cells are trypsinized and resuspended in Hanks buffer at 2×10$^7$ cells/mL. 100 μL of the cell suspension (2×10$^6$ cells) is aseptically injected into the subcutaneous space in the right dorsal flank of female NCR nude mice (age 7-10 weeks, Taconic) using a 23-ga needle. Seven days after implantation, the tumors are measured in two dimensions (length and width) with a caliper and the animal body weight is measured with a balance. Tumor volume is calculated with the following formula: tumor volume=L×W$^2$×0.5. When the average tumor volume reaches about 200 mm$^3$, the individual animals are assigned to different study groups using a random number generation method. The typical study consists of vehicle control, PLK1 inhibitor alone groups at various doses and schedules (10 animals/group). Tumor size and body weight are measured twice a week for three to four weeks. Once the tumor volume reaches over 10% of the body weight of the animal, or the mouse body weight loss is more than 20%, the mouse is euthanized. Data is collected and only those study groups which end the study with at least 7 animals are used for the analysis.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

The invention claimed is:

1. A compound of formula I:

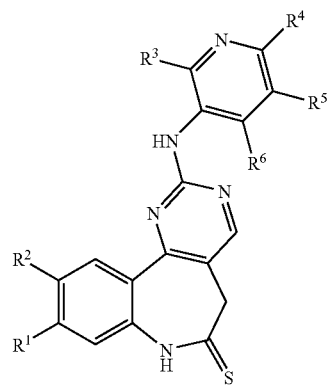

or a pharmaceutically acceptable salt thereof, wherein:

$R^1$ is selected from hydrogen, —CN, halogen, optionally substituted $C_{1-6}$aliphatic, or —YR$^{1a}$,
 wherein Y is —O—, —S—, or —NR$^{1a}$, and each occurrence of R$^{1a}$ is independently hydrogen, or optionally substituted $C_{1-6}$aliphatic;

$R^2$ is selected from hydrogen, halogen, —ZR$^{2a}$, or —OR$^{2b}$,
 wherein Z is an optionally substituted $C_{1-6}$ alkylene chain, and R$^{2a}$ is —OR$^{2b}$, —N(R$^{2b}$)$_2$, —SR$^{2b}$, —C(O)N(R$^{2b}$)$_2$, —N(R$^{2b}$)C(O)R$^{2b}$, —SO$_2$N(R$^{2b}$)$_2$, —NR$^{2b}$SO$_2$R$^{2b}$, —NR$^{2b}$C(O)N(R$^{2b}$)$_2$, or —NR$^{2b}$SO$_2$N(R$^{2b}$)$_2$, wherein each occurrence of R$^{2b}$ is independently hydrogen or optionally substituted $C_{1-6}$alkyl, or two occurrences of R$^{2b}$, taken together with a nitrogen atom to which they are bound, form an optionally substituted 3-7-membered heterocyclyl ring;

$R^3$ is selected from hydrogen, halogen, optionally substituted $C_{1-4}$alkyl, or optionally substituted $C_{1-4}$alkoxy;

$R^4$ is selected from hydrogen, optionally substituted $C_{1-6}$aliphatic, an optionally substituted 3-7-membered heterocyclyl ring, —(CH$_2$)$_x$NR$^{4a}$R$^{4b}$, —(CH$_2$)$_x$NR$^{4a}$C(O)R$^{4b}$, —(CH$_2$)$_x$NR$^{4a}$S(O)$_2$R$^{4b}$, —(CH$_2$)$_x$C(O)R$^{4b}$, —(CH$_2$)$_x$C(O)NR$^{4a}$R$^{4b}$, —(CH$_2$)$_x$S(O)$_2$NR$^{4a}$R$^{4b}$, or —(CH$_2$)$_x$OR$^{4b}$, wherein each occurrence of x is independently 0-6;

wherein R$^{4a}$ is hydrogen or optionally substituted $C_{1-6}$aliphatic, and

R$^{4b}$ is hydrogen, optionally substituted $C_{1-6}$aliphatic, optionally substituted $C_{3-7}$-heterocyclyl or $C_{3-7}$carbocyclyl ring, or is W—R$^{4c}$, wherein W is an optionally substituted $C_{2-6}$ alkylene chain, and R$^{4c}$ is an optionally substituted $C_{3-7}$-heterocyclyl ring, —OR$^{4d}$, —N(R$^{4d}$)$_2$, —SR$^{4d}$, —C(O)N(R$^{4d}$)$_2$, —N(R$^{4d}$)C(O)R$^{4d}$, —SO$_2$N(R$^{4d}$)$_2$, —NR$^{4d}$SO$_2$R$^{4d}$, —NR$^{4d}$C(O)N(R$^{4d}$)$_2$, or —NR$^{4d}$SO$_2$N(R$^{4d}$)$_2$, wherein each occurrence of R$^{4d}$ is independently hydrogen or optionally substituted C$_{1-6}$aliphatic, or two occurrences of R$^{4d}$, taken together with the nitrogen atom to which they are bound, form an optionally substituted 3-7-membered heterocyclyl ring;

or wherein R$^{4a}$ and R$^{4b}$, taken together with the nitrogen atom to which they are bound, form an optionally substituted 3-7-membered heterocyclyl ring;

R$^5$ is hydrogen, optionally substituted C$_{1-6}$aliphatic, an optionally substituted C$_{3-7}$-heterocyclyl ring, or is X—R$^{5a}$, wherein X is an optionally substituted C$_{2-6}$ alkylene chain or —NR$^{5c}$, wherein when X is an optionally substituted C$_{2-6}$ alkylene chain R$^{5a}$ is —OR$^{5b}$, —N(R$^{5b}$)$_2$, —SR$^{5b}$, —C(O)N(R$^{5b}$)$_2$, —N(R$^{5b}$)C(O)R$^{5b}$, —SO$_2$N(R$^{5b}$)$_2$, —NR$^{5b}$SO$_2$R$^{5b}$, —NR$^{5b}$C(O)N(R$^{5b}$)$_2$, or —NR$^{5b}$SO$_2$N(R$^{5b}$)$_2$; and when X is —NR$^{5c}$, R$^{5a}$ is hydrogen or optionally substituted C$_{1-6}$aliphatic, or R$^{5a}$ and R$^{5c}$, taken together with the nitrogen atom to which they are bound, form an optionally substituted 3-7-membered heterocyclyl ring;

wherein each occurrence of R$^{5b}$ and R$^{5c}$ is independently hydrogen or optionally substituted C$_{1-6}$aliphatic, or two occurrences of R$^{5b}$, or R$^{5a}$ and R$^{5c}$, taken together with the nitrogen atom to which they are bound, form an optionally substituted 3-7-membered heterocyclyl ring; or wherein R$^4$ and R$^5$, taken together, form an optionally substituted 5-7-membered cycloaliphatic or heterocyclyl ring; and R$^6$ is selected from hydrogen, halogen, optionally substituted C$_{1-4}$alkyl, or optionally substituted C$_{1-4}$alkoxy.

2. The compound of claim 1, wherein R$^2$, R$^4$, and R$^6$ are each hydrogen.

3. The compound of claim 1, wherein R$^2$, R$^5$, and R$^6$ are each hydrogen.

4. The compound of claim 1, wherein R$^1$ is optionally substituted C$_{1-4}$aliphatic, halogen, —CN, or —OMe.

5. The compound of claim 1, wherein R$^1$ is methyl, ethyl, —CF$_3$, Cl, —CN, —OMe, or cyclopropyl.

6. The compound of claim 1, wherein R$^2$ is hydrogen or —Z—R$^{2a}$, wherein Z is —(CH$_2$)$_{2-4}$ and R$^{2a}$ is N(R$^{2b}$)$_2$, wherein each occurrence of R$^{2b}$ is selected from hydrogen or C$_{1-4}$alkyl, or two occurrences of R$^{2b}$, taken together with the nitrogen atom to which they are bound, form an optionally substituted C$_{3-7}$-heterocyclyl ring.

7. The compound of claim 1, wherein R$^3$ is methyl or CF$_3$.

8. The compound of claim 1, wherein R$^4$ is methyl, or —NR$^{4a}$R$^{4b}$, wherein R$^{4a}$ and R$^{4b}$, taken together with the nitrogen atom to which they are bound, form an optionally substituted 3-7-membered heterocyclyl ring, or wherein R$^{4a}$ is hydrogen or C$_{1-4}$alkyl, and R$^{4b}$ is an optionally substituted C$_{3-7}$-heterocyclyl ring or is $^{W—R4c}$, wherein W is an optionally substituted C$_{2-6}$ alkylene chain, and R$^{4c}$ is an optionally substituted C$_{3-7}$-heterocyclyl ring.

9. The compound of claim 1, wherein R$^5$ is an optionally substituted C$_{3-7}$-heterocyclyl ring or is X—R$^{5a}$, wherein X is an optionally substituted C$_{2-6}$ alkylene chain, and R$^{5a}$ is —N(R$^{5b}$)$_2$, wherein each occurrence of R$^{5b}$ is independently hydrogen or C$_{1-6}$alkyl, or two occurrences of R$^{5b}$, taken together with the nitrogen atom to which they are bound, form an optionally substituted 3-7-membered heterocyclyl ring.

10. The compound of claim 1, wherein R$^4$ and R$^5$ are taken together to form a ring selected from:

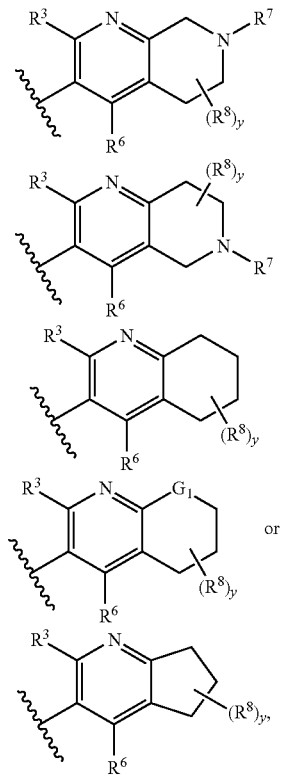

wherein
G$_1$ is —NH—, —O— or —N(CH$_3$)—
R$^7$ is selected from hydrogen or optionally substituted C$_{1-6}$aliphatic,
R$^8$ is selected from fluoro, optionally substituted C$_{1-6}$aliphatic, or —YR$^{1a}$, wherein Y is —O—, —S—, or —NR$^{1a}$, and each occurrence of R$^{1a}$ is independently hydrogen, or optionally substituted C$_{1-6}$aliphatic; and
y is 0-4.

11. The compound of claim 1 having the structure of formula I-A:

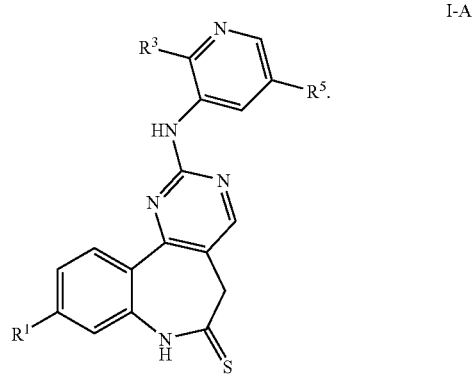

I-A

12. The compound of claim 11, wherein R$^1$ is optionally substituted C$_{1-4}$aliphatic, halogen, —CN, or —OMe.

13. The compound of claim 11, wherein R$^1$ is methyl, ethyl, —CF$_3$, Cl, —CN, —OMe, or cyclopropyl.

14. The compound of claim 11, wherein R$^3$ is methyl or CF$_3$.

15. The compound of claim 11, wherein $R^5$ is an optionally substituted $C_{3-7}$-heterocyclyl ring or is $X—R^{5a}$, wherein X is an optionally substituted $C_{2-6}$ alkylene chain, and $R^{5a}$ is $—N(R^{5b})_2$, wherein each occurrence of $R^{5b}$ is independently hydrogen or $C_{1-6}$alkyl, or two occurrences of $R^{5b}$, taken together with the nitrogen atom to which they are bound, form an optionally substituted 3-7-membered heterocyclyl ring.

16. The compound of claim 15, wherein $R^5$ is an optionally substituted pyrrolidinyl, morpholinyl, piperidinyl, or piperazinyl group, or is $X—R^{5a}$, wherein X is a $C_{2-4}$alkylene chain, and $R^{5a}$ is $—N(R^{5b})_2$, wherein each occurrence of $R^{5b}$ is independently hydrogen or $C_{1-6}$alkyl, or two occurrences of $R^{5b}$, taken together with the nitrogen atom to which they are bound, form an optionally substituted pyrrolidinyl, piperidinyl, piperazinyl, or morpholinyl group.

17. The compound of claim 16, wherein the pyrrolidinyl, morpholinyl, piperidinyl, or piperazinyl group is optionally substituted with 1-4 occurrences of $C_{1-4}$alkyl or $C_{1-4}$haloalkyl.

18. The compound of claim 11, wherein:
   a) $R^1$ is methyl, ethyl, propyl, $—CF_3$, Cl, —CN, —OMe, or cyclopropyl;
   b) $R^3$ is methyl or $CF_3$; and
   c) $R^5$ is an optionally substituted pyrrolidinyl, morpholinyl, piperidinyl, or piperazinyl group, or is $X—R^{5a}$, wherein X is a $C_{2-4}$alkylene chain, and $R^{5a}$ is $—N(R^{5b})_2$, wherein each occurrence of $R^{5b}$ is independently hydrogen or $C_{1-6}$alkyl, or two occurrences of $R^{5b}$, taken together with the nitrogen atom to which they are bound, form an optionally substituted pyrrolidinyl, piperidinyl, piperazinyl, or morpholinyl group.

19. The compound of claim 18, wherein $R^1$ is Cl or $CF_3$, and $R^3$ is methyl.

20. The compound of claim 1 having the structure of formula I—B:

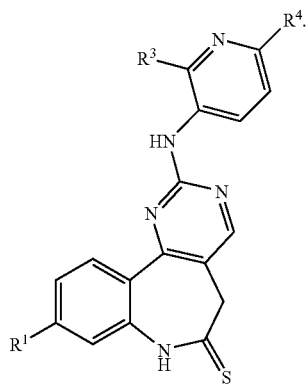

I-B

21. The compound of claim 20, wherein $R^1$ is optionally substituted $C_{1-4}$aliphatic, halogen, —CN, or —OMe.

22. The compound of claim 21, wherein $R^1$ is methyl, ethyl, $—CF_3$, Cl, —CN, —OMe, or cyclopropyl.

23. The compound of claim 20, wherein $R^3$ is methyl or $CF_3$.

24. The compound of claim 20, wherein $R^4$ is $—NR^{4a}R^{4b}$, wherein $R^{4a}$ and $R^{4b}$, taken together with the nitrogen atom to which they are bound, form an optionally substituted 3-7-membered heterocyclyl ring, or wherein $R^{4a}$ is hydrogen or $C_{1-4}$alkyl, and $R^{4b}$ is an optionally substituted $C_{3-7}$-heterocyclyl ring or is $W—R^{4c}$, wherein W is an optionally substituted $C_{2-4}$ alkylene chain, and $R^{4c}$ is an optionally substituted $C_{3-7}$-heterocyclyl ring, or $—N(R^{4d})_2$, wherein each occurrence of $R^{4d}$ is independently hydrogen or $C_{1-6}$alkyl, or two occurrences of $R^{4d}$, taken together with the nitrogen atom to which they are bound, form an optionally substituted 3-7-membered heterocyclyl ring.

25. The compound of claim 24, wherein $R^4$ is $—NR^{4a}R^{4b}$, wherein $R^{4a}$ and $R^{4b}$, taken together with the nitrogen atom to which they are bound, form an optionally substituted pyrrolidinyl, piperazinyl, piperidinyl, or morpholinyl ring, or wherein $R^{4a}$ is hydrogen or $C_{1-4}$alkyl, and $R^{4b}$ is an optionally substituted pyrrolidinyl, piperazinyl, piperidinyl, or morpholinyl ring, or is $W—R^{4c}$, wherein W is an optionally substituted $C_{2-4}$ alkylene chain, and $R^{4c}$ is an optionally substituted pyrrolidinyl, piperazinyl, piperidinyl, or morpholinyl ring, or $—N(R^{4d})_2$, wherein each occurrence of $R^{4d}$ is independently hydrogen or $C_{1-6}$alkyl, or two occurrences of $R^{4d}$, taken together with the nitrogen atom to which they are bound, form an optionally substituted pyrrolidinyl, piperazinyl, piperidinyl, or morpholinyl ring.

26. The compound of claim 20, wherein:
   a) $R^1$ is methyl, ethyl, propyl, $—CF_3$, Cl, —CN, —OMe, or cyclopropyl;
   b) $R^3$ is methyl or $CF_3$; and
   c) $R^4$ is $—NR^{4a}R^{4b}$, wherein $R^{4a}$ and $R^{4b}$, taken together with the nitrogen atom to which they are bound, form an optionally substituted pyrrolidinyl, piperazinyl, piperidinyl, or morpholinyl ring, or wherein $R^{4a}$ is hydrogen or $C_{1-4}$alkyl, and $R^{4b}$ is an optionally substituted pyrrolidinyl, piperazinyl, piperidinyl, or morpholinyl ring, or is $W—R^{4c}$, wherein W is an optionally substituted $C_{2-4}$ alkylene chain, and $R^{4c}$ is an optionally substituted pyrrolidinyl, piperazinyl, piperidinyl, or morpholinyl ring, or $—N(R^{4d})_2$, wherein each occurrence of $R^{4d}$ is independently hydrogen or $C_{1-6}$alkyl, or two occurrences of $R^{4d}$, taken together with the nitrogen atom to which they are bound, form an optionally substituted pyrrolidinyl, piperazinyl, piperidinyl, or morpholinyl ring.

27. The compound of claim 26, wherein $R^1$ is Cl or $CF_3$, and $R^3$ is methyl.

28. The compound of claim 1, wherein the compound is selected from:

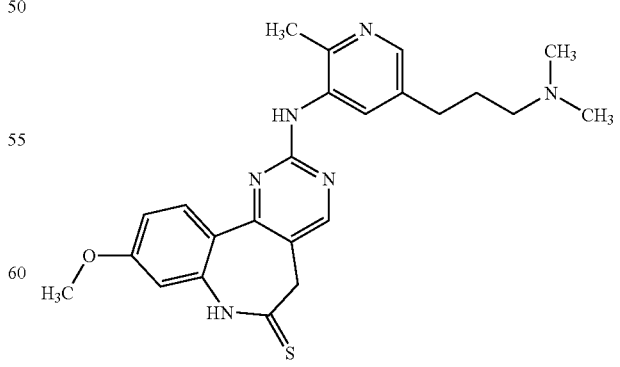

I-1

177
-continued
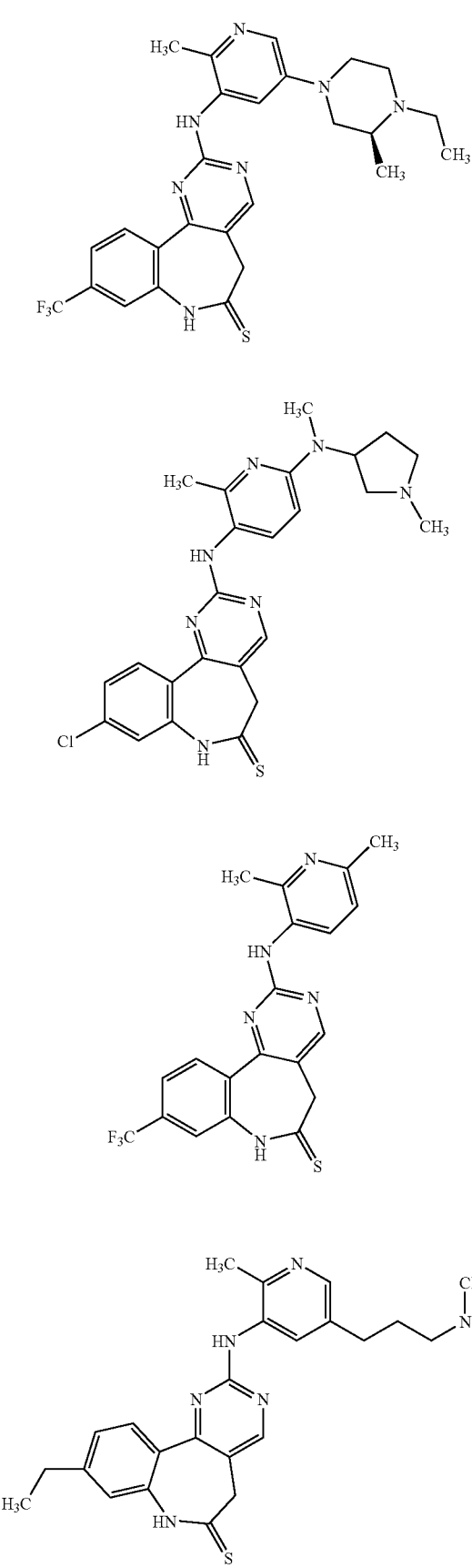
178
-continued
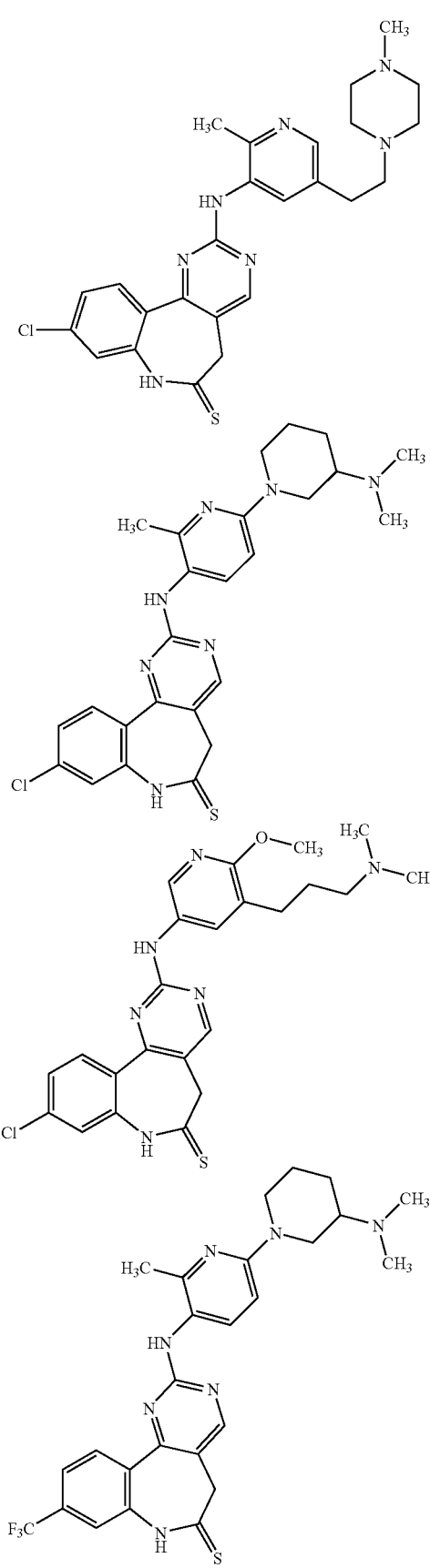

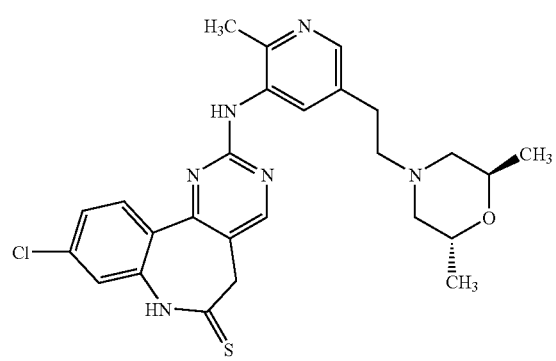
I-10
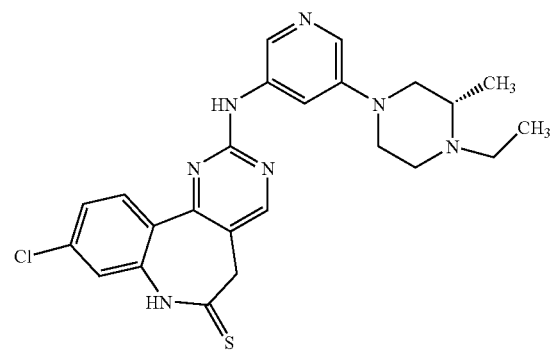
I-11
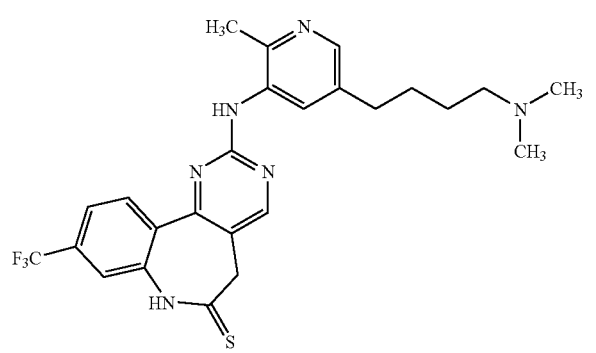
I-12
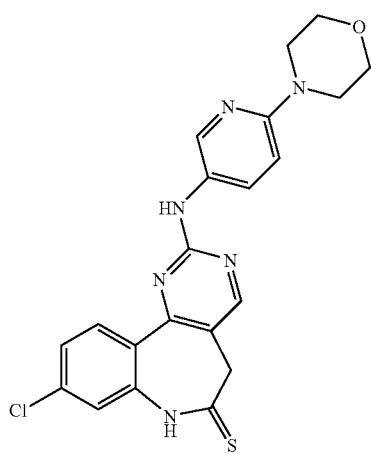
I-13
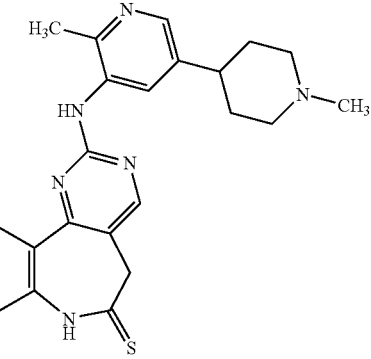
I-14
I-15
I-16
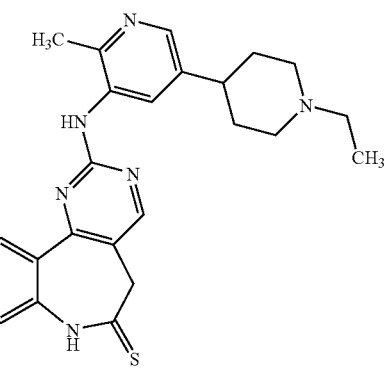
I-17

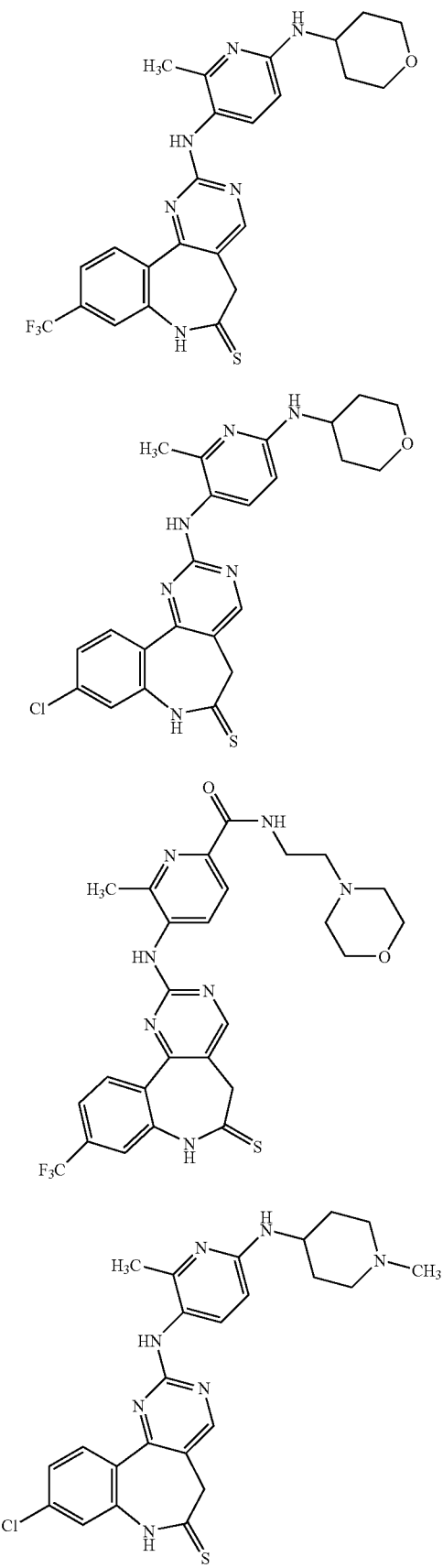
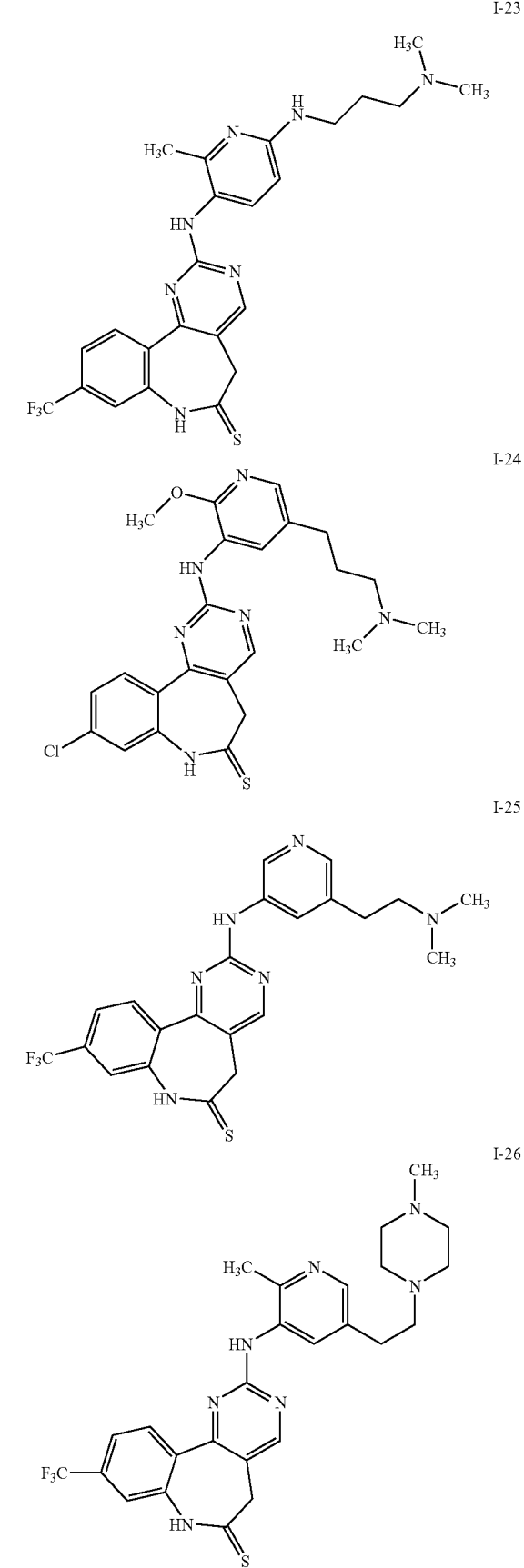

-continued
I-27
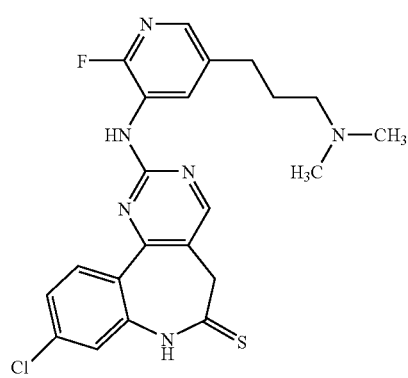
I-28
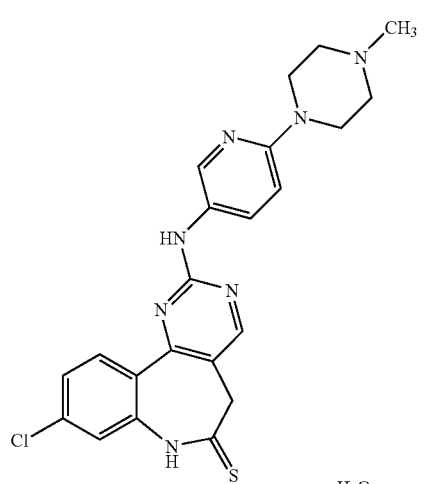
I-29
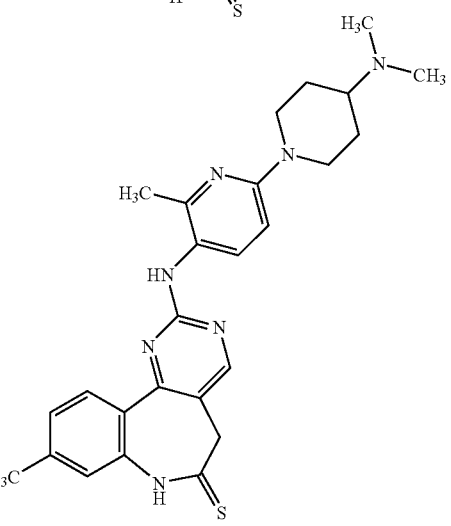
I-30
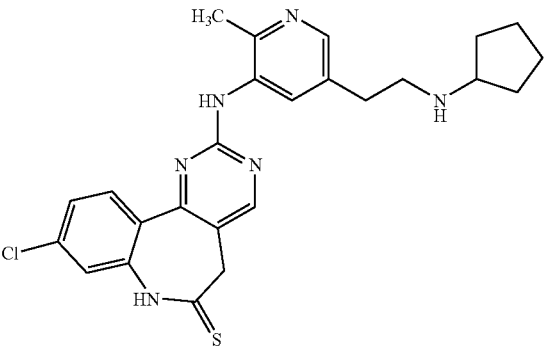
-continued
I-31
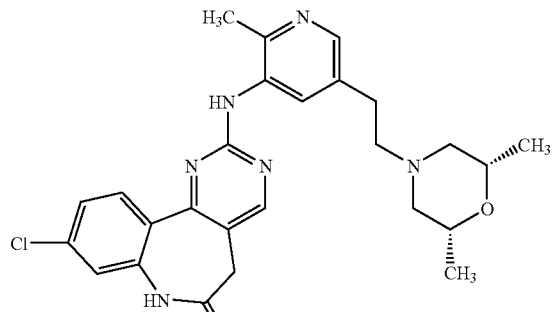
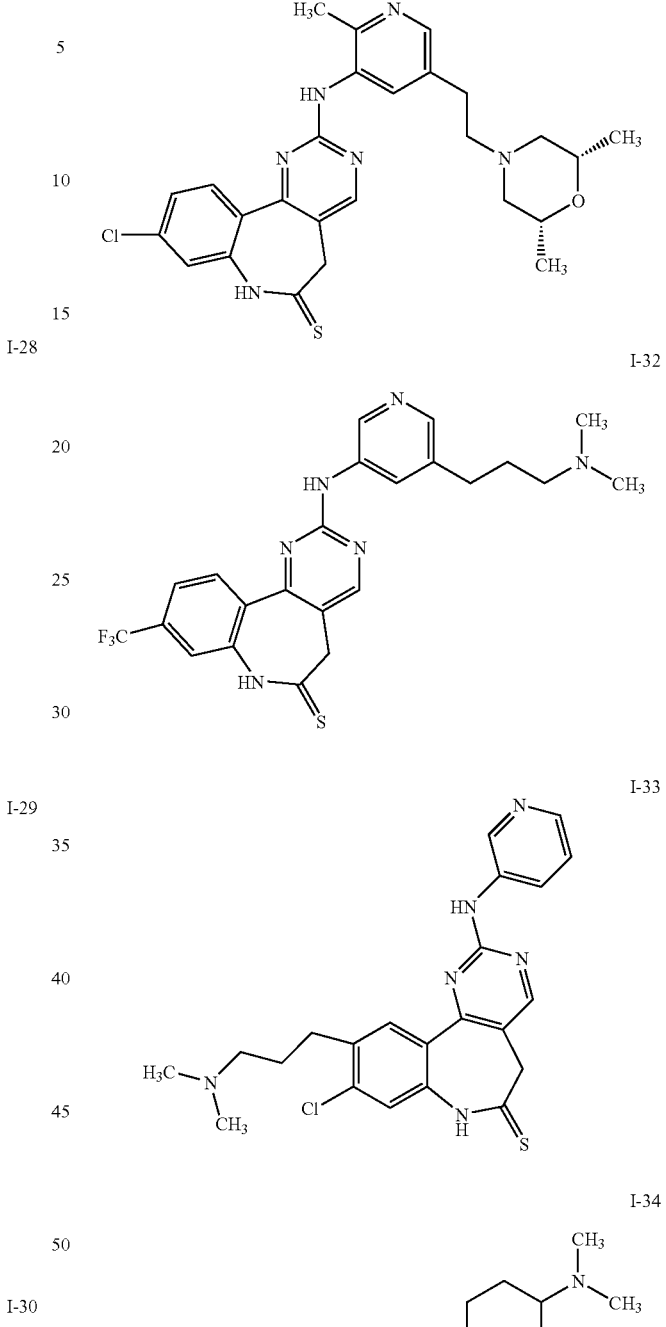

185
-continued
I-35
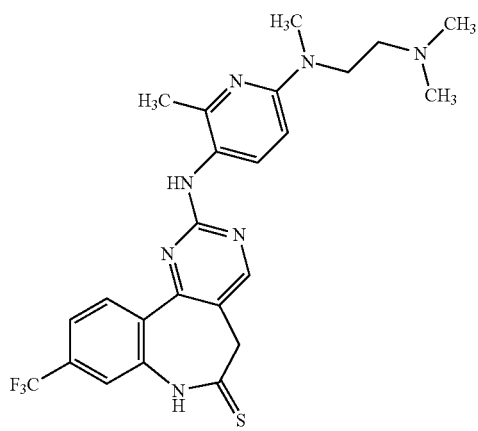
I-36
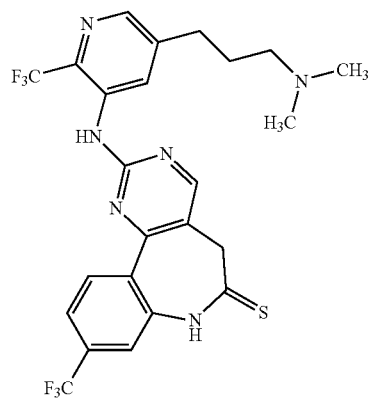
I-37
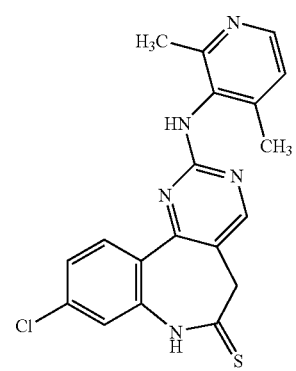
I-38
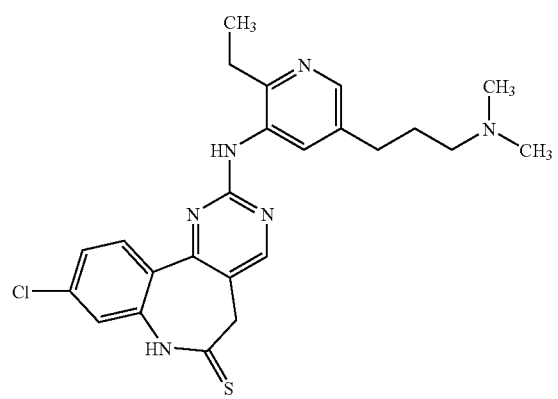
186
-continued
I-39
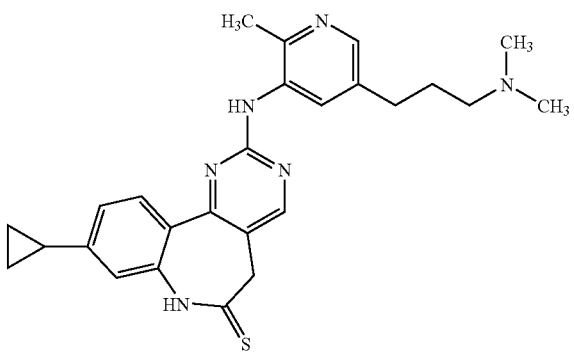
I-40
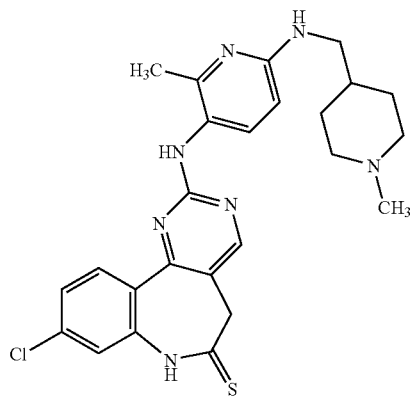
I-41
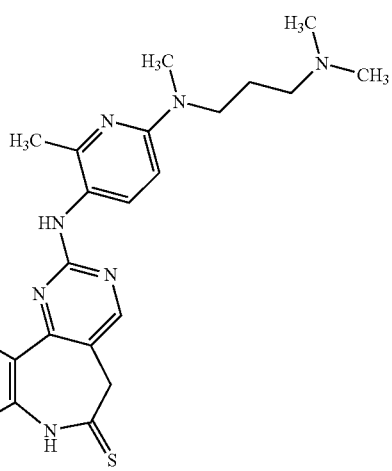
I-42
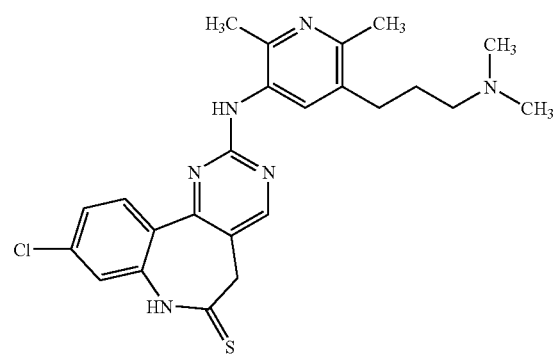

I-43
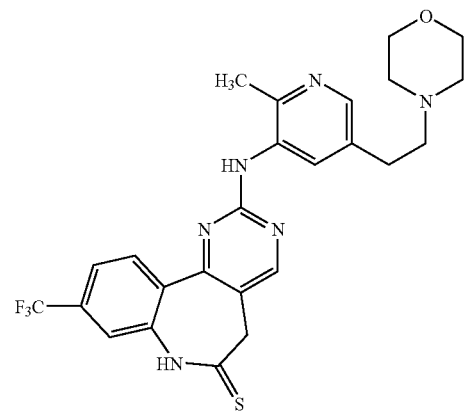
I-44
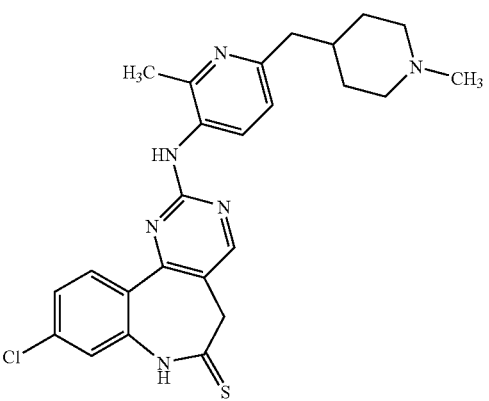
I-45
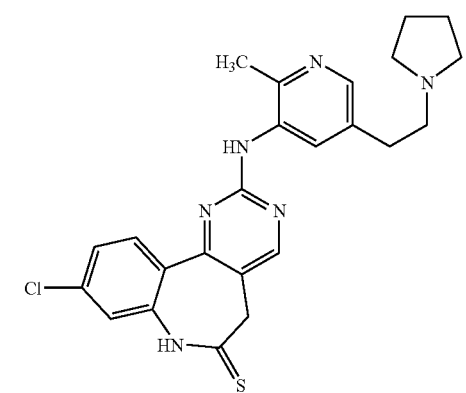
I-46
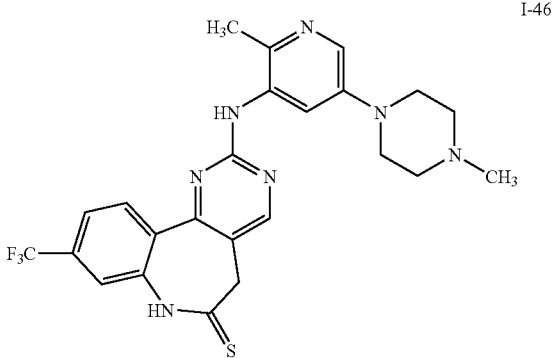
I-47
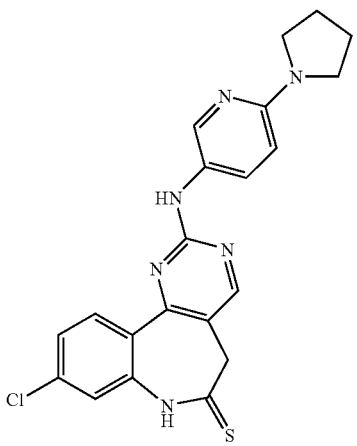
I-49
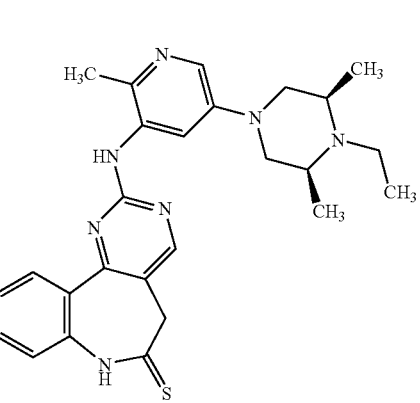
I-50
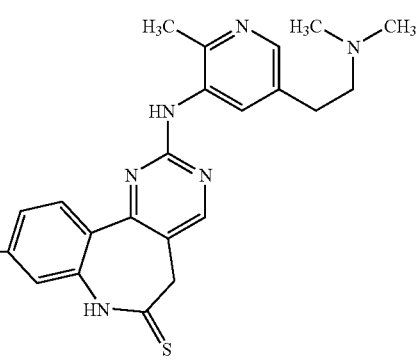
I-51
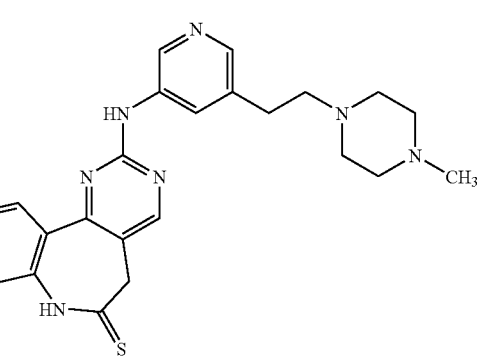

-continued
I-52
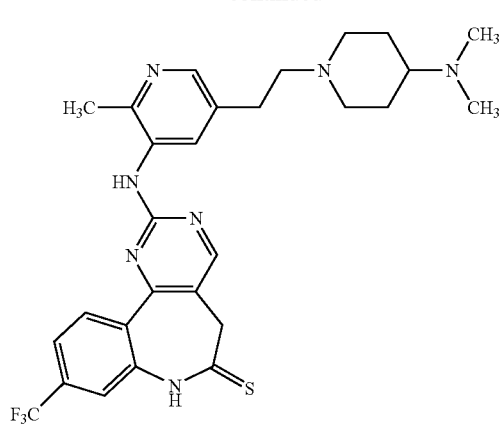
I-53
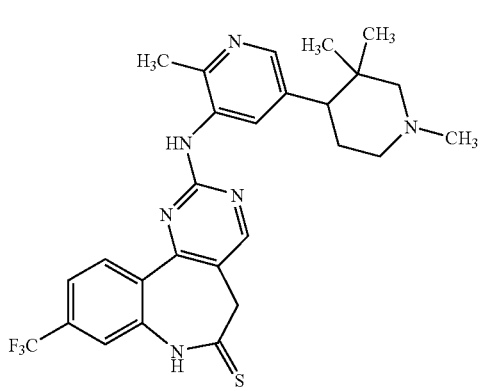
I-54
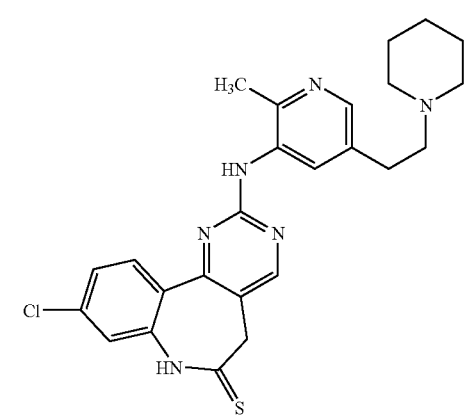
I-55
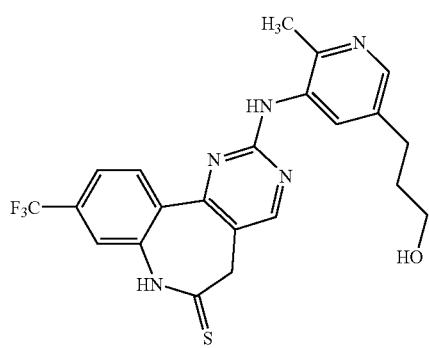
-continued
I-56
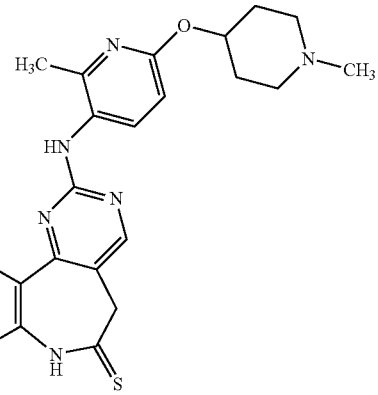
I-57
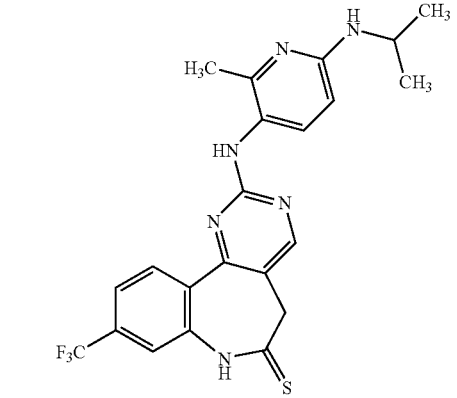
I-58
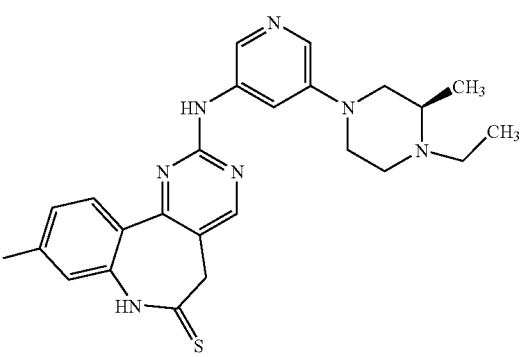
I-59
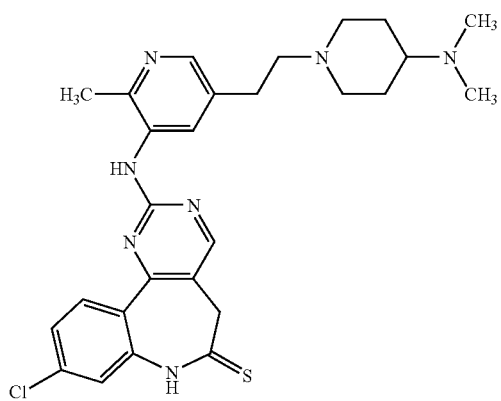

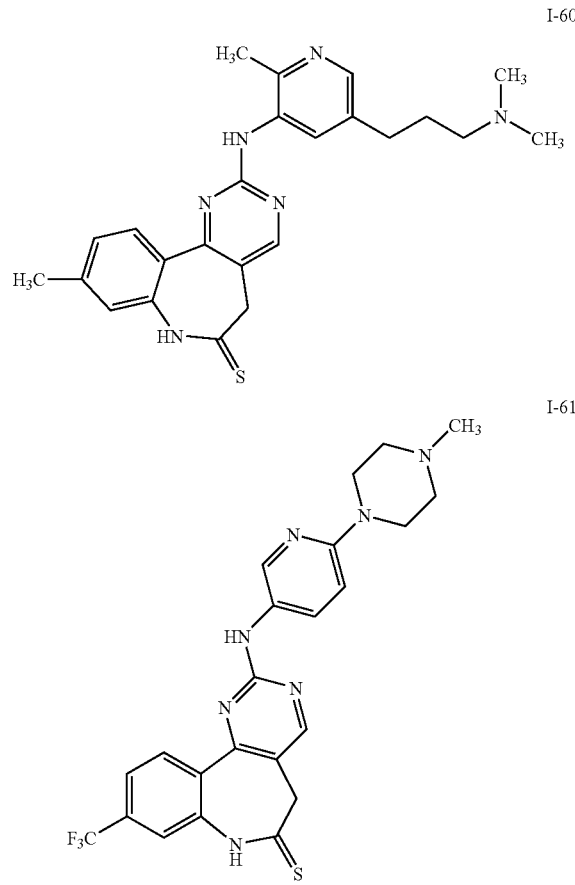
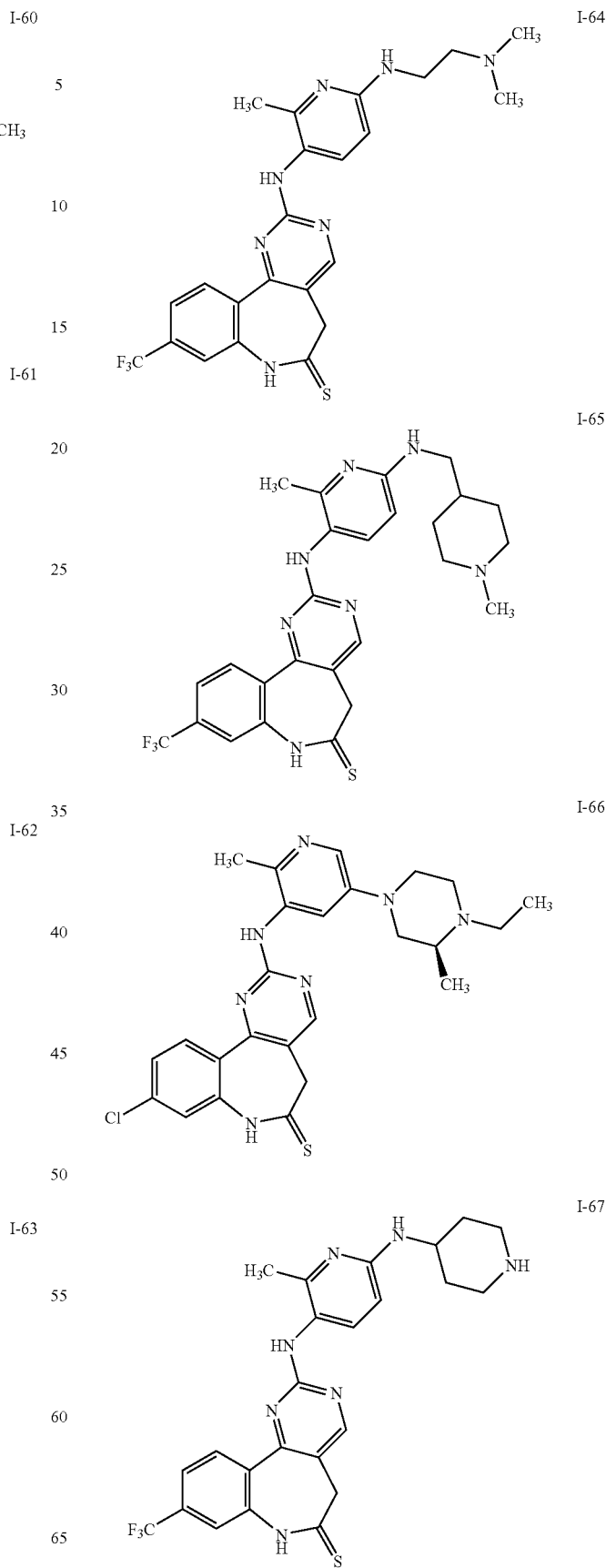

-continued
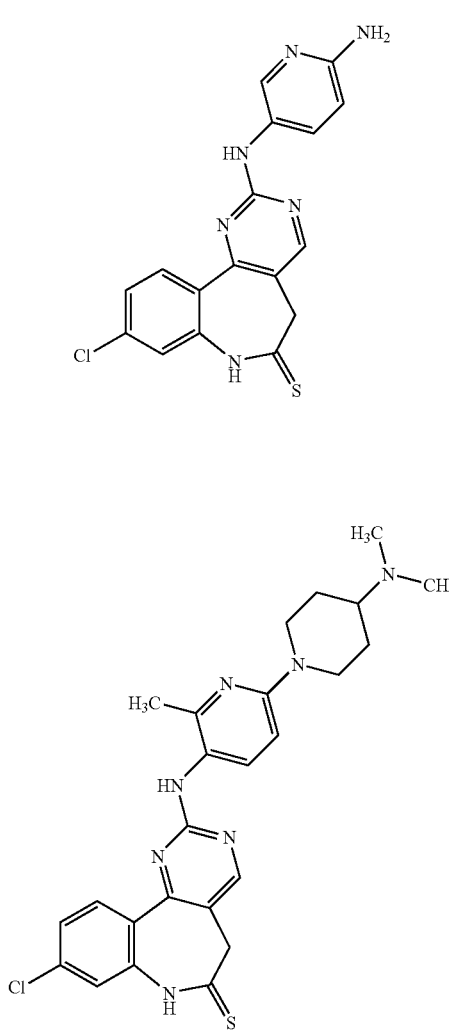
I-68
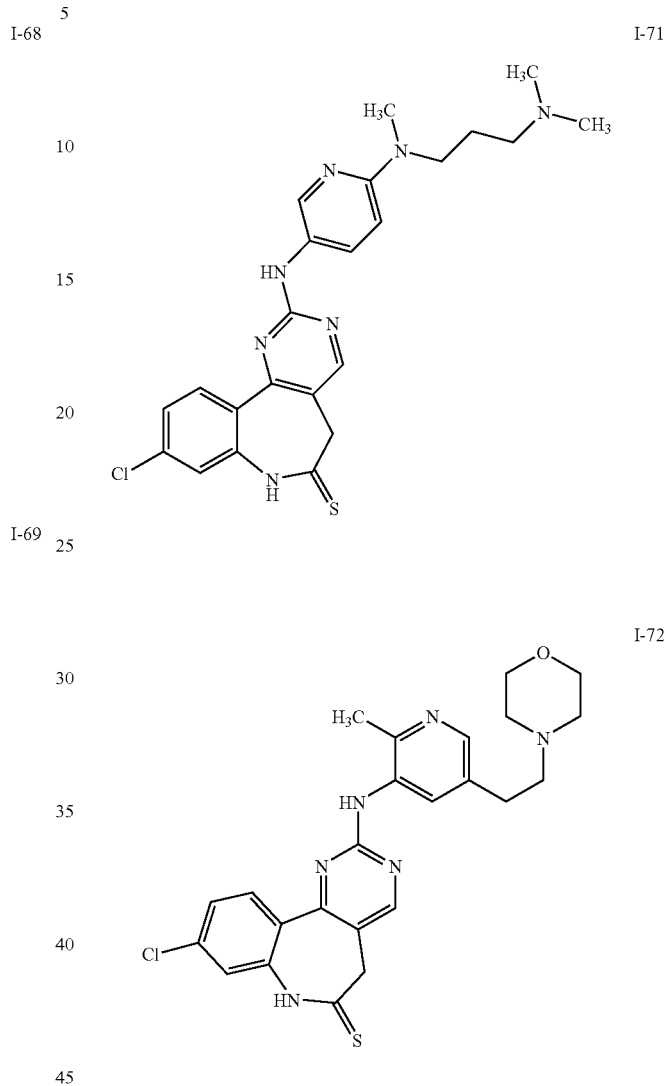
I-71
I-69
I-72
I-70
I-73

I-74 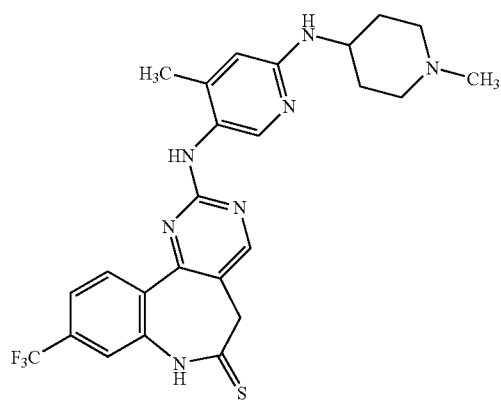
I-75 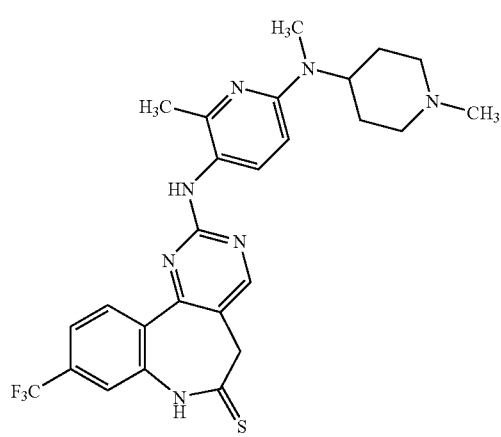
I-76 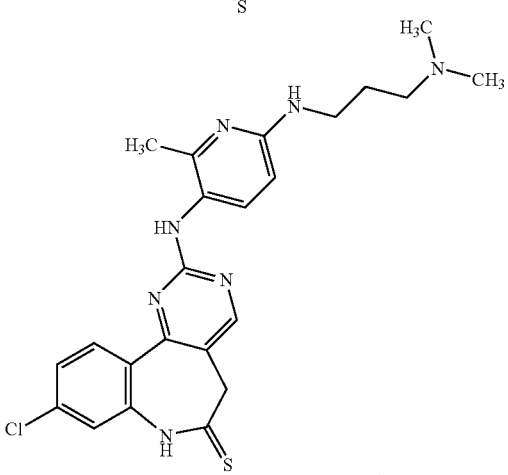
I-77 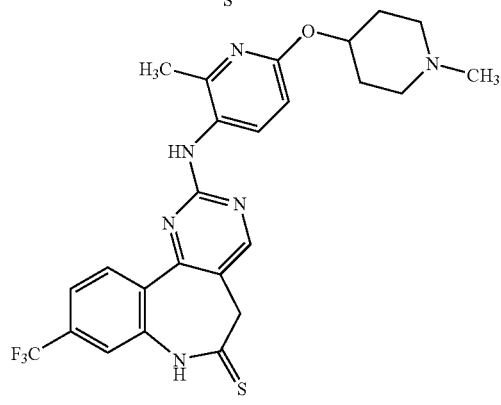
I-78 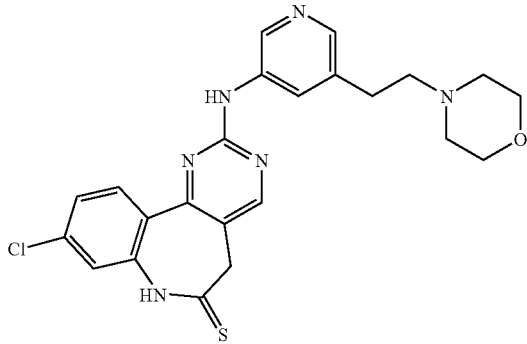
I-79 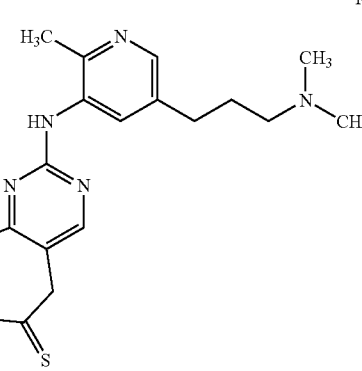
I-80 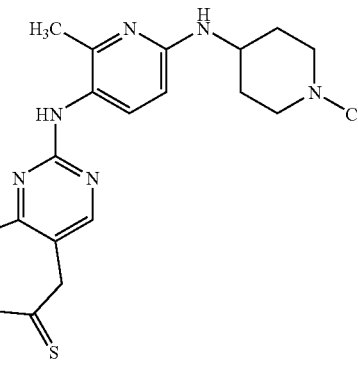
I-81 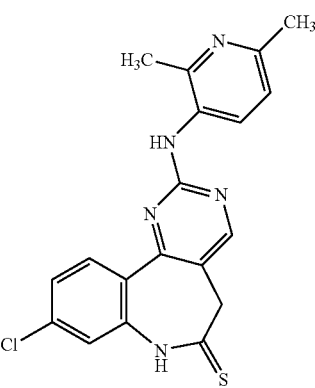

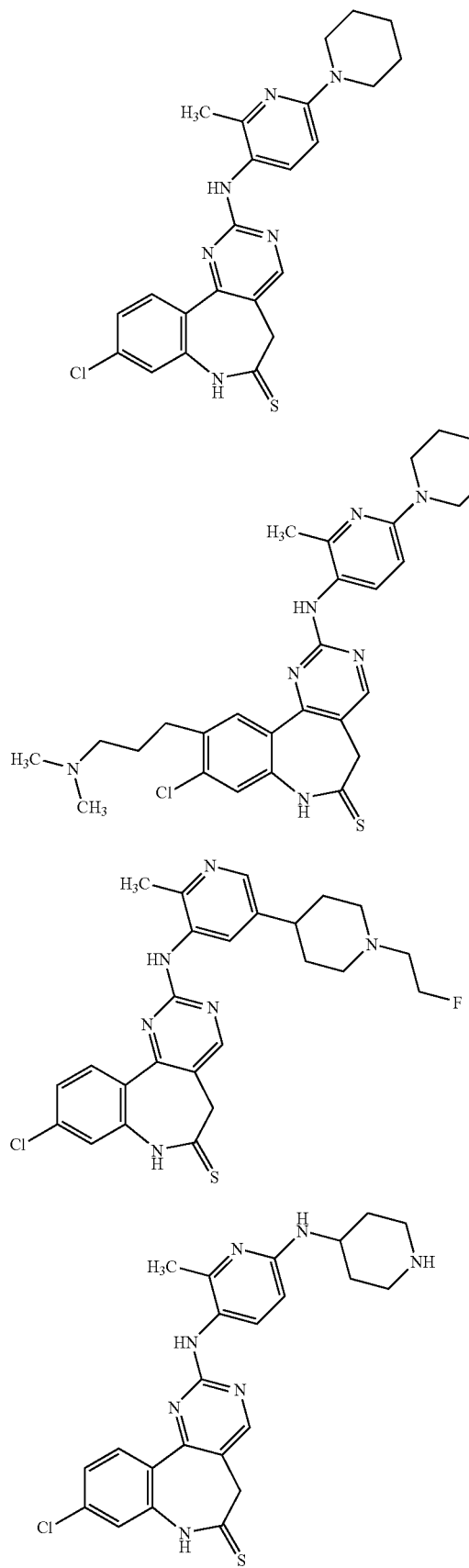
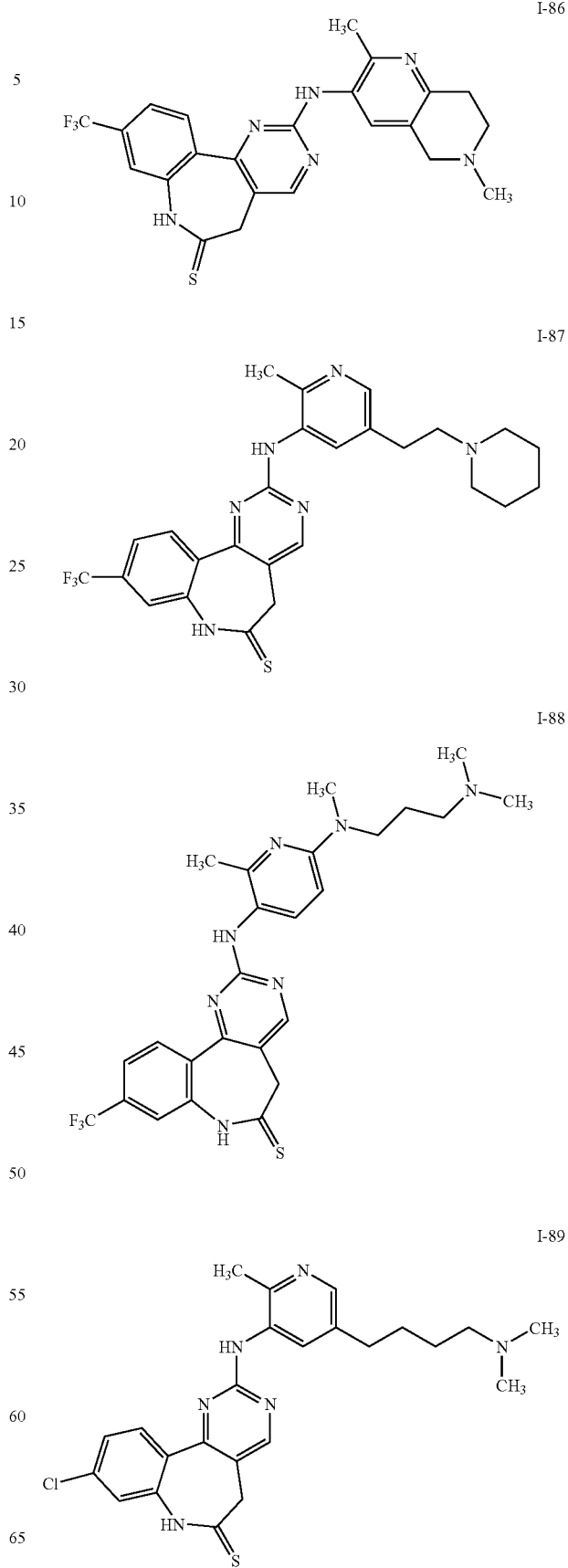

I-90 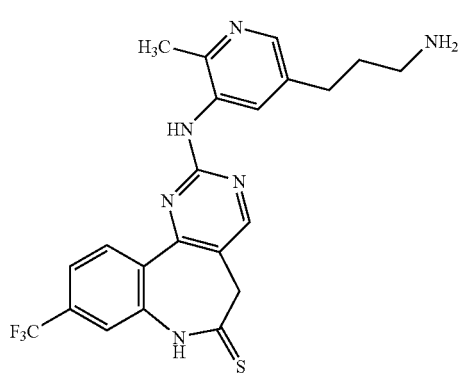
I-91 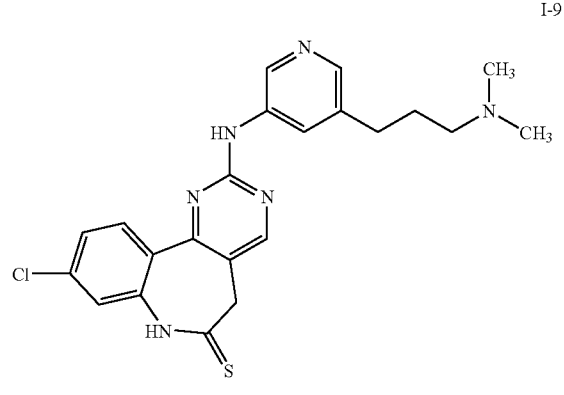
I-92 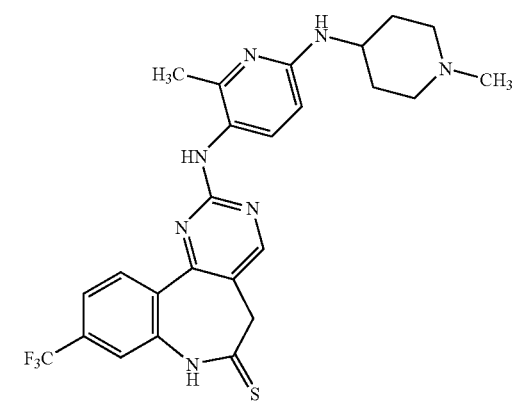
I-93 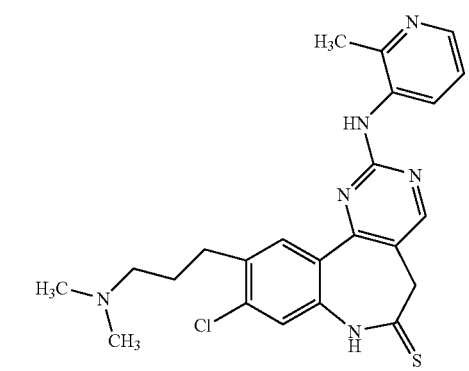
I-94 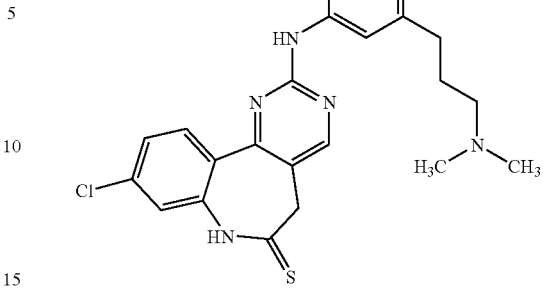
I-95 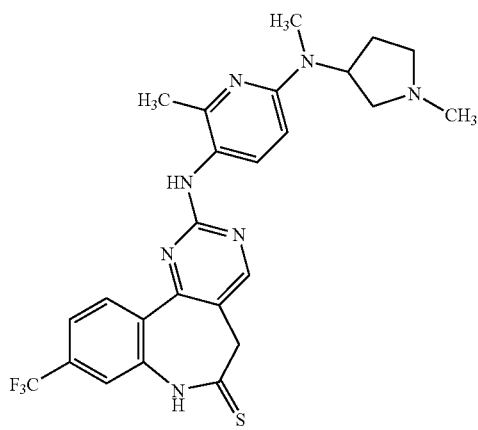
I-96 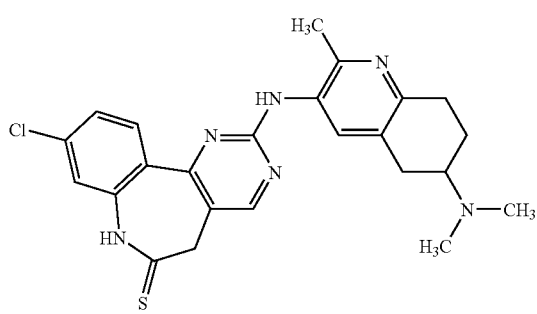
I-97 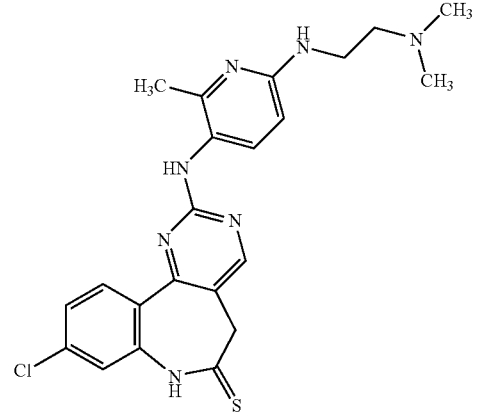

201
-continued
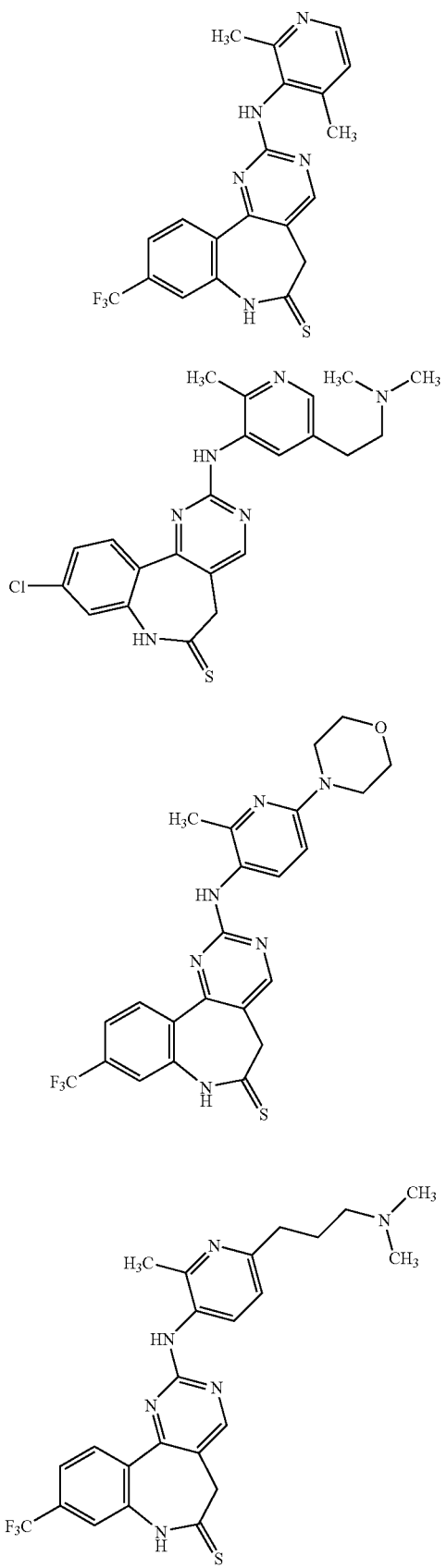
I-98
I-99
I-100
I-101
202
-continued
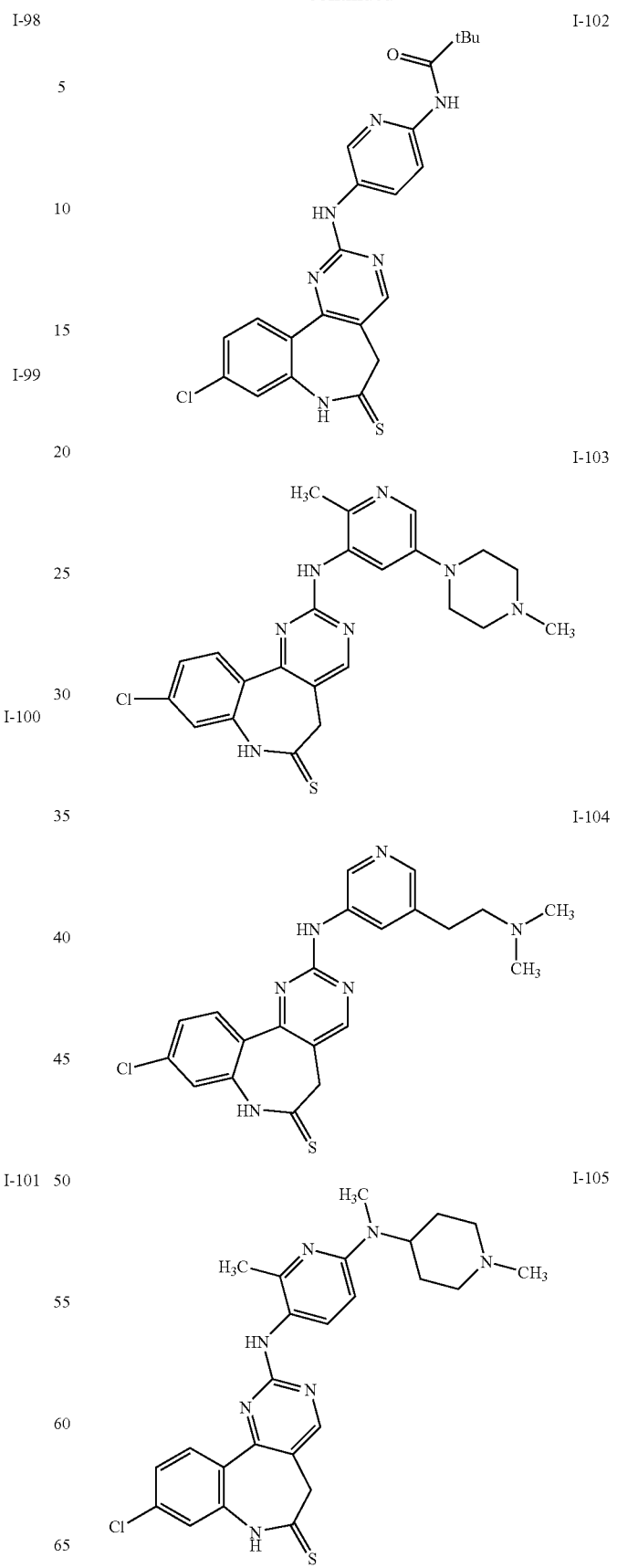
I-102
I-103
I-104
I-105

-continued
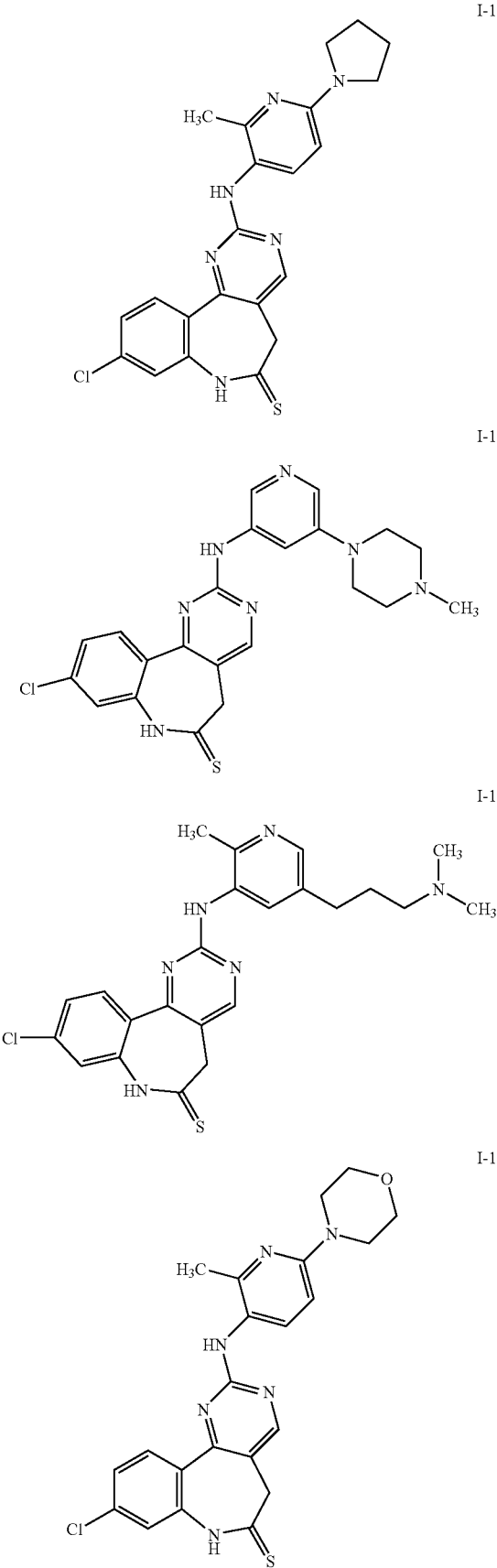
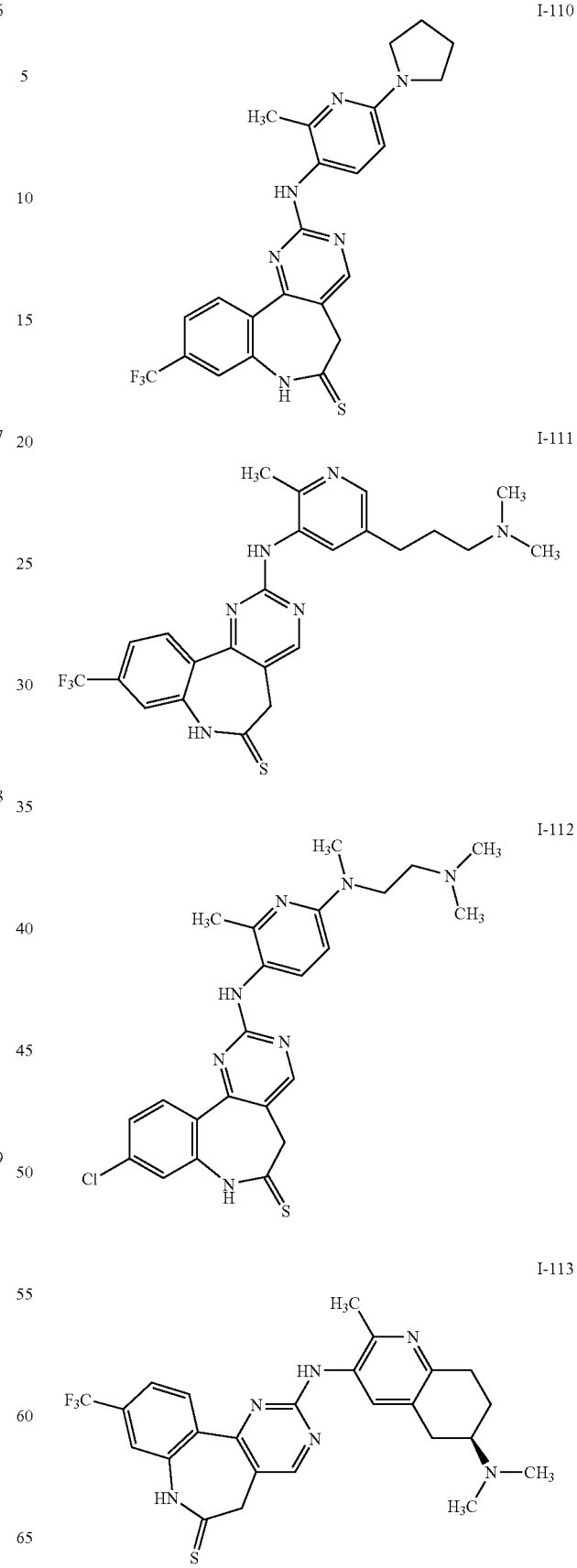

I-114
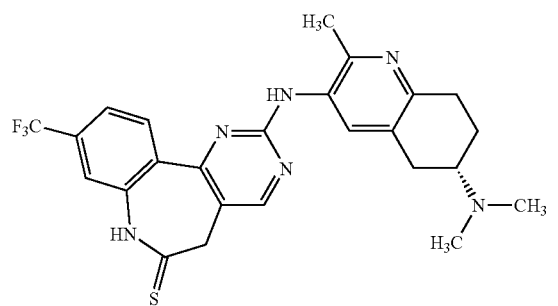
I-115
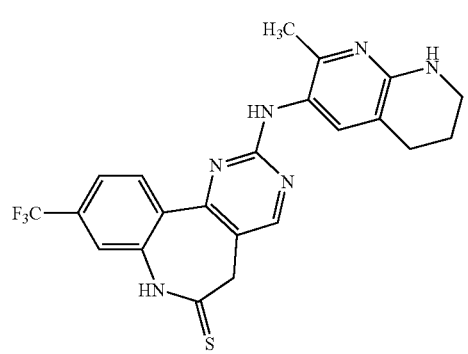
I-116
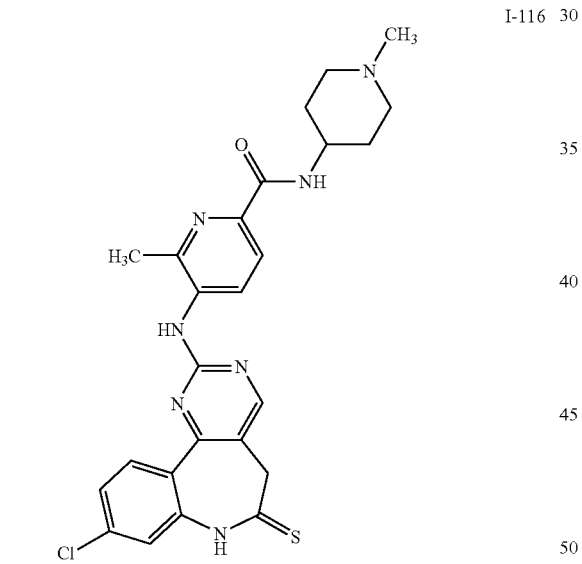
I-117
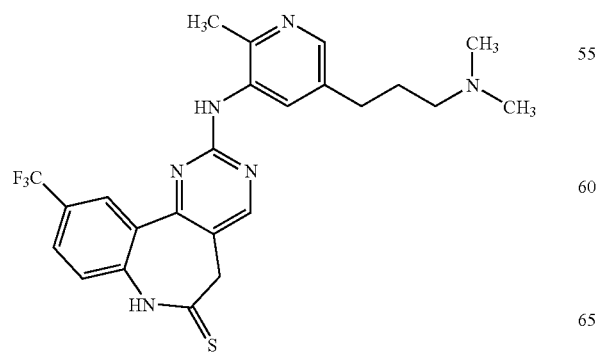
I-118
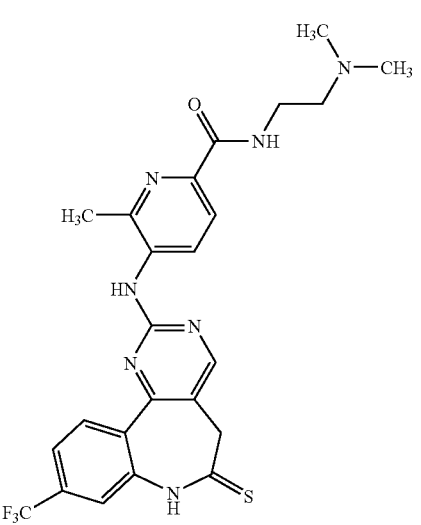
I-119
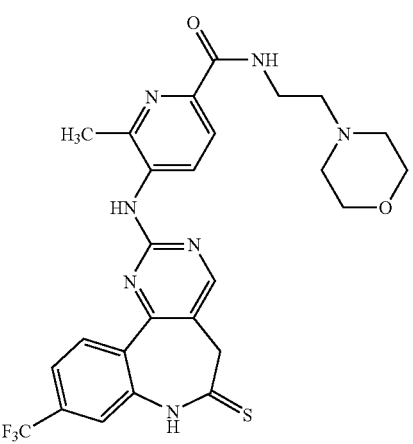
I-120
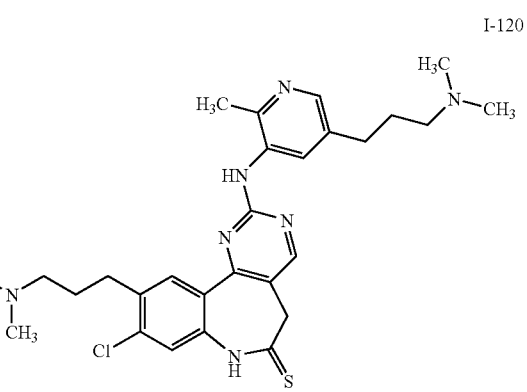

I-121
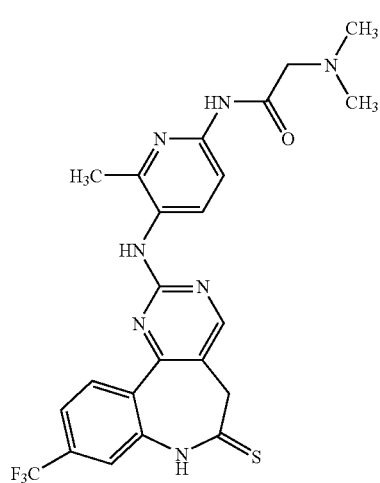
I-122
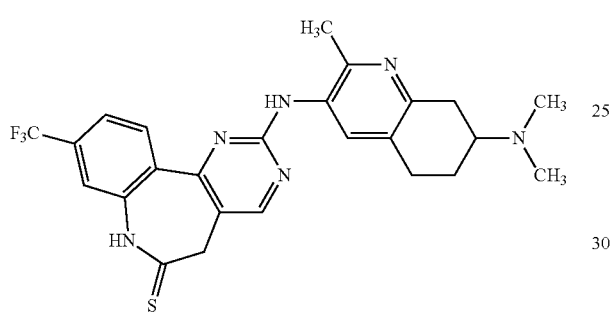
I-123
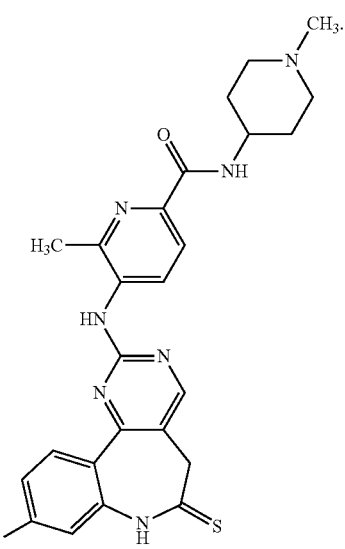
29. A pharmaceutical composition comprising a compound of claim 1, 11, 20 or 28 and a pharmaceutically acceptable carrier.
* * * * *

UNITED STATES PATENT AND TRADEMARK OFFICE
CERTIFICATE OF CORRECTION

| | | |
|---|---|---|
| PATENT NO. | : 7,998,952 B2 | Page 1 of 1 |
| APPLICATION NO. | : 12/631144 | |
| DATED | : August 16, 2011 | |
| INVENTOR(S) | : Indu T. Bharathan et al. | |

It is certified that error appears in the above-identified patent and that said Letters Patent is hereby corrected as shown below:

Please make the following corrections to the claims:

CLAIMS

In Column 173, Claim 1, Line 35, please delete, "$C_{1-4}$aikoxy" and replace with -- $C_{1-4}$alkoxy --

In Column 173, Claim 8, Line 58, please delete, "$W\text{-}R^{4c}$" and replace with -- $W\text{-}R^{4c}$ --

Signed and Sealed this
Twenty-fourth Day of July, 2012

David J. Kappos
*Director of the United States Patent and Trademark Office*